US010221164B2

(12) United States Patent
Makriyannis et al.

(10) Patent No.: US 10,221,164 B2
(45) Date of Patent: Mar. 5, 2019

(54) CANNABINERGIC NITRATE ESTERS AND RELATED ANALOGS

(71) Applicant: Northeastern University, Boston, MA (US)

(72) Inventors: Alexandros Makriyannis, Watertown, MA (US); Venkata Kiran Vemuri, Boston, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 15/401,791

(22) Filed: Jan. 9, 2017

(65) Prior Publication Data

US 2017/0210728 A1 Jul. 27, 2017

Related U.S. Application Data

(62) Division of application No. 14/770,331, filed as application No. PCT/US2014/018582 on Feb. 26, 2014, now Pat. No. 9,580,400.

(60) Provisional application No. 61/769,410, filed on Feb. 26, 2013.

(51) Int. Cl.
| | |
|---|---|
| *A61K 31/352* | (2006.01) |
| *A61K 31/435* | (2006.01) |
| *A61K 31/04* | (2006.01) |
| *C07D 405/14* | (2006.01) |
| *C07D 311/78* | (2006.01) |
| *C07D 311/80* | (2006.01) |
| *C07D 221/06* | (2006.01) |
| *C07D 231/56* | (2006.01) |
| *C07D 209/12* | (2006.01) |
| *C07C 203/04* | (2006.01) |
| *C07C 309/68* | (2006.01) |
| *C07C 203/00* | (2006.01) |
| *A61K 31/4433* | (2006.01) |
| *C07D 405/04* | (2006.01) |

(52) U.S. Cl.
CPC ............ *C07D 405/04* (2013.01); *A61K 31/04* (2013.01); *A61K 31/352* (2013.01); *A61K 31/435* (2013.01); *A61K 31/4433* (2013.01); *C07C 203/00* (2013.01); *C07C 203/04* (2013.01); *C07C 309/68* (2013.01); *C07D 209/12* (2013.01); *C07D 221/06* (2013.01); *C07D 231/56* (2013.01); *C07D 311/78* (2013.01); *C07D 311/80* (2013.01); *C07C 2601/14* (2017.05); *C07C 2601/16* (2017.05); *C07C 2602/42* (2017.05)

(58) Field of Classification Search
None
See application file for complete search history.

(56) References Cited

U.S. PATENT DOCUMENTS

| | | | |
|---|---|---|---|
| 5,219,747 | A | 6/1993 | McNally et al. |
| 7,745,424 | B2 * | 6/2010 | Ralston ................ A61K 31/235 514/124 |
| 9,580,400 | B2 | 2/2017 | Makriyannis et al. |
| 2007/0032544 | A1 | 2/2007 | Korthout et al. |
| 2007/0060638 | A1 | 3/2007 | Olmstead et al. |
| 2010/0152283 | A1 | 6/2010 | Gant |
| 2016/0108016 | A1 | 4/2016 | Makriyannis et al. |

FOREIGN PATENT DOCUMENTS

| | | |
|---|---|---|
| WO | WO 2007/136607 | 11/2007 |
| WO | 2014134127 | 9/2014 |

OTHER PUBLICATIONS

Database Registry Chemical Abstracts Service, Columbus, Ohio, Accession No. RN 131318-15-5, 131318-16-6, 131318-17-7, Entered STN: Jan. 11, 1991.*
Ito, Nobuyuki. Cancer Science 94(1), (2003) 3-8.*
Database Registry Chemical Abstracts Service, Columbus, Ohio, Accession No. RN 36235-17-3, Entered STN: Nov. 16, 1984.*
Bolla. M. et al. "Therapeutic Potential of Nitrate Esters of Commonly Used Drugs." Current Topics in Medicinal Chemistry. 2005. vol. 5. pp. 707-720.
Chang, C. A. et al. "Homology Modeling of Cannabinoid Receptors: Discovery of Cannabinoid Analogues for Therapeutic Use." Computational Drug Discovery and Design, Methods in Molecular Biology, Riccardo Baron (ed.). 2012. vol. 819. Chapter 35. pp. 595-611.
Fattore, L. et al. "Beyond THC: the new generation of cannabinoid designer drugs." Frontiers in Behavioral Neuroscience. 2011. vol. 5. Article 60, pp. 1-12.
International Search Report & Written Opinion on PCT/US2014/018582 dated Jun. 27, 2014.
Khanolkar, A. D. et al. "Cannabilactones: A Novel Class of CB2 Selective Agonists with Peripheral Analgesic Activity." J. Med. Chem. 2007. vol. 50. pp. 6493-6500.
Mercier, R. IV. et al. "Human Cannabinoid 2 GPCR Ligand-interaction Landscape: Cysteine Residues Critical to Biarylpyrazole Antagonist Binding Motif and Receptor Modulation." Chem Biol. 2010. vol. 17, No. 10, pp. 1132-1142.
Bodor, N., et al., "Soft drug design: General principles and recent applications", Medicinal Research Reviews, 20(1): 58-101 (Jan. 2000).
Buchwald, A., et al., "Soft cannabinoid analogues as potential anti-glaucoma agents", Pharmazie, 55(3): 196-201 (Mar. 2000).
Buchwald, A., et al., "Soft cannabinoid analogues as potential anti-glaucoma agents", Pharmazie, 57(2): 104-114 (Feb. 2002).

(Continued)

*Primary Examiner* — Samantha L Shterengarts
(74) *Attorney, Agent, or Firm* — Hamilton, Brook, Smith & Reynolds, P.C.

(57) ABSTRACT

The present technology relates to novel cannabinergic nitrate esters and related analogs, process of preparation, pharmaceutical compositions and their methods of use as medicaments, pharmacological tools and/or biomarkers. The novel cannabinergic nitrate ester compounds provide medicaments useful in treating a variety of diseases and medical disorders.

9 Claims, 15 Drawing Sheets

(56) References Cited

OTHER PUBLICATIONS

Minutolo, F., et al., "Metabolically labine cannabinoid esters: A 'soft drug' approach for the development of cannabinoid-based therapeutic drugs", Biorganic & Medicinal Chemistry Letters, 17(17): 4878-4881 (2007).
Boehncke, et al., "Concise International Chemical Assessment Document 6: Biphenyl", World Health Organization, Published 1999.
Stark, P., et al., "Cannabinoids. I. Behaviorial Effects", Journal of Phamacology and Experimental Therapeutics, 214 (1): 124-130 (1980).
Sullivan, H.R., et al., "Pharmacokinetics of Nabilone, a Psychotropically Active 9-Ketocannabinoid, in the Dog. Utilization of Quantitative Selected Ion Monitoring and Deuterium Labeling", Biomedical Mass Spectrometry, 5(4): 296-301 (1979).
Notification Concerning Transmittal of International Preliminary Report on Patentability for International Application No. PCT/US2014/018582, "Cannabinergic Nitrate Esters and Related Analogs", dated Sep. 11, 2015.

\* cited by examiner

CANNABINERGIC NITRATE ESTERS AND RELATED ANALOGS

CROSS-REFERENCE TO RELATED APPLICATIONS

This application is a divisional of U.S. application Ser. No. 14/770,331, now U.S. Pat. No. 9,580,400, which is a U.S. national stage application claiming the benefit of International Application No. PCT/US2014/018582, filed on Feb. 26, 2014, which claims the benefit of and priority to U.S. Provisional Patent Application No. 61/769,410, filed Feb. 26, 2013, the entire contents of which are incorporated herein by reference.

FIELD

The present technology generally relates to biologically active novel cannabinergic compounds. In particular, the present technology is related to novel cannabinergic nitrate esters and related analogs.

BACKGROUND

Human recreational use of the hemp plant *Cannabis sativa* ("marijuana") and anecdotal attempts to exploit it for potential therapeutic benefit have been documented throughout millennia. Some of marijuana's popularity as a recreational substance and medicament reflects its ability to alter sensory perception and relieve anxiety. Other medicinal effects of marijuana unrelated to its psychoactive properties, such as pain relief, have also been recorded in ancient texts. $\Delta^9$-tetrahydrocannabinol ($\Delta^9$-THC) and cannabidiol are the two major phytocannabinoids that were identified along with approximately 60 other phytocannabinoids present in *Cannabis*. $\Delta^9$-THC, cannabidiol, and some other phytocannabinoids are bioactive with, for example, intriguing anti-inflammatory, anticonvulsive, and anti-emetic effects of potential therapeutic value. However, $\Delta^9$-THC is regarded as the sole psychotropic cannabinoid in *Cannabis*. Given $\Delta^9$-THC's psychotropic effects, many biological investigations employed brain and brain plasma membranes as study-objects. Consensus data describing several key characteristics of cannabinoid action emerged: $\Delta^9$-THC, its synthetic analogs and related compounds elicit biological effects in a stereo- and structurally selective manner; their binding to brain plasma membranes is avid, saturable, stereospecific, concordant with in vitro and in vivo bioresponses (e.g., adenylyl cyclase inhibition, analgesia), and nonrandom in select brain regions.

These characteristics strongly implied that cannabinoid pharmacology is receptor-mediated, spurring the search for discrete mammalian cannabinoid receptors whose activation by $\Delta^9$-THC would elicit psychotropic effects. The search led to the discovery and cloning of two G protein-coupled receptors (GPCRs) for cannabinoids (CB), designated CB1 and CB2, which in humans share≈44% sequence homology. The CB1 receptor subtype is localized primarily in the central nervous system (CNS), reflecting its prevalence as the most abundant GPCR in brain. CB1 receptors are distributed among the cortex, cerebellum, hippocampus, and basal ganglia, brain regions that control motor, cognitive, emotional, and sensory functions. Hence, central CB1 receptor activation mediates most cannabinoid psychotropic and behavioral effects. The CB1 receptor is also present in high density in the brainstem, hypothalamus, and pituitary gland, loci influencing pain perception; hormonal activity; thermoregulation; and cardiovascular, gastrointestinal, and respiratory physiology. CB1 receptors at peripheral sites (e.g., adipocytes, liver, uterus) help regulate such basic physiological processes as energy balance and reproduction. Although detectable at exceedingly low levels in brain, CB2 receptors are expressed mainly by immune and hematopoietic cells, osteoclasts, and osteoblasts and mediate immune responses, inflammation, inflammatory and neuropathic pain, and bone remodeling. Largely because of this psychoactivity as well as its prevalence and early availability in synthetic form as a research tool, $\Delta^9$-THC attained the status of prototypic cannabinoid and became the focus of many pharmacological and mechanistic studies.

Much of this research in vivo was aimed at elucidating the effects of $\Delta^9$-THC in experimental animals as well as human subjects with the aid of newly-synthesized $\Delta^9$-THC analogs and related compounds such as nabilone, $\Delta^8$-tetrahydrocannabinol, 11-OH-$\Delta^9$-tetrahydrocannabinol, cannabidiol (ex., GWP42003), cannabinol, $\Delta^9$-tetrahydrocannabivarin (ex., GWP42004), CP-47,497, dexanabinol, Ajulemic acid, HU-210, 8-β-OH-tetrahydrocannabinol, 8-α-OH-tetrahydrocannabinol, SAB-378, nabitan, menabitan, A-40174, Org 28611, nonabine, BAY38-7271, GRC10693, S-777469, AZD¹940, GW-842,166X, GW-405,833, levonantradol, dimethylheptylpyran and the AM1703 analog PRS-211,375 (Cannabinor). Some of these compounds were radiolabeled and used as molecular probes as well. Virtually all cannabinoid-related medications granted regulatory approvals thus far are directly related to *Cannabis*, most of which act as agonists at the CB1 and CB2 receptors.

It has been suggested that tetrahydrocannabivarin acts as a CB1 neutral antagonist while $\Delta^9$-THC is known to act as a CB1 partial agonist. $\Delta^9$-THC (dronabinol, Marinol®) and its synthetic analog, the CB1/CB2 agonist, nabilone (Cesame®) are licensed as anti-nausea and anti-emetic medications for chemotherapy patients. Nabilone is also approved as an appetite stimulant to treat acquired immune deficiency syndrome-related cachexia. Sativex®, a standardized *Cannabis* extract containing an approximately equal mixture of the two phytocannabinoids ($\Delta^9$-THC and cannabidiol) formulated as a sublingual spray, was first licensed for alleviation of neuropathic pain in multiple sclerosis patients and subsequently approved for cancer pain relief. The low reported frequency of abuse and neurocognitive side-effects of *Cannabis* extracts/$\Delta^9$-THC derivatives has invited their continued clinical evaluation. Aside from nabilone, other synthetic cannabinoid-receptor activators such as CP55,940 have been studied clinically for alleviation of emesis; motor-related symptoms in patients with multiple sclerosis, Tourette's syndrome, or Parkinson's disease; intraocular pressure in glaucoma patients; neuropathic pain; or post-trauma brain damage.

SUMMARY

In one aspect, a compound of formula (I), or a pharmaceutically acceptable salt thereof is provided:

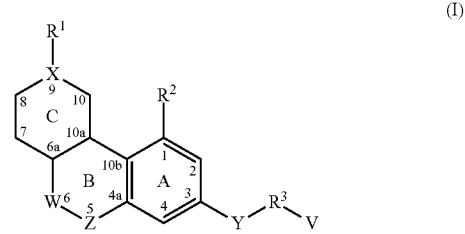

wherein:
C has zero, one, two or three double bonds;
X is C, CH, N, NH, C(CH$_2$)$_2$, S, O, SO, SO$_2$, or CF$_2$;

R is H, OH, =O, halogen, COOH, nitro, $ONO_2$, or optionally substituted alkyl, haloalkyl, alkenyl, alkynyl, acyl, aryl, heterocyclyl, heteroaryl, alkoxy, aryloxy, heteroalkoxy, heteroaryloxy, alkenyl, amino, thio, cyano, thiocynato, isothiocynato, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;

W is $C(CH_3)_2$, $CH(CH_3)$, C=O, C(O)-alkyl, C<$F_2$, C=S, C=$CH_2$, $C(CH_2)_2$, spirocyclic ring, S, SO, $SO_2$, or $C[CH_3(R^4)]$;

$R^4$ is an optionally substituted alkyl, alkenyl, or alkynyl group;

Z is O, S, SO, $SO_2$, NH, N—CN or N-alkyl;

R is H, OH, SH, $NH_2$, $CF_3$, COOH, halogen, $ONO_2$, alkyl-$ONO_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;

Y is a bond, $C(CH_3)_2$, $CF_2$, C=O, C(alkyl), COO, NHCO, CONH, alkyl, cycloalkyl, heterocyclyl, lactone, lactam, sultam, O, S, SO, $SO_2$, $OSO_2$, amine, diazine, alkenyl, or alkynyl group;

$R^3$ is absent, or is O, S, $SO_2$, $SO_2NH$, $NHSO_2$, $OSO_2$, alkyl, alkenyl, alkynyl, cycloalkyl, a carbocyclic, a spirocyclic, heterocyclyl, aryl, heteroaryl, carboxyl, acetate, amine, amide, or imide;

V is $V^1$ or $ONO_2$, wherein when any of rings A, B or C is substituted with a group comprising $ONO_2$ V is $V^1$, otherwise V is $ONO_2$; and $V^1$ is H, F, Cl, Br, I, haloalkyl, $N_3$, NCS, CN, $NO_2$, OH, alkoxy, amino, alkylamino, dialkylamino, trialkylamino, aryl, cycloalkyl, alkenyl, alkynyl, —C(O)aryl, —C(O)alkyl, —C(O)heteroaryl, —C(O)amino, —C(O)(dialkylamino), C(O)(trialkylamino), C(O)(heterocyclyl), C(O)heteroaryl, —OC(O)alkyl, $OSO_2H$, $OSO_2$(alkyl), $OSO_2$(aryl), $OSO_2NO_2$, $OSO_2$(alkyl)CN, $OSO_2$(alkyl)OH, $OSO_2$alkylamino), —SC(O)alkyl, —$SO_2$alkyl, —SO-alkyl, —$SC(CH_3)_2C(O)$Oalkyl, —$SC(CH_3)_2C(O)$Oaryl, —$SC(CH_3)_2C(O)$Oheteroaryl, —$SC(CH_3)_2C(O)$Oheterocyclyl, Si(alkyl)$_3$, —OC(O)aryl, NHC(O)alkyl, NHC(O)aryl, —C(O)H, C(O)Oalkyl, $SO_2$(amino), $SO_2$(heterocyclyl), $SO_2$(trialkylamino), $SO_2$(dialkylamino), a spirocyclic ring, heterocyclyl, heteroaryl, alkylthio, alkylamino, dialkylamino, alkylsulfinyl, alkylsulfonyl, boronic acid, boronate ester, $BF_3K$, or a biotin group tethered via an amide bond.

In Formula I, in some embodiments, C has at least one double bond at the C8-C9 position, the C9-C10 position, or the C6a-C10a position. In some embodiments, V is $ONO_2$. In other embodiments, $R^1$ is a group comprising $ONO_2$ and V is H. In other embodiments, $R^1$ is $ONO_2$, alkyl-$ONO_2$, O-alkyl-$ONO_2$, O—$SO_2$-alkyl-$ONO_2$, —C(O)O-alkyl-$ONO_2$, alkyl-C(O)O-alkyl-$ONO_2$, or alkyl-O-alkyl-$ONO_2$. In some embodiments, C has one, two or three double bonds, and at least one double bond is at the C8-C9 position, the C9-C10 position, or the C6a-C10a position; W is $C(CH_3)_2$, $CH(CH_3)$, C=O, or $CF_2$; Z is O or N; and V is H when $R^1$ is a group including $ONO_2$, or V is $ONO_2$. In any of the above embodiments, Y—$R^3$—V may be $ONO_2$, alkyl-$ONO_2$, O-alkyl-$ONO_2$, O—$SO_2$-alkyl-$ONO_2$, —C(O)O-alkyl-$ONO_2$, alkyl-C(O)O-alkyl-$ONO_2$, or alkyl-O-alkyl-$ONO_2$.

In any of the above embodiments of Formula I, C may be:

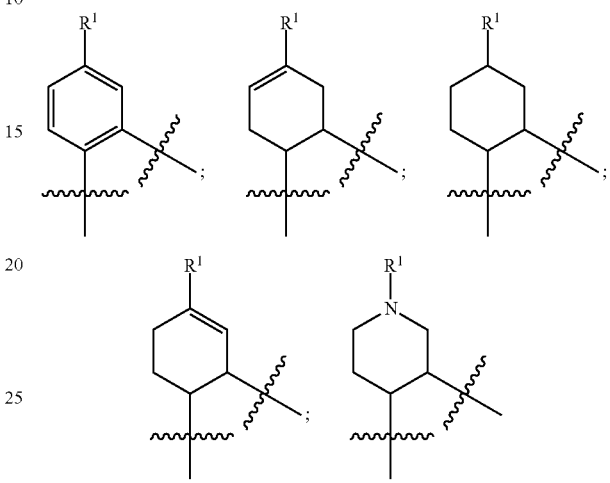

In any of the above embodiments of Formula I, B may be:

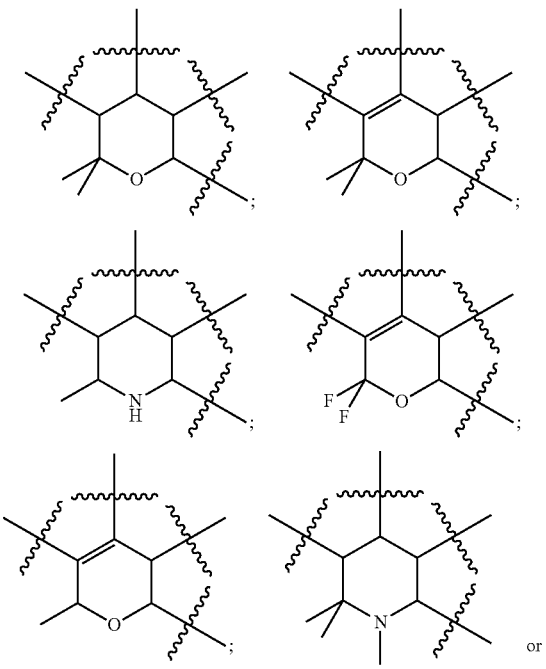

or

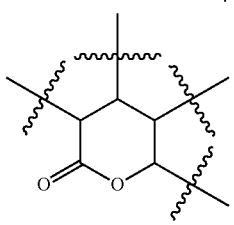

In any of the above embodiments of Formula I, C may be:

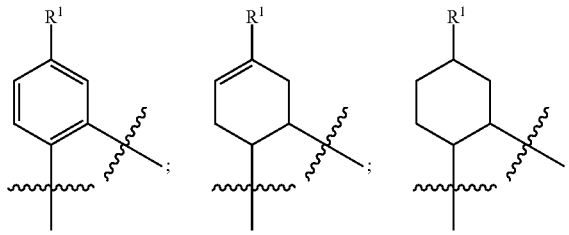

B may be:

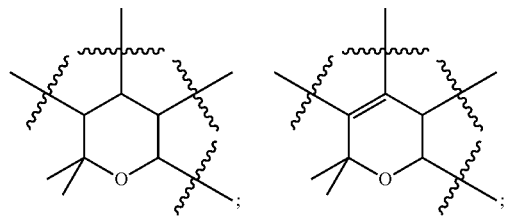

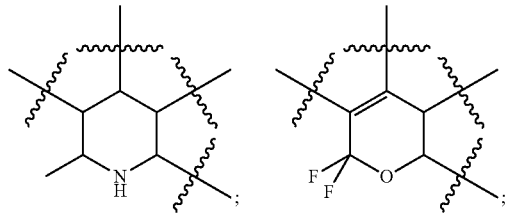

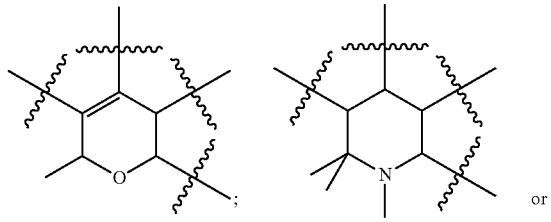

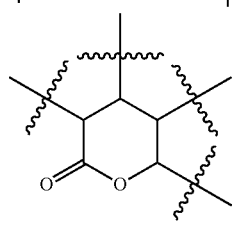

and V is ONO$_2$.

In another aspect, provided is a compound of Formula (II), or a pharmaceutically acceptable salt thereof:

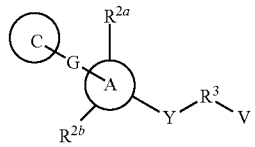

(II)

or a pharmaceutically acceptable salt thereof;
wherein:
C is carbocyclic, bicyclic, aryl, heterocyclyl, heteroaryl, or a terpene;
G is a bond, C=O, NH, CH$_2$, CONH, NHCO, C(O)O, OC(O), OCH$_2$, S, SO, SO$_2$, or O;
A is an aromatic ring, heteroaromatic ring, heterocyclic ring, or quinone;
R$^{2a}$ and R$^{2b}$ are each independently H, OH, SH, NH$_2$, CF$_3$, COOH, halogen, ONO$_2$, alkyl-ONO$_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;
Y is a bond, C(CH$_3$)$_2$, CF$_2$, C=O, C(alkyl), COO, NHCO, CONH, alkyl, cycloalkyl, heterocyclyl, lactone, lactam, sultam, O, S, SO, SO$_2$, OSO$_2$, amine, diazine, alkenyl, or alkynyl group;
R$^3$ is absent, or is O, S, SO$_2$, SO$_2$NH, NHSO$_2$, OSO$_2$, alkyl, alkenyl, alkynyl, cycloalkyl, a carbocyclic, a spirocyclic, heterocyclyl, aryl, heteroaryl, carboxyl, acetate, amine, amide, or imide; and
V is V$^1$ or ONO$_2$, wherein when any of rings A, B or C is substituted with a group comprising ONO$_2$ V is V$^1$, otherwise V is ONO$_2$; and
V$^1$ is H, F, Cl, Br, I, haloalkyl, N$_3$, NCS, CN, NO$_2$, OH, alkoxy, amino, alkylamino, dialkylamino, trialkylamino, aryl, cycloalkyl, alkenyl, alkynyl, —C(O)aryl, —C(O)alkyl, —C(O)heteroaryl, —C(O)amino, —C(O)(dialkylamino), C(O)(trialkylamino), C(O)(heterocyclyl), C(O)heteroaryl, —OC(O)alkyl, OSO$_2$H, OSO$_2$(alkyl), OSO$_2$(aryl), OSO$_2$NO$_2$, OSO$_2$(alkyl)CN, OSO$_2$(alkyl)OH, OSO$_2$alkylamino), —SC(O)alkyl, —SO$_2$alkyl, —SO-alkyl, —SC(CH$_3$)$_2$C(O)Oalkyl, —SC(CH$_3$)$_2$C(O)Oaryl, —SC(CH$_3$)$_2$C(O)Oheteroaryl, —SC(CH$_3$)$_2$C(O)Oheterocyclyl, Si(alkyl)$_3$, —OC(O)aryl, NHC(O)alkyl, NHC(O)aryl, —C(O)H, C(O)Oalkyl, SO$_2$(amino), SO$_2$(heterocyclyl), SO$_2$(trialkylamino), SO$_2$(dialkylamino), a spirocyclic ring, heterocyclyl, heteroaryl, alkylthio, alkylamino, dialkylamino, alkylsulfinyl, alkylsulfonyl, boronic acid, boronate ester, BF$_3$K, or a biotin group tethered via an amide bond.

In any of the above embodiments of Formula II, C may be:

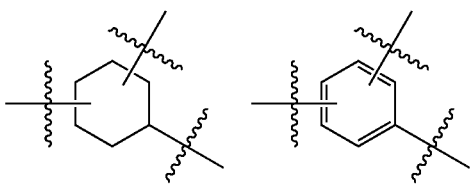

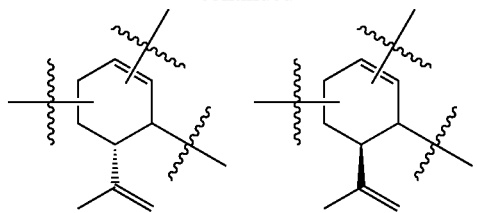
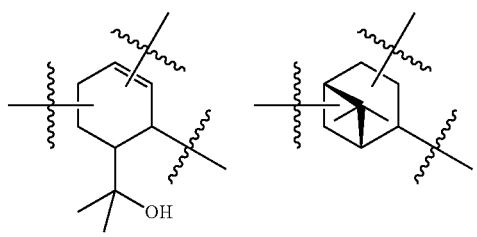
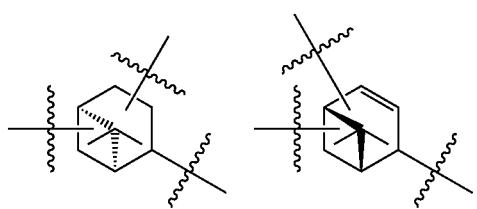
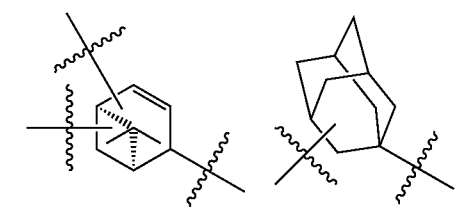
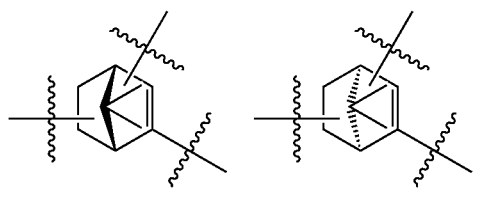
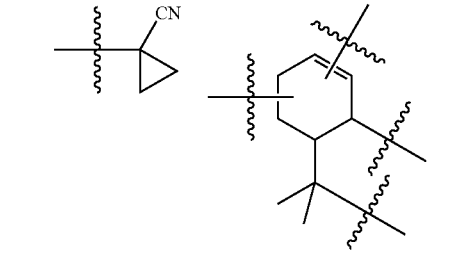
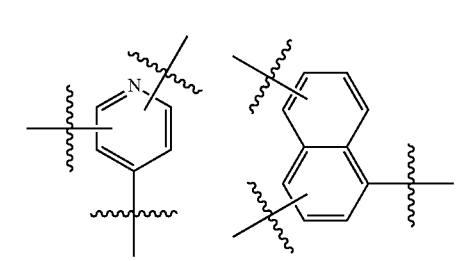
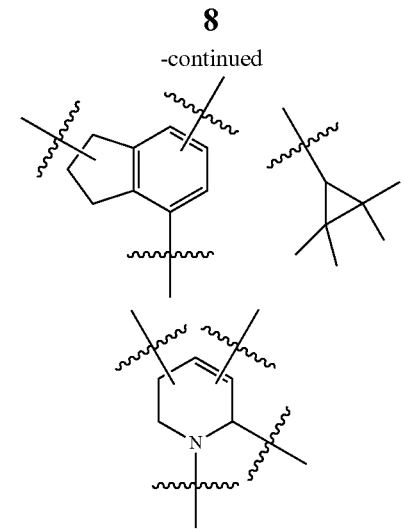
In any of the above embodiments of Formula II, A may be:
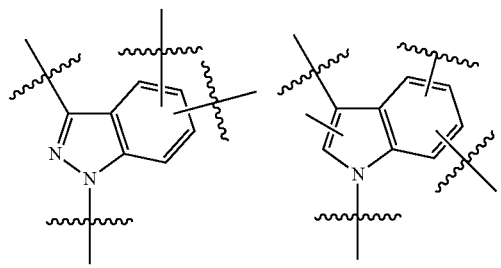
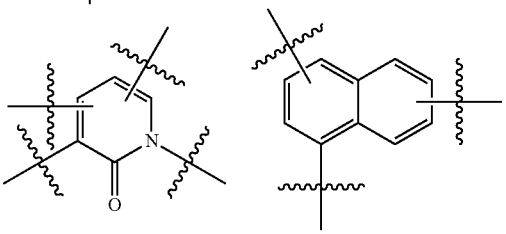
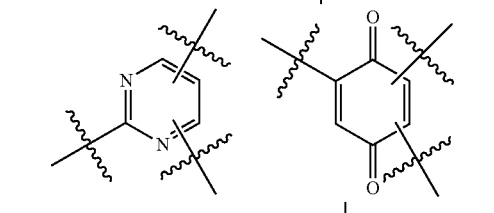
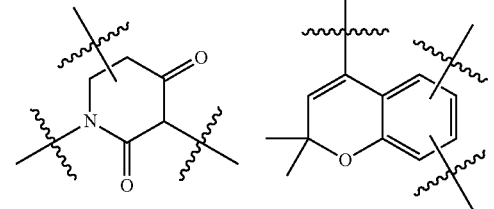
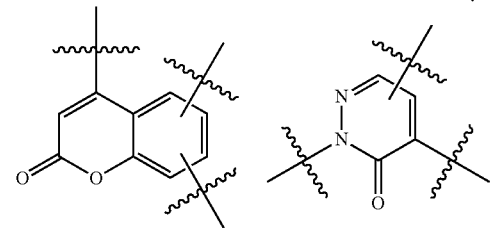

-continued

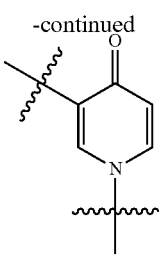

In another aspect, provided is a compound of Formula (III), or a pharmaceutically acceptable salt thereof:

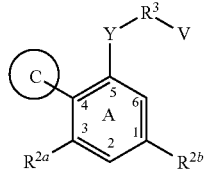

(III)

or a pharmaceutically acceptable salt thereof;
wherein:
C is carbocyclic, bicyclic, aryl, heterocyclyl, heteroaryl, or a terpene;
$R^{2a}$ and $R^{2b}$ are each independently H, OH, SH, $NH_2$, $CF_3$, COOH, halogen, $ONO_2$, alkyl-$ONO_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;
Y is a bond, $C(CH_3)_2$, $CF_2$, C=O, C(alkyl), COO, NHCO, CONH, alkyl, cycloalkyl, heterocyclyl, lactone, lactam, sultam, O, S, SO, $SO_2$, $OSO_2$, amine, diazine, alkenyl, or alkynyl;
$R^3$ is absent, O, S, $SO_2$, $SO_2NH$, $NHSO_2$, $OSO_2$, alkyl, alkenyl, alkynyl, cycloalkyl, a carbocyclic, a spirocyclic, heterocyclyl, aryl, heteroaryl, carboxyl, acetate, amine, amide, or imide; and
V is $V^1$ or $ONO_2$, wherein when any of rings A, B or C is substituted with a group comprising $ONO_2$ V is $V^1$, otherwise V is $ONO_2$; and
$V^1$ is H, F, Cl, Br, I, haloalkyl, $N_3$, NCS, CN, $NO_2$, OH, alkoxy, amino, alkylamino, dialkylamino, trialkylamino, aryl, cycloalkyl, alkenyl, alkynyl, —C(O)aryl, —C(O)alkyl, —C(O)heteroaryl, —C(O)amino, —C(O)(dialkylamino), C(O)(trialkylamino), C(O)(heterocyclyl), C(O)heteroaryl, —OC(O)alkyl, $OSO_2H$, $OSO_2$(alkyl), $OSO_2$(aryl), $OSO_2NO_2$, $OSO_2$(alkyl)CN, $OSO_2$(alkyl)OH, $OSO_2$alkylamino), —SC(O)alkyl, —$SO_2$alkyl, —SO-alkyl, —$SC(CH_3)_2C(O)Oalkyl$, —$SC(CH_3)_2C(O)Oaryl$, —$SC(CH_3)_2C(O)Oheteroaryl$, —$SC(CH_3)_2C(O)Oheterocyclyl$, Si(alkyl)$_3$, —OC(O)aryl, NHC(O)alkyl, NHC(O)aryl, —C(O)H, C(O)Oalkyl, $SO_2$(amino), $SO_2$(heterocyclyl), $SO_2$(trialkylamino), $SO_2$(dialkylamino), a spirocyclic ring, heterocyclyl, heteroaryl, alkylthio, alkylamino, dialkylamino, alkylsulfinyl, alkylsulfonyl, boronic acid, boronate ester, $BF_3K$, or a biotin group tethered via an amide bond.

In any of the above embodiments of Formula III, C may be:

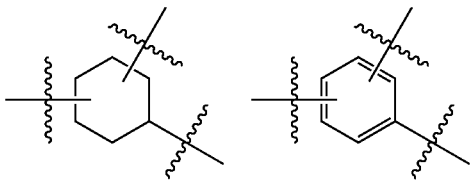

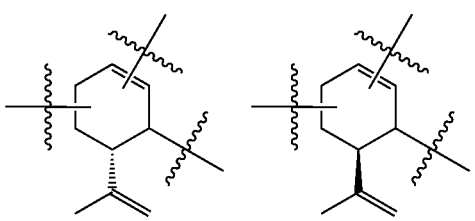

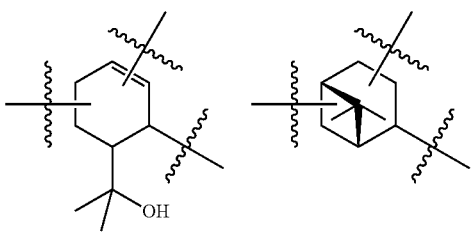

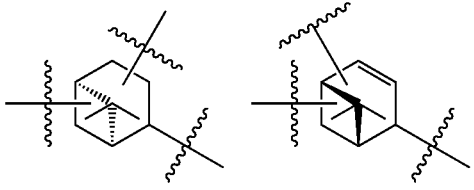

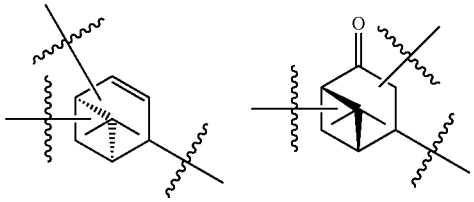

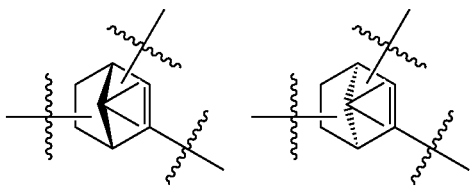

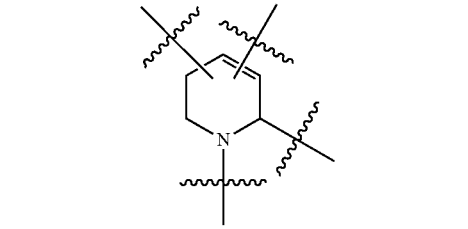

In another aspect, provided is a compound of Formula (IV), or a pharmaceutically acceptable salt thereof:

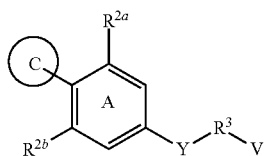

(IV)

or a pharmaceutically acceptable salt thereof;
wherein:

C is carbocyclic, bicyclic, acyl, heterocyclyl, heteroaryl, or a terpene;

$R^{2a}$ and $R^{2b}$ are each independently H, OH, SH, $NH_2$, $CF_3$, COOH, alkoxy, halogen, $ONO_2$, alkyl-$ONO_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;

Y is a bond, $C(CH_3)_2$, $CF_2$, C=O, C(alkyl), COO, NHCO, CONH, alkyl, cycloalkyl, heterocyclyl, lactone, lactam, sultam, O, S, SO, $SO_2$, $OSO_2$, amine, diazine, alkenyl, or, alkynyl;

$R^3$ is absent, or is O, S, $SO_2$, $SO_2NH$, $NHSO_2$, or $OSO_2$, alkyl, alkenyl, alkynyl, cycloalkyl, a carbocyclic, a spirocyclic, heterocyclyl, aryl, heteroaryl, carboxyl, acetate, amine, amide, or imide; and V is $V^1$ or $ONO_2$, wherein when any of rings A, B or C is substituted with a group comprising $ONO_2$ V is $V^1$, otherwise V is $ONO_2$; and $V^1$ is H, F, Cl, Br, T, haloalkyl, $N_3$, NCS, CN, $NO_2$, OH, alkoxy, amino, alkylamino, dialkylamino, trialkylamino, aryl, cycloalkyl, alkenyl, alkynyl, —C(O)aryl, —C(O)alkyl, —C(O)heteroaryl, —C(O)amino, —C(O)(dialkylamino), C(O)(trialkylamino), C(O)(heterocyclyl), C(O)heteroaryl, —OC(O)alkyl, $OSO_2H$, $OSO_2(alkyl)$, $OSO_2(aryl)$, $OSO_2NO_2$, $OSO_2(alkyl)CN$, $OSO_2(alkyl)OH$, $OSO_2$alkylamino), —SC(O)alkyl, —$SO_2$alkyl, —SO-alkyl, —$SC(CH_3)_2C(O)Oalkyl$, —$SC(CH_3)_2C(O)Oaryl$, —$SC(CH_3)_2C(O)Oheteroaryl$, —$SC(CH_3)_2C(O)Oheterocyclyl$, $Si(alkyl)_3$, —OC(O)aryl, NHC(O)alkyl, NHC(O)aryl, —C(O)H, C(O)Oalkyl, $SO_2(amino)$, $SO_2(heterocyclyl)$, $SO_2(trialkylamino)$, $SO_2(dialkylamino)$, spirocyclic ring, heterocyclyl, heteroaryl, alkylthio, alkylamino, dialkylamino, alkylsulfinyl, alkylsulfonyl, boronic acid, boronate ester, $BF_3K$, or a biotin group tethered via an amide bond.

In any of the above embodiments of Formula IV, C may be:

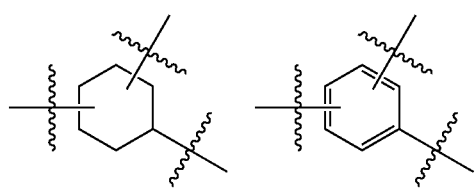

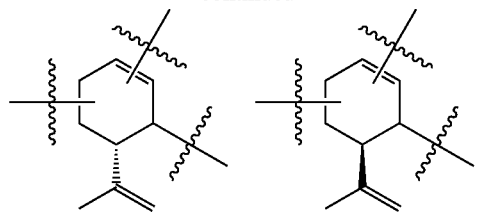

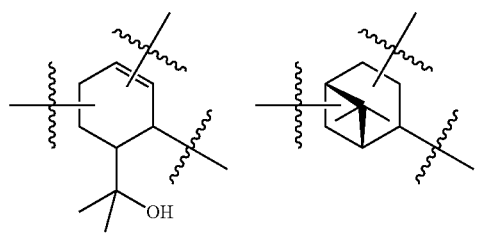

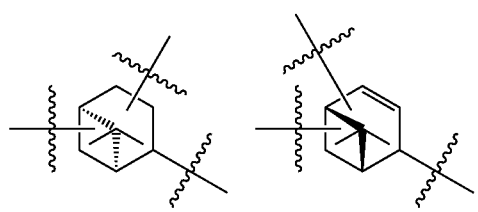

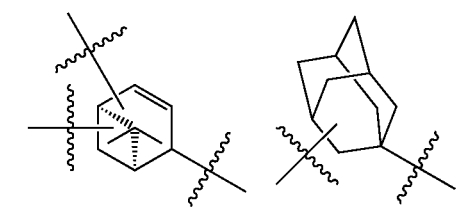

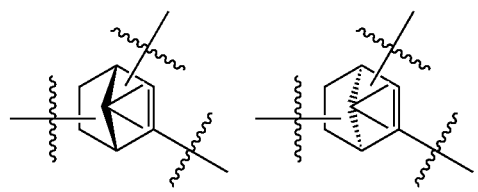

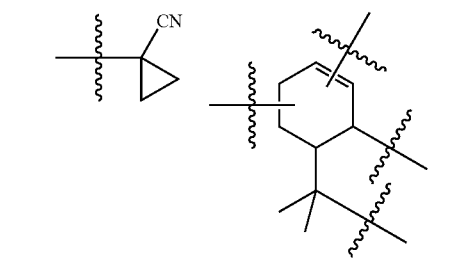

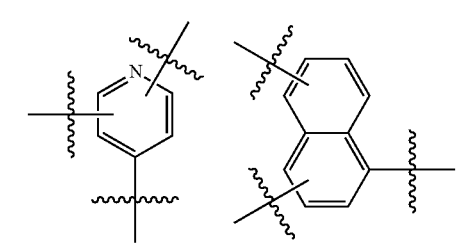

-continued

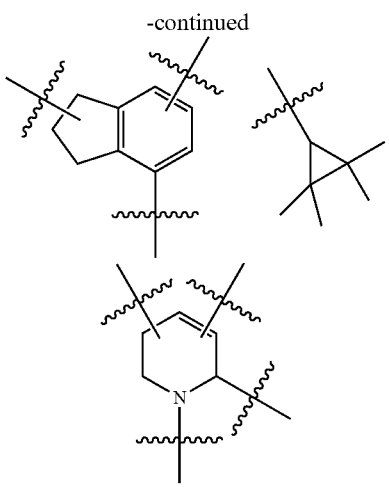

In another aspect, provided is a compound of Formula (V), or a pharmaceutically acceptable salt thereof:

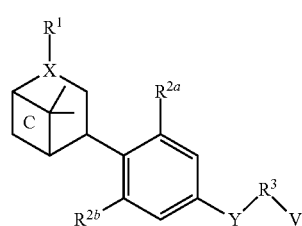

(V)

or a pharmaceutically acceptable salt thereof;
wherein:
X is C, CH, N, NH, $(CH_2)_2N$, S, O, SO, $SO_2$, or $CF_2$;
$R^1$ is H, OH, =O, halogen, COOH, nitro, $ONO_2$, alkyl, haloalkyl, alkenyl, alkynyl, acyl, aryl, heterocyclyl, heteroaryl, alkoxy, aryloxy, heteroalkoxy, heteroaryloxy, alkenyl, amino, thio, cyano, thiocynato, isothiocynato, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;
$R^{2a}$ and $R^{2b}$ are each independently H, OH, SH, $NH_2$, $CF_3$, COOH, alkoxy, halogen, $ONO_2$, alkyl-$ONO_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;
Y is a bond, $C(CH_3)_2$, $CF_2$, C=O, C(alkyl), COO, NHCO, CONH, cycloalkyl, heterocyclyl, lactone, lactam, sultam, O, S, SO, $SO_2$, $OSO_2$, amine, diazine, alkenyl, or alkynyl;
$R^3$ is absent, or is O, S, $SO_2$, $SO_2NH$, $NHSO_2$, or $OSO_2$, alkyl, alkenyl, alkynyl, cycloalkyl, a carbocyclic, a spirocyclic, heterocyclyl, aryl, heteroaryl, carboxyl, acetate, amine, amide, or imide; and
V is $V^1$ or $ONO_2$, wherein when any of rings A, B or C is substituted with a group comprising $ONO_2$ V is $V^1$, otherwise V is $ONO_2$; and $V^1$ is H, F, Cl, Br, I, haloalkyl, $N_3$, NCS, CN, $NO_2$, OH, alkoxy, amino, alkylamino, dialkylamino, trialkylamino, aryl, cycloalkyl, alkenyl, alkynyl, —C(O)aryl, —C(O)alkyl, —C(O)heteroaryl, —C(O)amino, —C(O)(dialkylamino), C(O)(trialkylamino), C(O)(heterocyclyl), C(O)heteroaryl, —OC(O)alkyl, $OSO_2H$, $OSO_2$(alkyl), $OSO_2$(aryl), $OSO_2NO_2$, $OSO_2$(alkyl)CN, $OSO_2$(alkyl)OH, $OSO_2$alkylamino), —SC(O)alkyl, —$SO_2$alkyl, —SO-alkyl, —$SC(CH_3)_2C(O)$Oalkyl, —$SC(CH_3)_2C(O)$Oaryl, —$SC(CH_3)_2C(O)$Oheteroaryl, —$SC(CH_3)_2C(O)$Oheterocyclyl, Si(alkyl)$_3$, —OC(O)aryl, NHC(O)alkyl, NHC(O)aryl, —C(O)H, C(O)Oalkyl, $SO_2$(amino), $SO_2$(heterocyclyl), $SO_2$(trialkylamino), $SO_2$(dialkylamino), a spirocyclic ring, heterocyclyl, heteroaryl, alkylthio, alkylamino, dialkylamino, alkylsulfinyl, alkylsulfonyl, boronic acid, boronate ester, $BF_3K$, or a biotin group tethered via an amide bond.

In another aspect, provided is a compound of Formula (VI), or a pharmaceutically acceptable salt thereof:

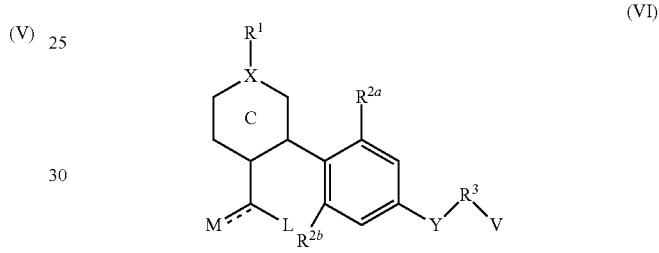

(VI)

or a pharmaceutically acceptable salt thereof;
wherein:
C is carbocyclic, bicyclic, aryl, heterocyclyl, heteroaryl, or a terpene;
M is $CH_2$ or alkyl-$T^1$;
L is $CH_3$ or alkyl-r; and
X is C, CH, N, NH, $(CH_2)_2N$, S, O, SO, $SO_2$, or $CF_2$;
$R^1$ is H, OH, =O, halogen, COOH, nitro, $ONO_2$, alkyl, haloalkyl, alkenyl, alkynyl, acyl, aryl, heterocyclyl, heteroaryl, alkoxy, aryloxy, heteroalkoxy, heteroaryloxy, alkenyl, amino, thio, cyano, thiocynato, isothiocynato, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;
$R^{2a}$ and $R^{2b}$ are each independently H, OH, SH, $NH_2$, $CF_3$, COOH, alkoxy, halogen, $ONO_2$, alkyl-$ONO_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;
Y is a bond, $C(CH_3)_2$, $CF_2$, C=O, C(alkyl), COO, NHCO, CONH, alkyl, cycloalkyl, heterocyclyl, lactone, lactam, sultam, O, S, SO, $SO_2$, $OSO_2$, amine, diazine, alkenyl, or alkynyl;
$R^3$ is absent, O, S, $SO_2$, $SO_2NH$, $NHSO_2$, $OSO_2$, alkyl, alkenyl, alkynyl, cycloalkyl, a carbocyclic, a spirocyclic, heterocyclyl, aryl, heteroaryl, carboxyl, acetate, amine, amide, or imide; and V is V¹ or ONO₂, wherein when any of rings A, B or C is substituted with a group comprising ONO, V is V¹, otherwise V is ONO₂; and V¹ is H, F, Cl, Br, I, haloalkyl, N₃, NCS, CN, NO₂, OH, alkoxy, amino, alkylamino, dialkylamino, trialkylamino, aryl, cycloalkyl, alkenyl, alkynyl, —C(O)aryl, —C(O)alkyl, —C(O)heteroaryl, —C(O)amino, —C(O)(dialkylamino), C(O)(trialkylamino), C(O)(heterocyclyl), C(O)heteroaryl, —OC(O)alkyl, OSO₂H, OSO₂(alkyl), OSO₂(aryl), OSO₂NO₂, OSO₂(alkyl)CN, OSO₂(alkyl)OH, OSO₂alkylamino), —SC(O)alkyl, —SO₂alkyl, —SO-alkyl, —SC(CH₃)₂C(O)Oalkyl, —SC(CH₃)₂C(O)Oaryl, —SC(CH₃)₂C(O)Oheteroaryl, —SC(CH₃)₂C(O)Oheterocyclyl, Si(alkyl)₃, —OC(O)aryl, NHC(O)alkyl, NHC(O)aryl, —C(O)H, C(O)Oalkyl, SO₂(amino), SO₂(heterocyclyl), SO₂(trialkylamino), SO₂(dialkylamino), a spirocyclic ring, heterocyclyl, heteroaryl, alkylthio, alkylamino, dialkylamino, alkylsulfinyl, alkylsulfonyl, boronic acid, boronate ester, BF₃K, or a biotin group tethered via an amide bond.

In any of the above embodiments of Formula VI, C may be:

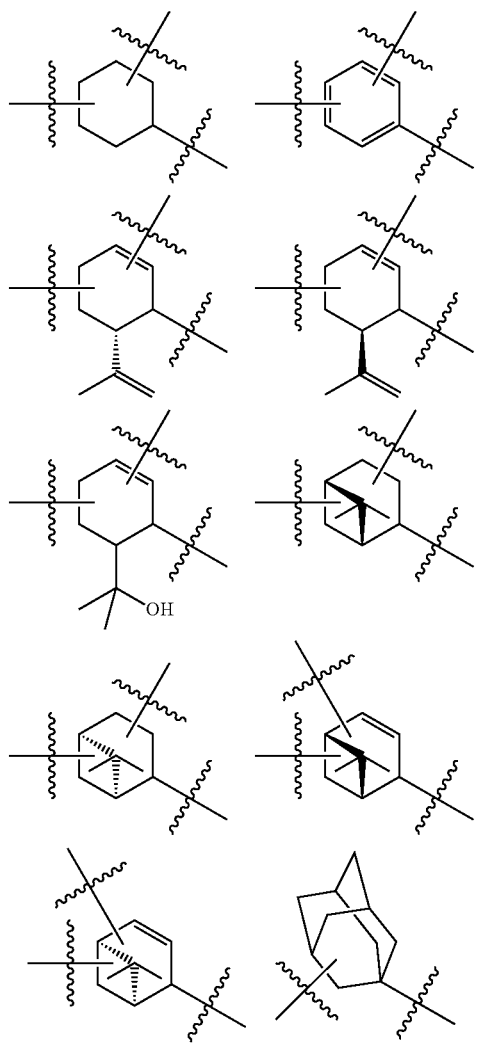

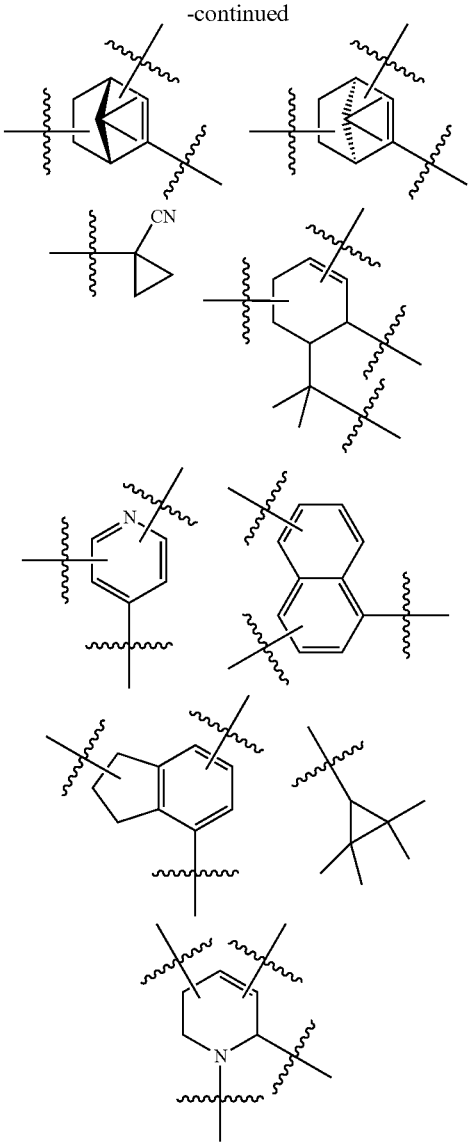

In another aspect, provided is a compound of Formula (VII), or a pharmaceutically acceptable salt thereof:

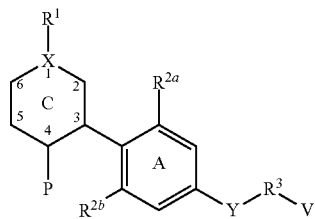

(VII)

or a pharmaceutically acceptable salt thereof;
wherein:
C is carbocyclic, bicyclic, aryl, heterocyclyl, heteroaryl, or a terpene;
P is H, alkyl, alkyl-OH or alkyl-ONO₂;
X is C, CH, N, NH, (CH₂)₂N, S, O, SO, SO₂, or CF₂;
R¹ is H, OH, =O, halogen, COOH, nitro, ONO₂, alkyl, haloalkyl, alkenyl, alkynyl, acyl, aryl, heterocyclyl, heteroaryl, alkoxy, aryloxy, heteroalkoxy, heteroaryloxy, alkenyl, amino, thio, cyano, thiocynato, isothiocynato, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;

$R^{2a}$ and $R^{2b}$ are each independently H, OH, SH, $NH_2$, $CF_3$, COOH, alkoxy, halogen, $ONO_2$, alkyl-$ONO_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;

Y is a bond, $C(CH_3)_2$, $CF_2$, C=O, C(alkyl), COO, NHCO, CONH, alkyl, cycloalkyl, heterocyclyl, lactone, lactam, sultam, O, S, SO, $SO_2$, $OSO_2$, amine, diazine, alkenyl, or alkynyl;

$R^3$ is absent, O, S, $SO_2$, $SO_2NH$, $NHSO_2$, $OSO_2$, alkyl, alkenyl, alkynyl, cycloalkyl, a carbocyclic, a spirocyclic, heterocyclyl, aryl, heteroaryl, carboxyl, acetate, amine, amide, or imide; and V is $V^1$ or $ONO_2$, wherein when any of rings A, B or C is substituted with a group comprising $ONO_2$ V is $V^1$, otherwise V is $ONO_2$; and $V^1$ is H, F, Cl, Br, I, haloalkyl, $N_3$, NCS, CN, $NO_2$, OH, alkoxy, amino, alkylamino, dialkylamino, trialkylamino, aryl, cycloalkyl, alkenyl, alkynyl, —C(O)aryl, —C(O)alkyl, —C(O)heteroaryl, —C(O)amino, —C(O)(dialkylamino), C(O)(trialkylamino), C(O)(heterocyclyl), C(O)heteroaryl, —OC(O)alkyl, $OSO_2H$, $OSO_2$(alkyl), $OSO_2$(aryl), $OSO_2NO_2$, $OSO_2$(alkyl)CN, $OSO_2$(alkyl)OH, $OSO_2$alkylamino), —SC(O)alkyl, —$SO_2$alkyl, —SO-alkyl, —$SC(CH_3)_2C(O)$Oalkyl, —$SC(CH_3)_2C(O)$Oaryl, —$SC(CH_3)_2C(O)$Oheteroaryl, —$SC(CH_3)_2C(O)$Oheterocyclyl, Si(alkyl)$_3$, —OC(O) aryl, NHC(O)alkyl, NH(O)aryl, —C(O)H, C(O)Oalkyl, $SO_2$(amino), $SO_2$(heterocyclyl), $SO_2$(trialkylamino), $SO_2$(dialkylamino), a spirocyclic ring, heterocyclyl, heteroaryl, alkylthio, alkylamino, dialkylamino, alkylsulfinyl, alkylsulfonyl, boronic acid, boronate ester, $BF_3K$, or a biotin group tethered via an amide bond.

In any of the above embodiments of Formula VII, C may be:

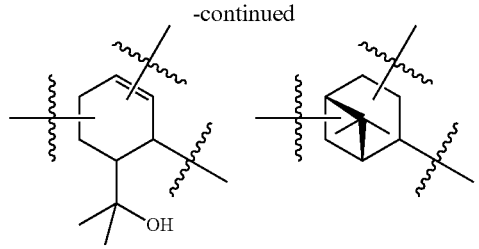
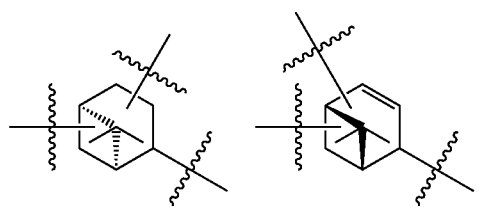

-continued

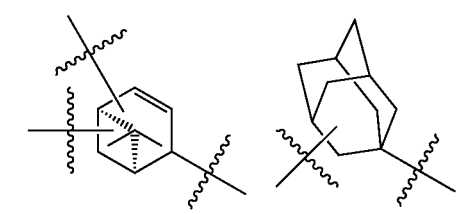
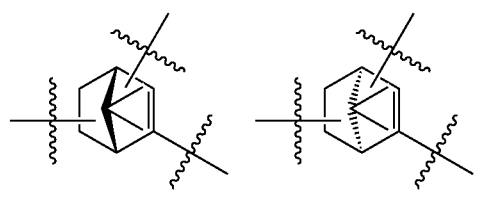
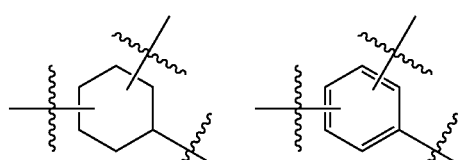
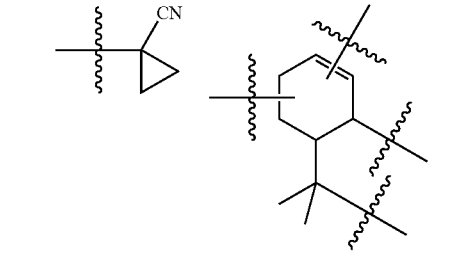
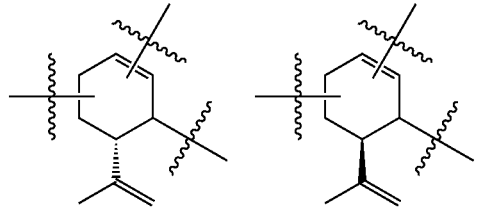
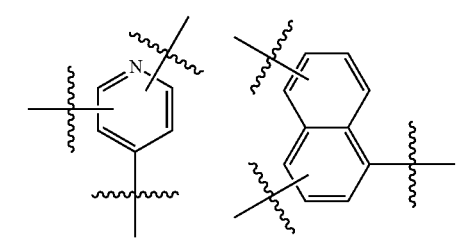
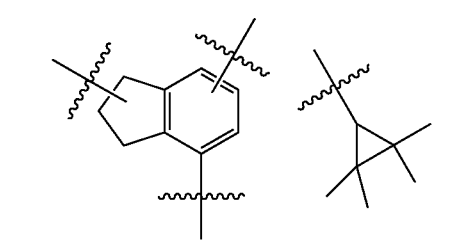

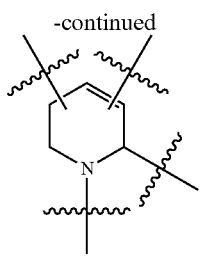

In another aspect, provided is a compound of Formula (VIII), or a pharmaceutically acceptable salt thereof:

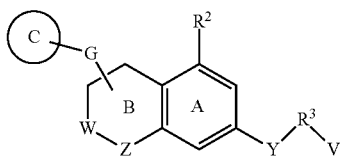

(VIII)

or a pharmaceutically acceptable salt thereof;
wherein:
C is carbocyclic, bicyclic, aryl, heterocyclyl, heteroaryl, or a terpene;
G is a bond, C=O, NH, $CH_2$, CONH, NHCO, C(O)O, OC(O), $OCH_2$, S, SO, $SO_2$, or O;
W is $C(CH_3)_2$, $CH(CH_3)$, C=O, C(O)-alkyl, $CF_2$, C=S, C=$CH_2$, $C(CH_2)_2$, spirocyclic ring, S, SO, $SO_2$, or $C[CH_3(R^4)]$;
$R^4$ is alkyl, alkenyl, or alkynyl group;
Z is O, S, SO, $SO_2$, NH, or N-alkyl;
$R^2$ is H, OH, SH, $NH_2$, $CF_3$, COOH, alkoxy, halogen, $ONO_2$, alkyl-$ONO_2$, alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;
Y is a bond, $C(CH_3)_2$, $CF_2$, C=O, C(alkyl), COO, NHCO, CONH, alkyl, cycloalkyl, heterocyclyl, lactone, lactam, sultam, O, S, SO, $SO_2$, $OSO_2$, amine, diazine, alkenyl, alkynyl;
$R^3$ is absent, O, S, $SO_2$, $SO_2NH$, $NHSO_2$, $OSO_2$, alkyl, alkenyl, alkynyl, cycloalkyl, a carbocyclic, a spirocyclic, heterocyclyl, aryl, heteroaryl, carboxyl, acetate, amine, amide, or imide; and
V is $V^1$ or $ONO_2$, wherein when any of rings A, B or C is substituted with a group comprising $ONO_2$ V is $V^1$, otherwise V is $ONO_2$; and
$V^1$ is H, F, Cl, Br, I, haloalkyl, $N_3$, NCS, CN, $NO_2$, OH, alkoxy, amino, alkylamino, dialkylamino, trialkylamino, aryl, cycloalkyl, alkenyl, alkynyl, —C(O)aryl, —C(O)alkyl, —C(O)heteroaryl, —C(O)amino, —C(O)(dialkylamino), C(O)(trialkylamino), C(O)(heterocyclyl), C(O)heteroaryl, —OC(O)alkyl, $OSO_2H$, $OSO_2$(alkyl), $OSO_2$(aryl), $OSO_2NO_2$, $OSO_2$(alkyl)CN, $OSO_2$(alkyl)OH, $OSO_2$alkylamino), —SC(O)alkyl, —$SO_2$alkyl, —SO-alkyl, —$SC(CH_3)_2C(O)$Oalkyl, —$SC(CH_3)_2C(O)$Oaryl, —$SC(CH_3)_2C(O)$Oheteroaryl, —$SC(CH_3)_2C(O)$Oheterocyclyl, Si(alkyl)$_3$, —OC(O)aryl, NHC(O)alkyl, NHC(O)aryl, —C(O)H, C(O)Oalkyl, $SO_2$(amino), $SO_2$(heterocyclyl), $SO_2$(trialkylamino), $SO_2$(dialkylamino), a spirocyclic ring, heterocyclyl, heteroaryl, alkylthio, alkylamino, dialkylamino, alkylsulfinyl, alkylsulfonyl, boronic acid, boronate ester, $BF_3K$, or a biotin group tethered via an amide bond.

In another aspect, provided is a compound of Formula (IX), or a pharmaceutically acceptable salt thereof:

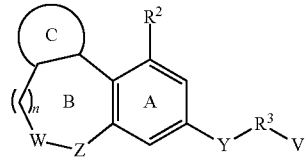

(IX)

or a pharmaceutically acceptable salt thereof;
wherein:
C is carbocyclic, bicyclic, aryl, heterocyclyl, heteroaryl, or a terpene;
n=0, 1
W is $C(CH_3)_2$, $CH(CH_3)$, C=O, C(O)-alkyl, $CF_2$, C=S, C=$CH_2$, $C(CH_2)_2$, spirocyclic ring, S, SO, $SO_2$, or $C[CH_3(R^4)]$;
$R^4$ is alkyl, alkenyl, or alkynyl;
Z is O, S, SO, $SO_2$, NH, or N-alkyl;
$R^2$ is H, OH, SH, $NH_2$, $CF_3$, COOH, alkoxy, halogen, $ONO_2$, alkyl-$ONO_2$, alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;
Y is a bond, $C(CH_3)_2$, $CF_2$, C=O, C(alkyl), COO, NHCO, CONH, alkyl, cycloalkyl, heterocyclyl, lactone, lactam, sultam, O, S, SO, $SO_2$, $OSO_2$, amine, diazine, alkenyl, or alkynyl;
$R^3$ is absent, O, S, $SO_2$, $SO_2NH$, $NHSO_2$, $OSO_2$, alkyl, alkenyl, alkynyl, cycloalkyl, a carbocyclic, a spirocyclic, heterocyclyl, aryl, heteroaryl, carboxyl, acetate, amine, amide, or imide; and
V is $V^1$ or $ONO_2$, wherein when any of rings A, B or C is substituted with a group comprising $ONO_2$ V is $V^1$, otherwise V is $ONO_2$; and
$V^1$ is H, F, Cl, Br, I, haloalkyl, $N_3$, NCS, CN, $NO_2$, OH, alkoxy, amino, alkylamino, dialkylamino, trialkylamino, aryl, cycloalkyl, alkenyl, alkynyl, —C(O)aryl, —C(O)alkyl, —C(O)heteroaryl, —C(O)amino, —C(O)(dialkylamino), C(O)(trialkylamino), C(O)(heterocyclyl), C(O)heteroaryl, —OC(O)alkyl, $OSO_2H$, $OSO_2$(alkyl), $OSO_2$(aryl), $OSO_2NO_2$, $OSO_2$(alkyl)CN, $OSO_2$(alkyl)OH, $OSO_2$alkylamino), —SC(O)alkyl, —$SO_2$alkyl, —SO-alkyl, —$SC(CH_3)_2C(O)$Oalkyl, —$SC(CH_3)_2C(O)$Oaryl, —$SC(CH_3)_2C(O)$Oheteroaryl, —$SC(CH_3)_2C(O)$Oheterocyclyl, Si(alkyl)$_3$, —OC(O)aryl, NHC(O)alkyl, NHC(O)aryl, —C(O)H, C(O)Oalkyl, $SO_2$(amino), $SO_2$(heterocyclyl), $SO_2$(trialkylamino), $SO_2$(dialkylamino), a spirocyclic ring, heterocyclyl, heteroaryl, alkylthio, alkylamino, dialkylamino, alkylsulfinyl, alkylsulfonyl, boronic acid, boronate ester, $BF_3K$, or a biotin group tethered via an amide bond.

In any of the above embodiments of Formula VII, C may be:

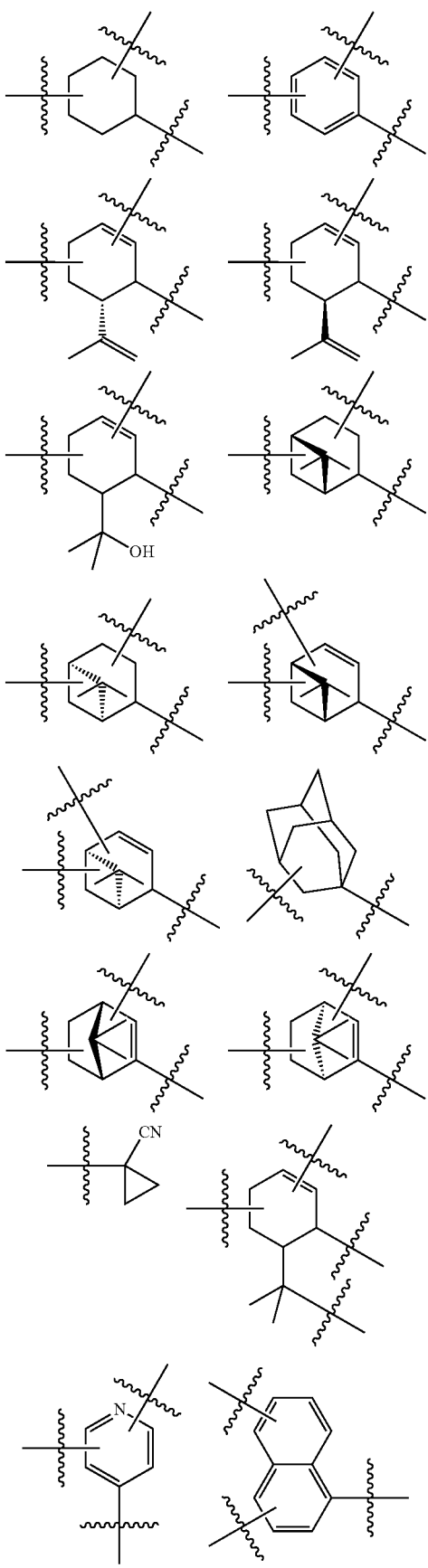
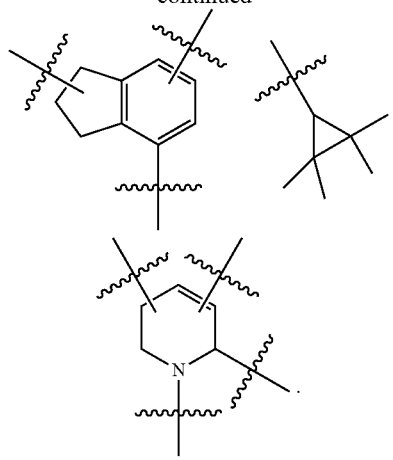

According to various embodiments, any of the above compounds may include where:

C is aromatic and A is aromatic, and G is C=O;
C is aromatic and A is heteroaromatic, and G is C=O;
C is aromatic and A is heteroaromatic, and G is CONH;
C is heterocyclic and A is heteroaromatic, and G is C=O;
C is heterocyclic and A is heteroaromatic, and G is C=O;
C is alkyl and A is heteroaromatic, and G is C=O;
C is carbocyclic and A is heteroaromatic, and G is C=O;
C is alkyl and A is heteroaromatic, and G is CONH;
C is heteroaromatic and A is heteroaromatic, and G is N(alkyl)SO$_2$;
C is aromatic and A is heteroaromatic, and G is NH;
C is bicyclic ring and A is aromatic, and G is O;
C is bicyclic ring and A is aromatic, and G is a direct bond;
C is a terpene;
C is carbocyclic and W is optionally present;
C is heteroaromatic and A is heteroaromatic, and G is OCH$_2$;
C is heterocyclic and A is aromatic, and G is CH$_2$;
C is aromatic and A is heterocyclic, and G is CH$_2$;
C is carbocyclic and A is heteroaromatic, and G is a COO or OCO;
C is heterocyclic and A is aromatic, and G is a direct bond;
C is heterocyclic and A is heteroaromatic, and G is a direct bond;
C is a terpene and A is aromatic, and G is a direct bond;
C is a terpene and A is quinone, and G is a direct bond;
C is a terpene and A is aromatic, and G is a direct bond;
C is heterocyclic and A is aromatic, and G is a direct bond;
C is aromatic and A is aromatic, and G is a direct bond;
C is aromatic and A is heterocyclic, and G is a direct bond;
C is alkyl and A is heteroaromatic, and G is a direct bond;
C is a terpene and A is aromatic, and G is a direct bond;
C is bicyclic and W is C=O; or
C is carbocyclic, B is carbocyclic and A is aromatic.

In another aspect, a compound is provided that is:
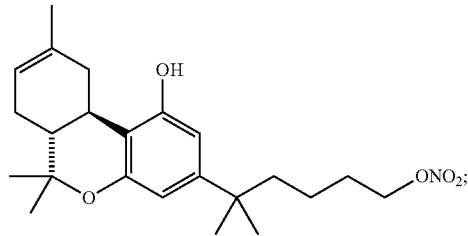
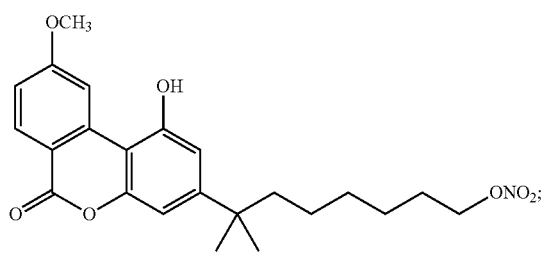
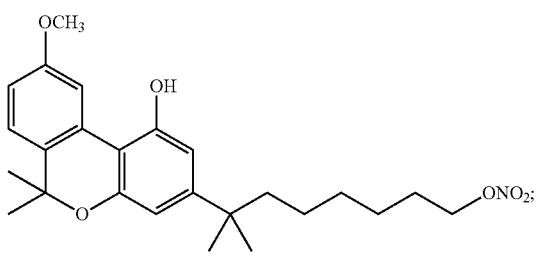
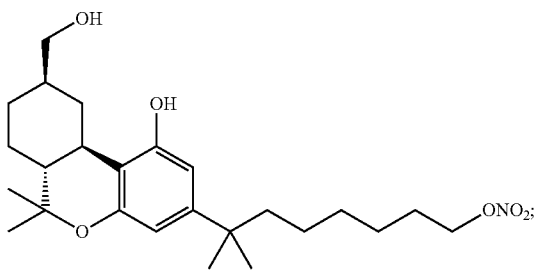
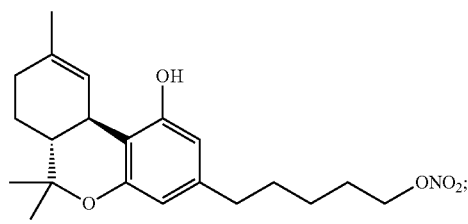
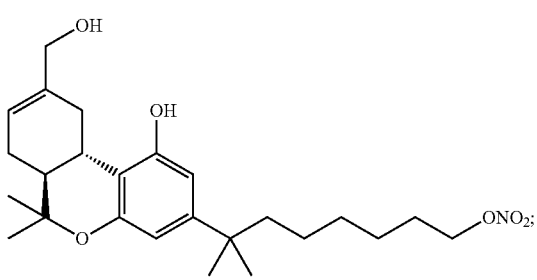
-continued
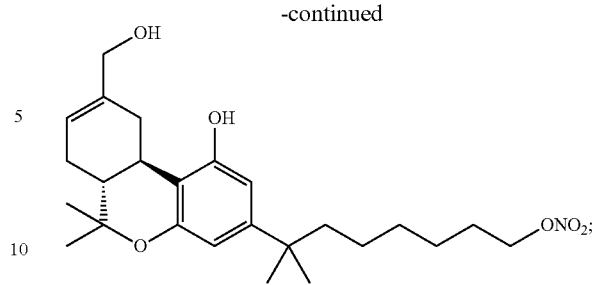
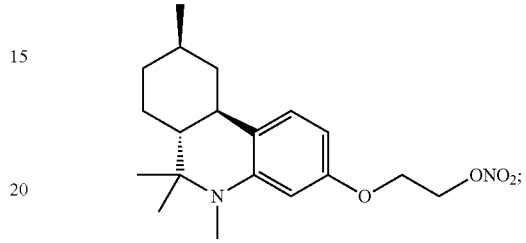
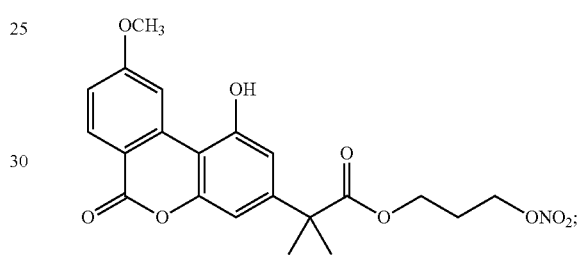
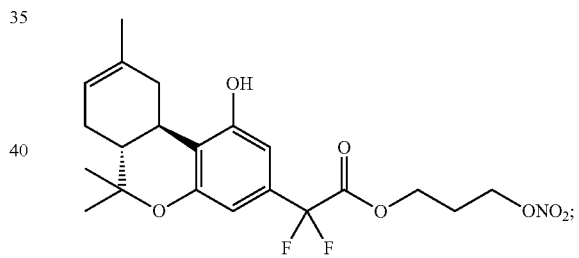
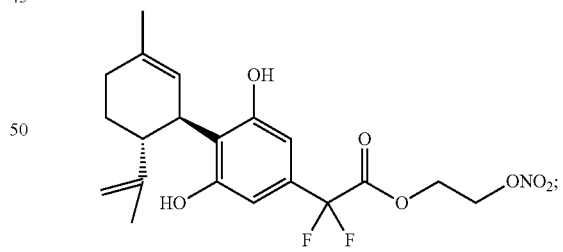
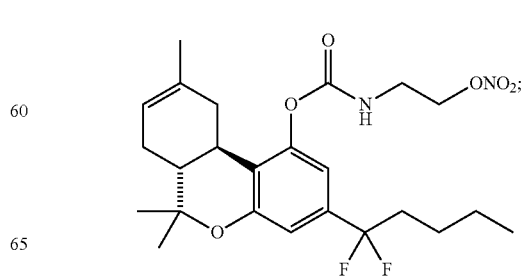

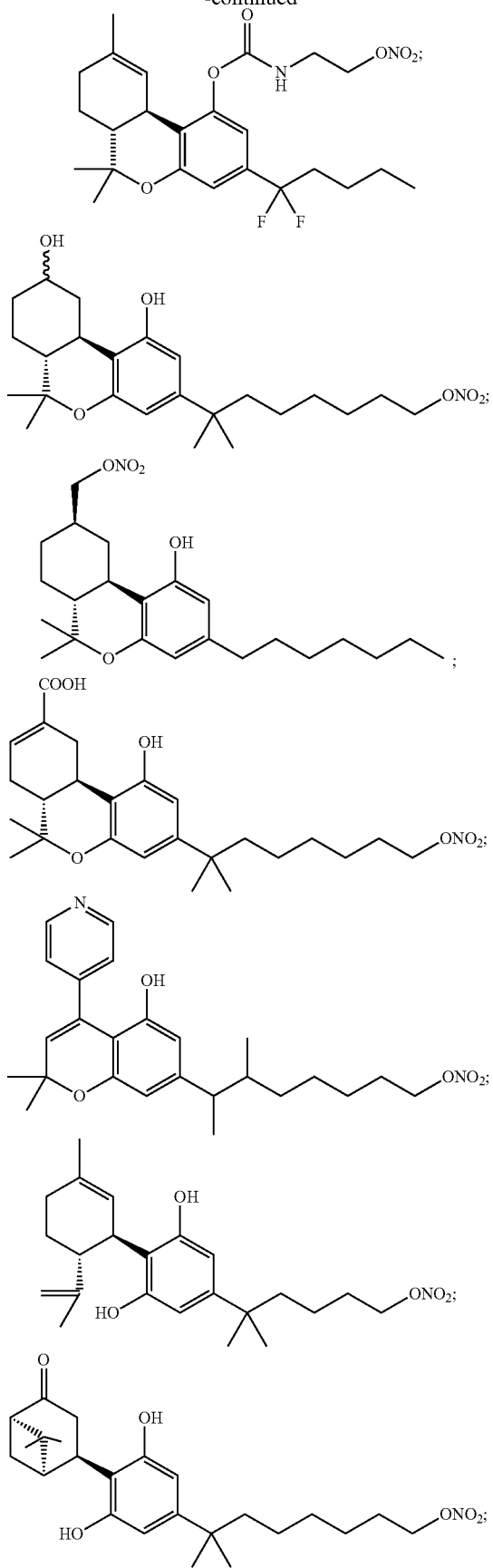
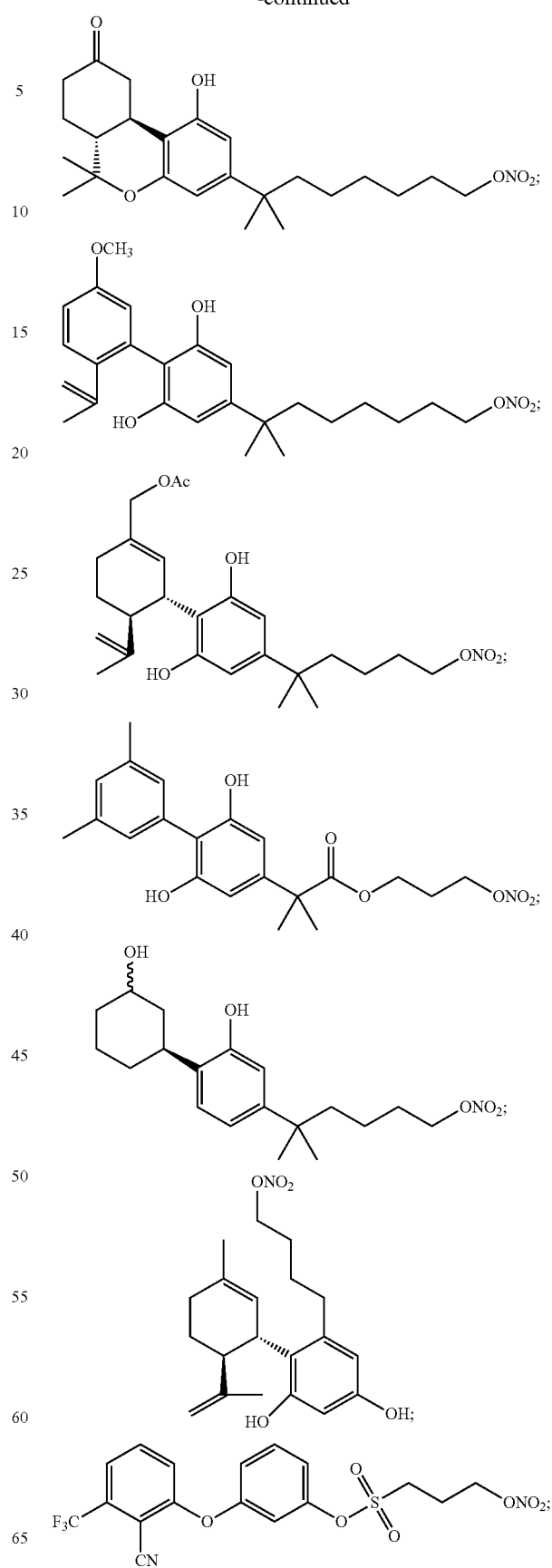

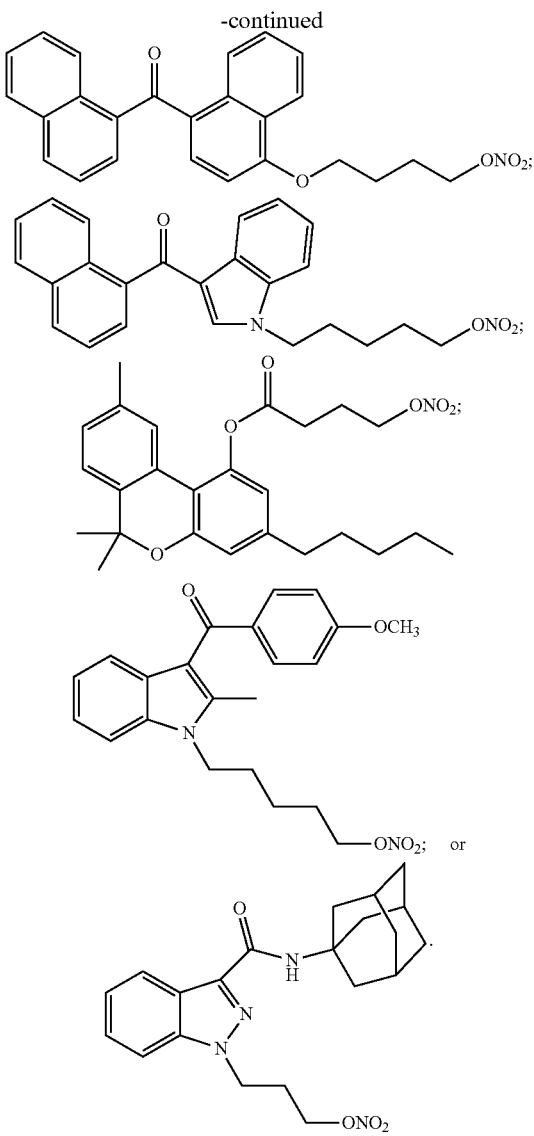

In another aspect, a composition is provided, the composition including any of the above compounds and at least one pharmaceutically acceptable excipient.

In another aspect, a method of agonizing activity of a cannabinoid 1 (CB1), cannabinoid 2 (CB2) or GPR55 receptor is provided, the method including contacting the cannabinoid 1 (CB1), cannabinoid 2 (CB2) or GPR55 receptor with a compound including a nitrate ester.

In another aspect, a method of agonizing activity of a cannabinoid 1 (CB1), cannabinoid 2 (CB2) or GPR55 receptor is provided, the method including contacting the cannabinoid 1 (CB1), cannabinoid 2 (CB2) or GPR55 receptor with any of the compounds described herein.

In another aspect, a method of antagonizing activity of a cannabinoid 1 (CB1), cannabinoid 2 (CB2) or GPR55 receptor is provided, the method including contacting the cannabinoid 1 (CB1), cannabinoid 2 (CB2) or GPR55 receptor with a compound including a nitrate ester.

In another aspect, a method of antagonizing activity of a cannabinoid 1 (CB1), cannabinoid 2 (CB2) or GPR55 receptor is provided, the method including contacting the cannabinoid 1 (CB1), cannabinoid 2 (CB2) or GPR55 receptor with any of the compounds described herein.

In another aspect, a method of inhibiting activity of a cannabinoid 1 (CB1), cannabinoid 2 (CB2) or GPR55 receptor is provided, the method including contacting the cannabinoid 1 (CB1), cannabinoid 2 (CB2) or GPR55 receptor with a compound including a nitrate ester.

In another aspect, a method of inhibiting activity of a cannabinoid 1 (CB1), cannabinoid 2 (CB2) or GPR55 receptor is provided, the method including contacting the cannabinoid 1 (CB1), cannabinoid 2 (CB2) or GPR55 receptor with any of the compounds described herein.

In any of the above methods, the compound that includes the nitrate ester may be compound of formula (T)

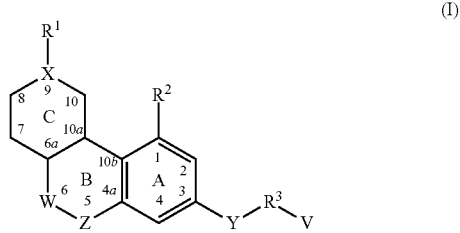

or a pharmaceutically acceptable salt thereof;
wherein:
C has zero, one, two or three double bonds;
X is C, CH, N, NH, $(CH_2)_2N$, S, O, SO, $SO_2$, or $CF_2$;
R is H, OH, =O, halogen, COOH, nitro, $ONO_2$, alkyl, haloalkyl, alkenyl, alkynyl, acyl, aryl, heterocyclyl, heteroaryl, alkoxy, aryloxy, heteroalkoxy, heteroaryloxy, alkenyl, amino, thio, cyano, thiocynato, isothiocynato, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, acetate group;
W is $C(CH_3)_2$, $CH(CH_3)$, C=O, C(O)-alkyl, $CF_2$, C=S, C=$CH_2$, $C(CH_2)_2$, spirocyclic ring, S, SO, $SO_2$, or $C[CH_3(R^4)]$;
$R^4$ is alkyl, alkenyl, or alkynyl;
Z is O, S, SO, $SO_2$, NH, or N-alkyl;
$R^2$ is H, OH, SH, $NH_2$, $CF_3$, COOH, halogen, $ONO_2$, alkyl-$ONO_2$, alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroaiylthio, heterocyclylthio, phosphonate, phosphate, or acetate;
Y is a bond, $C(CH_3)_2$, $CF_2$, C=O, C(alkyl), COO, NHCO, CONH, alkyl, cycloalkyl, heterocyclyl, lactone, lactam, sultam, O, S, SO, $SO_2$, $OSO_2$, amine, diazine, alkenyl, or alkynyl;
$R^3$ is absent, O, S, $SO_2$, $SO_2NH$, $NHSO_2$, $OSO_2$, alkyl, alkenyl, alkynyl, cycloalkyl, a carbocyclic, a spirocyclic, heterocyclyl, aryl, heteroaryl, carboxyl, acetate, amine, amide, or imide; and
V is $V^1$ or $ONO_2$, wherein when any of rings A, B or C is substituted with a group comprising $ONO_2$ V is $V^1$, otherwise V is $ONO_2$; and
$V^1$ is H, F, Cl, Br, I, haloalkyl, $N_3$, NCS, CN, $NO_2$, OH, alkoxy, amino, alkylamino, dialkylamino, trialkylamino, aryl, cycloalkyl, alkenyl, alkynyl, —C(O)aryl, —C(O)alkyl, —C(O)heteroaryl, —C(O)amino, —C(O)(dialkylamino), C(O)(trialkylamino), C(O)(heterocyclyl), C(O)heteroaryl, —OC(O)alkyl, OSO$_2$H, OSO$_2$(alkyl), OSO$_2$(aryl), OSO$_2$NO$_2$, OSO$_2$(alkyl)CN, OSO$_2$(alkyl)OH, OSO$_2$alkylamino), —SC(O)alkyl, —SO$_2$alkyl, —SO-alkyl, —SC(CH$_3$)$_2$C(O)Oalkyl, —SC(CH$_3$)$_2$C(O)Oaryl, —SC(CH$_3$)$_2$C(O)Oheteroaryl, —SC(CH$_3$)$_2$C(O)Oheterocyclyl, Si(alkyl)$_3$, —OC(O) aryl, NHC(O)alkyl, NHC(O)aryl, —C(O)H, C(O) Oalkyl, SO$_2$(amino), SO$_2$(heterocyclyl), SO$_2$(trialkylamino), SO$_2$(dialkylamino), spirocyclic ring, heterocyclyl, heteroaryl, alkylthio, alkylamino, dialkylamino, alkylsulfinyl, alkylsulfonyl, boronic acid, boronate ester, BF$_3$K, or a biotin group tethered via an amide bond.

In another aspect, a method is provided for treating a condition modulated by CB1, CB2 receptors and/or the GPR55 receptor activity, the method including administering to a subject in need thereof a therapeutically effective amount of any of the compounds described herein.

In another aspect, a method is provided for treating a condition modulated by CB1, CB2 receptors and/or the GPR55 receptor activity, the method including administering to a subject in need thereof a therapeutically effective amount of a compound including a nitrate ester moiety.

In another aspect, a use of a cannabinoid receptor agonist or a cannabinoid receptor antagonist for the manufacture of a medicament for the treatment of a condition modulated by CB1, CB2 receptors and/or the GPR55 receptor activity, wherein the cannabinoid receptor agonist or antagonist is compound including a nitrate ester moiety. In such embodiments, the compound may be an agonist or antagonist of a CB1, CB2 or GPR55 receptor, or combination of any two or more such receptors. In some such embodiments, the compound is a full agonist, a partial agonist, a neutral agonist, an inverse agonist, a full antagonist, a partial antagonist, a neutral antagonist, or an inverse antagonist. In some embodiments, the cannabinoid receptor inverse agonist or cannabinoid receptor neutral antagonist is a CB1 inverse agonist or a CB1 neutral antagonist or a CB2 inverse agonist or a CB2 neutral antagonist. In some embodiments, the cannabinoid receptor agonist or cannabinoid receptor antagonist is any of the compounds described herein.

In another aspect, the compounds described herein are capable of forming a covalent bond with an amino acid residue within the CB1, CB2 or GPR55 cannabinoid receptor. In some embodiments, the compound forms a covalent bond with an amino acid residue within the allosteric site or orthosteric site of the CB1, CB2 or GPR55 cannabinoid receptor. In some embodiments the compound acts as a nitric oxide donor. In some embodiments, the compound acts as a nitric oxide donor and forms a covalent bond with an amino acid residue within the cannabinoid receptor. In some embodiments, the compound acts as an allosteric modulator of the cannabinoid receptor. In some embodiments, the compound acts as an allosteric modulator and an orthosteric modulator of the cannabinoid receptor.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

Figure 1:
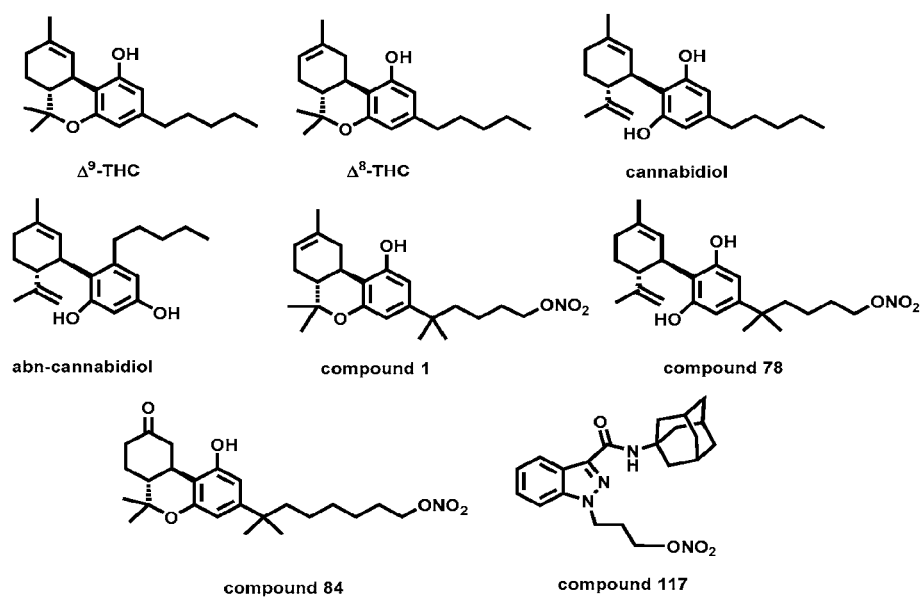
FIG. 1 illustrates chemical structures of $\Delta^8$-THC, $\Delta^9$-THC, cannabidiol, abnormal cannabidiol, compound 1, compound 78, compound 84 and compound 117.

As used herein and in the appended claims, the singular forms "a", "an", and "the" include plural referents unless the context clearly dictates otherwise. Thus, for example, reference to "a solvent" includes a plurality of such solvents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed technology. "Consisting of" shall mean excluding more than trace elements of other ingredients and substantial method steps. Embodiments defined by each of these transition terms are within the scope of this technology.

The term "compound(s) of the technology" as used herein means any of compounds of formulae (I)(IX), and may include stereoisomers, salts, tautomeric forms, hydrates and/or solvates thereof. The compounds of the present technology are prepared in different forms, such as pharmaceutically acceptable salts, hydrates, or solvates and the technology includes compositions and methods encompassing all variant forms of the compounds.

As used herein, C$_m$-C$_n$, such as C$_1$-C$_{12}$, C$_1$-C$_8$, or C$_1$-C$_6$ when used before a group refers to that group containing m to n carbon atoms.

Unless otherwise specifically defined, "acyl" refers to the general formula —C(O)alkyl.

Unless otherwise specifically defined, "acyloxy" refers to the general formula O-acyl.

Unless otherwise specifically defined, "alcohol" refers to the general formula alkyl-OH or carbocyclic-OH, cyclic alkyl-OH, and includes primary, secondary and tertiary variations. The alcohol can be protected with a protecting group selected from Peter G. M. Wuts, Theodora W. Greene, Greene's Protective Groups in Organic Synthesis, 4th Edition, 2006, Wiley; herein incorporated by reference in its entirety. Examples of protecting groups include methyl, benzyl and acetyl.

Unless otherwise specifically defined, "alkyl" or "lower alkyl" refers to a linear, branched or cyclic or cyclo-alkyl group having from 1 to 30 carbon atoms, 1 to 12 carbon atoms, and 1 to 7 carbon atoms including, for example, methyl, ethyl, propyl, butyl, hexyl, octyl, isopropyl, isobutyl, tert-butyl, cyclopropyl, cyclohexyl, and cyclooctyl. The alkyl group can be saturated or unsaturated. The alkyl group or the lower alkyl group can be unsubstituted, singly substituted or, if possible, multiply substituted, with substituent groups in any possible position. Unless otherwise specifically limited, a cyclic or cyclo-alkyl group includes monocyclic, bicyclic, tricyclic, tetracyclic and polycyclic rings, for example adamantyl, oxa-adamantyl, norbornyl, terpenes and related derivatives.

Unless otherwise specifically defined, "alkenyl" refers to a, straight or branched hydrocarbon chain containing 2 to 12 carbons and containing at least one carbon-carbon double bond. Representative alkenyl groups include vinyl, allyl, ethenyl, 2-propenyl, 2-methyl-2-propenyl, 2-methylhex-2-enyl, 3-butenyl, 2-methylpent-2-enyl, 3-methylocta-2,6-dienyl, 4-pentenyl, 5-hexenyl, 2-heptenyl, 2-methyl-1-heptenyl, and 3-decenyl. The "alkenyl" group can be unsubstituted, singly substituted or, if possible, multiply substituted, with substituent groups in any possible position.

Unless otherwise specifically defined, "alkenylene" refers to a divalent group derived from a straight or branched hydrocarbon chain containing 2 to 4 carbon atoms and containing at least one carbon-carbon double bond. Representative alkenylene groups include, CH=CH— and —CH$_2$CH=CH—. The "alkenylene" group can be unsubstituted, singly substituted or, if possible, multiply substituted, with substituent groups in any possible position.

Unless otherwise specifically defined, "alkynyl" refers to a straight or branched chain hydrocarbon group containing 2 to 10 carbon atoms and containing at least one carbon-carbon triple bond. Representative alkynyl groups include acetylenyl, 1-propynyl, 2-propynyl, 3-butynyl, 2-pentynyl, and 1-butynyl. The "alkynyl" group can be unsubstituted, singly substituted or, if possible, multiply substituted, with substituent groups in any possible position Unless otherwise specifically defined, "alkoxy" refers to the general formula O-alkyl. The "alkoxy" group can be unsubstituted, singly substituted or, if possible, multiply substituted, with substituent groups in any possible position Unless otherwise specifically defined, "alkylmercapto" refers to the general formula S-alkyl.

Unless otherwise specifically defined, "alkylamino" refers to the general formula —(NH)-alkyl.

Unless otherwise specifically defined, "di-alkylamino" refers to the general formula N-(alkyl)$_2$. Unless otherwise specifically limited di-alkylamino includes cyclic amine compounds such as piperidine and morpholine.

Unless otherwise specifically defined, an "aromatic" ring is an unsaturated ring structure having about 6 to 12, about 6 to 8 ring members, for example benzene and naphthalene. The aromatic ring structure can be unsubstituted, singly substituted or, if possible, multiply substituted, with substituent groups in any possible position.

Unless otherwise specifically defined, "aryl" refers to an aromatic ring system, for example phenyl, biphenyl or naphthyl. The aryl group can be unsubstituted, singly substituted or, if possible, multiply substituted, with substituent groups in any possible position. In certain embodiments, the aryl group will be fused to a carbocyclic ring having 5 to 8 ring atoms, for example as in 2,3-dihydro-1H-indene, 2,3-dihydro-1H-inden-2-yl)methanol and 2,2-dimethyl-2,3-dihydro-1H-indene. In certain embodiments, the aryl group will be fused to a heterocyclic ring having from 5 to 8 ring atoms, for example as in chromane and 2,3-dihydrobenzofuran.

Unless otherwise specifically defined, "aroyl" refers to the general formula —C(=O)aryl. The "aroyl" group can be unsubstituted, singly substituted or, if possible, multiply substituted, with substituent groups in any possible position Unless otherwise specifically defined, a "bicyclic" ring structure comprises 2 fused or bridged rings. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include, 2,3-dihydro-1H-indene, bicyclo[3.1.0]hexane, 2,3-dihydro-1H-inden-2-yl)methanol, bicyclooctane 7,7-dimethylbicyclo[2.2.1]hept-2-ene, 7,7-dimethylbicyclo[2.2.1]hept-2-en-1-yl)methanol, 7,7-dimethylbicyclo[2.2.1]heptane, 2,6-dioxabicyclo[3.3.0]octane, 6,6-dimethylbicyclo[3.1.1]heptan-2-one, tetralin, decalin and related terpenes such as caranc, trans-thujane, pinnae, camphene, isocamphane, fenchane, careen, chaminic acid, sabinene, thujene, thujol, thujanone, α-pinene, β-pinene, car-4-ene-3-ol, verbenol, verbenone, myrtenol, myrtenal, pinocarveol, pinocarvone, camphor, isoborneol, borneol, norbornane, fenchone, β-fenchol, α-fenchol, camphene and fenchene. The terpenes will encompass all related isomers and derivatives.

Unless otherwise specifically defined, a "carbocyclic" group and all its isomers is a non-aromatic ring structure, chiral or achiral, saturated or unsaturated, substituted or unsubstituted, with about 0 to 5 heteroatoms, and having about 3 to about 20 ring members, for example, 1- or 2-cyanocyclopropyl, 2,2,3,3-tetramethylcyclopropyl, cyclohexadiene, cyclohexanol, cycloheptane, cyclohexane, tetrahydropyran, cyclohexanone, cyclohexene, cyclohexadiene, lactone, lactam, sultone, sultam, quinone, and terpenes. The carbocyclic group and all of its isomers can be unsubstituted, singly substituted or, if possible, multiply substituted, with substituent groups in any possible position. Carobocyclic groups related to terpenes include (+)-cis/trans-p-mentha-2,8-dien-1-ol ((1S,4R)-1-methyl-4-(prop-1-en-2-yl)cyclohex-2-en-1-ol and (1R,4R)-1-methyl-4-(prop-1-en-2-yl)cyclohex-2-en-1-ol), p-mentha-1,8-diene-3-ol (isopiperitenol), nopinone and related derivatives, menthane, limonene, phellandrene, terpinolene, terpinene, menthol, isomenthol, neomenthol, neoisomenthol, pulegol, isopulegol, piperitol, terpineol, menth-1-en-8-thiol, carveol, perillaaldehyde, perillyl alcohol, menthone, isomenthone, pulegone, isopulegone, phellandral, piperitone, dihydrocarvone, carvenone, carvone, cymene, carvacrol, thymol, cymen-8-ol and cuminaldehyde. The terpenes will encompass all related isomers. In certain embodiments, the carbocylic group can be fused to another carbocyclic group, for example as in octahydro-1H-indene. Carobocyclic groups comprising of lactones include α-acetolactone, β-propiolactone, γ-butyrolactone, δ-valerolactone and ε-caprolactone. In some instances, a carbocyclic group can also be a cyclic or cycloalkyl group, a heteroalkyl or a heterocyclic group, or an alkyl group.

Unless otherwise specifically defined, an "alkaloid" is a natural product as defined in the publication Alkaloids—

Secrets of Life, Alkaloid Chemistry, Biological Significance, Applications and Ecological Role by Tadeusz Aniszewski, 2007, Elsevier B. V., herein incorporated by reference in its entirety. Examples include morphine, codeine, and thebaine. The "alkaloid" can be unsubstituted, singly substituted or, if possible, multiply substituted, with substituent groups in any possible position.

Unless otherwise specifically defined, a lactone is a cyclic ester having 4 to 8 ring members. The lactone can be unsubstituted, singly substituted or, if possible, multiply substituted, with substituent groups in any possible position.

Unless otherwise specifically defined, a lactam is a cyclic amide having 4 to 8 ring members. The lactam can be unsubstituted, singly substituted or, if possible, multiply substituted, with substituent groups in any possible position.

Unless otherwise specifically defined, a sultam is a cyclic sulfonamide having 4 to 8 ring members in which the S—N bond is part of the ring. The sultam can be unsubstituted, singly substituted or, if possible, multiply substituted, with substituent groups in any possible position.

Unless otherwise specifically defined, a "terpene" is a natural product as defined within and in the publication Terpenes—Flavors, Fragrances, Pharmaca, Pheromones (Eberhard Breitmaier, 2006, Wiley-VCH, incorporated herein by reference in its entirety). Examples of terpenes include camphor, pinene and menthol. The "terpene" can be unsubstituted, singly substituted or, if possible, multiply substituted, with substituent groups in any possible position. Unless otherwise specifically defined, a "terpene derivative" is a natural product or a synthetic compound that is obtained by a chemical modification of another parent terpene. For example, (+)-nopinone can be derived from β-pinene. Similarly, cis- and trans-isopiperitenol can be derived from (+)-limonene.

Unless otherwise specifically defined, "halogen" refers to an atom selected from fluorine, chlorine, bromine and iodine.

Unless otherwise specifically defined, a "heteroaromatic" ring is an unsaturated ring structure having about 5 to about 8 ring members independently selected from carbon atoms and one or more heteroatoms, including oxygen, nitrogen, phosphorous and/or sulfur, for example, thiophene, oxazole, isoxazole, imidazole, pyrazole, benzimidazole, triazolopyridine, benzotriazole, pyridine, pyridine 1-oxide, pyrimidine, indole, indazole, furan, quinoline, 1,2,4-triazole, 1,2,3-triazole, imidazole, tetrazole, 1H-pyrrolo[2,3-c]pyridine, 1H-pyrrolo[2,3-b]pyridine, 1-(cyclohexylmethyl)-1H-benzo[d]imidazole, 1-((1-methylpiperidin-2-yl)methyl)-1H-indole, 2,3,4,9-tetrahydro-1H-carbazole, 1,2,3,4-tetrahydropyrrolo[3,4-b]indole, 4-(alkylsulfonyl)-1,2,3,4-tetrahydropyrrolo[3,4-b]indole, quinazolin-4(3H)-one, 4-((1H-indol-1-yl)methyl)tetrahydro-2H-thiopyran 1,1-dioxide, isoindolin-1-one, nucleosides and their derivatives. The heteroaromatic ring can be unsubstituted, singly substituted or, if possible, multiply substituted, with substituent groups in any possible position. In certain embodiments, the heteroaryl group will be fused to a carbocyclic group having 5 to 8 ring atoms, for example as in 4,5,6,7-tetrahydrobenzo[b]thiophene, 4,4a,5,5a-tetrahydro-1H-cyclopropa[4,5]cyclopenta[1,2-c]pyrazole and 4,5,6,7-tetrahydro-1H-indole. In certain embodiments, the heteroaryl group will be fused to a heterocyclic ring having from 5 to 8 ring atoms, for example as in 5,6,7,8-tetrahydroquinoline.

Unless otherwise specifically defined, a "heterobicyclic" ring structure comprises 2 fused or bridged rings having ring members independently selected from carbon and one or more heteroatoms, including oxygen, nitrogen, phosphorous and/or sulfur. The heterobicyclic ring structure can be saturated or unsaturated. The heterobicyclic ring can be unsubstituted, singly substituted or, if possible, multiply substituted, with substituent groups in any possible position. The individual rings may or may not be of the same type. Examples of heterobicyclic ring structures include octahydropyrrolo[3,4-c]pyrrole and diazabicyclo[3.3.1]nonane and isobenzofuran.

Unless otherwise specifically defined, a "heterocyclic" ring is a saturated or unsaturated ring structure having about 3 to about 8 ring members independently selected from carbon atoms and one or more heteroatoms, including oxygen, nitrogen, phosphorous and/or sulfur; for example, azetidine, piperidine, morpholine, piperazine, (S) and (R)-1,2-dimethylpiperazine, 1-H-pyridine-2-one, dihydropyridine, tetrahydropyridine, pyridazin-3(2H)-one, piperidine-2,4-dione, pyrrolidine, thiomorpholine, 1,1-dioxothiomorpholine, tetrahydro-2H-thiopyran 1,1-dioxide, nucleosides and their derivatives. The heterocyclic ring can be unsubstituted, singly substituted or, if possible, multiply substituted, with substituent groups in any possible position.

Unless otherwise specifically defined, a "heterotricyclic" ring structure comprises 3 fused, bridged, or both fused and bridged rings having ring members independently selected from carbon and one or more heteroatoms, including oxygen, nitrogen, phosphorous and/or sulfur. The heterotricyclic ring structure may be saturated or unsaturated. The heterotricyclic ring structure can be unsubstituted, singly substituted or, if possible, multiply substituted, with substituent groups in any possible position. The individual rings may or may not be of the same type. Examples of heterotricyclic ring structures include carbazole, phenanthroline, phenazine, 2,4,10-trioxaadamantane and tetradecahydro-phenanthroline.

Unless otherwise specifically defined, a "heteropolycyclic" ring structure comprises more than 3 rings that may be fused, bridged or both fused and bridged and that have ring members independently selected from carbon and one or more heteroatoms, including oxygen, nitrogen, phosphorous and/or sulfur. The heteropolycyclic ring structure can be saturated or unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantane, oxa-adamantine, tropane, homotropane and 5-norbornene-2,3-dicarboximide.

Unless otherwise specifically defined, the term "phenacyl" refers to the general formula phenylacyl.

Unless otherwise specifically defined, a "polycyclic" ring structure comprises more than 3 rings that may be fused, bridged or both fused and bridged, and that includes carbon as ring atoms. The polycyclic ring structure can be saturated or unsaturated. The polycyclic ring structure can be unsubstituted, singly substituted or, if possible, multiply substituted, with substituent groups in any possible position. The individual rings may or may not be of the same type. Examples of polycyclic ring structures include adamantane, oxa-adamantane, bicyclooctane, norbornane and bicyclononanes.

Unless otherwise specifically defined, a glycol is an alcohol containing compound with two hydroxyl groups. The glycol group can be unsubstituted, singly substituted or, if possible, multiply substituted, with substituent groups in any possible position. Examples of glycol include 1,2-ethanediol, 1,3-propanediol and 1,4-butanediol.

Unless otherwise specifically defined, a polyol is an alcohol containing compound more than two hydroxyl groups. The polyol group can be unsubstituted, singly substituted or, if possible, multiply substituted, with substituent groups in any possible position.

Unless otherwise specifically defined, "PEG", "PEG$_n$", "PEG$_r$", and "PEG$_s$" independently refer to the polyether entity tethered or conjugated to the compounds directly, via an alkyl group or via another linker to improve the physicochemical properties such as water solubility of the compounds. "PEG", "PEG$_n$", "PEG$_r$", and "PEG$_s$" can be represented by the formula —(CH$_2$—CH$_2$—O—)$_m$CH$_3$ where m is 1-15. Examples of a linker are the amide group, carbamate, carbonate and the ester group. The linker can be hydrolyzed physiologically or enzymatically. The definitions and immediate applications of the PEG technology can be adapted from Valentino J. Stella (editor), Prodrugs: Challenges and Rewards, 2007, Springer (volumes 1 and 2); herein incorporated by reference in its entirety.

Unless otherwise specifically defined, the term "cannabinergic" refers to being related to the endocannabinoid system comprising of CB1 and CB2 receptors and additionally the orphan receptors GPR55 and GPR119.

Unless otherwise specifically defined, the term "related analogs" refers to compounds disclosed in the technology that have the same properties as cannabinergic nitrate esters. For example, the related analogs bind covalently to the cannabinoid receptors and/or can act as nitric oxide donors while behaving as cannabinergic agonists, antagonists, partial agonists or allosteric modulators.

Unless otherwise specifically defined, the term "dual functional behavior" refers to compounds disclosed in the technology that have more than one kind of an effect as shown in a standard in vitro assay. For example, a compound of the present technology can behave as a CB1 antagonist as well as a CB2 agonist. The standard in vitro assay can be one or more selected from the cAMP accumulation assay, GTP-γS binding assay, cell impedance assay, calcium mobilization assay or the β-arrestin recruitment assay. In some instances, a compound disclosed in the invention can behave as an orthosteric ligand, allosteric ligand or a biotopic ligand for the cannabinoid receptors. Unless otherwise specifically defined, an orthosteric ligand binds to an orthosteric site which refers to the endogenous agonist-binding site on a receptor. Unless otherwise specifically defined, an allosteric ligand binds to an allosteric site which refers to a binding site on the receptor that is topographically distinct from the endogenous agonist-binding (orthosteric) site. Bitopic ligands that have both orthosteric ligand-binding properties as well as a secondary element that is able to bind to a neighbouring allosteric site on the receptor. (Annu Rev Pharmacol Toxicol. 2012; 52:153-78, Nat Rev Drug Discov. 2013; 12(1):25-34, Annu Rev Pharmacol Toxicol. 2013; 53:531-56; herein incorporated by reference in its entirety).

Unless otherwise specifically defined, the term "nitric oxide donor" refers to compounds that can donate nitric oxide (NO). In some instances, the term "nitric oxide donor" is used to designate a chemical entity with the potential to elicit a NO(-like) response in living systems. Such compounds need not, in a literal sense, donate (or even spontaneously evolve) bioactive NO under physiological conditions.

Unless otherwise specifically defined, the term "bind covalently to cannabinoid receptors" and "label the cannabinoid receptors" refers to the cannabinoid receptors being temporarily or permanently modified. The modification happens when a chemical species belonging to the compounds attaches itself to the amino acid residues such as serines and cysteines of the cannabinoid receptors via a covalent bond.

Unless otherwise specifically defined, the term "agonist" refers to a compound which decreases the cAMP levels; an "antagonist" or "neutral antagonist" has no effect on cAMP levels; a "partial agonist" induces sub-maximal decrease in cAMP levels; and an "inverse agonist" increases the cAMP levels.

Unless otherwise specifically defined, the term "physicochemical properties" refers to certain physical and chemical descriptive properties that the compounds possess. For example, compound 1 has a better ClogP (octanol-water partition coefficient) and tPSA (total polar surface area) value of 4.2 and 90.5 respectively as compared to $\Delta^9$-THC which has a ClogP and tPSA of 7.2 and 29.4.

Unless otherwise specifically defined, a "spirocyclic" ring is a non-aromatic ring structure wherein two rings are fused at one carbon atom and each ring can have 3 to 6 ring members independently selected from carbon atoms and one or more heteroatoms, including oxygen, nitrogen, phosphorous and/or sulfur or a combination thereof and S can exist as S, SO or SO$_2$. Examples include azaspiro[3.3]heptane, azaspiro[3.5]nonane, spiro[3.3]heptane, azaspiro[5.5]undecane, azaspiro[3.4]octane, azaspiro[2.4]heptane, diazaspiro[4.5]decane, diazaspiro[3.5]nonane, diazaspiro[3.3]heptane, diazaspiro[4.4]nonane, diazaspiro[6.6]tridecane, thia-6-azaspiro[3.3]heptane, dioxo-thia-6-azaspiro[3.3]heptane, oxa-6-azaspiro[3.3]heptane.

Unless otherwise specifically defined, a tricyclic ring structure comprises 3 rings that may be fused, bridged or both fused and bridged, and that includes carbon as ring atoms. The tricyclic ring structure can be saturated or unsaturated. The tricyclic ring structure can be unsubstituted, singly substituted or, if possible, multiply substituted, with substituent groups in any possible position. The individual rings may or may not be of the same type. Examples of tricyclic ring structures include fluorene and anthracene.

In general, "substituted" or "optionally substituted" refers to groups (e.g., an alkyl group, an aryl group) in which one or more bonds to a hydrogen atom contained therein may be replaced by a bond to non-hydrogen or non-carbon atoms. As used herein, and unless otherwise excluded, any alkyl, alkenyl, alkynyl, alkenylene, carbocyclyl, aryl, heteroaryl, cyclyl, or heterocyclyl may be substituted. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Substituent groups for the above moieties useful in the technology are those groups that do not significantly diminish the biological activity of the compound. Examples of substituent groups include, but are not limited to, alkyl, alkynyl, alkenyl, alcohol, halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. In some embodiments, suitable substituents also include, terpene, boronic acid, boronate ester, BF$_3$K, biotin group tethered via an amide bond (e.g., alkyl, alkoxy or another linker attached to biotin via an amide bond), CF$_2$, CF$_3$, CF$_2$H, N$_3$, NCS, CN, NQ$^1$Q$^2$, =O, OQ$^3$, SQ$^3$, NHQ$^3$, =CH$_2$, =NOH, OAc, O-acyl, O-aryl, CH$_2$-aryl, O-aroyl, NH-acyl, NH-aroyl, CHO, C(halogen)$_3$, (halogen)$_2$, COOQ$^3$, SO$_2$-halogen, OSO$_2$CF$_3$, SO$_3$H, SO$_3$alkyl, SO$_2$NQ$^1$Q$^2$, CONQ$^1$Q$^2$, =CH$_2$, OH, alkyl-OH, OH, ONO$_2$, alkyl-ONO$_2$, spirocyclic, alkylmercapto, aryl, aroyl, alkylamino, di-alkylamino, polycyclic, carbocyclic group, heterocyclic ring, aromatic ring, heteroaromatic ring, CO-T$^1$, —C(O)OP(O)(Oalkyl)$_2$, O—PO(OX$^1$)(OY$^1$), O-alkyl-(CH$_2$)$_p$—O—PO(OX$^1$)(OY$^1$) wherein p is 0-6, OSO$_3$H, OCO-alkyl-COOH, OCO-alkenyl-COOH, OPO$_3$H$_2$, O—SO$_2$alkyl-T$^1$, O—SO$_2$-T$^1$, OT$^1$, Oalkyl-T$^1$, NHSO$_2$-T$^1$, Nalkyl-SO$_2$-T$^1$, —O—COalkyl-T$^1$, NHCO-T$^1$, OCONH-T$^1$, O—CO-T$^1$, O—CO—O-T$^1$, OCO-alkyl-NH-T$^1$, OCO-alkyl-N(T$^1$)$_2$, OCO-alkyl-T$^1$, O-alkyl-T$^1$, O-alkyl-OCO-T$^1$, O-T$^1$-T$^1$, O-alkyl-PO(OX$^1$)(OY$^1$), OCO(glycol), OCO-alkyl(glycol), OCO-PEG$_r$, O—CO—O-PEG$_r$, O—COCO—O-PEG$_r$, and O-PEG$_r$; wherein T$^1$ is H, alkyl, halogen, OH, CF$_3$, CF$_2$H, COOH, COOalkyl, alkaloid, immunogen, terpene, O—PO(OX$^1$)(OY$^1$), SO$_3$H, ONO$_2$ a heterocyclic ring, NQ$^1$Q$^2$ or T$^1$ is an ammonium group, wherein said ammonium group can be independently substituted one or more times with a C1 to C6 alkyl radical, or is a C3 to C7 heterocycle containing a nitrogen heteroatom for bond formation, wherein the said heterocycle can contain one or more heteroatoms independently selected from N, O or S, and wherein said heterocycle can be substituted with one or more independently chosen substituents;

r is 0 to 10;

wherein any of the above groups can be optionally substituted in any possible position;

Q$^1$ and Q$^2$ are each independently H, alkyl, or alkyl-ONO$_2$, or

Q$^1$ and Q$^2$ together are part of a heterocyclic ring having about 4 to about 7 ring members and optionally one additional heteroatom selected from O, N or S, or Q$^1$ and Q$^2$ together are part of an imide ring having about 5 to about 6 members;

Q$^3$ is H, alkyl, heterocyclic ring, aromatic ring, heteroaromatic ring hydroxyloweralkyl, or alkyl-NQ$^1$Q$^2$;

X$^1$ and Y$^1$ are independently H, alkyl-OCO-alkyl, alkyl-O—CO—O-alkyl, alkali metals or alkaline earth metals; and PEG$_r$ refers to a polyether PEGylated group tethered via a linker.

The term "group comprising ONO$_2$" as used herein includes any moiety having a terminal —ONO$_2$ group. Such moieties include, but are not limited to, ONO$_2$, alkyl-ONO$_2$, O-alkyl-ONO$_2$, O—SO$_2$-alkyl-ONO$_2$, —C(O)O-alkyl-ONO$_2$, alkyl-C(O)O-alkyl-ONO$_2$, alkyl-O-alkyl-ONO$_2$, and the like. In some embodiments, the alkyl group is substituted with one or more groups selected from hydroxyl, carboxyl, carboalkoxy, amide, amino, cycloalkyl, aryl, heteroaryl, or heterocyclyl groups.

In various embodiments, the compounds disclosed herein may suitably include isomers, pharmaceutically acceptable salts, solvates, hydrates, amides, esters, ethers, chemically protected forms, tautomers, polymorphs and prodrugs thereof.

The term "composition(s) of the technology" as used herein means compositions comprising any of compounds described herein, such as for example, compounds of formulae (I) (IX), or salts, tautomeric forms, hydrates, and solvates thereof.

The term "method(s) of the technology" as used herein means methods comprising treatment with the compounds and/or compositions of the technology.

The term "solvate" as used herein means a compound, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

A "pharmaceutical composition" refers to a mixture of one or more of the compounds described herein, or pharmaceutically acceptable salts, tautomers, solvates, or hydrates thereof, with other chemical components, such as physiologically acceptable carriers and excipients. The purpose of a pharmaceutical composition is to facilitate administration of a compound to an organism.

The term "pharmaceutically acceptable" refers to safe and non-toxic for in vivo, preferably, human administration.

The term "pharmaceutically acceptable salt" is intended to include salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic, oxalic, propionic, and other acids. Salts may also exist as solvates or hydrates. Other exemplary pharmaceutically acceptable salts are described herein.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated C1-C20 aliphatic carboxylic acids, which are optionally substituted by halogen or by hydroxyl groups, or C6-C12 aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of (+) or (−) 20 percent, 10 percent, 5 percent or 1 percent.

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of an affliction, or one or more symptoms thereof, prevent the advancement of conditions related to an affliction, prevent the recurrence, development, or onset of one or more symptoms associated with an affliction, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "in need thereof" refers to the need for symptomatic or asymptomatic relief from a condition.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in "Remington's Pharmaceutical Sciences" by E. W. Martin (herein incorporated by reference in its entirety).

As used herein, the terms "animal," "subject" and "patient" as used herein include all members of the animal kingdom including, but not limited to, mammals, animals (e.g., cats, dogs, horses, swine, etc.) and humans. In some embodiments, an "individual" refers to a human. In some embodiments, an "animal" refers to, for example, nonhuman-primates such as monkeys and baboons; veterinary animals, such as rodents, dogs, cats, horses and the like; and farm animals, such as cows, pigs and the like. In some embodiments, the subject or patient is a human.

In one aspect, novel cannabinergic nitrate esters (CNE) and related analogs are provided. The cannabinergic nitrate ester compounds have a range of useful medical applications by acting as agonists, partial agonists, neutral antagonists, inverse-agonists or allosteric modulators for the CB1, CB2 receptors and/or the GPR55 receptor. In some embodiments, the compounds exhibit dual functional behavior. In another aspect combination therapy, pharmaceutical preparations, and compositions employing the CNE analogs are provided. In yet another aspect, methods of administering therapeutically effective amounts of the CNE analogs to provide a physiological effect are provided.

In certain aspects, the technology relates to new cannabinergic nitrate ester compounds. Such compounds may act as nitric oxide donors; bind covalently to and/or label the CB1, CB2 receptors and/or the GPR55 receptor; act as agonists, partial agonists, neutral antagonists, inverse-agonists or allosteric modulators for the CB1, CB2 receptors and/or the GPR55 receptor; have a predictable onset and duration of action; and/or have improved physicochemical properties.

The cannabimimetic nitrate esters can be represented by general formulae I-IX; and encompasses all isomers including enantiomers, diastereomers, geometric isomers, racemates, tautomers, rotamers, and atropisomers, N-oxides, salts, solvates, and/or hydrates, metabolites and pharmaceutically acceptable salts. In general, the compositions of the technology may be alternately formulated to comprise, consist of, or consist essentially of, any appropriate components herein disclosed. The compositions of the technology may additionally, or alternatively, be formulated so as to be devoid, or substantially free, of any components, materials, ingredients, adjuvants or species or that are otherwise not necessary to the achievement of the function and/or objectives of the present technology.

In certain aspects, compounds of formula (I), isomers thereof or pharmaceutically acceptable salts thereof, are provided:

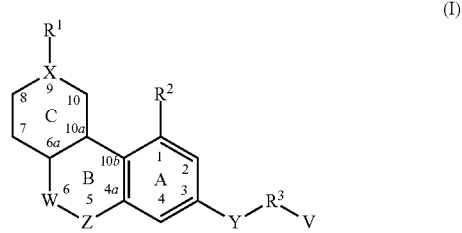

(I)

wherein

C has zero, one, two or three double bonds, and if present, at least one double bond is preferably in the C8-C9 position, the C9-C10 position, or the C6a-C10a position;

wherein A, B and C are optionally substituted in any possible position;

X is C, CH, $C(CH_2)_2$, N, S, O, SO, or $SO_2$;

wherein when X is C, N or CH, $R^1$ is $(CH_2)_p$— $R^6$ wherein p=0-6;

$R^6$ is H, alkyl, alkynyl, alkenyl, halogen, alcohol, alkoxy, $C(halogen)_2H$, $N_3$, NCS, CN, $NQ^1Q^2$, =O, $=CH_2$, $F_2$, $OQ^3$, $SQ^3$, $NHQ^3$, =NOH, OAc, O-acyl, O-aryl, 0-aroyl, NH-acyl, NH-aroyl, CHO, $C(halogen)_3$, $COOQ^3$, $SO_2$-halogen, $OSO_2CF_3$, $SO_3H$, $SO_3$alkyl, $SO_2NQ^1Q^2$, $CONQ^1Q^2$, $ONO_2$, alkyl-$T^1$, alkenyl-$T^1$, alkynyl-$T^1$, carbocyclic-$T^1$, spirocyclic, alkyl-$ST^1$, aroyl, alkylamino, di-alkylamino, heterocyclic ring, carbocyclic group, aromatic ring, heteroaromatic ring, CO-$T^1$, O—PO$(OX^1)(OY^1)$, O-alkyl-$(CH_2)_r$—O—PO$(OX^1)(OY^1)$, $OSO_3H$, OCO-alkyl-COOH, OCO-alkenyl-COOH, $OPO_3H_2$, O—$SO_2$alkyl-$T^1$, O—$SO_2$-$T^1$, $OT^1$, $NHSO_2$-$T^1$, Nalkyl-$SO_2$-$T^1$, NHCO-$T^1$, OCONH-$T^1$, O—CO-$T^1$, O—CO—O-$T^1$, OCO-alkyl-NH-$T^1$, OCO—NH-alkyl-$T^1$, OCO-alkyl-$N(T^1)_2$, OCO-alkyl-$T^1$, O-alkyl-$T^1$, O-alkyl-OCO-$T^1$, O-$T^1$-$T^1$, O-alkyl-PO$(OX^1)(OY^1)$, OCO(glycol), OCO-alkyl(glycol), OCO(polyol), OCO-alkyl(polyol), OCO-alkyl(BT), OCO-PEG$_r$, O—CO—O-PEG$_r$, O—COCO—O-PEG$_r$, or O-PEG$_r$; wherein $T^1$ is H, alkyl, halogen, OH, $CF_3$, $CF_2H$, COOH, COOalkyl, carbocyclic group, aromatic ring, heteroaromatic ring, alkaloid, terpene, immunogen, O—PO$(OX^1)(OY^1)$, $SO_3H$, $ONO_2$ a heterocyclic ring, $NQ^1Q^2$ or $T^1$ is an ammonium group, wherein said ammonium group can be independently substituted one or more times with a C1 to C6 alkyl radical, or is a C3 to C7 heterocycle containing a nitrogen heteroatom for bond formation, wherein the said heterocycle can contain one or more heteroatoms independently selected from N, O or S, and wherein said heterocycle can be substituted with one or more independently chosen substituents;

r is 0 to 10;

wherein any of the above groups can be optionally substituted in any possible position;

$Q^1$ and $Q^2$ each independently are H or alkyl, alkyl-$ONO_2$; or $Q^1$ and $Q^2$ together are part of a heterocyclic ring having about 4 to about 7 ring members and optionally one additional heteroatom selected from O, N or S; or $Q^1$ and $Q^2$ together are part of an imide ring having about 5 to about 6 members;

$Q^3$ is H, alkyl, heterocyclic ring, aromatic ring, heteroaromatic ring, hydroxyloweralkyl, —P(O)(Oalkyl)$_2$ or alkyl-$NQ^1Q^2$;

$X^1$ and $Y^1$ are H, alkyl-OCO-alkyl, alkyl-O—CO—O-alkyl, alkali metals or alkaline earth metals;

BT is a Biotin group tethered via an amide bond; and

PEG$_r$ refers to a polyether PEGylated group tethered via a linker;

W is C(CH$_3$)$_2$, CH(CH$_3$), C=O, CF$_2$, C=S, C=CH$_2$, C(CH$_2$)$_2$, spirocyclic ring, S, SO, SO$_2$, or C[CH$_3$(R$^4$)];

Z is a bond, O, S, SO, SO$_2$, NH, N—CN or N-alkyl;

R$^4$ is CH$_2$R$^5$, C=(CH$_2$)$_n$—R$^5$, or C(CH$_2$)$_n$—R$^5$;

n=0 or 1;

R$^5$ is alkyl, alkenyl, alkynyl, H, OH, N$_3$, NCS, ONO$_2$, CHO, halogen, COOH, COOalkyl, CONHalkyl, heterocyclic ring, or heteroaromatic ring;

R$^2$ is H, OH, SH, NH$_2$, CF$_3$, COOH, alkyl-OH, halogen, NHCOalkyl, NHalkyl, N(dialkyl), OC(S)N(dialkyl), NHSO$_2$alkyl, SC(O)N(dialkyl), O—PO(OX$^{11}$)(OY$^{11}$), O-alkyl-(CH$_2$)$_s$—O—PO(OX$^{11}$)(OY$^{11}$), O-alkyl-(CH$_2$)$_s$—C(O)O—PO(OX$^{11}$)(OY$^{11}$), OSO$_3$H, OCO-alkyl-COOH, OCO-alkenyl-COOH, OPO$_3$H$_2$, OSO$_2$alkyl-T$^{11}$, O—SO$_z$ T$^{11}$, OT$^{11}$, NHCO-T$^{11}$, CONH-T$^{11}$, alkyl-T$^{11}$, OCONH-alkyl-T$_H$, —O—COalkyl-T$^{11}$, OCONH-T$^{11}$, O—CO-T$^{11}$, O—CO—O-T$^{11}$, OCO-alkyl-NH-T$^{11}$, OCO-alkyl-N(T$^{11}$)$_2$O-alkyl-OCO-T$^{11}$, O-T$^{11}$-O-alkyl-PO(OX$^{11}$)(OY$^{11}$), OCO(glycol), OCO-alkyl(glycol), OCO(polyol), OCO-alkyl(polyol), OCOalkyl(BT), OCO-PEG$_s$, O—CO—O—PEG$_s$, O—COCO—O—PEG, O-PEG$_s$;

T$^{11}$ is H, alkyl, carbocyclic group, halogen, OH, NO$_2$, ONO$_2$, CF$_3$, CF$_2$H, COOH, COOalkyl, alkaloid, terpene, immunogen, O—PO(OX$^{11}$)(OY$^{11}$), SO$_3$H, N$_3$, NCS, aromatic ring, heteroaromatic ring, a heterocyclic ring, or NQ$^{11}$Q$^{12}$, or T$^{11}$ is an ammonium group, wherein said ammonium group can be independently substituted one or more times with a C1 to C6 alkyl radical, or is a C3 to C7 heterocycle containing a nitrogen heteroatom for bond formation, wherein the said heterocycle can contain one or more heteroatoms independently selected from nitrogen, oxygen or sulfur, and wherein said heterocycle can be substituted with one or more independently chosen substituents;

s is 0 to 10;

X$^{11}$ and Y$^{11}$ are H, alkyl, alkyl-OCO-alkyl, alkyl-O—CO—O-alkyl, alkali metals or alkaline earth metals;

Q$^{11}$ and Q$^{12}$ are each independently H or alkyl, or

Q$^{11}$ and Q$^{12}$ together are part of a heterocyclic ring having about 4 to about 7 ring members and optionally one additional heteroatom selected from O, N or S, or Q$^{11}$ and Q$^{12}$ together are part of an imide ring having about 5 to about 6 members;

Q$^{13}$ is H, alkyl, hydroxyloweralkyl, or alkyl-NQ$^{11}$Q$^{12}$;

BT is a Biotin group tethered via an amide bond; and

PEG$_s$ refers to a polyether PEGylated group tethered via a linker;

Y is a bond, C(CH$_3$)$_2$, C(halogen)$_2$, C=O, C(alkyl), C(carbocyclic), C(heterocyclic), COO, NHCO, CONH, alkyl, cycloalkyl, heterocyclic ring, a lactone, lactam, sultam, O, S, SO, SO$_2$, OSO$_2$, NH, N-alkyl, a carbon atom directly as part of R$^3$, N=N, CH=CH, CH= or C≡C;

R$^3$ is -D$^1$-J$^1$-J$^2$;

D$^1$ is a bond or an optionally substituted alkyl group, alkenyl group, alkenylene, alkynyl group, cycloalkyl, a carbocyclic group, a spirocyclic ring, a polycyclic ring, a heterocyclic ring, an aromatic ring, a heteroaromatic ring, C=O(O), O(C=O), CONH, NHCO, O, S, SO$_2$, SO$_2$NH, NHSO$_2$, NH(alkyl), N(alkyl), NH, or OSO$_2$; and J$^1$ and J$^2$ are absent or are each independently selected from alkyl, O, NH, N, COO, OCO, O—CO—O, CONH, CONHalkyl, NHCO, NHCOalkyl, OSO$_2$, SO$_2$NH, and NHSO$_2$;

V is V$^1$ when either A, B or C are substituted with a group comprising ONO$_2$, or V is ONO$_2$;

V$^1$ is H, halogen, CF$_3$, CF$_2$H, N$_3$, NCS, CN, NO$_2$, NX$^1$X$^2$OX$^3$, SX$^3$, OAc, OSO$_2$X$^3$, O-acyl, S-acyl, SO$_2$-alkyl, SO-alkyl, SC(CH$_3$)$_2$COOX$^8$, OC(CH$_3$)$_2$COOX$^8$, C(CH$_3$)$_2$COOX$^8$, Si(alkyl)$_3$, alkyl-CN, O-aroyl, O(CH$_2$)$_j$OX$^3$, O(CH$_2$)$_j$NX$^1$X$^2$, NH-acyl, NH-aroyl, CHO, C(halogen)$_3$, COOX$^3$, COOX$^7$, SO$_3$H, SO$_2$NX$^1$X$^2$, CONX$^1$X$^2$, NHC(O)O-alkyl, NHSO2-alkyl, alkoxy, alkyl, alkenyl group, alkenylene, alkynyl group, cycloalkyl, a carbocyclic group, a spirocyclic ring, a polycyclic ring, a heterocyclic ring, an aromatic ring, a heteroaromatic ring, alcohol, alkylmercapto, alkylamino, di-alkylamino, alkylsulfinyl or alkylsulfonyl, boronic acid, boronate ester, BF$_3$K, biotin group tethered via an amide bond, CX$^4$X$^5$X$^6$, —CH=CHX$^8$, —C≡CX$^8$;

X$^1$ and X$^2$ each independently comprise H or alkyl, or

X$^1$ and X$^2$ together comprise part of a heterocyclic ring having about 4 to about 7 ring members and optionally one additional heteroatom selected from O, N or S, or X$^1$ and X$^2$ together comprise part of an imide ring having about 5 to about 6 members, X$^3$ comprises H, alkyl, aryl, NO$_2$, (CH$_2$)$_m$CN, hydroxyloweralkyl, or alkyl-NX$^1$X$^2$, X$^4$, X$^5$, and X$^6$ each independently comprise H, alkyl, carbocyclic group, hydroxyloweralkyl, alkyl-OH, halogen, CN, SNO, S(SO$_2$)alkyl, NX$^1$X$^2$, COOX$^3$, CONX$^3$, OX$^7$, or O-alkyl-X$^7$ wherein X$^7$ comprises H, alkyl, NO$_2$, NO, P(O)(OX$^8$)$_2$, PH(O)(OX$^8$), S(O)$_k$N(alkyl)$_2$, S(O)$_k$X$^8$, S(O)$_k$OX$^8$, COOX$^8$, CONX$^8$, SO$_3$H, COX$^8$, wherein X$^8$ comprises H, alkyl, carbocyclic group, heterocyclic ring, aromatic ring, heteroaromatic ring, or —CX$^9$=CHX$^{10}$ wherein X$^9$ and X$^{10}$ each independently comprise H or alkyl m is an integer from 0 to 7 j is an integer from 0 to about 6, and k is an integer from 0 to about 2.

In some embodiments, C has zero, one, two or three double bonds, and if present, at least one double bond is in the C8-C9 position, the C9-C10 position, or the C6a-C10a position;

wherein A, B and C are optionally substituted in any possible position;

X is C, CH, (CH$_2$)$_2$, or N;

wherein when X is C, N or CH,

R$^1$ is (CH$_2$)$_p$— R$^6$ wherein p=0-2;

R$^6$ is H, alkyl, alkynyl, alkenyl, alcohol, alkoxy, =O, ONO$_2$, alkyl-ONO$_2$, heteroaromatic ring, or COOH;

W is C(CH$_3$)$_2$, CH(CH$_3$), C=O, or CF$_2$;

Z is O, NH, or N-alkyl;

R$^2$ is H, OH, Oalkyl-T$^{11}$, alkyl-T$^{11}$, —O—COalkyl-T$^{11}$, O—CO-T$^{11}$, OCO-alkyl-NH-T$^{11}$, or OCO-alkyl-N(T$^{11}$)$_2$;

wherein, T$^{11}$ is H, alkyl, ONO$_2$, or a heterocyclic ring;

Y is C(CH$_3$)$_2$, C(halogen)$_2$, CH(alkyl), alkyl, or O;

R$^3$ is D$^1$-J$^1$-J$^2$;

$D^1$ is an alkyl group, alkenyl group, alkynyl group, or $CO_2$-alkyl; or a pharmaceutically acceptable salt thereof; and V is H when $R^6$ or is $ONO_2$, or V is $ONO_2$.

In certain aspects, compounds of formula (I), isomers thereof or pharmaceutically acceptable salts thereof, are provided:

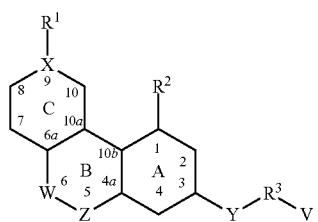

(I)

wherein

A is an optionally substituted aromatic ring, heteroaromatic ring, heterocyclic ring, quinone, alkaloid, terpene or a related derivative;

W is absent, or is $C(CH_3)_2$, $CH(CH_3)$, C=O, $CF_2$, C=S, C=CH$_2$, $C(CH_2)_2$, spirocyclic ring, S, SO, $SO_2$, or $C[CH_3(R^4)]$;

Z is absent or is a bond, OH, O, S, N, SO, $SO_2$, NH, N—CN or N-alkyl; and remaining variables are are as previously defined.

In some embodiments, C is selected from the group consisting of:

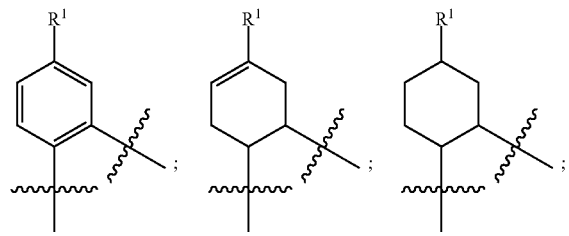

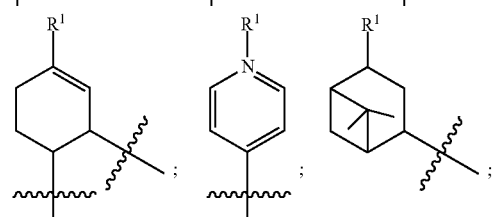

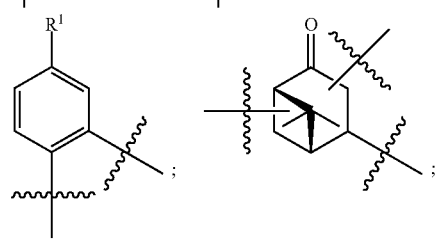

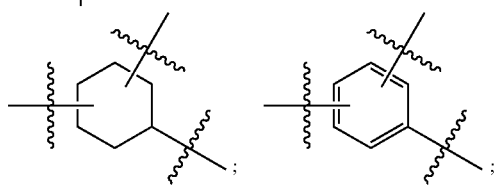

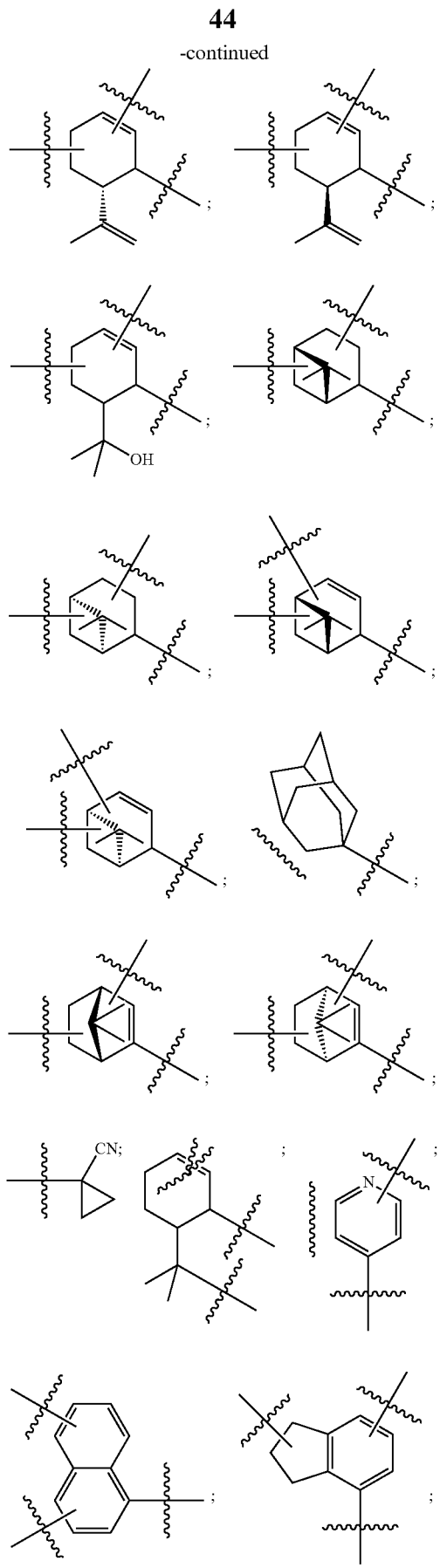

-continued

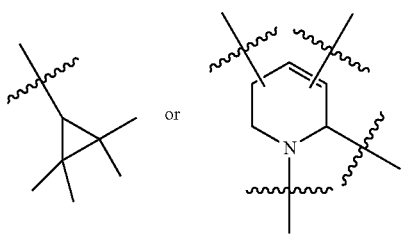

In some embodiments, B is selected from the group consisting of:

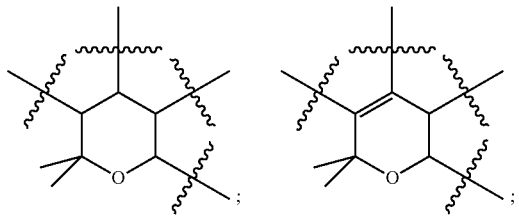

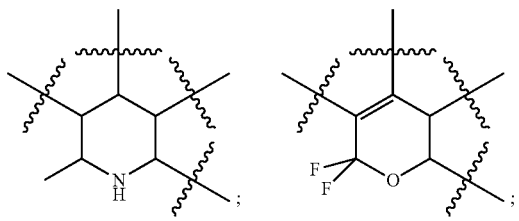

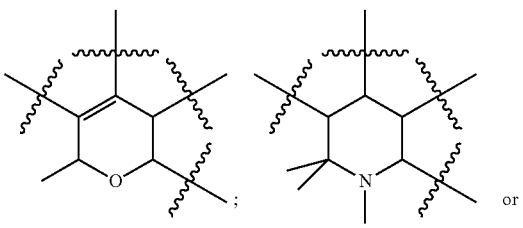

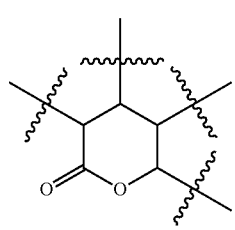

In some embodiments, A is selected from the group consisting of:

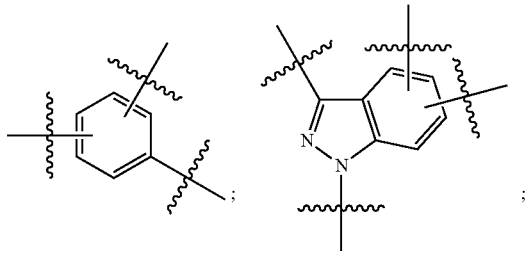

-continued

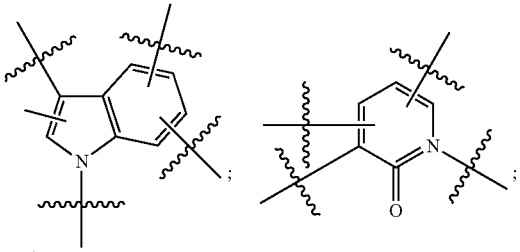

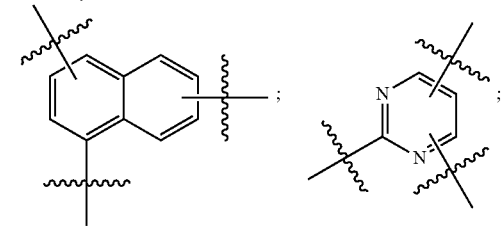

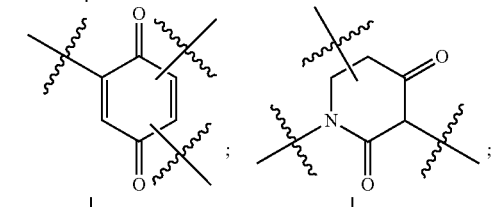

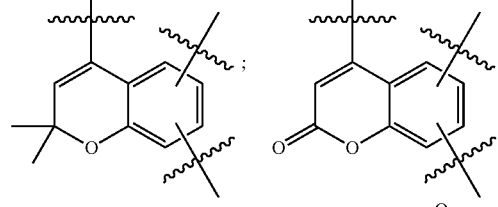

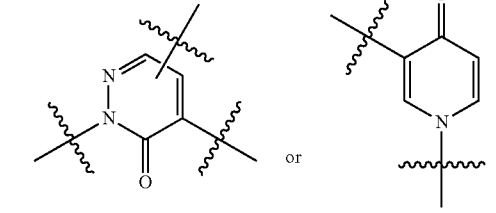

In some embodiments, compounds of formula (I), isomers thereof or pharmaceutically acceptable salts thereof, are provided:

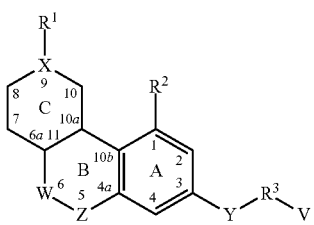

(I)

wherein:
C has zero, one, two or three double bonds;
X is C, CH, N, NH, $(CH_2)_2N$, S, O, SO, $SO_2$, or $CF_2$;
$R^1$ is H, OH, =O, halogen, COOH, nitro, $ONO_2$, or optionally substituted alkyl, haloalkyl, alkenyl, alkynyl, acyl, aryl, heterocyclyl, heteroaryl, alkoxy, aryloxy, heteroalkoxy, heteroaryloxy, alkenyl, amino, thio, cyano, thiocynato, isothiocynato, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate and acetate group;

W is $C(CH_3)_2$, $CH(CH_3)$, $C=O$, $C(O)$-alkyl, $CF_2$, $C=S$, $C=CH_2$, $C(CH_2)_2$, spirocyclic ring, S, SO, $SO_2$, or $C[CH_3 (R^4)]$;

$R^4$ is an optionally substituted alkyl, alkenyl, or alkynyl group;

Z is O, S, SO, $SO_2$, NH, or N-alkyl;

$R^2$ is H, OH, SH, $NH_2$, $CF_3$, COOH, alkoxy, halogen, $ONO_2$, alkyl-$ONO_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate or acetate group;

Y is a bond, $C(CH_3)_2$, $CF_2$, $C=O$, C(alkyl), COO, NHCO, CONH, or optionally substituted alkyl, cycloalkyl, heterocyclyl, lactone, lactam, sultam, O, S, SO, $SO_2$, $OSO_2$, amine, diazine, alkenyl, or alkynyl group;

$R^3$ is absent, or is O, S, $SO_2$, $SO_2NH$, $NHSO_2$, or $OSO_2$ or is an optionally substituted alkyl, alkenyl, alkynyl, cycloalkyl, a carbocyclic, a spirocyclic, heterocyclyl, aryl, heteroaryl, carboxyl, acetate, amine, amide, imide groups; and V is $V^1$ or $ONO_2$, wherein when A, B or C is substituted with a group comprising $ONO_2$ in any position, V is $V^1$, otherwise V is $ONO_2$.

In some embodiments, C has at least one double bond at the C8-C9 position, the C9-C10 position, or the C6a-C10a position. In some embodiments, V is $ONO_2$. In some embodiments, $R^1$ is a group comprising $ONO_2$ and V is $V^1$. In some embodiments, $R^1$ is $ONO_2$, alkyl-$ONO_2$, O-alkyl-$ONO_2$, O—$SO_2$-alkyl-$ONO_2$, —C(O)O-alkyl-$ONO_2$, alkyl-C(O)O-alkyl-$ONO_2$, or alkyl-O-alkyl-$ONO_2$.

In some embodiments, C has one, two or three double bonds, and at least one double bond is at the C8-C9 position, the C9-C10 position, or the C6a-C10a position; W is $C(CH_3)_2$, $CH(CH_3)$, $C=O$, or $CF_2$; Z is O or N; and V is $V^1$ when $R^1$ is a group comprising $ONO_2$, or V is $ONO_2$. In some embodiments, Y—$R^3$—V is $ONO_2$, alkyl-$ONO_2$, O-alkyl-$ONO_2$, O—$SO_2$-alkyl-$ONO_2$, —C(O)O-alkyl-$ONO_2$, alkyl-C(O)O-alkyl-$ONO_2$, or alkyl-O-alkyl-$ONO_2$.

In some embodiments of compound of formula (I), C is selected from the group consisting of:

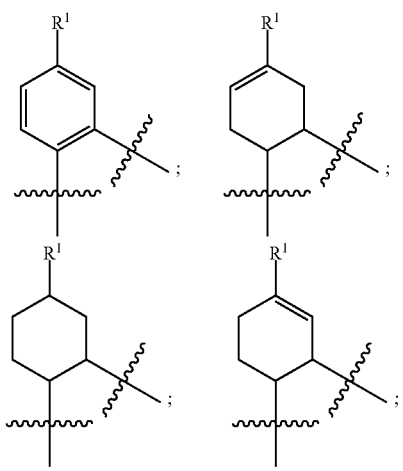

In some embodiments of compound of formula (I), B is selected from the group consisting of:

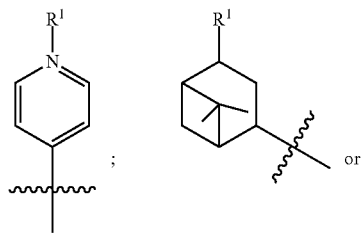

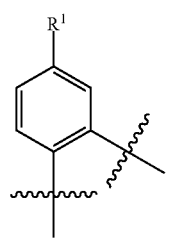

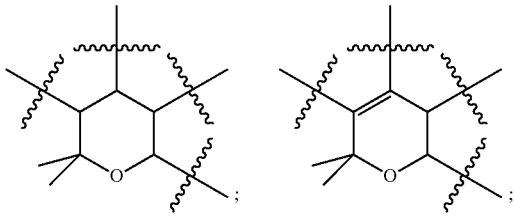

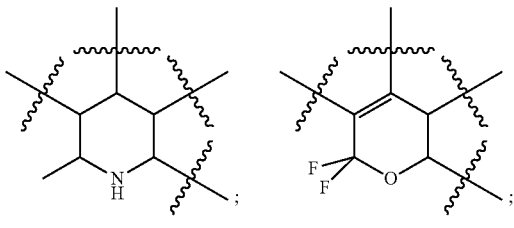

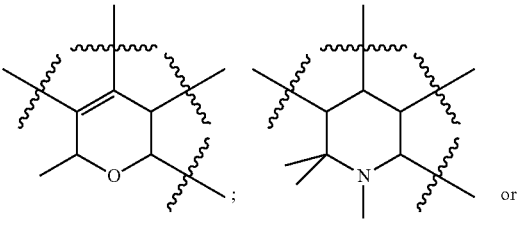

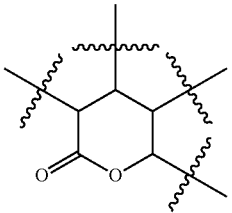

In another embodiment, compounds of formula (II), isomers thereof or pharmaceutically acceptable salts thereof, are provided.

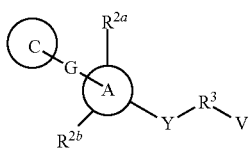

(II)

wherein,

C is optionally substituted alkyl, alkenyl, alkynyl, a carbocyclic group, bicyclic ring, aromatic ring, heterocyclic ring, heteroaromatic ring, alkaloid, terpene or a related derivative;

G is optionally present and when present is a direct bond or a group selected from C=O, NH, $CH_2$, CONH, NHCO, CONH(alkyl)-, COO, OCO, $OCH_2$, alkyl, S, SO, $SO_2$, and O;

A is an optionally substituted aromatic ring, heteroaromatic ring, heterocyclic ring, quinone, alkaloid, terpene or a related derivative;

$R^{2a}$ and $R^{2b}$ are each independently $R^2$; and
$R^2$, $R^3$, V and Y are as previously defined.

In some embodiments of compound of formula (II), C is selected from a ring system comprising

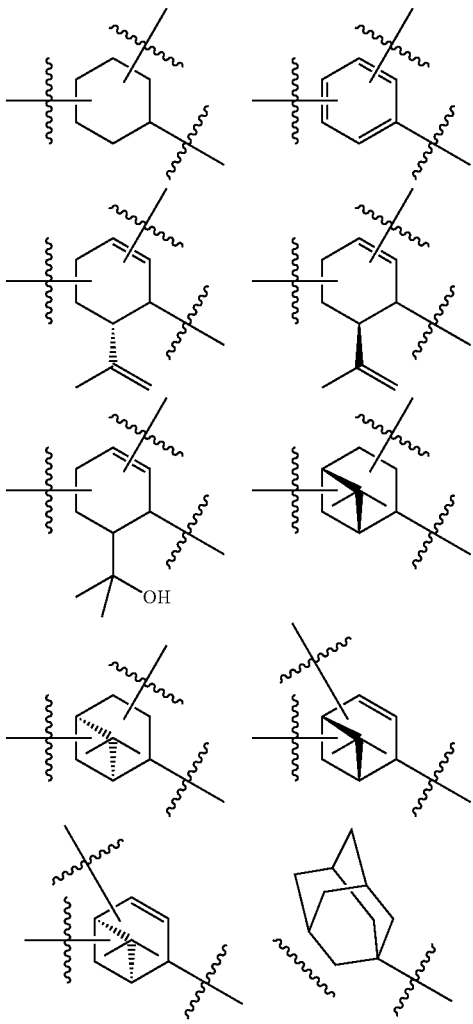

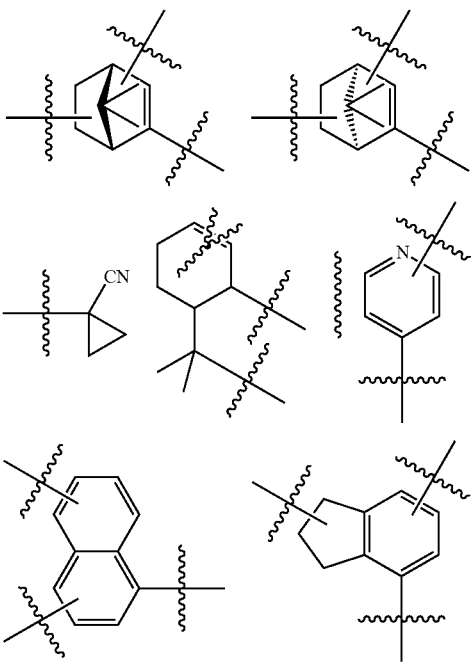

In some embodiments of compound of formula (II), A is selected from a ring system comprising

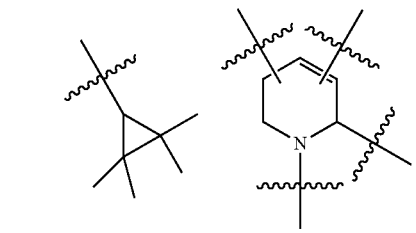

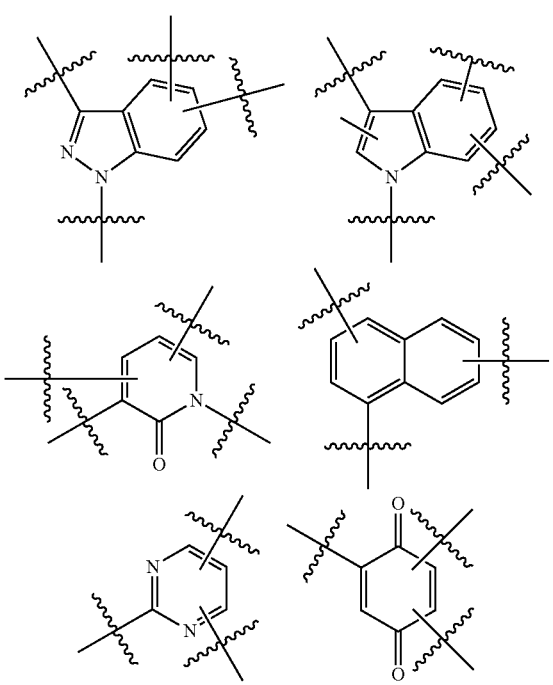

-continued

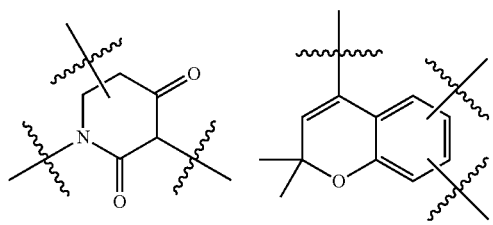
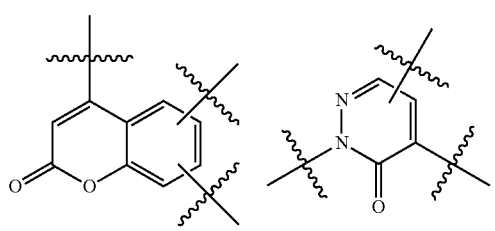
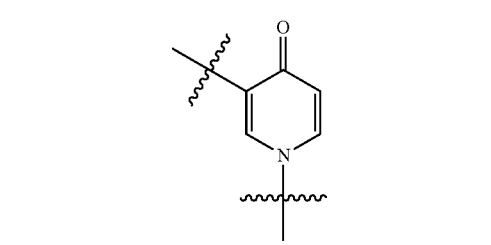

In yet another embodiment, compounds of formula (III), isomers thereof or pharmaceutically acceptable salts thereof, are provided.

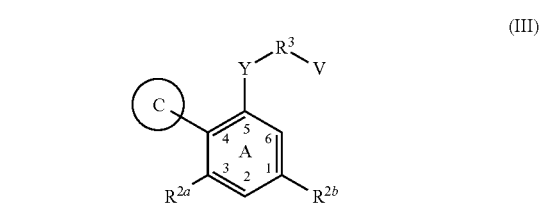

(III)

wherein,

C is an optionally substituted carbocyclic group, bicyclic ring, aromatic ring, heterocyclic ring, heteroaromatic ring, alkaloid, terpene or a related derivative;

$R^{2a}$ and $R^{2b}$ are each independently $R^2$; and $R^2$, $R^3$, V and Y are as previously defined.

In some embodiments of the compound of formula (III), V is $ONO_2$.

In some embodiments of compound of formula (III), C is selected from a ring system comprising

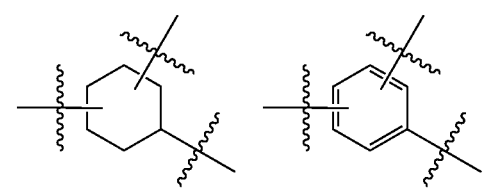

-continued

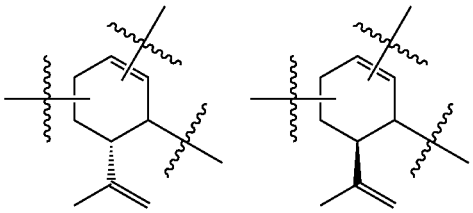
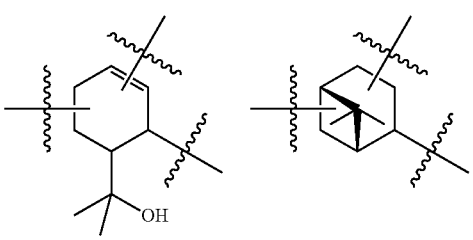
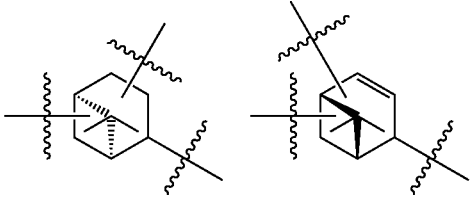
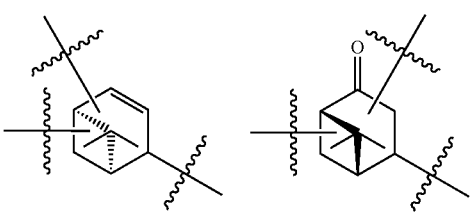
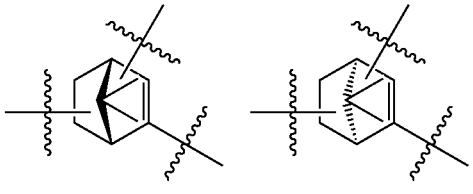
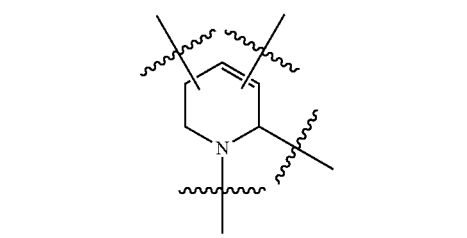
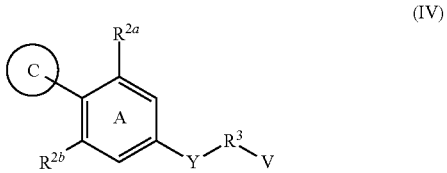

In some embodiments, compounds of formula (IV), isomers thereof or pharmaceutically acceptable salts thereof, are provided.

(IV)

wherein,

C is optionally substituted alkyl, alkenyl, alkynyl, a carbocyclic group, bicyclic ring, aromatic ring, heterocyclic ring, heteroaromatic ring, alkaloid, terpene or a related derivative;

$R^{2a}$ and $R^{2b}$ are each independently $R^2$; and $R^2$, $R^3$, V and Y are as previously defined.

In some embodiments of compound of formula (IV), C is selected from a ring system comprising

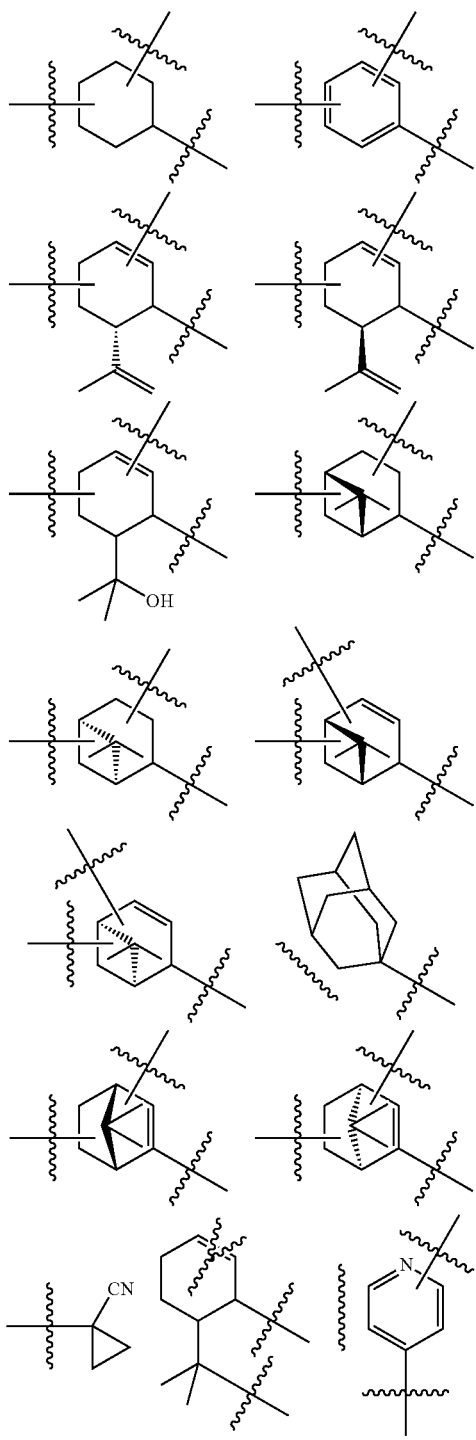

-continued

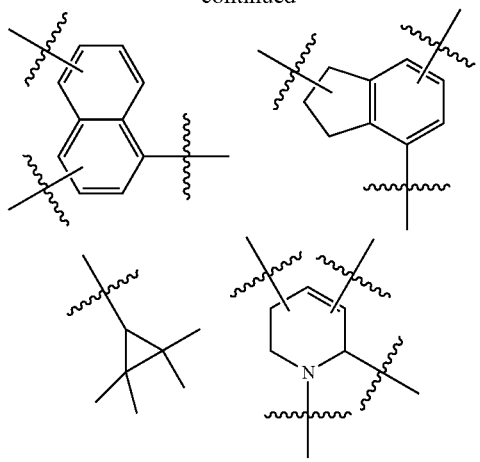

In some embodiments, compounds of formula (V), isomers thereof or pharmaceutically acceptable salts thereof, are provided.

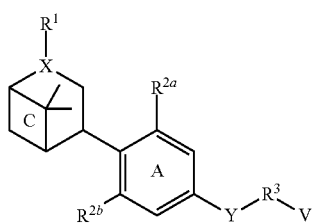

(V)

wherein,

C has zero or one double bond, and if present, the double bond is preferably in the C2-C3 position or C3-C4 position;

$R^{2a}$ and $R^{2b}$ are each independently $R^2$; and $R^1$, $R^2$, $R^3$, V, X and Y are as previously defined.

In some embodiments, compounds of formula (VI), isomers thereof or pharmaceutically acceptable salts thereof, are provided.

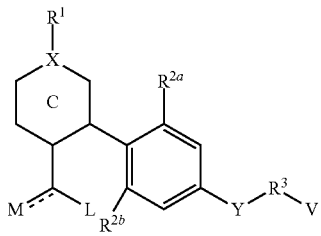

(VI)

wherein,

C has zero, one or three double bonds, and if present, at least one double bond is preferably in the C1-C2 position;

C8-C9 is a double bond and optionally a single bond;

$R^{2a}$ and $R^{2b}$ are each independently $R^2$;

M is $CH_2$ or alkyl-$T^1$;

L is $CH_3$ or alkyl-$T^1$; and $R^1$, $R^2$, $R^3$, V, X and Y are as previously defined.

In some embodiments of compound of formula (VI), C is selected from a ring system comprising

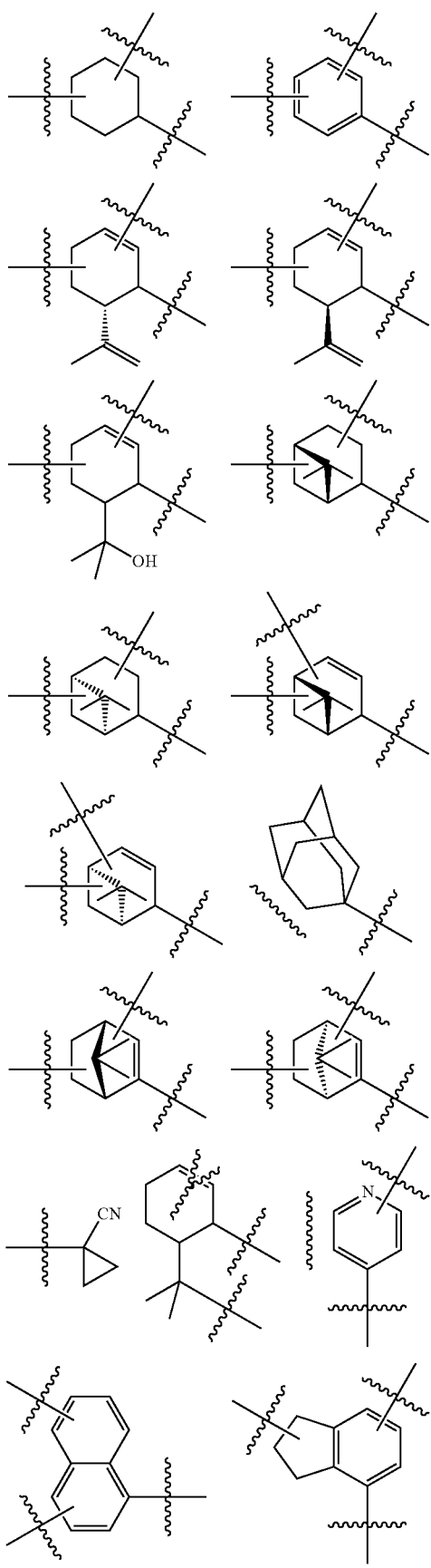

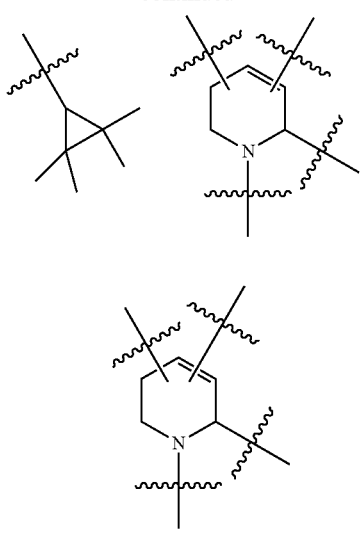

In some embodiments of compounds of formula (VII), isomers thereof or pharmaceutically acceptable salts thereof, are provided.

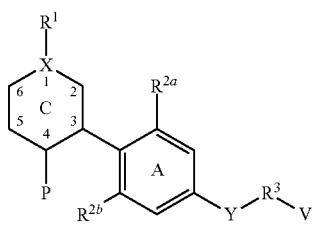

(VII)

wherein,

C has zero, one or three double bonds;

P is H, alkyl-OH, C(CH$_3$)$_2$(T$^1$) or alkyl-ONO$_2$;

R$^{2a}$ and R$^{2b}$ are each independently R$^2$; and

R$^1$, R$^2$, R$^3$, V, X and Y are as previously defined.

In some embodiments of compound of formula (VII), C is selected from a ring system comprising

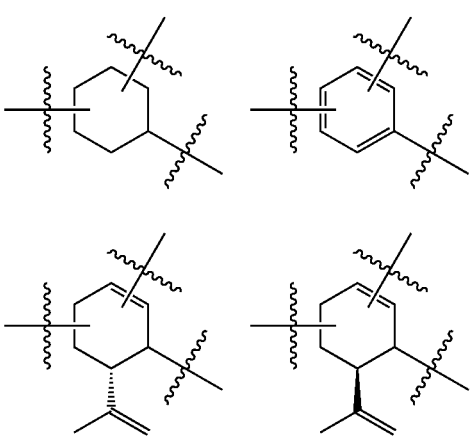

-continued

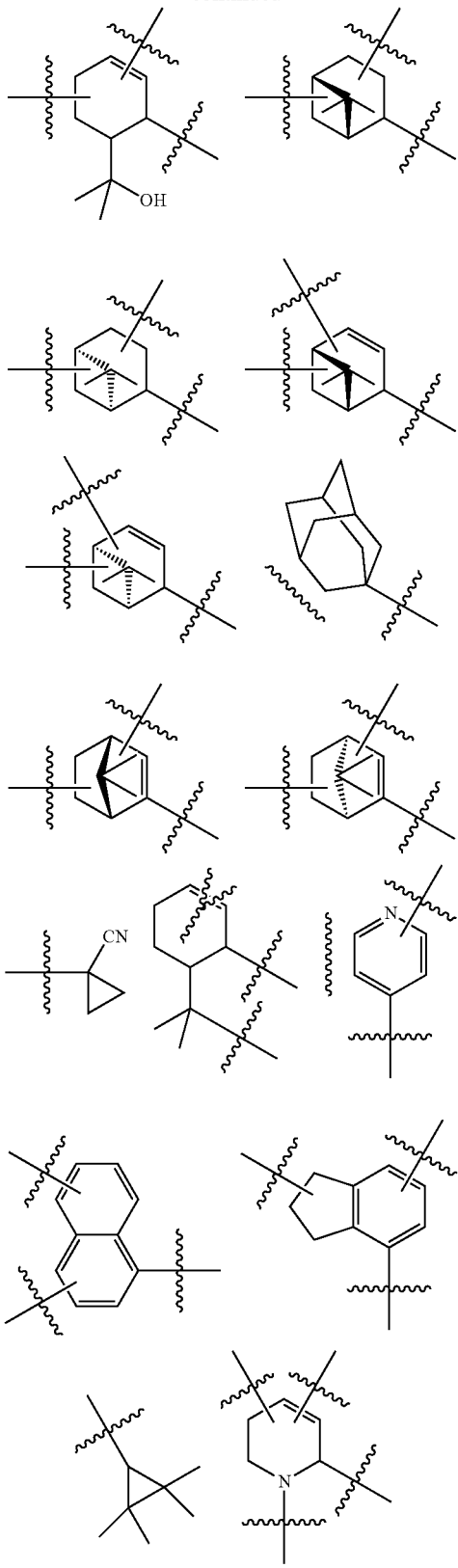

In another embodiment, compounds of formula (VIII), isomers thereof or pharmaceutically acceptable salts thereof, are provided.

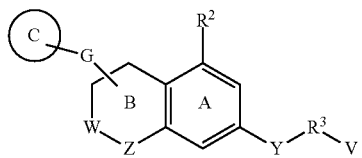

wherein,
C is an optionally substituted carbocyclic group, bicyclic ring, aromatic ring, heterocyclic ring, heteroaromatic ring, alkaloid, terpene or a related derivative;
G is a bond or a group selected from C=O, NH, CH$_2$, CONH, NHCO, S and O;
W is a bond, C(CH$_3$)$_2$, CH(CH$_3$), C=O, CF$_2$, C=S, C=CH$_2$, C(CH$_2$)$_2$, spirocyclic ring, S, SO, SO$_2$, or C[CH$_3$(R$^4$)];
Z is O, S, SO, SO$_2$, NH, or N-alkyl; and
R$^2$, R$^3$, R$^4$, V and Y are as defined herein for formula (I).
In some embodiments, compounds of formula (IX), isomers thereof or pharmaceutically acceptable salts thereof, are provided.

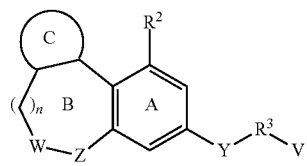

wherein,
C is as defined previously for formulae (I-VIII) and n=0, 1; and
R$_2$, R$_3$, V, W, Z, and Y are as defined herein for formula (I).
In some embodiments, C is aromatic and A is aromatic, and G is C=O;
C is aromatic and A is heteroaromatic, and G is C=O;
C is aromatic and A is heteroaromatic, and G is CONH;
C is heterocyclic and A is heteroaromatic, and G is C=O;
C is heterocyclic and A is heteroaromatic, and G is C=O;
C is alkyl and A is heteroaromatic, and G is C=O;
C is carbocyclic and A is heteroaromatic, and G is C=O;
C is alkyl, and A is heteroaromatic, and G is CONH;
C is carbocyclic and A is heteroaromatic, and G is C=O;
C is alkyl, and A is heteroaromatic, and G is CONH;
C is heteroaromatic and A is heteroaromatic, and G is N(alkyl)SO$_2$;
C is aromatic and A is heteroaromatic, and G is NH;
C is bicyclic ring and A is aromatic, and G is O;
C is bicyclic ring and A is aromatic, and G is a direct bond;
C is a terpene;
C is carbocyclic and W is optionally present;
C is heteroaromatic and A is heteroaromatic, and G is OCH$_2$;
C is heterocyclic and A is aromatic, and G is CH$_2$;
C is aromatic and A is heterocyclic, and G is CH$_2$;
C is carbocyclic and A is heteroaromatic, and G is a COO or OCO;
C is heterocyclic and A is aromatic, and G is a direct bond;
C is heterocyclic and A is heteroaromatic, and G is a direct bond;
C is a terpene and A is aromatic, and G is a direct bond;
C is a terpene and A is quinone, and G is a direct bond;

C is a terpene and A is aromatic, and G is a direct bond;
C is heterocyclic and A is aromatic, and G is a direct bond;
C is aromatic and A is aromatic, and G is a direct bond;
C is aromatic and A is heteroaromatic, and G is a direct bond;
C is alkyl and A is heteroaromatic, and G is a direct bond;
C is a terpene and A is aromatic, and G is a direct bond;
C is bicyclic and W is C=O; or
C is carbocyclic, B is carbocyclic and A is aromatic.

In any of the above embodiments of Formula IX, C may be:

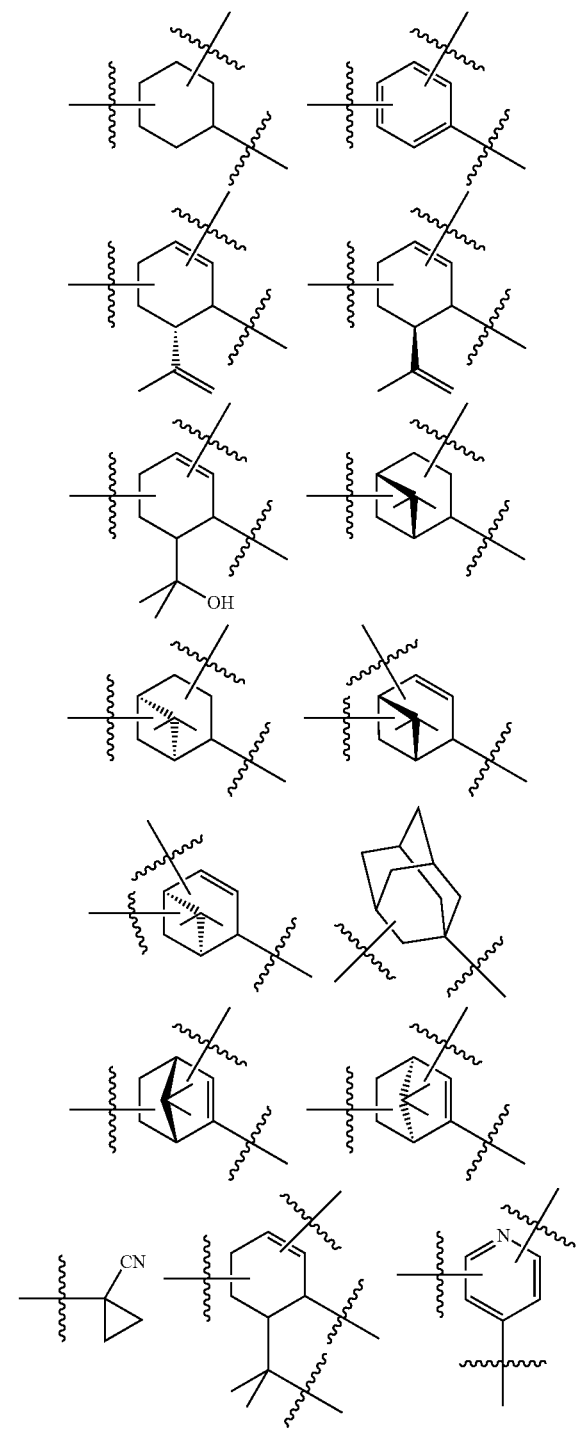

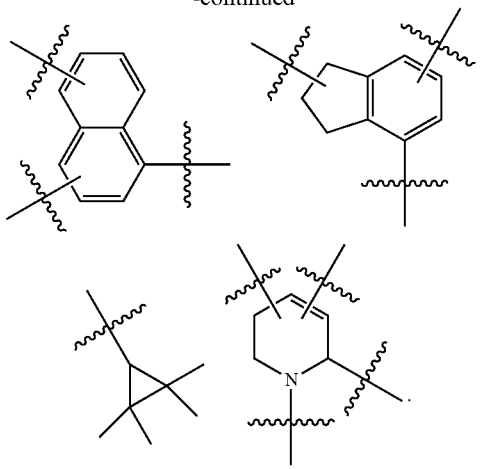

In some embodiments of the compound of formula (I), the compound has the formula (Ia):

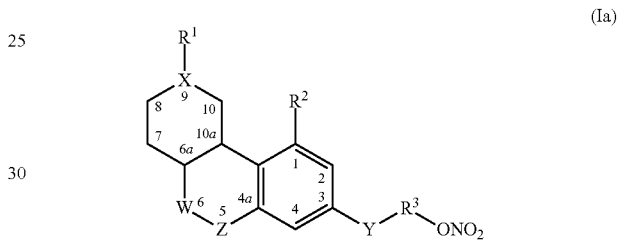

(Ia)

wherein the substituents are as previously defined.

In some embodiments of formula (I) and (Ia), C is carbocyclic and W is C=O.

In some embodiments of formula (I) and (Ia), C is carbocyclic and W is C[CH$_3$(R$^4$)].

In some embodiments of the compound of formula (II), C is an optionally substituted carbocyclic group, bicyclic ring, aromatic ring, heterocyclic ring, heteroaromatic ring, or a terpene;

A is an optionally substituted aromatic ring, heteroaromatic ring, or quinone;

G is a bond, C=O, NH, CH$_2$, or O; and

R$^{2a}$ and R$^{2b}$ are each independently R$^2$.

In some embodiments of the compound of formula (II), the compound has the formula (IIa):

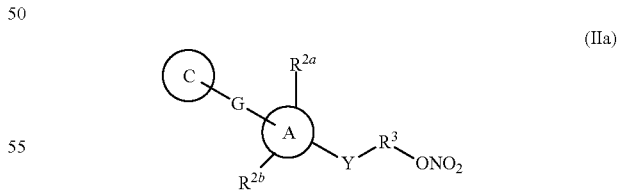

(IIa)

wherein,

C is an optionally substituted carbocyclic group, bicyclic ring, aromatic ring, heterocyclic ring, heteroaromatic ring, or a terpene;

G is a bond or a group selected from C=O, NH, CH$_2$, CONH, NHCO, COO, OCO, OCH$_2$, S, SO, SO$_2$ and O;

A is an optionally substituted aromatic ring, heteroaromatic ring, heterocyclic ring, or quinone;

R$^{2a}$ and R$^{2b}$ are each independently R$^2$; and

R$^2$, R$^3$ and Y are as previously defined.

In some embodiments of formulae (II) or (IIa), C is aromatic and A is aromatic; and G is C=O.

In some embodiments of formulae (II) or (IIa), C is aromatic and A is heteroaromatic; and G is C=O.

In some embodiments of formulae (II) or (IIa), C is aromatic and A is heteroaromatic; and G is CONH.

In some embodiments of formulae (II) or (IIa), C is heterocyclic and A is heteroaromatic; and G is C=O.

In some embodiments of formulae (II) or (IIa), C is alkyl and A is heteroaromatic; and G is C=O.

In some embodiments of formulae (II) or (IIa), C is heteroaromatic and A is heteroaromatic; and G is N(alkyl)SO$_2$.

In some embodiments of formulae (II) or (IIa), C is aromatic and A is heteroaromatic; and G is NH.

In some embodiments of formulae (II) or (IIa), C is bicyclic ring and A is aromatic; and G is O.

In some embodiments of formulae (II) or (IIa), C is bicyclic ring and A is aromatic; and G is a direct bond.

In some embodiments of formulae (II) or (IIa), C is heterocyclic and A is aromatic; and G is CH$_2$.

In some embodiments of formulae (II) or (IIa), C is heterocyclic and A is aromatic; and G is a direct bond.

In some embodiments of formulae (II) or (IIa), C is a terpene and A is aromatic; and G is a direct bond.

In some embodiments of formulae (II) or (IIa), C is a terpene and A is quinone; and G is a direct bond.

In some embodiments of formulae (II) or (IIa), C is a terpene and A is aromatic; and G is a direct bond.

In some embodiments of the compound of formula (III), the compound has the formula (IIIa):

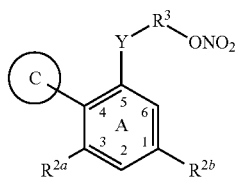

(IIIa)

wherein,

C is an optionally substituted carbocyclic group, bicyclic ring, aromatic ring, heterocyclic ring, heteroaromatic ring, or a terpene;

$R^{2a}$ and $R^{2b}$ are each independently $R^2$; and $R^2$, $R^3$ and Y are as previously defined.

In some embodiments of formulae (III) or (IIIa), C is heterocyclic and A is aromatic; and G is a direct bond.

In some embodiments of formulae (III) or (IIIa), C is a terpene and A is aromatic; and G is a direct bond.

In some embodiments of the compound of formula (IV), the compound has the formula (IVa):

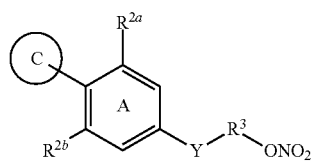

(IVa)

wherein, C is an optionally substituted carbocyclic group, bicyclic ring, aromatic ring, heterocyclic ring, heteroaromatic ring, or a terpene;

$R^{2a}$ and $R^{2b}$ are each independently $R^2$; and $R^2$, $R^3$ and Y are as previously defined.

In some embodiments of formulae (IV) or (IVa), C is a terpene.

In some embodiments of formulae (IV) or (IVa), C is an aromatic ring.

In some embodiments of formulae (IV) or (IVa), C is carbocyclic.

In some embodiments of the compound of formula (V), the compound has the formula (Va):

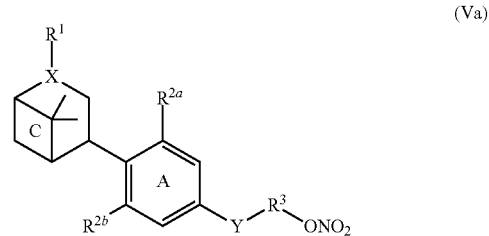

(Va)

wherein, C has within zero or one double bond, and if present, the double bond is preferably in the C2-C3 position or C3-C4 position;

$R^{2a}$ and $R^{2b}$ are each independently $R^2$; and $R^1$, $R^2$, $R^3$, X and Y are as previously defined.

In some embodiments of the compound of formula (VI), the compound has the formula (VIa):

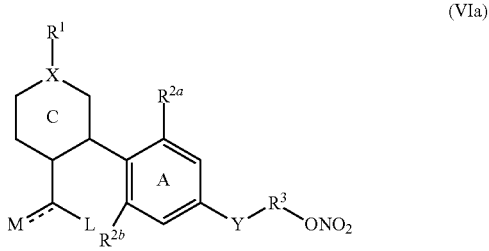

(VIa)

wherein, C has zero, one or three double bonds, and if present, at least one double bond is preferably in the C1-C2 position;

C8-C9 is a double bond and optionally a single bond;

$R^{2a}$ and $R^{2b}$ are each independently $R^2$; and

M is CH$_2$ or alkyl-T$^1$;

L is CH$_3$ or alkyl-T$^1$; and $R^1$, $R^2$, $R^3$, X and Y are as previously defined.

In some embodiments of the compound of formula (VII), the compound has the formula (VIIa):

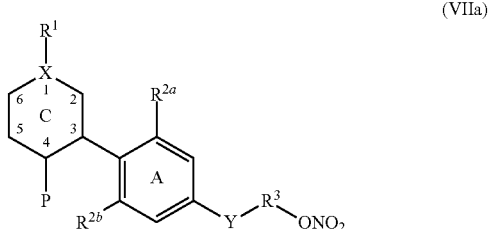

(VIIa)

wherein, C has zero, one or three double bonds;

P is H, alkyl-OH or alkyl-ONO$_2$;

$R^{2a}$ and $R^{2b}$ are each independently $R^2$; and $R^1$, $R^2$, $R^3$, X and Y are as previously defined.

In some embodiments of the formula (VIII), the compound has the formula (VIIIa):

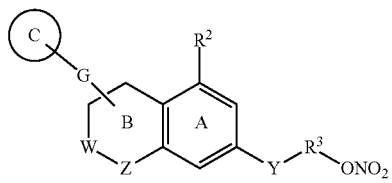
(VIIIa)

wherein,

C is an optionally substituted carbocyclic group, bicyclic ring, aromatic ring, heterocyclic ring, heteroaromatic ring, or a terpene;

G is a bond or a group selected from C=O, NH, CH$_2$, CONH, NHCO, S and O;

W is a bond, C(CH$_3$)$_2$, CH(CH$_3$), C=O, CF$_2$, C=S, C=CH$_2$, C(CH$_2$)$_2$, spirocyclic ring, S, SO, SO$_2$, or C[CH$_3$(R$^4$)];

Z is O, S, SO, SO$_2$, NH, or N-alkyl

R$^2$, R$^3$, R$^4$ and Y are as defined herein for compounds of formula (I).

In some embodiments, C has zero double bonds. In some embodiments, C has one double bond in the C8-C9 position, the C9-C10 position, or the C6a-C10a position. In some embodiments, C has two double bonds. In some embodiments, C has three double bonds.

In some embodiments, W is C(CH$_3$)$_2$, CH(CH$_3$), C=O, CF$_2$, C=S, C=CH$_2$, C(CH$_2$)$_2$, spirocyclic ring, S, SO, SO$_2$, or C[CH$_3$(R$^4$)]. In some embodiments, W is a C(CH$_3$)$_2$, CH(CH$_3$), C=O, CF$_2$, C=S, C=CH$_2$, C(CH$_2$)$_2$, spirocyclic ring, S, SO, SO$_2$, or C[CH$_3$(R$^4$)]. In some embodiments, W is C(CH$_3$)$_2$, CH(CH$_3$), C=O, CF$_2$, C=S, C=CH$_2$, C(CH$_2$)$_2$, S, SO$_2$, or C[CH$_3$(R$^4$)]. In some embodiments, W is C(CH$_3$)$_2$, CH(CH$_3$), C=O, CF$_2$, C(CH$_2$)$_2$, S, or SO$_2$. In some embodiments, W is C(CH$_3$)$_2$, CH(CH$_3$), C=O, CF$_2$, or C(CH$_2$)$_2$.

In some embodiments, W is C(CH$_3$)$_2$, C=O, CF$_2$, or C(CH$_2$)$_2$. In some embodiments, W is C(CH$_3$)$_2$, C=O, CF$_2$, or C(CH$_2$)$_2$. In some embodiments, W is C(CH$_3$)$_2$, C=O, or CF$_2$. In some embodiments, W is C(CH$_3$)$_2$ or CF$_2$. In some embodiments, W is C(CH$_3$)$_2$. In some embodiments, W is CF$_2$.

In some embodiments, V is V$^1$ when A or C are substituted with a group comprising ONO$_2$, or V is ONO$_2$. In some embodiments, V is V' when R$^6$ or T$^{11}$ are ONO$_2$, or V is ONO$_2$. In some embodiments, V is H when R$^1$ comprises ONO$_2$, or V is ONO$_2$. In some embodiments, V is V$^1$ when R$^1$ comprises ONO$_2$ or P is ONO$_2$ or V is ONO$_2$. In some embodiments, V is H or ONO$_2$. In some embodiments, V is H. In some embodiments, V is ONO$_2$.

In some embodiments, R$^4$ is CH$_2$R$^5$, C=(CH$_2$)$_n$—R$^5$, or C≡(CH$_2$)$_n$—R$^5$. In some embodiments, R$^4$ is CH$_2$R$^5$ or C=(CH$_2$)$_n$—R$^5$. In some embodiments, R$^4$ is CH$_2$R$^5$ or C=(CH$_2$)$_n$—R$^5$. In some embodiments, R$^4$ is C=(CH$_2$)$_n$—R$^5$ or C≡(CH$_2$)$_n$—R$^5$. In some embodiments, R$^4$ is CH$_2$R$^5$. In some embodiments, R$^4$ is C=(CH$_2$)$_n$—R$^5$. In some embodiments, R$^4$ is C(CH$_2$)$_n$—R$^5$.

In some embodiments, n is 0 or 1. In some embodiments, n is 0. In some embodiments, n is 1.

In some embodiments, R$^5$ is alkyl, alkenyl, alkynyl, H, OH, N$_3$, NCS, ONO$_2$, CHO, halogen, COOH, COOalkyl, CONHalkyl, heterocyclic ring, or heteroaromatic ring. In some embodiments, R$^5$ is alkyl, alkenyl, alkynyl, OH, N$_3$, ONO$_2$, halogen, COOH, COOalkyl, CONHalkyl, heterocyclic ring, or heteroaromatic ring. In some embodiments, R$^5$ is alkyl, ONO$_2$, halogen, heterocyclic ring, or heteroaromatic ring. In some embodiments, R$^5$ is alkyl, heterocyclic ring, or heteroaromatic ring. In some embodiments, R$^5$ is alkyl.

In some embodiments, X is C, CH, (CH$_2$)$_2$, N, S, O, SO, or SO$_2$. In some embodiments, X is C, CH, or (CH$_2$)$_2$. In some embodiments, X is C, CH, or N. In some embodiments, X is C or CH. In some embodiments, X is C. In some embodiments, X is CH.

In some embodiments, p is 0-6. In some embodiments, p is 0-3. In some embodiments, p is 0-2. In some embodiments, p is 0-1. In some embodiments, p is 0. In some embodiments, p is 1.

6 In some embodiments, R H, alkyl, alkynyl, alkenyl, halogen, alcohol, alkoxy, CF$_2$H, N$_3$, NCS, CN, ONO$_2$, NQ$^1$Q$^2$, =O, OQ$^3$, SQ$^3$, NHQ$^3$, =CH$_2$, OAc, O-acyl, O-aryl, O-aroyl, NH-acyl, NH-aroyl, C(halogen)$_3$, (halogen)$_2$, COOQ$^3$, SO$_2$-halogen, OSO$_2$CF$_3$, SO$_3$H, SO$_3$alkyl, SO$_2$NQ$^1$Q$^2$, CONQ$^1$Q$^2$, alkyl-OH, ONO$_2$, alkyl-ONO$_2$, spirocyclic, alkylmercapto, aroyl, alkylamino, di-alkylamino, heterocyclic ring, aromatic ring, heteroaromatic ring, CO-T$^1$, O—PO(OX$^1$)(OY$^1$), O-alkyl-(CH$_2$)$_r$—O—PO(OX$^1$)(OY$^1$), OSO$_3$H, OCO-alkyl-COOH, OCO-alkenyl-COOH, OPO$_3$H$_2$, O—SO$_2$alkyl-T$^1$, O—SO$_2$-T$^1$, OT$^1$, Oalkyl-T$^1$, NHSO$_2$-T$^1$, Nalkyl-SO$_2$-T$^1$, —O—COalkyl-T$^1$, NHCO-T$^1$, OCONH-T$^1$, O—CO-T$^1$, O—CO—O-T$^1$T$^1$, OCO-alkyl-N(T$^1$)$_2$, OCO-alkyl-T$^1$, O-alkyl-T$^1$, O-alkyl-OCO-T$^1$, O-T$^1$-T$^1$, O-alkyl-PO(OX$^1$)(OY$^1$), OCO(glycol), OCO-alkyl(glycol), OCO(polyol), OCO-alkyl(polyol), OCO-alkyl(BT), OCO-PEG$_r$, O—CO—O-PEG$_r$, O—COCO—O-PEG$_r$, or O-PEG$_r$.

In some embodiments, R$^6$ is H, alkyl, alkynyl, halogen, alcohol, alkoxy, CN, CO$_2$H, ONO$_2$, =O, =CH$_2$, OAc, O-acyl, O-aryl, O-aroyl, NH-acyl, NH-aroyl, C(halogen)$_3$, (halogen)$_2$, alkyl-ONO$_2$, heterocyclic ring, aromatic ring, or heteroaromatic ring. In some embodiments, R$^6$ is H, alkyl, alkynyl, alcohol, alkoxy, CO$_2$H, ONO$_2$, =O, =CH$_2$, heterocyclic ring, aromatic ring, or heteroaromatic ring. In some embodiments, R$^6$ is H, alkyl, alkynyl, alcohol, alkoxy, CO$_2$H, ONO$_2$, =O, =CH$_2$, heterocyclic ring, aromatic ring, or heteroaromatic ring. In some embodiments, R$^6$ is H, alkyl, alkynyl, alcohol, alkoxy, CO$_2$H, ONO$_2$, =o, or =CH$_2$.

In some embodiments, T$^1$ is H, alkyl, halogen, OH, CF$_3$, CF$_2$H, COOH, COOalkyl, O—PO(OX$^1$)(OY$^1$), SO$_3$H, ONO$_2$ a heterocyclic ring, NQ$^1$Q$^2$ or T$^1$ is an ammonium group, wherein said ammonium group can be independently substituted one or more times with a C1 to C6 alkyl radical, or is a C3 to C7 heterocycle containing a nitrogen heteroatom for bond formation, wherein the said heterocycle can contain one or more heteroatoms independently selected from N, O or S, and wherein said heterocycle can be substituted with one or more independently chosen substituents. In some embodiments, T$^1$ is H, alkyl, CF$_3$, CF$_2$H, O—PO(OX$^1$)(OY$^1$), ONO$_2$ a heterocyclic ring, NQ$^1$Q$^2$ or T$^1$ is an ammonium group, wherein said ammonium group can be independently substituted one or more times with a C1 to C6 alkyl radical, or is a C3 to C7 heterocycle containing a nitrogen heteroatom for bond formation, wherein the said heterocycle can contain one or more heteroatoms independently selected from N, O or S, and wherein said heterocycle can be substituted with one or more independently chosen substituents. In some embodiments, T$^1$ is H, alkyl, a heterocyclic ring, or T$^1$ is an ammonium group, wherein said ammonium group can be independently substituted one or more times with a C1 to C6 alkyl radical, or is a C3 to C7 heterocycle containing a nitrogen heteroatom for bond formation, wherein the said heterocycle can contain one or more heteroatoms independently selected from N, O or S, and wherein said heterocycle can be substituted with one or more independently chosen substituents. In some embodiments, $T^1$ is H, alkyl, or a heterocyclic ring. In some embodiments, $T^1$ is H or alkyl. In some embodiments, $T^1$ is H. In some embodiments, $T^1$ is alkyl.

In some embodiments, r is 0 to 10. In some embodiments, r is 0 to 6. In some embodiments, r is 0 to 4. In some embodiments, r is 0 to 2. In some embodiments, r is 0 to 1. In some embodiments, r is 0. In some embodiments, r is 1.

In some embodiments, $Q^1$ and $Q^2$ each independently are H, alkyl or alkyl-$ONO_2$; or $Q^1$ and $Q^2$ together are part of a heterocyclic ring having about 4 to about 7 ring members and optionally one additional heteroatom selected from O, N or S. In some embodiments, $Q^1$ and $Q^2$ each independently are H, alkyl or alkyl-$ONO_2$; or $Q^1$ and $Q^2$ together are part of a heterocyclic ring having about 4 to about 7 ring members. In some embodiments, $Q^1$ and $Q^2$ each independently are H, alkyl or alkyl-$ONO_2$. In some embodiments, $Q^1$ and $Q^2$ together are part of a heterocyclic ring having about 4 to about 7 ring members. In some embodiments, $Q^1$ and $Q^2$ each independently are H or alkyl. In some embodiments, $Q^1$ and $Q^2$ each independently are H or alkyl-$ONO_2$. In some embodiments, $Q^1$ and $Q^2$ each independently are alkyl or alkyl-$ONO_2$. In some embodiments, $Q^1$ and $Q^2$ are H. In some embodiments, $Q^1$ and $Q^2$ are alkyl. In some embodiments, $Q^1$ and $Q^2$ are alkyl-$ONO_2$.

In some embodiments, $X^1$ and $Y^1$ are H, alkyl-OCO-alkyl, or alkyl-O—CO—O-alkyl. In some embodiments, $X^1$ and $Y^1$ are H or alkyl-OCO-alkyl. In some embodiments, $X^1$ is H, alkyl-OCO-alkyl, alkyl-O—CO—O-alkyl, alkali metal or alkaline earth metal. In some embodiments, $X^1$ is H, alkyl-OCO-alkyl, or alkyl-O—CO—O-alkyl. In some embodiments, $X^1$ is H. In some embodiments, $Y^1$ is H, alkyl-OCO-alkyl, alkyl-O—CO—O-alkyl, alkali metal or alkaline earth metal. In some embodiments, $Y^1$ is H, alkyl-OCO-alkyl or alkyl-O—CO—O-alkyl. In some embodiments, $Y^1$ is H.

In some embodiments, Y is $C(CH_3)_2$, $CF_2$, C(alkyl), COO, CONH, alkyl, O, S, SO, $SO_2$, $OSO_2$, NH, or N-alkyl. In some embodiments, Y is $C(CH_3)_2$, $CF_2$, COO, CONH, alkyl, O, $OSO_2$, NH, or N-alkyl. In some embodiments, Y is $C(CH_3)_2$, $CH_2$, $CF_2$, O, or $OSO_2$. In some embodiments, Y is $C(CH_3)_2$, $CH_2$, $CF_2$, or O. In some embodiments, Y is $C(CH_3)_2$, $CH_2$, or $CF_2$. In some embodiments, Y is $C(CH_3)_2$. In some embodiments, Y is $CH_2$. In some embodiments, Y is $CF_2$.

In some embodiments, Z is O, $SO_2$, NH, or N-alkyl. In some embodiments, Z is O, NH, or N-alkyl. In some embodiments, Z is O, or N-alkyl. In some embodiments, Z is O, or N-methyl. In some embodiments, Z is O. In some embodiments, Z is N-methyl. In some embodiments, Z and/or W are a bond.

In some embodiments, $R^2$ is H, OH, SH, $CF_3$, COOH, alkyl-OH, halogen, NHCOalkyl, NHalkyl, N(dialkyl), $NHSO_2$alkyl, OCO-alkyl-COOH, OCO-alkenyl-COOH, $OSO_2$alkyl-$T^{11}$, O—$SO_2$-$T^{11}$, $OT^{11}$, alkyl-$T^{11}$, —O—COalkyl-$T^{11}$, OCONH-$T^{11}$, O—CO-$T^{11}$, O—CO—O-$T^{11}$, OCO-alkyl-NH-$T^{11}$, OCO-alkyl-N($T^{11}$)$_2$, O-alkyl-OCO-$T^{11}$, or O-$T^{11}$. In some embodiments, $R^2$ is H, OH, SH, $CF_3$, COOH, alkyl-OH, halogen, OCONH-alkyl-$T^{11}$, or —O—COalkyl-$T^{11}$. In some embodiments, $R^2$ is H, OH, $CF_3$, COOH, OCONH-alkyl-$T^{11}$, or —O—COalkyl-$T^{11}$. In some embodiments, $R^2$ is H. In some embodiments, $R^2$ is OH. In some embodiments, $R^2$ is $CF_3$. In some embodiments, $R^2$ is COOH. In some embodiments, $R^2$ is OCONH-alkyl-$T^{11}$. In some embodiments, $R^2$ is —O—COalkyl-$T^{11}$.

In some embodiments, $T^{11}$ is H, alkyl, halogen, OH, $CF_3$, $CF_2H$, COOH, COOalkyl, $ONO_2$, aromatic ring, heteroaromatic ring, a heterocyclic ring, or $NQ^{11}Q^{12}$, or $T^{11}$ is an ammonium group, wherein said ammonium group can be independently substituted one or more times with a C1 to C6 alkyl radical, or is a C3 to C7 heterocycle containing a nitrogen heteroatom for bond formation. In some embodiments, $T^{11}$ is H, alkyl, halogen, OH, $CF_3$, $CF_2H$, COOH, COOalkyl, $ONO_2$, aromatic ring, heteroaromatic ring, a heterocyclic ring, or $NQ^{11}Q^{12}$, or $T^1$ is an ammonium group, wherein said ammonium group can be independently substituted one or more times with a C1 to C6 alkyl radical. In some embodiments, $T^{11}$ is H, alkyl, halogen, OH, $CF_3$, $CF_2H$, COOH, COOalkyl, $ONO_2$, aromatic ring, heteroaromatic ring, a heterocyclic ring, or $NQ^{11}Q^{12}$. In some embodiments, $T^{11}$ is H, alkyl, halogen, OH, $CF_3$, $CF_2H$, COOH, COOalkyl, $ONO_2$, or $NQ^{11}Q^{12}$. In some embodiments, $T^{11}$ is H, alkyl, halogen, OH, $CF_3$, $CF_2H$, COOH, COOalkyl, or $ONO_2$. In some embodiments, $T^{11}$ is H, alkyl, halogen, $CF_3$, $CF_2H$, COOH or COOalkyl. In some embodiments, is H, alkyl, halogen, $CF_3$, or $CF_2H$. In some embodiments, $T^{11}$ is H, alkyl, or $CF_3$. In some embodiments, is H or alkyl. In some embodiments, $T^{11}$ is H or methyl. In some embodiments, $T^{11}$ is H. In some embodiments, $T^{11}$ is methyl.

In some embodiments, s is 0 to 10. In some embodiments, s is 0 to 6. In some embodiments, s is 0 to 4. In some embodiments, s is 0 to 2. In some embodiments, s is 0 or 1. In some embodiments, s is 0. In some embodiments, s is 1.

In some embodiments, $X^{11}$ and $Y^{11}$ are H, alkyl-OCO-alkyl, or alkyl-O—CO—O-alkyl. In some embodiments, $X^{11}$ and $Y^{11}$ are H or alkyl-OCO-alkyl. In some embodiments, $X^{11}$ is H, alkyl-OCO-alkyl, alkyl-O—CO—O-alkyl, alkali metal or alkaline earth metal. In some embodiments, $X^{11}$ is H, alkyl-OCO-alkyl, or alkyl-O—CO—O-alkyl. In some embodiments, $X^{11}$ is H. In some embodiments, is H, alkyl-OCO-alkyl, alkyl-O—CO—O-alkyl, alkali metal or alkaline earth metal. In some embodiments, $Y^{11}$ is H, alkyl-OCO-alkyl or alkyl-O—CO—O-alkyl. In some embodiments, $Y^{11}$ is H.

In some embodiments, $Q^{11}$ and $Q^{12}$ are each independently H or alkyl, or $Q^{11}$ and $Q^{12}$ together are part of a heterocyclic ring having about 4 to about 7 ring members and optionally one additional heteroatom selected from O, N or S. In some embodiments, $Q^{11}$ and $Q^{12}$ are each independently H or alkyl. In some embodiments, $Q^{11}$ and $Q^{12}$ are each independently H or methyl. In some embodiments, $Q^{11}$ and $Q^{12}$ are each H. In some embodiments, $Q^{11}$ and $Q^{12}$ are each methyl.

In some embodiments, $Q^{13}$ is H, alkyl, or alkyl-$NQ^{11}Q^{12}$. In some embodiments, $Q^{13}$ is H or alkyl. In some embodiments, $Q^{13}$ is H or methyl. In some embodiments, $Q^{13}$ is H. In some embodiments, $Q^{13}$ is H or alkyl. In some embodiments, $Q^{13}$ is methyl.

In some embodiments, $D^1$ is an optionally substituted alkyl group, alkenyl group, alkenylene, alkynyl group, cycloalkyl, a carbocyclic group, a spirocyclic ring, a polycyclic ring, a heterocyclic ring, an aromatic ring, a heteroaromatic ring, C=O(O), O(C=O), CONH, NHCO, O, S, $SO_2$, $SO_2NH$, $NHSO_2$, NH(alkyl), NH, or $OSO_2$. In some embodiments, $D^1$ is a alkyl group, alkenyl group, alkenylene, alkynyl group, cycloalkyl, a carbocyclic group, a heterocyclic ring, an aromatic ring, a heteroaromatic ring, C=O(O), O(C=O), CONH, NHCO, O, S, $SO_2$, $SO_2NH$, NHSO$_2$, NH(alkyl), NH, or OSO$_2$. In some embodiments, D$^1$ is a alkyl group, alkenyl group, alkenylene, alkynyl group, cycloalkyl, a carbocyclic group, an aromatic ring, C=O(O), O(C=O), CONH, NHCO, O, S, SO$_2$, SO$_2$NH, NHSO$_2$, NH(alkyl), NH, or OSO$_2$. In some embodiments, D$^1$ is a alkyl group, alkenyl group, alkenylene, alkynyl group, cycloalkyl, C=O(O), O(C=O), CONH, NHCO, O, S, SO$_2$, SO$_2$NH, NHSO$_2$, NH(alkyl), NH, or OSO$_2$. In some embodiments, D$^1$ is a alkyl group, alkenyl group, alkenylene, alkynyl group or cycloalkyl. In some embodiments, D$^1$ is a alkyl group. In some embodiments, D$^1$ is a —(C1-C6)-alkyl group. In some embodiments, D$^1$ is a —(C1-C3)-alkyl group. In some embodiments, D$^1$ is a methyl group.

In some embodiments, J$^1$ and J$^2$ are each independently selected from alkyl, O, NH, N, COO, OCO, O—CO—O, CONH, NHCO, OSO$_2$, SO$_2$NH, and NHSO$_2$. In some embodiments, J$^1$ and J$^2$ are each independently selected from alkyl. In some embodiments, J$^1$ and J$^2$ are each present. In some embodiments, J$^1$ is present. In some embodiments, J$^1$ and J$^2$ are absent.

In some embodiments, C is an optionally substituted cyclohexyl ring, bicyclic ring, aromatic ring, heterocyclic ring, heteroaromatic ring, or terpene. In some embodiments, C is an optionally substituted cyclohexyl ring, cyclodecyl ring, phenyl ring, naphthyl ring, piperazine ring, heteroaromatic ring or terpene. In some embodiments, C is an optionally substituted cyclohexyl ring, phenyl ring, naphthyl ring, piperazine ring, or terpene. In some embodiments, C is a cyclohexyl ring. In some embodiments, C is a phenyl ring. In some embodiments, C is a terpene.

In some embodiments, A is an optionally substituted aromatic ring, heteroaromatic ring, or heterocyclic ring. In some embodiments, A is an optionally substituted phenyl ring, naphthyl ring, indole ring, or hydroxypyridine ring. In some embodiments, A is a phenyl ring or naphthyl ring. In some embodiments, A is a phenyl ring.

In some embodiments, G is a direct bond or a group selected from C=O, NH, CH$_2$, CONH, NHCO, S, SO, SO$_2$, and O. In some embodiments, G is not present. In some embodiments, G is a direct bond or a group selected from C=O, NH, CH$_2$, and O. In some embodiments, G is a direct bond or a group selected from C=O, NH, and O. In some embodiments, G is a direct bond or a group selected from C=O, NH, and O. In some embodiments, G is a direct bond. In some embodiments, G is C=O. In some embodiments, G is NH. In some embodiments, G is CH$_2$. In some embodiments, G is O.

In some embodiments, M is CH$_2$. In some embodiments, M is alkyl-V. In some embodiments, M is alkyl.

In some embodiments, L is alkyl. In some embodiments, L is alkyl-V. In some embodiments, L is CH$_3$.

In some embodiments, P is H or alkyl-ONO$_2$. In some embodiments, P is H.

In some embodiments, P is alkyl-ONO$_2$.

In some embodiments, the compounds of Formula (I)-(IX) includes: 2-((6aR,10aR)-1-hydroxy-6,6,9-trimethyl-6a,7,10,10a-tetrahydro-6H-benzo[c]chromen-3-yl)ethyl nitrate; 3-((6 aR,10 aR)-1-hydroxy-6,6,9-trimethyl-6a,7,10,10a-tetrahydro-6H-benzo[c]chromen-3-yl)propyl nitrate; 4-((6aR,10aR)-1-hydroxy-6,6,9-trimethyl-6a, 7,10,10a-tetrahydro-6H-benzo[c]chromen-3-yl)butyl nitrate; 4-((6aR,10aR)-1-hydroxy-6,6,9-trimethyl-6a,7,10,10a-tetrahydro-6H-benzo[c]chromen-3-yl)pentyl nitrate; 6-((6aR,10aR)-1-hydroxy-6,6,9-trimethyl-6a,7,10,10a-tetrahydro-6H-benzo[c]chromen-3-yl)hexyl nitrate; 7-((6aR,10aR)-1-hydroxy-6, 6,9-trimethyl-6a,7,10,10a-tetrahydro-6H-benzo[c]chromen-3-yl)heptyl nitrate; 8-((6aR,10aR)-1-hydroxy-6,6,9-trimethyl-6a,7,10,10a-tetrahydro-6H-benzo[c]chromen-3-yl)octyl nitrate; 9-((6aR,10aR)-1-hydroxy-6,6,9-trimethyl-6a,7,10,10a-tetrahydro-6H-benzo[c]chromen-3-yl)nonyl nitrate; 2-((6aR,10aR)-1-hydroxy-6,6,9-trimethyl-6a,7,10,10a-tetrahydro-6H-benzo[c]chromen-3-yl)-2-methylpropyl nitrate; 3-((6aR,10aR)-1-hydroxy-6,6,9-trimethyl-6a,7,10,10a-tetrahydro-6H-benzo[c]chromen-3-yl)-3-methylbutyl nitrate; 4-((6aR,10aR)-1-hydroxy-6,6,9-trimethyl-6a,7,10,10a-tetrahydro-6H-benzo[c]chromen-3-yl)-4-methylpentyl nitrate; 5-((6aR,10aR)-1-hydroxy-6,6,9-trimethyl-6a,7,10,10a-tetrahydro-6H-benzo[c]chromen-3-yl)-5-methylhexyl nitrate; 6-((6aR,10aR)-1-hydroxy-6,6,9-trimethyl-6a,7,10,10a-tetrahydro-6H-benzo[c]chromen-3-yl)-6-methylheptyl nitrate; 7-((6aR,10aR)-1-hydroxy-6,6,9-trimethyl-6a, 7,10,10a-tetrahydro-6H-benzo[c]chromen-3-yl)-7-methyloctyl nitrate; 8-((6aR,10aR)-1-hydroxy-6,6,9-tri methyl-6a,7,10,10a-tetrahydro-6H-benzo[c]chromen-3-yl)-8-methylnonyl nitrate; (6aR,10aR)-6,6,9-trimethyl-3-(nitrooxy)pentyl)-6a,7,10,10a-tetrahydro-6H-benzo[c]chromen-1-yl 2-propylpentanoate; (6aR,10aR)-6,6,9-trimethyl-3-(2-methyl-8-(nitrooxy)octan-2-yl)-6a,7,10,10a-tetrahydro-6H-benzo[c]chromen-1-yl 2-propylpentanoate; (6aR,10aR)-6,6,9-trimethyl-3-(2-methyloctan-2-yl)-6a,7,10,10a-tetrahydro-6H-benzo[c]chromen-1-yl 4-(nitrooxy)butanoate; (6aR,10aR)-6,6,9-trimethyl-3-pentyl-6a,7,10,10a-tetrahydro-6H-benzo[c]chromen-1-yl 4-(nitrooxy)butanoate; (6aR,10aR)-6,6,9-trimethyl-3-propyl-6a,7,10,10a-tetrahydro-6H-benzo[c]chromen-1-yl 4-(nitrooxy)butanoate; 2-((6aR,10aR)-1-hydroxy-6,6,9-trimethyl-6a,7,8,10a-tetrahydro-6H-benzo[c]chromen-3-yl)ethyl nitrate; 3-((6aR,10aR)-1-hydroxy-6,6,9-trimethyl-6a,7,8,10a-tetrahydro-6H-benzo[c]chromen-3-yl)propyl nitrate; 4-((6aR,10aR)-1-hydroxy-6,6,9-trimethyl-6a,7,8,10a-tetrahydro-6H-benzo[c]chromen-3-yl)butyl nitrate; 5-((6aR,10aR)-1-hydroxy-6,6,9-trimethyl-6a,7,8,10a-tetrahydro-6H-benzo[c]chromen-3-yl)pentyl nitrate; 6-((6aR,10aR)-1-hydroxy-6,6,9-trimethyl-6a,7,8,10a-tetrahydro-6H-benzo[c]chromen-3-yl)hexyl nitrate; 7-((6aR,10aR)-1-hydroxy-6,6,9-trimethyl-6a,7,8,10a-tetrahydro-6H-benzo[c]chromen-3-yl)heptyl nitrate; 8-((6aR,10aR)-1-hydroxy-6,6,9-trimethyl-6a,7,8,10a-tetrahydro-6H-benzo[c]chromen-3-yl)octyl nitrate; 9-((6aR,10aR)-1-hydroxy-6,6,9-trimethyl-6a,7,8,10a-tetrahydro-6H-benzo[c]chromen-3-yl)nonyl nitrate; 2-((6aR,10aR)-1-hydroxy-6,6,9-trimethyl-6a,7,8,10a-tetrahydro-6H-benzo[c]chromen-3-yl)-2-methylpropyl nitrate; 3-((6aR,10aR)-1-hydroxy-6,6,9-trimethyl-6a,7,8,10a-tetrahydro-6H-benzo[c]chromen-3-yl)-3-methylbutyl nitrate; 4-((6aR,10aR)-1-hydroxy-6,6,9-trimethyl-6a,7,8,10a-tetrahydro-6H-benzo[c]chromen-3-yl)-4-methylpentyl nitrate; 5-((6aR,10aR)-1-hydroxy-6,6,9-trimethyl-6a,7,8,10a-tetrahydro-6H-benzo[c]chromen-3-yl)-5-methylhexyl nitrate; 6-((6aR,10aR)-1-hydroxy-6,6,9-trimethyl-6a,7,8,10a-tetrahydro-6H-benzo[c]chromen-3-yl)-6-methylheptyl nitrate; 7-((6aR,10aR)-1-hydroxy-6,6,9-trimethyl-6a,7,8,10a-tetrahydro-6H-benzo[c]chromen-3-yl)-7-methyloctyl nitrate; 8-46aR,10aR)-1-hydroxy-6,6,9-trimethyl-6a,7,8,10a-tetrahydro-6H-benzo[c]chromen-3-yl)-8-methylnonyl nitrate; (6aR,10aR)-6,6,9-trimethyl-3-(5-(nitrooxy)pentyl)-6a,7,8,10a-tetrahydro-6H-benzo[c]chromen-1-yl 2-propylpentanoate; (6aR,10aR)-6,6,9-trimethyl-3-(2-methyl-8-(nitrooxy)octan-2-yl)-6a,7,8,10a-tetrahydro-6H-benzo[c]chromen-1-yl 2-propylpentanoate; (6aR,10aR)-6,6,9-trimethyl-3-(2-methyloctan-2-yl)-6a,7,8,10a-tetrahydro-6H-benzo[c]chromen-1-yl 4-(nitrooxy)butanoate; (6aR,10aR)-6,6,9-trimethyl-3-pentyl-6a,7,8,10a-tetrahydro-6H-benzo[c]chromen-1-yl 4-(nitrooxy)butan oate; (6aR,10aR)-6,6,9-trimethyl-3-propyl-6a,7,8,10a-tetrahydro-6H-benzo[c]chromen-1-yl 4-(nitrooxy)butanoate; (E)-4-oxo-4-(((6aR, 10aR)-6,6,9-trimethyl-3-(5-(nitro oxy)pentyl)-6a,7,8,10a-tetrahydro-6H-benzo[c]chromen-1-yl)oxy)but-2-enoic acid; (E)-4-oxo-4-(((6aR,10aR)-6,6,9-trimethyl-3-(5-(nitrooxy)pentyl)-6a,7,10,10a-tetrahydro-6H-benzo[c]chromen-1-yl)oxy)but-2-enoic acid; (E)-4-oxo-4-(((6aR,10aR)-6,6,9-trimethyl-3-(3-(nitrooxy)propyl)-6a,7,8,10a-tetrahydro-6H-benzo[c]chromen-1-yl)oxy)but-2-enoic acid; (E)-4-oxo-4-(((6aR,10aR)-6,6,9-trimethyl-3-(3-(nitrooxy)propyl)-6a,7,10,10a-tetrahydro-6H-benzo[c]chromen-1-yl)oxy)but-2-enoic acid; (Z)-4-oxo-4-(((6aR,10aR)-6,6,9-trimethyl-3-(5-(nitrooxy)pentyl)-6a,7,8,10a-tetrahydro-6H-benzo[c]chromen-1-yl)oxy)but-2-enoic acid; (Z)-4-oxo-4-(((6aR,10aR)-6,6,9-trimethyl-3-(5-(nitro oxy)pentyl)-6a,7,10,10a-tetrahydro-6H-benzo[c]chromen-1-yl)oxy)but-2-enoic acid; (Z)-4-oxo-4-(((6aR,10aR)-6,6,9-trimethyl-3-(3-(nitrooxy)propyl)-6a,7,8,10a-tetrahydro-6H-benzo[c]chromen-1-yl)oxy)but-2-enoic acid; (Z)-4-oxo-4-(((6aR,10aR)-6,6,9-trimethyl-3-(3-(nitrooxy)propyl)-6a,7,10,10a-tetrahydro-6H-benzo[c]chromen-1-yl)oxy)but-2-enoic acid; (6aR,10aR)-6,6,9-trimethyl-3-(5-(nitrooxy)pentyl)-6a,7,10,10a-tetrahydro-6H-benzo[c]chromen-1-yl 2,5,8,11,14,17,20-heptaoxadocosan-22-oate; (6aR,10aR)-6,6,9-trimethyl-3-(2-(nitro oxy)ethyl)-6a,7,10,10a-tetrahydro-6H-benzo[c]chromen-1-yl 2,5,8,11,14,17,20-heptaoxadocosan-22-oate; 4-oxo-4-(((6aR,10aR)-6,6,9-trimethyl-3-(5-(nitro oxy)pentyl)-6a,7,8,10a-tetrahydro-6H-benzo[c]chromen-1-yl)oxy)butanoic acid; 4-oxo-4-(((6aR,10aR)-6,6,9-trimethyl-3-(5-(nitrooxy)pentyl)-6a,7,10,10a-tetrahydro-6H-benzo[c]chromen-1-yl)oxy)butanoic acid; (6aR,10aR)-6,6,9-trimethyl-3-(5-(nitrooxy)pentyl)-6a,7,8,10a-tetrahydro-6H-benzo[c]chromen-1-yl 2,5,8,11,14,17,20-heptaoxadocosan-22-oate; (6aR,10aR)-6,6,9-trimethyl-3-(5-(nitro oxy)pentyl)-6a,7,10,10a-tetrahydro-6H-benzo[c]chromen-1-yl 2,5,8,11,14,17,20-heptaoxadocosan-22-oate; (6aR,10aR)-6,6,9-trimethyl-3-(5-(nitrooxy)pentyl)-6a,7,8,10a-tetrahydro-6H-benzo[c]chromen-1-yl 4-methylbenzenesulfonate; (6aR,10aR)-6,6,9-trimethyl-3-(5-(nitro oxy)pentyl)-6a,7,8,10a-tetrahydro-6H-benzo[c]chromen-1-yl benzylcarbamate; (6aR,10aR)-3-(adamantan-1-yl)-6,6,9-trimethyl-6a,7,10,10a-tetrahydro-6H-benzo[c]chromen-1-yl 4-(nitrooxy)butanoate; 7-((6aR,10aR)-1-methoxy-6,6-dimethyl-9-methylene-6a,7,8,9,10,10a-hexahydro-6H-benzo[c]chromen-3-yl)-7-methyloctyl nitrate; (6aR,10aR)-6,6-dimethyl-9-methylene-3-(2-methyloctan-2-yl)-6a,7,8,9,10,10a-hexahydro-6H-benzo[c]chromen-1-yl nitrate; 7-(1-hydroxy-6,6,9-trimethyl-7,8,9,10-tetrahydro-6H-benzo[c]chromen-3-yl)-6-methyloctyl nitrate; 6,6,9-trimethyl-3-(3-methyloctan-2-yl)-7,8,9,10-tetrahydro-6H-benzo[c]chromen-1-yl 4-(nitrooxy)butanoate; 2-((1S,2S,5 S)-6,6-dimethyl-4-oxobicyclo[3.1.1]heptan-2-yl)-3-hydroxy-5-(2-methyloct-7-yn-2-yl)phenyl 4-(nitrooxy)butanoate; 8-((6aR,10aR)-1-hydroxy-6,6,9-trimethyl-6a,7,10,10a-tetrahydro-6H-benzo[c]chromen-3-yl)nonyl nitrate; 5-((6aS,10aR)-1-hydroxy-9-methyl-6a,7,8,10a-tetrahydro-6H-benzo[c]chromen-3-yl)pentyl nitrate; 5-((6aS,10aS)-1-hydroxy-9-methyl-6a,7,10,10a-tetrahydro-6H-benzo[c]chromen-3-yl)pentyl nitrate; 6-((6aR,10aR)-1-hydroxy-6,6,9-trimethyl-6a,7,8,10a-tetrahydro-6H-benzo[c]chromen-3-yl)heptyl nitrate; N,N,N-trimethyl-2-oxo-2-(((6aR,10aR)-6,6,9-trimethyl-3-(5-(nitrooxy)pentyl)-6a,7,8,10a-tetrahydro-6H-benzo[c]chromen-1-yl)oxy)ethanaminium iodide; 3-(((6aR,10aR)-3-((1s,3 S)-adamantan-1-yl)-6,6,9-trimethyl-6a,7,10,10a-tetrahydro-6H-benzo[c]chromen-1-yl)oxy)propyl nitrate; 7-((6aR,10aR)-1-hydroxy-6,6,9-trimethyl-6a,7,10,10a-tetrahydro-6H-benzo[c]chromen-3-yl)hept-5-en-1-yl nitrate; 7-((6aR,10aR)-1-hydroxy-6,6,9-trimethyl-6a,7,10,10a-tetrahydro-6H-benzo[c]chromen-3-yl)hept-5-yn-1-yl nitrate; 5-((6aR,10aR)-6,6-difluoro-1-hydroxy-9-methyl-6a,7,10,10a-tetrahydro-6H-benzo[c]chromen-3-yl)pentyl nitrate; (6aR,10aR)-6,6-difluoro-9-methyl-3-(2-methyl-6-(nitrooxy)hexan-2-yl)-6a,7,10,10a-tetrahydro-6H-benzo[c]chromen-1-yl 2-propylpentanoate; 7-((6aR,10aR)-6,6-difluoro-1-hydroxy-9-methyl-6a,7,10,10a-tetrahydro-6H-benzo[c]chromen-3-yl)-7-methyl-6-oxooctyl nitrate; (E)-4-(((6aR,10aR)-6,6-difluoro-9-methyl-3-(2-methyl-8-(nitrooxy)-3-oxooctan-2-yl)-6a,7,10,10a-tetrahydro-6H-benzo[c]chromen-1-yl)oxy)-4-oxobut-2-enoic acid; (6aR,10aR)-6,6-difluoro-9-methyl-3-(2-methyl-3-oxooctan-2-yl)-6a,7,10,10a-tetrahydro-6H-benzo[c]chromen-1-yl 4-(nitrooxy)butanoate; 3-(1,9-dihydroxy-6-oxo-6H-benzo[c]chromen-3-yl)-3-methylbutyl nitrate; 4-(1,9-dihydroxy-6-oxo-6H-benzo[c]chromen-3-yl)-4-methylpentyl nitrate; 5-(1,9-dihydroxy-6-oxo-6H-benzo[c]chromen-3-yl)-5-methylhexyl nitrate; 6-(1,9-dihydroxy-6-oxo-6H-benzo[c]chromen-3-yl)-6-methylheptyl nitrate; 7-(1,9-dihydroxy-6-oxo-6H-benzo[c]chromen-3-yl)-7-methyloctyl nitrate; 1-hydroxy-3-(2-methyloctan-2-yl)-6-oxo-6H-benzo[c]chromen-9-yl nitrate; 6-((l-hydroxy-9-methoxy-6-oxo-6H-benzo[c]chromen-3-yl)(methyl)amino)hexyl nitrate; 3-(1-hydroxy-9-methoxy-6-oxo-6H-benzo[c]chromen-3-yl)-3-methylbutyl nitrate; 4-(1-hydroxy-9-methoxy-6-oxo-6H-benzo[c]chromen-3-yl)-4-methylpentyl nitrate; 5-(1-hydroxy-9-methoxy-6-oxo-6H-benzo[c]chromen-3-yl)-5-methylhexyl nitrate; 6-(1-hydroxy-9-methoxy-6-oxo-6H-benzo[c]chromen-3-yl)-6-methylheptyl nitrate; 7-(1-hydroxy-9-methoxy-6-oxo-6H-benzo[c]chromen-3-yl)-7-methyloctyl nitrate; 9-methoxy-3-(2-methyl-8-(nitrooxy)octan-2-yl)-6-oxo-6H-benzo[c]chromen-1-yl 2-propylpentanoate; 9-methoxy-3-(2-methyl octan-2-yl)-6-oxo-6H-benzo[c]chromen-1-yl 4-(nitrooxy)butanoate; (E)-4-((9-methoxy-3-(2-methyloctan-2-yl)-6-oxo-6H-benzo[c]chromen-1-yl)oxy)-4-oxobut-2-enoic acid; (Z)-4-((9-methoxy-3-(2-methyloctan-2-yl)-6-oxo-6H-benzo[c]chromen-1-yl)oxy)-4-oxobut-2-enoic acid; 9-methoxy-3-(2-methyl-8-(nitrooxy)octan-2-yl)-6-oxo-6H-benzo[c]chromen-1-yl 2,5,8,11,14,17,20-heptaoxadocosan-22-oate; 4-((9-methoxy-3-(2-methyloctan-2-yl)-6-oxo-6H-benzo[c]chromen-1-yl)oxy)-4-oxobutanoic acid; 3-(1-hydroxy-9-methoxy-6,6-dimethyl-6H-benzo[c]chromen-3-yl)-3-methylbutyl nitrate; 4-(1-hydroxy-9-methoxy-6,6-dimethyl-6H-benzo[c]chromen-3-yl)-4-methylpentyl nitrate; 5-(1-hydroxy-9-methoxy-6,6-dimethyl-6H-benzo[c]chromen-3-yl)-5-methylhexyl nitrate; 6-(1-hydroxy-9-methoxy-6,6-dimethyl-6H-benzo[c]chromen-3-yl)-6-methylheptyl nitrate; 7-(1-hydroxy-9-methoxy-6,6-dimethyl-6H-benzo[c]chromen-3-yl)-7-methyloctyl nitrate; 9-methoxy-6,6-dimethyl-3-(2-methyloctan-2-yl)-6H-benzo[c]chromen-1-yl 4-(nitro oxy)butanoate; (3-((1s,3 s)-adamantan-1-yl)-1-hydroxy-6,6-dimethyl-6H-benzo[c]chromen-9-yl)methyl nitrate; 3-((6aR,9R,10aR)-1-hydroxy-9-(hydroxymethyl)-6,6-dimethyl-6a,7,8,9,10,10a-hexahydro-6H-benzo[c]chromen-3-yl)-3-methylbutyl nitrate; 4-((6aR,9R,10aR)-1-hydroxy-9-(hydroxymethyl)-6,6-dimethyl-6a,7,8,9,10,10a-hexahydro-6H-benzo[c]chromen-3-yl)-4-methylpentyl nitrate; 5-((6aR,9R,10aR)-1-hydroxy-9-(hydroxymethyl)-6,6-dimethyl-6a,7,8,9,10,10a-hexahydro-6H-benzo[c]chromen-3-yl)-5-methylhexyl nitrate; 6-((6aR,9R,10aR)-1-hydroxy-9-(hydroxymethyl)-6,6-dimethyl-6a,7,8,9,10,10a-hexahydro-6H-benzo[c]chromen-3-yl)-6-methylheptyl nitrate; 7-((6aR,9R,10aR)-1-hydroxy-9-(hydroxymethyl)-6,6-dimethyl-6a,7,8,9,10,10a-hexahydro-6H-benzo[c]chromen-3-yl)-7-methyloctyl nitrate; ((6aR,9R,10aR)-1-hydroxy-6,6-dimethyl-3-(2-methyloctan-2-yl)-6a,7,8,9,10,10a-hexahydro-6H-benzo[c]chromen-9-yl)methyl nitrate;

4-(nitrooxy)butyl 2-((6aR,9R,10aR)-1-hydroxy-9-(hydroxymethyl)-6,6-dimethyl-6a,7,8,9,10,10a-hexahydro-6H-benzo[c]chromen-3-yl)-2-methylpropanoate; ((6R,6aR,9R,10aR)-3-((1s,3S)-adamantan-1-yl)-6-ethynyl-1-hydroxy-6-methyl-6a,7,8,9,10,10a-hexahydro-6H-benzo[c]chromen-9-yl)methyl nitrate; ((6aR,9R,10aR)-3-((1s,3S)-adamantan-1-yl)-1-hydroxy-6,6-dimethyl-6a,7,8,9,10,10a-hexahydro-6H-benzo[c]chromen-9-yl)methyl nitrate; (6R,6aR,9R,10aR)-3-((1s,3S)-adamantan-1-yl)-6,9-bis(hydroxymethyl)-6-methyl-6a,7,8,9,10,10a-hexahydro-6H-benzo[c]chromen-1-yl 4-(nitrooxy)butanoate; (6R,6aR,9R,10aR)-6,9-bis(hydroxymethyl)-6-methyl-3-(2-methyloctan-2-yl)-6a,7,8,9,10,10a-hexahydro-6H-benzo[c]chromen-1-yl 4-(nitrooxy)butanoate; 4-(nitrooxy)butyl 2,2-difluoro-2-((6aR,9R,10aR)-1-hydroxy-9-(hydroxymethyl)-6,6-dimethyl-6a,7,8,9,10,10a-hexahydro-6H-benzo[c]chromen-3-yl)acetate; (6aR,9R,10aR)-1-hydroxy-6,6-dimethyl-3-(tert-pentyl)-6a,7,8,9,10,10a-hexahydro-6H-benzo[c]chromen-9-yl nitrate; (6aR,9R,10aR)-1-hydroxy-6,6-dimethyl-3-(2-methylpentan-2-yl)-6a,7,8,9,10,10a-hexahydro-6H-benzo[c]chromen-9-yl nitrate; (6aR,9R,10aR)-1-hydroxy-6,6-dimethyl-3-(2-methylhexan-2-yl)-6a,7,8,9,10,10a-hexahydro-6H-benzo[c]chromen-9-yl nitrate; (6aR,9R,10 aR)-1-hydroxy-6,6-dimethyl-3-(2-methylheptan-2-yl)-6a,7,8,9,10,10a-hexahydro-6H-benzo[c]chromen-9-yl nitrate; (6aR,9R,10aR)-1-hydroxy-6,6-dimethyl-3-(2-methyloctan-2-yl)-6a,7,8,9,10,10a-hexahydro-6H-benzo[c]chromen-9-yl nitrate; 3-((6aR,10aR)-1-hydroxy-6,6-dimethyl-9-oxo-6a,7,8,9,10,10a-hexahydro-6H-benzo[c]chromen-3-yl)-3-methylbutyl nitrate; 4-((6aR,10aR)-1-hydroxy-6,6-dimethyl-9-oxo-6a,7,8,9,10,10a-hexahydro-6H-benzo[c]chromen-3-yl)-4-methylpentyl nitrate; 5-((6aR,10aR)-1-hydroxy-6,6-dimethyl-9-oxo-6a,7,8,9,10,10a-hexahydro-6H-benzo[c]chromen-3-yl)-5-methylhexyl nitrate; 6-((6aR,10aR)-1-hydroxy-6,6-dimethyl-9-oxo-6a,7,8,9,10,10a-hexahydro-6H-benzo[c]chromen-3-yl)-6-methylheptyl nitrate; 7-((6aR,10aR)-1-hydroxy-6,6-dimethyl-9-oxo-6a,7,8,9,10,10a-hexahydro-6H-benzo[c]chromen-3-yl)-7-methyloctyl nitrate; 1-(((((6aR,10aR)-6,6-dimethyl-3-(2-methyl-8-(nitrooxy)octan-2-yl)-9-oxo-6a,7,8,9,10,10a-hexahydro-6H-benzo[c]chromen-1-yl)oxy)carbonyl)oxy)ethyl isobutyrate; 7-((6aS,10aR)-1-hydroxy-6,6-dimethyl-9-oxo-6a,7,8,9,10,10a-hexahydro-6H-benzo[c]chromen-3-yl)-7-methyloctyl nitrate; (6aR,10aR)-6,6-dimethyl-3-(2-methyl-8-(nitrooxy)octan-2-yl)-9-oxo-6a,7,8,9,10,10a-hexahydro-6H-benzo[c]chromen-1-yl 2-propylpentanoate; (6aS,10aR)-6,6-dimethyl-3-(2-methyl-8-(nitrooxy)octan-2-yl)-9-oxo-6a,7,8,9,10,10a-hexahydro-6H-benzo[c]chromen-1-yl 2-propylpentanoate; (E)-4-(((6aR,10 aR)-6,6-dimethyl-3-(2-methyl-8-(nitrooxy)octan-2-yl)-9-oxo-6a,7,8,9,10,10a-hexahydro-6H-benzo[c]chromen-1-yl)oxy)-4-oxobut-2-enoic acid; (E)-4-(((6aS,10aR)-6,6-dimethyl-3-(2-methyl-8-(nitrooxy)octan-2-yl)-9-oxo-6a,7,8,9,10,10a-hexahydro-6H-benzo[c]chromen-1-yl)oxy)-4-oxobut-2-enoic acid; (Z)-4-(((6aR,10aR)-6,6-dimethyl-3-(2-methyl-8-(nitrooxy)octan-2-yl)-9-oxo-6a,7,8,9,10,10a-hexahydro-6H-benzo[c]chromen-1-yl)oxy)-4-oxobut-2-enoic acid; (Z)-4-(((6aS,10aR)-6,6-dimethyl-3-(2-methyl-8-(nitrooxy)octan-2-yl)-9-oxo-6a,7,8,9,10,10a-hexahydro-6H-benzo[c]chromen-1-yl)oxy)-4-oxobut-2-enoic acid; (6aR,10aR)-6,6-dimethyl-3-(2-methyl-8-(nitrooxy)octan-2-yl)-9-oxo-6a,7,8,9,10,10a-hexahydro-6H-benzo[c]chromen-1-yl 2,5,8,11,14,17,20-heptaoxadocosan-22-oate; 4-(((6aR,10aR)-6,6-dimethyl-3-(2-methyl-8-(nitrooxy)octan-2-yl)-9-oxo-6a,7,8,9,10,10a-hexahydro-6H-benzo[c]chromen-1-yl)oxy)-4-oxobutanoic acid; 7,7-difluoro-7-((6aR,10aR)-1-hydroxy-6,6-dimethyl-9-oxo-6a,7,8,9,10,10a-hexahydro-6H-benzo[c]chromen-3-yl)heptyl nitrate; 7,7-difluoro-7-((6aS,10aR)-1-hydroxy-6,6-dimethyl-9-oxo-6a,7,8,9,10,10a-hexahydro-6H-benzo[c]chromen-3-yl)heptyl nitrate; 4-(nitrooxy)butyl 2-((6aS,10aR)-1-hydroxy-6,6-dimethyl-9-oxo-6a,7,8,9,10,10a-hexahydro-6H-benzo[c]chromen-3-yl)-2-methylpropanoate; 4-(nitrooxy)butyl 2,2-difluoro-2-((6aS,10 aR)-1-hydroxy-6,6-dimethyl-9-oxo-6a,7,8,9,10,10a-hexahydro-6H-benzo[c]chromen-3-yl)acetate; 4-(nitrooxy)butyl 2,2-difluoro-2-((6aR,10aR)-1-hydroxy-6,6-dimethyl-9-oxo-6a,7,8,9,10,10a-hexahydro-6H-benzo[c]chromen-3-yl)acetate; 4-(nitrooxy)butyl 2-((6aR,10aR)-1-hydroxy-6,6-dimethyl-9-oxo-6a,7,8,9,10,10a-hexahydro-6H-benzo[c]chromen-3-yl)-2-methylpropan oate; 4-(nitrooxy)butyl 2-((6aR,10aR)-1-hydroxy-6,6-dimethyl-9-oxo-6a,7,8,9,10,10a-hexahydro-6H-benzo[c]chromen-3-yl)propanoate; (E)-4-(((6aR,10aR)-3-(1,1-difluoro-7-(nitrooxy)heptyl)-6,6-dimethyl-9-oxo-6a,7,8,9,10,10a-hexahydro-6H-benzo[c]chromen-1-yl)oxy)-4-oxobut-2-enoic acid; (Z)-4-(((6aR,10aR)-3-(1,1-difluoro-7-(nitrooxy)heptyl)-6,6-dimethyl-9-oxo-6a,7,8,9,10,10a-hexahydro-6H-benzo[c]chromen-1-yl)oxy)-4-oxobut-2-enoic acid; (6S,6aR,9R,10aR)-9-hydroxy-6-methyl-3-(((R)-5-phenylpentan-2-yl)oxy)-5,6,6a,7,8,9,10,10a-octahydrophenanthridin-1-yl 4-(nitrooxy)butanoate; 3-((6aR,9R,10 aR)-1,9-dihydroxy-6,6-dimethyl-6a,7,8,9,10,10a-hexahydro-6H-benzo[c]chromen-3-yl)-3-methylbutyl nitrate; 4-((6aR,9R,10 aR)-1,9-dihydroxy-6,6-dimethyl-6a,7,8,9,10,10a-hexahydro-6H-benzo[c]chromen-3-yl)-4-methylpentyl nitrate; 5-((6aR,9R,10aR)-1,9-dihydroxy-6,6-dimethyl-6a,7,8,9,10,10a-hexahydro-6H-benzo[c]chromen-3-yl)-5-methylhexyl nitrate; 6-((6aR,9R,10aR)-1,9-dihydroxy-6,6-dimethyl-6a,7,8,9,10,10a-hexahydro-6H-benzo[c]chromen-3-yl)-6-methylheptyl nitrate; 7-((6aR,9R,10aR)-1,9-dihydroxy-6,6-dimethyl-6a,7,8,9,10,10a-hexahydro-6H-benzo[c]chromen-3-yl)-7-methyloctyl nitrate; 7-((6aR,9S,10aR)-1,9-dihydroxy-6,6-dimethyl-6a,7,8,9,10,10a-hexahydro-6H-benzo[c]chromen-3-yl)-7-methyloctyl nitrate; 7-((6aR,10aR)-9-((1H-imidazol-1-yl)methyl)-1-hydroxy-6,6-dimethyl-6a,7,10,10a-tetrahydro-6H-benzo[c]chromen-3-yl)-7-methyloctyl nitrate; 3-((6aR,10aR)-1-hydroxy-9-(hydroxymethyl)-6,6-dimethyl-6 a,7,10,10a-tetrahydro-6H-benzo[c]chromen-3-yl)-3-methylbutyl nitrate; 4-((6aR,10aR)-1-hydroxy-9-(hydroxymethyl)-6,6-dimethyl-6a,7,10,10a-tetrahydro-6H-benzo[c]chromen-3-yl)-4-methylpentyl nitrate; 5-((6aR,10aR)-1-hydroxy-9-(hydroxymethyl)-6,6-dimethyl-6a,7,10,10a-tetrahydro-6H-benzo[c]chromen-3-yl)-5-methylhexyl nitrate; 6-((6aR,10aR)-1-hydroxy-9-(hydroxymethyl)-6,6-dimethyl-6a,7,10,10a-tetrahydro-6H-benzo[c]chromen-3-yl)-6-methylheptyl nitrate; 7-((6aR,10aR)-1-hydroxy-9-(hydroxymethyl)-6,6-dimethyl-6a,7,10,10a-tetrahydro-6H-benzo[c]chromen-3-yl)-7-methyloctyl nitrate; ((6aR,10aR)-1-hydroxy-6,6-dimethyl-3-(2-methylnonan-2-yl)-6a,7,10,10a-tetrahydro-6H-benzo[c]chromen-9-yl)methyl nitrate; 7-((6aS,10aS)-1-hydroxy-9-(hydroxymethyl)-6,6-dimethyl-6a,7,10,10a-tetrahydro-6H-benzo[c]chromen-3-yl)-7-methyloctyl nitrate; 3-((6aR,10aR)-1-hydroxy-9-(hydroxymethyl)-6,6-dimethyl-6a,7,8,10a-tetrahydro-6H-benzo[c]chromen-3-yl)-3-methylbutyl nitrate; 4-((6aR,10aR)-1-hydroxy-9-(hydroxymethyl)-6,6-dimethyl-6a,7,8,10a-tetrahydro-6H-benzo[c]chromen-3-yl)-4-methylpentyl nitrate; 5-((6aS,10aS)-1-hydroxy-9-(hydroxymethyl)-6,6-dimethyl-6a,7,8,10a-tetrahydro-6H-benzo[c]chromen-3-yl)-5-methylhexyl nitrate; 6-((6aS,10aS)-1-hydroxy-9-(hydroxymethyl)-6,6-dimethyl-6a, 7,8,10a-tetrahydro-6H-benzo[c]chromen-3-yl)-6-methylheptyl nitrate; 7-((6aR,10aR)-1-hydroxy-9-(hydroxymethyl)-6,6-dimethyl-6a,7,8,10a-tetrahydro-6H-benzo[c]chromen-3-yl)-7-methyloctyl nitrate; 2-(((6aR,9R,10aR)-5,6,6,9-tetramethyl-5,6,6a,7,8,9, 10,10a-octahydrophenanthridin-3-yl)oxy)ethyl nitrate; 3-(((6aR,9R,10aR)-5,6,6,9-tetramethyl-5,6,6a,7,8,9,10,10a-octahydrophenanthridin-3-yl)oxy)propyl nitrate; 4-(((6aR, 9R,10aR)-5,6,6,9-tetramethyl-5,6,6a,7,8,9,10,10a-octahydrophenanthridin-3-yl)oxy)butyl nitrate; 5-(((6aR,9R, 10aR)-5,6,6,9-tetramethyl-5,6,6a,7,8,9,10,10a-octahydrophenanthridin-3-yl)oxy)pentyl nitrate; 6-(((6aR, 9R,10aR)-5,6,6,9-tetramethyl-5,6,6a,7,8,9,10,10a-octahydrophenanthridin-3-yl)oxy)hexyl nitrate; 2-(nitrooxy) ethyl 2-(1-hydroxy-9-methoxy-6-oxo-6H-benzo[c] chromen-3-yl)-2-methylpropanoate; 3-(nitrooxy)propyl 2-(1-hydroxy-9-methoxy-6-oxo-6H-benzo[c]chromen-3-yl)-2-methylpropanoate; 4-(nitrooxy)butyl 2-(1-hydroxy-9-methoxy-6-oxo-6H-benzo[c]chromen-3-yl)-2-methylpropanoate; 5-(nitrooxy)pentyl 2-(1-hydroxy-9-methoxy-6-oxo-6H-benzo[c]chromen-3-yl)-2-methylpropanoate; (E)-4-((9-methoxy-3-(2-methyl-1-((5-(nitrooxy)pentyl)oxy)-1-oxopropan-2-yl)-6-oxo-6H-benzo[c]chromen-1-yl)oxy)-4-oxobut-2-enoic acid; (Z)-4-((9-methoxy-3-(2-methyl-1-((5-(nitrooxy)pentyl)oxy)-1-oxopropan-2-yl)-6-oxo-6H-benzo [c]chromen-1-yl)oxy)-4-oxobut-2-enoic acid; 9-methoxy-3-(2-methyl-1-((5-(nitrooxy)pentyl)oxy)-1-oxopropan-2-yl)-6-oxo-6H-benzo[c]chromen-1-yl 2,5,8,11,14,17,20-heptaoxadocosan-22-oate; 4-((9-methoxy-3-(2-methyl-1-((5-(nitrooxy)pentyl)oxy)-1-oxopropan-2-yl)-6-oxo-6H-benzo[c]chromen-1-yl)oxy)-4-oxobutanoic acid; 9-methoxy-3-(2-methyl-1-((5-(nitrooxy)pentyl)oxy)-1-oxopropan-2-yl)-6-oxo-6H-benzo[c]chromen-1-yl 2-propylpentanoate; 3-(1-(hexyloxy)-2-methyl-1-oxopropan-2-yl)-9-methoxy-6-oxo-6H-benzo[c]chromen-1-yl 4-(nitrooxy) butanoate; 2-(nitrooxy)ethyl 2,2-difluoro-2-(1-hydroxy-6,6, 9-trimethyl-6a,7,10,10a-tetrahydro-6H-benzo[c]chromen-3-yl)acetate; 3-(nitrooxy)propyl 2,2-difluoro-2-(1-hydroxy-6, 6,9-trimethyl-6a,7,10,10a-tetrahydro-6H-benzo[c]chromen-3-yl)acetate; 4-(nitrooxy)butyl 2,2-difluoro-2-(1-hydroxy-6, 6,9-trimethyl-6a,7,10,10a-tetrahydro-6H-benzo[c]chromen-3-yl)acetate; 5-(nitrooxy)pentyl 2,2-difluoro-2-(1-hydroxy-6,6,9-trimethyl-6a,7,10,10a-tetrahydro-6H-benzo[c] chromen-3-yl)acetate; 3-(1,1-difluoro-2-(4-(nitrooxy) butoxy)-2-oxoethyl)-6,6,9-trimethyl-6a,7,10,10a-tetrahydro-6H-benzo[c]chromen-1-yl 2-propylpentanoate; 3-(1,1-difluoro-2-oxo-2-(pentyloxy)ethyl)-6,6,9-trimethyl-6a,7,10,10a-tetrahydro-6H-benzo[c]chromen-1-yl 4-(nitrooxy)butanoate; (6aR,10aR)-3-(1,1-difluoropropyl)-6,6,9-trimethyl-6a,7,10,10a-tetrahydro-6H-benzo[c]chromen-1-yl 4-(nitrooxy)butanoate; (6aR,10aR)-3-(1,1-difluorobutyl)-6, 6,9-trimethyl-6a,7,10,10a-tetrahydro-6H-benzo[c]chromen-1-yl 4-(nitrooxy)butanoate; (6aR,10aR)-3-(1,1-difluoropentyl)-6,6,9-trimethyl-6a,7,10,10a-tetrahydro-6H-benzo[c] chromen-1-yl 4-(nitrooxy)butanoate; (6aR,10aR)-3-(1,1-difluorohexyl)-6,6,9-trimethyl-6a,7,10,10a-tetrahydro-6H-benzo[c]chromen-1-yl 4-(nitrooxy)butanoate; (6aR,10aR)-3-(1,1-difluoroheptyl)-6,6,9-trimethyl-6a,7,10,10a-tetrahydro-6H-benzo[c]chromen-1-yl 4-(nitrooxy) butanoate; (6aR,10aR)-3-(1,1-difluoropropyl)-6,6,9-trimethyl-6a,7,8,10a-tetrahydro-6H-benzo[c]chromen-1-yl 4-(nitrooxy)butanoate; (6aR,10aR)-3-(1,1-difluorobutyl)-6, 6,9-trimethyl-6a,7,8,10a-tetrahydro-6H-benzo[c]chromen-1-yl 4-(nitrooxy)butanoate; (6aR,10aR)-3-(1,1-difluoropentyl)-6,6,9-trimethyl-6a,7,8,10a-tetrahydro-6H-benzo[c] chromen-1-yl 4-(nitrooxy)butanoate; (6aR,10aR)-3-(1,1-difluorohexyl)-6,6,9-trimethyl-6a,7,8,10a-tetrahydro-6H-benzo[c]chromen-1-yl 4-(nitrooxy)butanoate; (6aR,10aR)-3-(1,1-difluoroheptyl)-6,6,9-trimethyl-6a,7,8,10a-tetrahydro-6H-benzo[c]chromen-1-yl 4-(nitrooxy) butanoate; (6aR,10aR)-1-hydroxy-6,6-dimethyl-3-(2-methyl-4-(nitrooxy)butan-2-yl)-6a,7,10,10a-tetrahydro-6H-benzo[c]chromene-9-carboxylic acid; (6aR,10aR)-1-hydroxy-6,6-dimethyl-3-(2-methyl-5-(nitrooxy)pentan-2-yl)-6a,7,10,10a-tetrahydro-6H-benzo[c]chromene-9-carboxylicacid; (6aR,10aR)-1-hydroxy-6,6-dimethyl-3-(2-methyl-6-(nitrooxy)hexan-2-yl)-6a,7,10,10a-tetrahydro-6H-benzo[c]chromene-9-carboxylic acid; (6aR,10aR)-1-hydroxy-6,6-dimethyl-3-(2-methyl-7-(nitro oxy)heptan-2-yl)-6a,7,10,10a-tetrahydro-6H-benzo[c]chromene-9-carboxylicacid; (6aR,10aR)-1-hydroxy-6,6-dimethyl-3-(2-methyl-8-(nitrooxy)octan-2-yl)-6a, 7,10,10a-tetrahydro-6H-benzo[c]chromene-9-carboxylic acid; (6aR,10aR)-6,6-dimethyl-3-(2-methyl-8-(nitrooxy)octan-2-yl)-1-((2-propylpentanoyl)oxy)-6a,7,10,10a-tetrahydro-6H-benzo[c] chromene-9-carboxylic acid; sodium (6aR,10aR)-1-hydroxy-6,6-dimethyl-3-(2-methyl-8-(nitrooxy)octan-2-yl)-6a,7,10,10a-tetrahydro-6H-benzo[c]chromene-9-carboxylate; (6aR,10aR)-1-hydroxy-6,6-dimethyl-3-(3-(nitrooxy)propyl)-6a,7,8,10a-tetrahydro-6H-benzo[c] chromene-9-carboxylic acid; (6aR,10aR)-1-hydroxy-6,6-dimethyl-3-(4-(nitrooxy)butyl)-6a,7,8,10a-tetrahydro-6H-benzo[c]chromene-9-carboxylic acid; (6aS,10aS)-1-hydroxy-6,6-dimethyl-3-(5-(nitrooxy)pentyl)-6a, 7,8,10a-tetrahydro-6H-benzo[c]chromene-9-carboxylic acid; (6aS, 10aS)-1-hydroxy-6,6-dimethyl-3-(6-(nitrooxy)hexyl)-6a, 7,8,10a-tetrahydro-6H-benzo[c]chromene-9-carboxylic acid; (6aR,10aR)-1-hydroxy-6,6-dimethyl-3-(7-(nitrooxy) heptyl)-6a, 7,8,10a-tetrahydro-6H-benzo[c]chromene-9-carboxylic acid; sodium (6aR,10aR)-1-hydroxy-6,6-di methyl-3-(7-(nitrooxy)heptyl)-6a,7,8,10a-tetrabydro-6H-benzo[c] chromene-9-carboxylate; ((1R,3R,4R)-3-(4-((1s,3S)-adamantan-1-yl)-2,6-dihydroxyphenyl)-4-(prop-1-en-2-yl) cyclohexyl)methyl nitrate; 5,5-dimethyl-8-(3-methyl-8-(nitrooxy)octan-2-yl)-2-(prop-2-yn-1-yl)-2,3,4,5-tetrahydro-1H-chromeno[4,3-c]pyridin-10-yl 4-(piperidin-1-yl)butanoate; 6-(5-hydroxy-2,2-dimethyl-4-(pyridin-4-yl)-2H-chromen-7-yl)-5-methylheptyl nitrate; 7-(5-hydroxy-2,2-dimethyl-4-(pyridin-4-yl)-2H-chromen-7-yl)-6-methyloctyl nitrate; 6-(5-hydroxy-2-oxo-4-(pyridin-4-yl)-2H-chromen-7-yl)-5-methylheptyl nitrate; 7-(5-hydroxy-2-oxo-4-(pyridin-4-yl)-2H-chromen-7-yl)-6-methyloctyl nitrate; 7-(5-hydroxy-2-oxo-4-(pyridin-4-ylmethyl)-2H-chromen-7-yl)-7-methyloctyl nitrate; 6-(5-methoxy-2-oxo-4-(pyridin-4-ylmethyl)-2H-chromen-7-yl)-6-methylheptyl nitrate; 3-((1'R,2'R)-2,6-dihydroxy-5'-methyl-2'-(prop-1-en-2-yl)-1',2',3',4'-tetrahydro-[1,1'-biphenyl]-4-yl)-3-methylbutyl nitrate; 4-((1'R,2'R)-2,6-dihydroxy-5'-methyl-2'-(prop-1-en-2-yl)-1',2',3',4'-tetrahydro-[1,1'-biphenyl]-4-yl)-4-methylpentyl nitrate; 5-((1'R,2'R)-2,6-dihydroxy-5'-methyl-2'-(prop-1-en-2-yl)-1',2',3',4'-tetrahydro-[1,1'-biphenyl]-4-yl)-5-methylhexyl nitrate; 6-((1'R,2'R)-2,6-dihydroxy-5'-methyl-2'-(prop-1-en-2-yl)-1',2',3',4'-tetrahydro-[1,1'-biphenyl]-4-yl)-6-methylheptyl nitrate; 7-((1'R,2'R)-2,6-dihydroxy-5'-methyl-2'-(prop-1-en-2-yl)-1',2',3',4'-tetrahydro-[1,1'-biphenyl]-4-yl)-7-methyloctyl nitrate; 3-((1'R,2R')-2,6-dihydroxy-5'-methyl-2'-(prop-1-en-2-yl)-1',2',3',4'-tetrahydro-[1,1'-biphenyl]-4-yl)propyl nitrate; 4-((1'R,2'R)-2,6-dihydroxy-5'-methyl-2'-(prop-1-en-2-yl)-1',2',3',4'-tetrahydro-[1,1'-biphenyl]-4-yl)butyl nitrate; 5-((1'R,2'R)-2,6-dihydroxy-5'-(hydroxymethyl)-2'-(prop-1-en-2-yl)-1',2',3',4'-tetrahydro-[1,1'-biphenyl]-4-yl)pentyl nitrate; 6-((1'R,2'R)-2,6-dihydroxy-5'-methyl-2'-(prop-1-en-2-yl)-1',2',3',4'-tetrahydro-[1,1'-biphenyl]-4-yl)hexyl nitrate; 7-((1'R,2'R)-2,6-dihydroxy-5'-methyl-2'-(prop-1-en-2-yl)-1',2',3',4'-tetrahydro-[1,1'-biphenyl]-4-yl)heptyl nitrate; 3-((1'S,2'S)-2,6-dihydroxy-5'-methyl-2'-(prop-1-en-2-yl)-1', 2',3',4'-tetrahydro-[1,1'-biphenyl]-4-yl)propyl nitrate;

4-((1'S,2'S)-2,6-dihydroxy-5'-methyl-2'-(prop-1-en-2-yl)-1',2',3',4'-tetrahydro-[1,1'-biphenyl]-4-yl)-4-methylpentyl nitrate; 5-((1'S,2'S)-2,6-dihydroxy-5'-methyl-2'-(prop-1-en-2-yl)-1',2',3',4'-tetrahydro-[1,1'-biphenyl]-4-yl)-5-methylhexyl nitrate; 6-((1'S,2'S)-2,6-dihydroxy-5'-methyl-2'-(prop-1-en-2-yl)-1',2',3',4'-tetrahydro-[1,1'-biphenyl]-4-yl)-6-methylheptyl nitrate; 7-((1'S,2'S)-2,6-dihydroxy-5'-methyl-2'-(prop-1-en-2-yl)-1',2',3',4'-tetrahydro-[1,1'-biphenyl]-4-yl)-7-methyloctyl nitrate; ((1S,6S)-2',6'-dihydroxy-4'-(2-methyl-4-(nitrooxy)butan-2-yl)-6-(prop-1-en-2-yl)-1,4,5,6-tetrahydro-[1,1'-biphenyl]-3-yl)methyl acetate; ((1S,6S)-2',6'-dihydroxy-4'-(2-methyl-5-(nitrooxy)pentan-2-yl)-6-(prop-1-en-2-yl)-1,4,5,6-tetrahydro-[1,1'-biphenyl]-3-yl) methyl acetate; ((1S,6S)-2',6'-dihydroxy-4'-(2-methyl-6-(nitrooxy)hexan-2-yl)-6-(prop-1-en-2-yl)-1,4,5,6-tetrahydro-[1,1'-biphenyl]-3-yl)methyl acetate; ((1S,6S)-2',6'-dihydroxy-4'-(2-methyl-7-(nitrooxy)heptan-2-yl)-6-(prop-1-en-2-yl)-1,4,5,6-tetrahydro-[1,1'-biphenyl]-3-yl) methyl acetate; 41S,6S)-2',6'-dihydroxy-4'-(2-methyl-8-(nitrooxy)octan-2-yl)-6-(prop-1-en-2-yl)-1,4,5,6-tetrahydro-[1,1'-biphenyl]-3-yl)methyl acetate; 3-((1'S,2'S)-2,6-dihydroxy-5'-(hydroxymethyl)-2'-(prop-1-en-2-yl)-1',2',3',4'-tetrahydro-[1,1'-biphenyl]-4-yl)propyl nitrate; 4-((1'S,2'S)-2,6-dihydroxy-5'-(hydroxymethyl)-2'-(prop-1-en-2-yl)-1',2',3',4'-tetrahydro-[1,1'-biphenyl]-4-yl)butyl nitrate; 5-((1'S,2'S)-2,6-dihydroxy-5'-(hydroxymethyl)-2'-(prop-1-en-2-yl)-1',2',3',4'-tetrahydro-[1,1'-biphenyl]-4-yl)-5-methylhexyl nitrate; 6-((1'S,2'S)-2,6-dihydroxy-5'-(hydroxymethyl)-2'-(prop-1-en-2-yl)-1',2',3',4'-tetrahydro-[1,1'-biphenyl]-4-yl)hexyl nitrate; 7-((1'S,2'S)-2,6-dihydroxy-5'-(hydroxymethyl)-2'-(prop-1-en-2-yl)-1',2',3',4'-tetrahydro-[1,1'-biphenyl]-4-yl)-7-methyloctyl nitrate; (1S,6S)-2',6'-dihydroxy-4'-(3-(nitrooxy)propyl)-6-(prop-1-en-2-yl)-1,4,5,6-tetrahydro-[1,1'-biphenyl]-3-carboxylic acid; (1S,6S)-2',6'-dihydroxy-4'-(4-(nitrooxy)butyl)-6-(prop-1-en-2-yl)-1,4,5,6-tetrahydro-[1,1'-biphenyl]-3-carboxylic acid; (1S,6S)-2',6'-dihydroxy-4'-(2-methyl-6-(nitrooxy)hexan-2-yl)-6-(prop-1-en-2-yl)-1,4,5,6-tetrahydro-[1,1'-biphenyl]-3-carboxylic acid; (1S,6S)-2',6'-dihydroxy-4'-(6-(nitrooxy)hexyl)-6-(prop-1-en-2-yl)-1,4,5,6-tetrahydro-[1,1'-biphenyl]-3-carboxylic acid; (1S,6S)-2',6'-dihydroxy-4'-(2-methyl-8-(nitrooxy)octan-2-yl)-6-(prop-1-en-2-yl)-1,4,5,6-tetrahydro-[1,1'-biphenyl]-3-carboxylic acid; (E)-4-(((1'R,2'R)-6-hydroxy-5'-methyl-4-(2-methyl-8-(nitrooxy)octan-2-yl)-2'-(prop-1-en-2-yl)-1',2',3',4'-tetrahydro-[1,1'-biphenyl]-2-yl)oxy)-4-oxobut-2-enoic acid; (Z)-4-(((1'R,2'R)-6-hydroxy-5'-methyl-4-(2-methyl-8-(nitrooxy)octan-2-yl)-2'-(prop-1-en-2-yl)-1',2',3',4'-tetrahydro-[1,1'-biphenyl]-2-yl)oxy)-4-oxobut-2-enoic acid; 1-(((((1'S,2'S)-6-hydroxy-5'-methyl-4-(2-methyl-6-(nitrooxy)hexan-2-yl)-2'-(prop-1-en-2-yl)-1',2',3',4'-tetrahydro-[1,1'-biphenyl]-2-yl)oxy)carbonyl)oxy) ethyl isobutyrate; 4-(((1'R,2'R)-6-hydroxy-5'-methyl-4-(7-(nitrooxy)heptyl)-2'-(prop-1-en-2-yl)-1',2',3',4'-tetrahydro-[1,1'-biphenyl]-2-yl)oxy)-4-oxobutanoic acid; (1'S,2'S)-6-hydroxy-5'-methyl-4-(2-methyl-8-(nitrooxy)octan-2-yl)-2'-(prop-1-en-2-yl)-1',2',3',4'-tetrahydro-[1,1'-biphenyl]-2-yl 2-propylpentanoate; sodium (1S,6S)-2',6'-dihydroxy-4'-(2-methyl-8-(nitrooxy)octan-2-yl)-6-(prop-1-en-2-yl)-1,4,5,6-tetrahydro-[1,1'-biphenyl]-3-carboxylate; (1'S,2'S)-6-hydroxy-5'-methyl-4-(2-methyl-6-(nitrooxy)hexan-2-yl)-2'-(prop-1-en-2-yl)-1',2',3',4'-tetrahydro-[1,1'-biphenyl]-2-yl 2,5,8,11,14,17,20-heptaoxadocosan-22-oate; (1'S,2'S)-5'-(acetoxymethyl)-6-hydroxy-4-(2-methyloctan-2-yl)-2'-(prop-1-en-2-yl)-1',2',3',4'-tetrahydro-[1,1'-biphenyl]-2-yl 4-(nitrooxy)butanoate; 7-((1'S,2'S)-2,6-dimethoxy-5'-methyl-2'-(prop-1-en-2-yl)-1',2',3',4'-tetrahydro-[1,1'-biphenyl]-4-yl)-7-methyloctyl nitrate; 2-(((1'S,2'S)-6-hydroxy-5'-methyl-4-(2-methyl-6-(nitrooxy)hexan-2-yl)-2'-(prop-1-en-2-yl)-1',2',3',4'-tetrahydro-[1,1'-biphenyl]-2-yl)oxy)-N,N,N-trimethyl-2-oxoethanaminium iodide; (2E,2'E)-4,4'-(((1'R,2'R)-5'-methyl-4-(2-methyl-8-(nitrooxy)octan-2-yl)-2'-(prop-1-en-2-yl)-1',2',3',4'-tetrahydro-[1,1'-biphenyl]-2,6-diyl)bis(oxy))bis(4-oxobut-2-enoic acid); 3-(4-((1R,2R,5R)-6,6-dimethyl-4-oxobicyclo[3.1.1]heptan-2-yl)-3,5-dihydroxyphenyl)-3-methylbutyl nitrate; 4-(4-((1R,2R,5R)-6,6-dimethyl-4-oxobicyclo[3.1.1]heptan-2-yl)-3,5-dihydroxyphenyl)-4-methylpentyl nitrate; 5-(4-((1R,2R,5R)-6,6-dimethyl-4-oxobicyclo[3.1.1]heptan-2-yl)-3,5-dihydroxyphenyl)-5-methylhexyl nitrate; 6-(4-((1R,2R,5R)-6,6-dimethyl-4-oxobicyclo[3.1.1]heptan-2-yl)-3,5-dihydroxyphenyl)-6-methylheptyl nitrate; 7-(4-((1R,2R,5R)-6,6-dimethyl-4-oxobicyclo[3.1.1]heptan-2-yl)-3,5-dihydroxyphenyl)-7-methyloctyl nitrate; 3-(4-((1S,2S,5S)-6,6-dimethyl-4-oxobicyclo[3.1.1]heptan-2-yl)-3,5-dihydroxyphenyl)-3-methylbutyl nitrate; 4-(4-((1S,2S,5S)-6,6-dimethyl-4-oxobicyclo[3.1.1]heptan-2-yl)-3,5-dihydroxyphenyl)-4-methylpentyl nitrate; 5-(4-((1S,2S,5S)-6,6-dimethyl-4-oxobicyclo[3.1.1]heptan-2-yl)-3,5-dihydroxyphenyl)-5-methylhexyl nitrate; 6-(4-((1S,2S,5S)-6,6-dimethyl-4-oxobicyclo[3.1.1]heptan-2-yl)-3,5-dihydroxyphenyl)-6-methylheptyl nitrate; 7-(4-((1S,2S,5S)-6,6-dimethyl-4-oxobicyclo[3.1.1]heptan-2-yl)-3,5-dihydroxyphenyl)-7-methyloctyl nitrate; (E)-4-(2-((1R,2R,5R)-6,6-dimethyl-4-oxobicyclo[3.1.1]heptan-2-yl)-3-hydroxy-5-(2-methyl-7-(nitrooxy)heptan-2-yl)phenoxy)-4-oxobut-2-enoic acid; (E)-4-(2-((1R,2R,5R)-6,6-dimethyl-4-oxobicyclo[3.1.1]heptan-2-yl)-3-hydroxy-5-(2-methyl-8-(nitrooxy)octan-2-yl)phenoxy)-4-oxobut-2-enoic acid; (Z)-4-(2-((1R,2R,5R)-6,6-dimethyl-4-oxobicyclo[3.1.1]heptan-2-yl)-3-hydroxy-5-(2-methyl-8-(nitro oxy)octan-2-yl)phenoxy)-4-oxobut-2-enoic acid; 4-(2-((1R,2R,5R)-6,6-dimethyl-4-oxobicyclo[3.1.1]heptan-2-yl)-3-hydroxy-5-(2-methyl-8-(nitrooxy)octan-2-yl)phenoxy)-4-oxobutanoic acid; 4,4'-((2-((1R,2R,5R)-6,6-dimethyl-4-oxobicyclo[3.1.1]heptan-2-yl)-5-(2-methyl-8-(nitrooxy)octan-2-yl)-1,3-phenylene)bis(oxy))bis(4-oxobutanoic acid); 2-((1R,2R,5R)-6,6-dimethyl-4-oxobicyclo[3.1.1]heptan-2-yl)-3-hydroxy-5-(2-methyl-8-(nitro oxy)octan-2-yl)phenyl 2,5,8,11,14,17,20-heptaoxadocosan-22-oate; 2-((1R,2R,5R)-6,6-dimethyl-4-oxobicyclo[3.1.1]heptan-2-yl)-3-hydroxy-5-(2-methyl-8-(nitro oxy)octan-2-yl)phenyl 2-propylpentanoate; 1-(((2-((1R,2R,5R)-6,6-dimethyl-4-oxobicyclo[3.1.1]heptan-2-yl)-3-hydroxy-5-(2-methyl-8-(nitrooxy)octan-2-yl) phenoxy)carbonyl)oxy)ethyl isobutyrate; 2-((1R,2S,5R)-6,6-dimethyl-4-oxobicyclo[3.1.1]heptan-2-yl)-3-hydroxy-5-(2-methyloctan-2-yl)phenyl 4-(nitrooxy)butanoate; 2-(2-((1R,2S,5R)-6,6-dimethyl-4-oxobicyclo[3.1.1]heptan-2-yl)-3-hydroxy-5-(2-methyl-8-(nitro oxy)octan-2-yl)phenoxy)-N,N,N-trimethyl-2-oxoethanaminium iodide; (E)-4-(2-((1S,2S,5S)-6,6-dimethyl-4-oxobicyclo[3.1.1]heptan-2-yl)-3-hydroxy-5-(2-methyl-6-(nitrooxy)hexan-2-yl)phenoxy)-4-oxobut-2-enoic acid; (E)-4-(2-((1S,2S,5S)-6,6-dimethyl-4-oxobicyclo[3.1.1]heptan-2-yl)-3-hydroxy-5-(2-methyl-8-(nitrooxy)octan-2-yl)phenoxy)-4-oxobut-2-enoic acid; (Z)-4-(2-((1S,2S,5S)-6,6-dimethyl-4-oxobicyclo[3.1.1]heptan-2-yl)-3-hydroxy-5-(2-methyl-8-(nitro oxy)octan-2-yl)phenoxy)-4-oxobut-2-enoic acid; 4-(2-((1S,2S,5S)-6,6-dimethyl-4-oxobicyclo[3.1.1]heptan-2-yl)-3-hydroxy-5-(2-methyl-8-(nitrooxy)octan-2-yl)phenoxy)-4-oxobutanoic acid; 4,4'-((2-((1S,2S,5S)-6,6-dimethyl-4-oxobicyclo[3.1.1]heptan-2-yl)-5-(2-methyl-8-(nitrooxy)octan-2-yl)-1,3-phenylene)bis(oxy))bis(4-oxobutanoic acid); 2-((1S,2S,5S)-6,6-dimethyl-4-oxobicyclo[3.1.1]heptan-2-yl)-3-hydroxy-5-(2-methyl-8-(nitrooxy)octan-2-yl)phenyl 2,5,8,11,14,17,20- heptaoxadocosan-22-oate; 2-((1S,2S,5S)-6,6-dimethyl-4-oxobicyclo[3.1.1]heptan-2-yl)-3-hydroxy-5-(2-methyl-8-(nitrooxy)octan-2-yl)phenyl 2-propylpentanoate; 1-(((2-((1S,2S,5 S)-6,6-dimethyl-4-oxobicyclo[3.1.1]heptan-2-yl)-3-hydroxy-5-(2-methyl-8-(nitrooxy)octan-2-yl)phenoxy) carbonyl)oxy)ethyl isobutyrate; 2-((1S,2S,5 S)-6,6-dimethyl-4-oxobicyclo[3.1.1]heptan-2-yl)-3-hydroxy-5-(2-methyloctan-2-yl)phenyl 4-(nitrooxy)butanoate; 2-(2-((1S,2S,5S)-6,6-dimethyl-4-oxobicyclo[3.1.1]heptan-2-yl)-3-hydroxy-5-(2-methyl-8-(nitrooxy)octan-2-yl)phenoxy)-N,N,N-trimethyl-2-oxoethanaminium iodide; 5-benzoyl-2-((1S,2S,5S)-6,6-dimethyl-4-oxobicyclo[3.1.1]heptan-2-yl)-3-hydroxyphenyl 4-(nitrooxy)butanoate; ((1R,3R,4R)-3-(4-((1s,3S)-adamantan-1-yl)-2,6-dihydroxyphenyl)-4-(prop-1-en-2-yl)cyclohexyl)methyl nitrate; ((1R,3R,4S)-3-(4-((1s,3S)-adamantan-1-yl)-2,6-dihydroxyphenyl)-4-isopropylcyclohexyl)methyl nitrate; 7-((1'R,6'R)-2-hydroxy-3'-methyl-3,6-dioxo-6'-(prop-1-en-2-yl)-[1,1'-bi(cyclohexane)]-1,2',4-trien-4-yl)-7-methyloctyl nitrate; 5-((1'R,6'R)-2-hydroxy-3'-methyl-3,6-dioxo-6'-(prop-1-en-2-yl)-[1,1'-bi(cyclohexane)]-1,2',4-trien-4-yl)pentyl nitrate; 2-(nitrooxy)ethyl 2-((1'R,2'R)-2,6-dihydroxy-5'-methyl-2'-(prop-1-en-2-yl)-1',2',3',4'-tetrahydro-[1,1'-biphenyl]-4-yl)-2-methylpropanoate; 3-(nitrooxy)propyl 2-((1'R,2'R)-2,6-dihydroxy-5'-methyl-2'-(prop-1-en-2-yl)-1',2',3',4'-tetrahydro-[1,1'-biphenyl]-4-yl)-2-methylpropanoate; 4-(nitrooxy)butyl 2-((1'R,2'R)-2,6-dihydroxy-5'-methyl-2'-(prop-1-en-2-yl)-1',2',3',4'-tetrahydro-[1,1'-biphenyl]-4-yl)-2-methylpropanoate; 5-(nitrooxy)pentyl 2-((1'R,2'R)-2,6-dihydroxy-5'-methyl-2'-(prop-1-en-2-yl)-1',2',3',4'-tetrahydro-[1,1'-biphenyl]-4-yl)-2-methylpropanoate; 6-(nitrooxy)hexyl 2-((1'R,2'R)-2,6-dihydroxy-5'-methyl-2'-(prop-1-en-2-yl)-1',2',3',4'-tetrahydro-[1,1'-biphenyl]-4-yl)-2-methylpropanoate; 2-(nitrooxy)ethyl 2-((1'S,2'S)-5'-(acetoxymethyl)-2,6-dihydroxy-2'-(prop-1-en-2-yl)-1',2',3',4'-tetrahydro-[1,1'-biphenyl]-4-yl)-2-methylpropanoate; 3-(nitrooxy)propyl 2-((1'S,2'S)-5'-(acetoxymethyl)-2,6-dihydroxy-2'-(prop-1-en-2-yl)-1',2',3',4'-tetrahydro-[1,1'-biphenyl]-4-yl)-2-methylpropanoate; 4-(nitrooxy)butyl 2-((1'S,2'S)-5'-(acetoxymethyl)-2,6-dihydroxy-2'-(prop-1-en-2-yl)-1',2',3',4'-tetrahydro-[1,1'-biphenyl]-4-yl)-2-methylpropanoate; 5-(nitrooxy)pentyl 2-((1'S,2'S)-5'-(acetoxymethyl)-2,6-dihydroxy-2'-(prop-1-en-2-yl)-1',2',3',4'-tetrahydro-[1,1'-biphenyl]-4-yl)-2-methylpropanoate; 6-(nitrooxy)hexyl 2-((1'S,2'S)-5'-(acetoxymethyl)-2,6-dihydroxy-2'-(prop-1-en-2-yl)-1',2',3',4'-tetrahydro-[1,1'-biphenyl]-4-yl)-2-methylpropanoate; (E)-4-(((1'R,2'R)-6-hydroxy-5'-methyl-4-(2-methyl-1-(4-(nitrooxy)butoxy)-1-oxopropan-2-yl)-2'-(prop-1-en-2-yl)-1',2',3',4'-tetrahydro-[1,1'-biphenyl]-2-yl)oxy)-4-oxobut-2-enoic acid; (1'R,2'R)-6-hydroxy-5'-methyl-4-(2-methyl-1-(4-(nitrooxy)butoxy)-1-oxopropan-2-yl)-2'-(prop-1-en-2-yl)-1',2',3',4'-tetrahydro-[1,1'-biphenyl]-2-yl 4-(nitrooxy)butanoate; (1'R,2'R)-6-hydroxy-5'-methyl-4-(2-methyl-1-(4-(nitrooxy)butoxy)-1-oxopropan-2-yl)-2'-(prop-1-en-2-yl)-1',2',3',4'-tetrahydro-[1,1'-biphenyl]-2-yl 2,5,8,11,14,17,20-heptaoxadocosan-22-oate; (1'S,2'S)-5'-(acetoxymethyl)-6-hydroxy-4-(2-methyl-1-oxo-1-propoxypropan-2-yl)-2'-(prop-1-en-2-yl)-1',2',3',4'-tetrahydro-[1,1'-biphenyl]-2-yl 4-(nitrooxy)butanoate; (1'S,2'S)-5'-(acetoxymethyl)-6-hydroxy-4-(2-methyl-1-(3-(nitrooxy)propoxy)-1-oxopropan-2-yl)-2'-(prop-1-en-2-yl)-1',2',3',4'-tetrahydro-[1,1'-biphenyl]-2-yl 2-propylpentanoate; 4,4'-(((1'S,2'S)-5'-(acetoxymethyl)-4-(2-methyl-1-(4-(nitrooxy)butoxy)-1-oxopropan-2-yl)-2'-(prop-1-en-2-yl)-1',2',3',4'-tetrahydro-[1,1'-biphenyl]-2,6-diyl)bis(oxy))bis(4-oxobutanoic acid); (1'S,2'S)-5'-(acetoxymethyl)-4-(1-(hexyloxy)-2-methyl-1-oxopropan-2-yl)-6-hydroxy-2'-(prop-1-en-2-yl)-1',2',3',4'-tetrahydro-[1,1'-biphenyl]-2-yl 4-(nitrooxy)butanoate; 2-(((1'S,2'S)-5'-(acetoxymethyl)-6-hydroxy-4-(2-methyl-1-((6-(nitrooxy)hexyl)oxy)-1-oxopropan-2-yl)-2'-(prop-1-en-2-yl)-1',2',3',4'-tetrahydro-[1,1'-biphenyl]-2-yl)oxy)-N,N,N-trimethyl-2-oxoethanaminium iodide; 2-(nitrooxy)ethyl 2-((1'R,2'R)-2,6-dihydroxy-5'-methyl-2'-(prop-1-en-2-yl)-1',2',3',4'-tetrahydro-[1,1'-biphenyl]-4-yl)-2,2-difluoroacetate; 3-(nitrooxy)propyl 2-((1'R,2'R)-2,6-dihydroxy-5'-methyl-2'-(prop-1-en-2-yl)-1',2',3',4'-tetrahydro-[1,1'-biphenyl]-4-yl)-2,2-difluoroacetate; 4-(nitrooxy)butyl 2-((1'R,2'R)-2,6-dihydroxy-5'-methyl-2'-(prop-1-en-2-yl)-1',2',3',4'-tetrahydro-[1,1'-biphenyl]-4-yl)-2,2-difluoroacetate; 5-(nitrooxy)pentyl 2-((1'R,2'R)-2,6-dihydroxy-5'-methyl-2'-(prop-1-en-2-yl)-1',2',3',4'-tetrahydro-[1,1'-biphenyl]-4-yl)-2,2-difluoroacetate; 6-(nitrooxy)hexyl 2-((1'R,2'R)-2,6-dihydroxy-5'-methyl-2'-(prop-1-en-2-yl)-1',2',3',4'-tetrahydro-[1,1'-biphenyl]-4-yl)-2,2-difluoroacetate; 2-(nitrooxy)ethyl 2-((1'S, 2'S)-5'-(acetoxymethyl)-2,6-dihydroxy-2'-(prop-1-en-2-yl)-1',2',3',4'-tetrahydro-[1,1'-biphenyl]-4-yl)-2,2-difluoroacetate; 3-(nitrooxy)propyl 2-((1'S,2'S)-5'-(acetoxymethyl)-2,6-dihydroxy-2'-(prop-1-en-2-yl)-1',2',3',4'-tetrahydro-[1,1'-biphenyl]-4-yl)-2,2-difluoro acetate; 4-(nitrooxy)butyl 2-((1'S,2'S)-5'-(acetoxymethyl)-2,6-dihydroxy-2'-(prop-1-en-2-yl)-1',2',3',4'-tetrahydro-[1,1'-biphenyl]-4-yl)-2,2-difluoroacetate; 5-(nitrooxy)pentyl 2-((1'S, 2'S)-5'-(acetoxymethyl)-2,6-dihydroxy-2'-(prop-1-en-2-yl)-1',2',3',4'-tetrahydro-[1,1'-biphenyl]-4-yl)-2,2-difluoroacetate; 6-(nitrooxy)hexyl 2-((1'S,2'S)-5'-(acetoxymethyl)-2,6-dihydroxy-2'-(prop-1-en-2-yl)-1',2',3',4'-tetrahydro-[1,1'-biphenyl]-4-yl)-2,2-difluoroacetate; (1'R,2'R)-4-(1,1-difluoro-2-(4-(nitrooxy)butoxy)-2-oxoethyl)-6-hydroxy-5'-methyl-T-(prop-1-en-2-yl)-1',2',3',4'-tetrahydro-[1,1'-biphenyl]-2-yl 4-(nitrooxy)butanoate; (1'R,2'R)-4-(1,1-difluoro-2-(4-(nitrooxy)butoxy)-2-oxoethyl)-6-hydroxy-5'-methyl-T-(prop-1-en-2-yl)-1',2',3',4'-tetrahydro-[1,1'-biphenyl]-2-yl 2,5,8,11,14,17,20-heptaoxadocosan-22-oate; (E)-4-(((1'R,2'R)-4-(1,1-difluoro-2-(4-(nitrooxy)butoxy)-2-oxoethyl)-6-hydroxy-5'-methyl-2'-(prop-1-en-2-yl)-1',2',3',4'-tetrahydro-[1,1'-biphenyl]-2-yl)oxy)-4-oxobut-2-enoic acid; (1'S,2'S)-5'-(acetoxymethyl)-4-(1,1-difluoro-2-oxo-2-propoxyethyl)-6-hydroxy-2'-(prop-1-en-2-yl)-1',2',3',4'-tetrahydro-[1,1'-biphenyl]-2-yl 4-(nitrooxy)butanoate; (1'S, 2'S)-5'-(acetoxymethyl)-4-(1,1-difluoro-2-(3-(nitrooxy) propoxy)-2-oxoethyl)-6-hydroxy-2'-(prop-1-en-2-yl)-1',2',3',4'-tetrahydro-[1,1'-biphenyl]-2-yl 2-propylpentanoate; 4,4'-(((1'S,2'S)-5'-(acetoxymethyl)-4-(1,1-difluoro-2-(4-(nitrooxy)butoxy)-2-oxo ethyl)-2'-(prop-1-en-2-yl)-1',2',3',4'-tetrahydro-[1,1'-biphenyl]-2,6-diyl)bis(oxy))bis(4-oxobutanoic acid); (1'S,2'S)-5'-(acetoxymethyl)-4-(1,1-difluoro-2-(hexyloxy)-2-oxoethyl)-6-hydroxy-2'-(prop-1-en-2-yl)-1',2',3',4'-tetrahydro-[1,1'-biphenyl]-2-yl 4-(nitrooxy)butanoate; 2-(((1'S,2'S)-5'-(acetoxymethyl)-4-(1,1-difluoro-2-((6-(nitrooxy)hexyl)oxy)-2-oxoethyl)-6-hydroxy-2'-(prop-1-en-2-yl)-1',2',3',4'-tetrahydro-[1,1'-biphenyl]-2-yl)oxy)-N,N,N-trimethyl-2-oxoethanaminium iodide; 2-(nitrooxy)ethyl 2-(4-((1S,2S,5 S)-6,6-dimethyl-4-oxobicyclo[3.1.1]heptan-2-yl)-3,5-dihydroxyphenyl)-2-methylpropanoate; 3-(nitrooxy)propyl 2-(4-((1S,2S,5 S)-6,6-dimethyl-4-oxobicyclo[3.1.1]heptan-2-yl)-3,5-dihydroxyphenyl)-2-methylpropanoate; 4-(nitrooxy)butyl 2-(4-((1S,2S,5S)-6,6-dimethyl-4-oxobicyclo[3.1.1]heptan-2-yl)-3,5-dihydroxyphenyl)-2-methylpropanoate; 5-(nitrooxy)pentyl 2-(4-((1S,2S,5S)-6,6-dimethyl-4-oxobicyclo[3.1.1]heptan-2-yl)-3,5-dihydroxyphenyl)-2-methylpropanoate; 6-(nitrooxy)hexyl 2-(4-((1S,2S,5S)-6,6-dimethyl-4-oxobicyclo[3.1.1]heptan-2-yl)-3,5-dihydroxyphenyl)-2- methylpropanoate; 2-(nitrooxy)ethyl 2-(4-((1R,2R,5R)-6,6-dimethyl-4-oxobicyclo[3.1.1]heptan-2-yl)-3,5-dihydroxyphenyl)-2-methylpropanoate; 3-(nitrooxy)propyl 2-(4-((1R,2R,5R)-6,6-dimethyl-4-oxobicyclo[3.1.1]heptan-2-yl)-3,5-dihydroxyphenyl)-2-methylpropanoate; 4-(nitrooxy)butyl 2-(4-((1R,2R,5R)-6,6-dimethyl-4-oxobicyclo[3.1.1]heptan-2-yl)-3,5-dihydroxyphenyl)-2-methylpropanoate; 5-(nitrooxy)pentyl 2-(4-((1R,2R,5R)-6,6-dimethyl-4-oxobicyclo[3.1.1]heptan-2-yl)-3,5-dihydroxyphenyl)-2-methylpropanoate; 6-(nitrooxy)hexyl 2-(4-((1R,2R,5R)-6,6-dimethyl-4-oxobicyclo[3.1.1]heptan-2-yl)-3,5-dihydroxyphenyl)-2-methylpropanoate; (E)-4-(2-((1S,2S,5S)-6,6-dimethyl-4-oxobicyclo[3.1.1]heptan-2-yl)-3-hydroxy-5-(2-methyl-1-(4-(nitrooxy)butoxy)-1-oxopropan-2-yl)phenoxy)-4-oxobut-2-enoic acid; 2-((1S,2S,5S)-6,6-dimethyl-4-oxobicyclo[3.1.1]heptan-2-yl)-3-hydroxy-5-(2-methyl-1-(3-(nitrooxy)propoxy)-1-oxopropan-2-yl)phenyl 2-propylpentanoate; 4,4'-((2-((1S,2S,5 S)-6,6-dimethyl-4-oxobicyclo[3.1.1]heptan-2-yl)-5-(2-fluoro-1-(4-(nitrooxy)butoxy)-1-oxopropan-2-yl)-1,3-phenylene)bis(oxy))bis(4-oxobutanoic acid); 2-((1S,2S,5S)-6,6-dimethyl-4-oxobicyclo[3.1.1]heptan-2-yl)-5-(1-(hexyloxy)-2-methyl-1-oxopropan-2-yl)-3-hydroxyphenyl 4-(nitrooxy)butanoate; 2-(2-((1S,2S,5S)-6,6-dimethyl-4-oxobicyclo[3.1.1]heptan-2-yl)-3-hydroxy-5-(2-methyl-1-((6-(nitrooxy)hexyl)oxy)-1-oxopropan-2-yl)phenoxy)-N,N,N-trimethyl-2-oxoethanaminium iodide; 2-((1R,2R,5R)-6,6-dimethyl-4-oxobicyclo[3.1.1]heptan-2-yl)-3-hydroxy-5-(2-methyl-1-oxo-1-(pentyloxy)propan-2-yl)phenyl 4-(nitrooxy)butanoate; 2-((1R,2R,5R)-6,6-dimethyl-4-oxobicyclo[3.1.1]heptan-2-yl)-3-hydroxy-5-(2-methyl-1-(4-(nitrooxy)butoxy)-1-oxopropan-2-yl)phenyl 2,5,8,11,14,17,20-heptaoxadocosan-22-oate; (E)-4-(2-41R,2R,5R)-6,6-dimethyl-4-oxobicyclo[3.1.1]heptan-2-yl)-3-hydroxy-5-(2-methyl-1-(4-(nitrooxy)butoxy)-1-oxopropan-2-yl)phenoxy)-4-oxobut-2-enoic acid; 2-(nitrooxy)ethyl 2-(4-((1R,2R,5R)-6,6-dimethyl-4-oxobicyclo[3.1.1]heptan-2-yl)-3-hydroxy-5-(((1-(isobutyryloxy)ethoxy)carbonyl)oxy)phenyl)-2-methylpropanoate; 2-((1S,2S,5S)-6,6-dimethyl-4-oxobicyclo[3.1.1]heptan-2-yl)-3-hydroxy-5-(2-methyl-8-(nitrooxy)octan-2-yl)phenyl 2-propylpentanoate; 3-(nitrooxy)propyl 2-(4-((1S,2S,5S)-6,6-dimethyl-4-oxobicyclo[3.1.1]heptan-2-yl)-3,5-dihydroxyphenyl)-2,2-difluoroacetate; 4-(nitrooxy)butyl 2-(4-((1S,2S,5 S)-6,6-dimethyl-4-oxobicyclo[3.1.1]heptan-2-yl)-3,5-dihydroxyphenyl)-2,2-difluoroacetate; 5-(nitrooxy)pentyl 2-(4-((1S,2S,5S)-6,6-dimethyl-4-oxobicyclo[3.1.1]heptan-2-yl)-3,5-dihydroxyphenyl)-2,2-difluoroacetate; 6-(nitrooxy)hexyl 2-(4-((1S,2S,5S)-6,6-dimethyl-4-oxobicyclo[3.1.1]heptan-2-yl)-3,5-dihydroxyphenyl)-2,2-difluoroacetate; 2-(nitrooxy)ethyl 2-(4-((1R,2R,5R)-6,6-dimethyl-4-oxobicyclo[3.1.1]heptan-2-yl)-3,5-dihydroxyphenyl)-2,2-difluoroacetate; 3-(nitrooxy)propyl 2-(4-((1R,2R,5R)-6,6-dimethyl-4-oxobicyclo[3.1.1]heptan-2-yl)-3,5-dihydroxyphenyl)-2,2-difluoroacetate; 4-(nitrooxy)butyl 2-(4-((1R,2R,5R)-6,6-dimethyl-4-oxobicyclo[3.1.1]heptan-2-yl)-3,5-dihydroxyphenyl)-2,2-difluoroacetate; 5-(nitrooxy)pentyl 2-(4-((1R,2R,5R)-6,6-dimethyl-4-oxobicyclo[3.1.1]heptan-2-yl)-3,5-dihydroxyphenyl)-2,2-difluoroacetate; 6-(nitrooxy)hexyl 2-(4-((1R,2R,5R)-6,6-dimethyl-4-oxobicyclo[3.1.1]heptan-2-yl)-3,5-dihydroxyphenyl)-2,2-difluoroacetate; (E)-4-(5-(1,1-difluoro-2-(4-(nitrooxy)butoxy)-2-oxoethyl)-2-((1S,2S,5 S)-6,6-dimethyl-4-oxobicyclo[3.1.1]heptan-2-yl)-3-hydroxyphenoxy)-4-oxobut-2-enoic acid; 5-(1,1-difluoro-2-(3-(nitrooxy)propoxy)-2-oxoethyl)-2-((1S,2S,5 S)-6,6-dimethyl-4-oxobicyclo[3.1.1]heptan-2-yl)-3-hydroxyphenyl 2-propylpentanoate; 4,4'-((5-(1,1-difluoro-2-(4-(nitrooxy)butoxy)-2-oxoethyl)-2-((1S,2S,5S)-6,6-dimethyl-4-oxobicyclo[3.1.1]heptan-2-yl)-1,3-phenylene)bis(oxy))bis(4-oxobutanoic acid); 5-(1,1-difluoro-2-(hexyloxy)-2-oxoethyl)-2-((1S,2S,5S)-6,6-dimethyl-4-oxobicyclo[3.1.1]heptan-2-yl)-3-hydroxyphenyl 4-(nitrooxy)butanoate; 2-(5-(1,1-difluoro-2-((6-(nitrooxy)hexyl)oxy)-2-oxoethyl)-2-((1S,2S,5 S)-6,6-dimethyl-4-oxobicyclo[3.1.1]heptan-2-yl)-3-hydroxyphenoxy)-N,N,N-trimethyl-2-oxo ethanaminium iodide; 5-(1,1-difluoro-2-oxo-2-(pentyloxy)ethyl)-2-((1R,2R,5R)-6,6-dimethyl-4-oxobicyclo[3.1.1]heptan-2-yl)-3-hydroxyphenyl 4-(nitrooxy)butanoate; 5-(1,1-difluoro-2-(4-(nitrooxy)butoxy)-2-oxoethyl)-2-((1R,2R,5R)-6,6-dimethyl-4-oxobicyclo[3.1.1]heptan-2-yl)-3-hydroxyphenyl 2,5,8,11,14,17,20-heptaoxadocosan-22-oate; (E)-4-(5-(1,1-difluoro-2-(4-(nitrooxy)butoxy)-2-oxoethyl)-2-((1R,2R,5R)-6,6-dimethyl-4-oxobicyclo[3.1.1]heptan-2-yl)-3-hydroxyphenoxy)-4-oxobut-2-enoic acid; 1-(((5-(1,1-difluoro-2-(2-(nitrooxy)ethoxy)-2-oxoethyl)-2-41R,2R,5R)-6,6-dimethyl-4-oxobicyclo[3.1.1]heptan-2-yl)-3-hydroxyphenoxy)carbonyl)oxy)ethyl isobutyrate; ((1S,6S)-2',6'-dihydroxy-4'-(2-methyloctan-2-yl)-6-(prop-1-en-2-yl)-1,4,5,6-tetrahydro-[1,1'-biphenyl]-3-yl)methyl nitrate; ((1R,6R)-2',6'-dihydroxy-4'-(2-methyloctan-2-yl)-6-(prop-1-en-2-yl)-1,4,5,6-tetrahydro-[1,1'-biphenyl]-3-yl)methyl nitrate; ((1S,6S)-2',6'-dihydroxy-4'-pentyl-6-(prop-1-en-2-yl)-1,4,5,6-tetrahydro-[1,1'-biphenyl]-3-yl)methyl nitrate; ((1R,6R)-2',6'-dihydroxy-4'-pentyl-6-(prop-1-en-2-yl)-1,4,5,6-tetrahydro-[1,1'-biphenyl]-3-yl)methyl nitrate; 6-(2,6-dihydroxy-5'-methoxy-2'-(prop-1-en-2-yl)-[1,1'-biphenyl]-4-yl)-6-methylheptyl nitrate; 7-(2,6-dihydroxy-5'-methoxy-2'-(prop-1-en-2-yl)-[1,1'-biphenyl]-4-yl)-7-methyloctyl nitrate; 7-(2,6-dihydroxy-5'-methoxy-2'-(prop-1-en-2-yl)-[1,1'-biphenyl]-4-yl)-7,7-difluoroheptyl nitrate; 2-(nitrooxy)ethyl 2-(2,6-dihydroxy-5'-methoxy-2'-(prop-1-en-2-yl)-[1,1'-biphenyl]-4-yl)-2-methylpropanoate; (S)-6-hydroxy-5'-methoxy-4-pentyl-2'-(prop-1-en-2-yl)-[1,1'-biphenyl]-2-yl 4-(nitrooxy)butanoate; 4,4-difluoro-4-(1-hydroxy-9-methoxy-6,6-dimethyl-6H-benzo[c]chromen-3-yl)butyl nitrate; 4-(nitrooxy)butyl 2-(1-hydroxy-9-methoxy-6,6-dimethyl-6H-benzo[c]chromen-3-yl)-2-methylpropanoate; 4-(nitrooxy)butyl 2,2-difluoro-2-(1-hydroxy-9-methoxy-6,6-dimethyl-6H-benzo[c]chromen-3-yl)acetate; 7-(4-((1S,2S,5 S)-4-(hydroxymethyl)-6,6-dimethylbicyclo[3.1.1]hept-3-en-2-yl)-3,5-dimeth oxyphenyl)-7-methyl octyl nitrate; 5-(4-((1S,2S,5S)-4-(hydroxymethyl)-6,6-dimethylbicyclo[3.1.1]hept-3-en-2-yl)-3,5-dimethoxyphenyl)pentyl nitrate; 4-(nitrooxy)butyl 2-(4-((1S,2S,5 S)-4-(hydroxymethyl)-6,6-dimethylbicyclo[3.1.1]hept-3-en-2-yl)-3,5-dimethoxyphenyl)-2-methylpropanoate; ((1S,4S,5S)-4-(2,6-dimethoxy-4-(2-methylnonan-2-yl)phenyl)-6,6-dimethylbicyclo[3.1.1]hept-2-en-2-yl)methyl nitrate; 7,7-difluoro-7-(4-((1S,2S,5 S)-4-(hydroxymethyl)-6,6-dimethylbicyclo[3.1.1]hept-3-en-2-yl)-3,5-dimethoxyphenyl)heptyl nitrate; pentyl 2-(4-((1S,2S,5S)-6,6-dimethyl-4-((nitrooxy)methyl)bicyclo[3.1.1]hept-3-en-2-yl)-3,5-dimethoxyphenyl)-2-methylpropanoate; ((1S,4S,5S)-4-(4-(1,1-difluorooctyl)-2,6-dimethoxyphenyl)-6,6-dimethylbicyclo[3.1.1]hept-2-en-2-yl)methyl nitrate; pentyl 2-(4-((1S,2S,5S)-6,6-dimethyl-4-((nitrooxy)methyl)bicyclo[3.1.1]hept-3-en-2-yl)-3,5-dimethoxyphenyl)-2,2-difluoroacetate; 7-(2,6-dihydroxy-3',5'-dimethyl-[1,1'-biphenyl]-4-yl)-7-methyloctyl nitrate; 5-(2,6-dihydroxy-3',5'-dimethyl-[1,1'-biphenyl]-4-yl)-5-methylhexyl nitrate; 7-(2-hydroxy-3',5'-dimethyl-[1,1'-biphenyl]-4-yl)-7-methyloctyl nitrate; 2'-cyano-3'-(trifluoromethyl)-[1,1'-biphenyl]-3-yl 3-(nitrooxy)propane-1-sulfonate; 2'-cyano-3'-(trifluoromethyl)-[1,1'-biphenyl]-3-yl 5-(nitrooxy)pentane-1-sulfonate; 3-(2-cyano-3-(trifluoromethyl)phenoxy)phenyl 3-(nitrooxy)propane-1-sulfonate; 4-hydroxy-3-((2R)-2-(hydroxymethyl)-2,3-dihydro-1H-inden-1-yl)phenyl 3-(nitrooxy)propane-1-sulfonate; 4-hydroxy-3-((2S)-2-(hydroxymethyl)-2,3-dihydro-1H-inden-1-yl)phenyl 3-(nitrooxy)propane-1-sulfonate; 4-(nitrooxy) butyl 2-(2,6-dihydroxy-3',5'-dimethyl-[1,1'-biphenyl]-4-yl)-2-methylpropanoate; 4-(nitrooxy)butyl 2-(2,6-dihydroxy-3',5'-dimethyl-[1,1'-biphenyl]-4-yl)-2,2-difluoroacetate; 5-(3-hydroxy-4-((1S,3R)-3-hydroxycyclohexyl)phenyl)-5-methylhexyl nitrate; 7-(3-hydroxy-4-((1S,3R)-3-hydroxycyclohexyl)phenyl)-7-methyloctyl nitrate; 5-(3-hydroxy-4-((1S,3S)-3-hydroxycyclohexyl)phenyl)-5-methylhexyl nitrate; 7-(3-hydroxy-4-((1S,3S)-3-hydroxycyclohexyl)phenyl)-7-methyloctyl nitrate; 4-(nitrooxy)butyl 2-(3-hydroxy-4-((1S,3R)-3-hydroxycyclohexyl)phenyl)-2-methylpropanoate; 4-(nitrooxy)butyl 2-(3-hydroxy-4-((1S,3S)-3-hydroxycyclohexyl)phenyl)-2-methylpropanoate; 8-(3-hydroxy-4-((1S,3R)-3-hydroxycyclohexyl)phenyl)-8-methylnonyl nitrate; 4-(nitrooxy)butyl 2,2-difluoro-2-(3-hydroxy-4-((1S,3S)-3-hydroxycyclohexyl)phenyl)acetate; 4-(nitrooxy)butyl 2,2-difluoro-2-(3-hydroxy-4-((1S,3R)-3-hydroxycyclohexyl)phenyl)acetate; 8-(3-hydroxy-4-((1S,3S)-3-hydroxycyclohexyl)phenyl)-8-methylnonyl nitrate; 7-(3-hydroxy-4-((1R,2R,5R)-5-hydroxy-2-(3-hydroxypropyl)cyclohexyl)phenyl)-7-methyloctyl nitrate; 7-(3-hydroxy-4-((1R,3R,4aS,7S,8aR)-3-hydroxy-7-(hydroxymethyl)decahydronaphthalen-1-yl) phenyl)-7-methyloctyl nitrate; 2-((1'R,2'R)-4,6-dihydroxy-5'-methyl-2'-(prop-1-en-2-yl)-1',2',3',4'-tetrahydro-[1,1'-biphenyl]-2-yl)ethyl nitrate; 3-((1'R,2'R)-4,6-dihydroxy-5'-methyl-2'-(prop-1-en-2-yl)-1',2',3',4'-tetrahydro-[1,1'-biphenyl]-2-yl)propyl nitrate; 3-((1'R,2'R)-4,6-dihydroxy-5'-methyl-2'-(prop-1-en-2-yl)-1',2',3',4'-tetrahydro-[1,1'-biphenyl]-2-yl)propyl nitrate; 5-((1'R,2'R)-4,6-dihydroxy-5'-methyl-2'-(prop-1-en-2-yl)-1',2',3',4'-tetrahydro-[1,1'-biphenyl]-2-yl)pentyl nitrate; 7-((1'R,2'R)-4,6-dihydroxy-5'-methyl-2'-(prop-1-en-2-yl)-1',2',3',4'-tetrahydro-[1,1'-biphenyl]-2-yl)-7-methyloctyl nitrate; 2-((1'S,2'S)-4,6-dihydroxy-5'-methyl-2'-(prop-1-en-2-yl)-1',2',3',4'-tetrahydro-[1,1'-biphenyl]-2-yl)ethyl nitrate; 3-((1'S,2'S)-4,6-dihydroxy-5'-methyl-2'-(prop-1-en-2-yl)-1',2',3',4'-tetrahydro-[1,1'-biphenyl]-2-yl)propyl nitrate; 3-((1'S,2'S)-4,6-dihydroxy-5'-methyl-2'-(prop-1-en-2-yl)-1',2',3',4'-tetrahydro-[1,1'-biphenyl]-2-yl)propyl nitrate; 5-((1'S,2'S)-4,6-dihydroxy-5'-methyl-2'-(prop-1-en-2-yl)-1',2',3',4'-tetrahydro-[1,1'-biphenyl]-2-yl)pentyl nitrate; 7-((1'S,2'S)-4,6-dihydroxy-5'-methyl-2'-(prop-1-en-2-yl)-1',2',3',4'-tetrahydro-[1,1'-biphenyl]-2-yl)-7-methyloctyl nitrate; 7-((1'R,2'R)-4,6-dihydroxy-5'-methyl-2'-(prop-1-en-2-yl)-1',2',3',4'-tetrahydro-[1,1'-biphenyl]-2-yl)-7,7-difluoroheptyl nitrate; 7-((1'S,2'S)-4,6-dihydroxy-5'-methyl-2'-(prop-1-en-2-yl)-1',2',3',4'-tetrahydro-[1,1'-biphenyl]-2-yl)-7,7-difluoroheptyl nitrate; 4-(nitrooxy)butyl 2-((1'R,2'R)-4,6-dihydroxy-5'-methyl-2'-(prop-1-en-2-yl)-1',2',3',4'-tetrahydro-[1,1'-biphenyl]-2-yl)-2-methylpropanoate; 4-(nitrooxy)butyl 2-((1'S,2'S)-4,6-dihydroxy-5'-methyl-2'-(prop-1-en-2-yl)-1',2',3',4'-tetrahydro-[1,1'-biphenyl]-2-yl)-2-methylpropanoate; 4-(nitrooxy)butyl 2-((1'R,2'R)-4,6-dihydroxy-5'-methyl-2'-(prop-1-en-2-yl)-1',2',3',4'-tetrahydro-[1,1'-biphenyl]-2-yl)-2,2-difluoroacetate; 4-(nitrooxy)butyl 2-((1'S,2'S)-4,6-dihydroxy-5'-methyl-2'-(prop-1-en-2-yl)-1',2',3',4'-tetrahydro-[1,1'-biphenyl]-2-yl)-2,2-difluoroacetate; 3-(((1'R,2'R)-2-hydroxy-5'-methyl-6-(5-(nitrooxy)pentyl)-2'-(prop-1-en-2-yl)-1',2',3',4'-tetrahydro-[1,1'-biphenyl]-4-yl)oxy)-3-oxopropanoic acid; (E)-4-(((1'S,2'S)-2-hydroxy-5'-methyl-6-(5-(nitrooxy)pentyl)-2'-(prop-1-en-2-yl)-1',2', 3',4'-tetrahydro-[1,1'-biphenyl]-4-yl)oxy)-4-oxobut-2-enoic acid; (Z)-4-(((1'S,2S)-2-hydroxy-5'-methyl-6-(5-(nitrooxy) pentyl)-2'-(prop-1-en-2-yl)-1',2',3',4'-tetrahydro-[1,1'-biphenyl]-4-yl)oxy)-4-oxobut-2-enoic acid; (1'R,2'R)-2-hydroxy-5'-methyl-6-pentyl-2'-(prop-1-en-2-yl)-1',2',3',4'-tetrahydro-[1,1'-biphenyl]-4-yl 4-(nitrooxy)butan oate; 3,5-dihydroxy-2-((1R,2S,5 S)-4,6,6-trimethylbicyclo[3.1.1]hept-3-en-2-yl) phenethyl nitrate; 4-(3,5-dihydroxy-2-((1R,2S,5S)-4,6,6-trimethylbicyclo[3.1.1]hept-3-en-2-yl)phenyl)butyl nitrate; 7-(3,5-dihydroxy-2-((1R,2S,5S)-4,6,6-trimethylbicyclo [3.1.1]hept-3-en-2-yl)phenyl)-7-methyloctyl nitrate; (E)-4-(3-hydroxy-5-(4-(nitrooxy)butyl)-4-((1R,2S,5S)-4,6,6-trimethylbicyclo[3.1.1]hept-3-en-2-yl)phenoxy)-4-oxobut-2-enoic acid; 3-hexyl-5-hydroxy-4-((1R,2S,5S)-4,6,6-trimethylbicyclo[3.1.1]kept-3-en-2-yl)phenyl 4-(nitrooxy) butanoate; 4-(nitrooxy)butyl 2-(3,5-dihydroxy-2-((1R,2S, 5S)-4,6,6-trimethylbicyclo[3.1.1]hept-3-en-2-yl)phenyl)-2-methylpropanoate; 4-(nitrooxy)butyl 2-(3,5-dihydroxy-2-((1R,2S,5 S)-4,6,6-trimethylbicyclo[3.1.1]hept-3-en-2-yl) phenyl)-2,2-difluoroacetate; 5-(3,5-dihydroxy-2-((1R,2R,5 S)-4,6,6-trimethylbicyclo[3.1.1]hept-3-en-2-yl)phenyl)pentyl nitrate; 5-(3,5-dihydroxy-2-((1R,2R,5S)-4,6,6-trimethylbicyclo[3.1.1]hept-3-en-2-yl)phenyl)-5,5-difluoropentyl nitrate; 2-(1,4-dimethyl-1,2,5,6-tetrahydropyridin-2-yl)-3,5-dihydroxyphenethyl nitrate; 5-(3,5-dihydroxy-2-(1-isopropyl-4-methyl-1,2,5,6-tetrahydropyridin-2-yl)phenyl)pentyl nitrate; 3-hexyl-5-hydroxy-4-(1-isopropyl-4-methyl-1,2,5, 6-tetrahydropyridin-2-yl)phenyl 5-(nitrooxy)pentanoate; 4-(nitrooxy)butyl 2-(3,5-dihydroxy-2-(1-isopropyl-4-methyl-1,2,5,6-tetrahydropyridin-2-yl)phenyl)-2-methylpropanoate; 5-(2-cyclohexyl-3,5-dihydroxyphenyl)pentyl nitrate; 4-cyclohexyl-3-hydroxy-5-pentylphenyl 5-(nitrooxy)pentanoate; 7-(2-cyclohexyl-3,5-dihydroxyphenyl)-7-methyl-6-oxooctyl nitrate; 5-(2-((1S,2S,5S)-6,6-dimethyl-4-oxobicyclo[3.1.1]heptan-2-yl)-3,5-dihydroxyphenyl) pentyl nitrate; 5-(2-((1R,2R,5R)-6,6-dimethyl-4-oxobicyclo [3.1.1]heptan-2-yl)-3,5-dihydroxyphenyl)pentyl nitrate; 3-(nitrooxy)propyl 1-(6-ethyl-1-(4-fluorobenzyl)-5-methyl-2-oxo-1,2-dihydropyridine-3-carboxamido)cyclohexanecarboxylate; 4-(nitrooxy)butyl 1-(6-ethyl-1-(4-fluorobenzyl)-5-methyl-2-oxo-1,2-dihydropyridine-3-carboxamido) cyclohexanecarboxylate; 3-(nitrooxy)propyl 1-(6-ethyl-1-(4-fluorobenzyl)-5-methyl-2-oxo-1,2-dihydropyridine-3-carboxamido)cyclopentanecarboxylate; 3-(nitrooxy)propyl 2-(6-ethyl-1-(4-fluorobenzyl)-5-methyl-2-oxo-1,2-dihydropyridine-3-carboxamido)-2-methylpropanoate; 3-(nitrooxy) propyl 3-(2-(1-(cyclohexylmethyl)-2-oxo-1,2,5,6,7,8,9,10-octahydrocycloocta[b]pyridine-3-carboxamido)thiazol-4-yl)propan oate; ((R)-1-((R)-5-(3,3-dimethylbutanamido)-3-(4-isopropylphenyl)-4,6-dimethyl-2,3-dihydrobenzofuran-7-yl)ethoxy)methyl nitrate; 3-(((R)-7-((R)-1-hydroxyethyl)-3-(4-isopropylphenyl)-4,6-dimethyl-2,3-dihydrobenzofuran-5-yl)amino)-3-oxopropyl nitrate; (R)-2-((1-(cyclohexylmethyl)-3-(3,4-dimethylpiperazine-1-carbonyl)-1H-indol-7-yl)oxy)ethyl nitrate; (R)-3-(4-(1-(cyclohexylmethyl)-7-methoxy-1H-indole-3-carbonyl)-2-methylpiperazin-1-yl)propyl nitrate; 1-(cyclohexylmethyl)-3-((3S,5R)-3,4,5-trimethylpiperazine-1-carbonyl)-1H-indol-7-yl nitrate; (R)-5-(3-(3,4-dimethylpiperazine-1-carbonyl)-7-methoxy-1H-indol-1-yl)pentyl nitrate; 5-(3-(1-naphthoyl)-1H-indol-1-yl)pentyl nitrate; 4-((4-(1-naphthoyl)naphthalen-1-yl)oxy)butyl nitrate; 5-(3-(2,2,3,3-tetramethylcyclopropanecarbonyl)-1H-indol-1-yl)pentyl nitrate; 5-(3-((1-cyanocyclopropyl)carbamoyl)-1H-indol-1-yl)pentyl nitrate; 4-(nitrooxy)butyl 1-(3-chlorophenyl)-2,4-dioxopiperidine-3-carboxylate; 4-*(2-(2,5-dichlorophenyl)-3-oxo-2,3-dihydropyridazin-4-yl)oxy)butyl nitrate; 5-((2-

(4-hydroxyphenethyl)-5-methoxy-1-oxoisoindolin-4-yl) amino)pentyl nitrate; 5-((3-((benzo[d][1,3]dioxol-5-ylmethyl)carbamoyl)-7-methoxy-2-oxo-1,2-dihydroquinolin-8-yl)oxy)pentyl nitrate; 3-(4-((2-((2,4-dichlorophenyl)amino)-4-(trifluoromethyl)pyrimidine-5-carboxamido)methyl)piperidin-1-yl)propyl nitrate; 3-(4-(2-(1-(2,3-dichlorobenzoyl)-5-methoxy-2-methyl-1H-indol-3-yl)ethyl)piperazin-1-yl)propyl nitrate; 2-((1-(2,3-dichlorobenzoyl)-2-methyl-3-(2-morpholinoethyl)-1H-indol-5-yl)oxy)ethyl nitrate; ((1R,3r)-3-((6aR,10aR)-1-hydroxy-6,6-dimethyl-9-oxo-6a,7,8,9,10,10a-hexahydro-6H-benzo[c]chromen-3-yl)adamantan-1-yl)methyl nitrate; ((1R,3r)-3-(4-((1S,2R,5S)-6,6-dimethyl-4-oxobicyclo[3.1.1]heptan-2-yl)-3,5-dihydroxyphenyl)adamantan-1-yl)methyl nitrate; 2-(((1R,3r)-3-((6aR,10aR)-1-hydroxy-6,6-dimethyl-9-oxo-6a,7,8,9,10,10a-hexahydro-6H-benzo[c]chromen-3-yl)adamantan-1-yl)methoxy)ethyl nitrate; ((1R,3r)-3-((1'R,2'R)-2,6-dihydroxy-5'-methyl-2'-(prop-1-en-2-yl)-1',2',3',4'-tetrahydro-[1,1'-biphenyl]-4-yl)adamantan-1-yl)methyl nitrate; ((1R,3r)-3-((6aR,10aR)-1-hydroxy-6,6,9-trimethyl-6a,7,8,10a-tetrahydro-6H-benzo[c]chromen-3-yl)adamantan-1-yl)methyl nitrate; ((1R,3r)-3-((6aR,10aR)-1-hydroxy-6,6,9-trimethyl-6a,7,10,10a-tetrahydro-6H-benzo[c]chromen-3-yl)adamantan-1-yl)methyl nitrate; ((1S,3r)-3-((1'S,2'S)-2,6-dihydroxy-5'-(hydroxymethyl)-2'-(prop-1-en-2-yl)-1',2',3',4'-tetrahydro-[1,1'-biphenyl]-4-yl)adamantan-1-yl)methyl nitrate; 2-((1R,3r)-3-((6aR,10aR)-1-hydroxy-6,6-dimethyl-9-oxo-6a,7,8,9,10,10a-hexahydro-6H-benzo[c]chromen-3-yl)adamantane-1-carboxamido)ethyl nitrate; 2-((1R,3r)-3-(4-((1S,2R,5S)-6,6-dimethyl-4-oxobicyclo[3.1.1]heptan-2-yl)-3,5-dihydroxyphenyl)adamantane-1-carboxamido)ethyl nitrate; 2-(((1R,3r)-3-(4-((1S,2R,5S)-6,6-dimethyl-4-oxobicyclo[3.1.1]heptan-2-yl)-3,5-dihydroxyphenyl)adamantan-1-yl)methoxy)ethyl nitrate; 3-(1-(3-(nitrooxy)propyl)-1H-indazole-3-carboxamido)adamantane-1-carboxylic acid; 3-(3-((1-cyanocyclopropyl)carbamoyl)-1H-indazol-1-yl)propyl nitrate; 2-(3-(adamantan-1-ylcarbamoyl)-1H-indazol-1-yl)ethyl nitrate; or a pharmaceutically acceptable salt of any such compound.

In certain embodiments, a compound is provided, wherein the compound is:

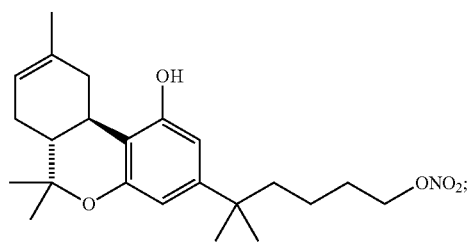

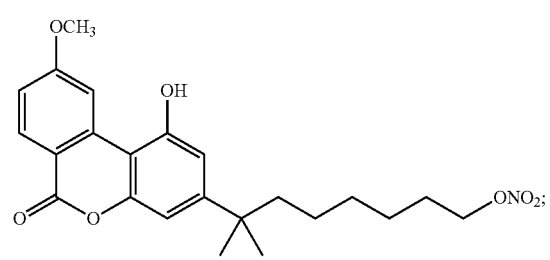

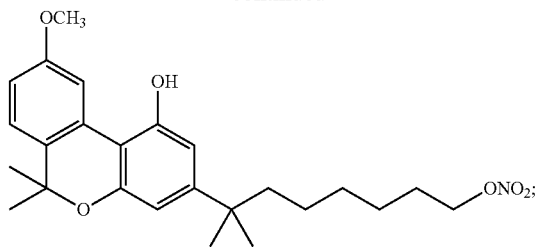

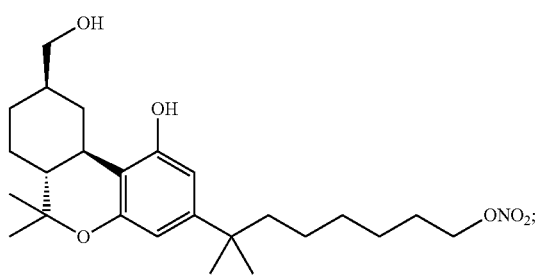

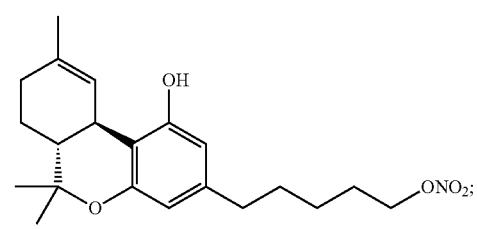

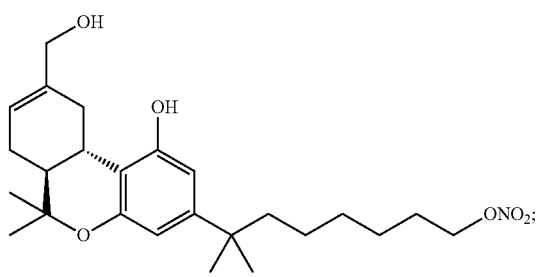

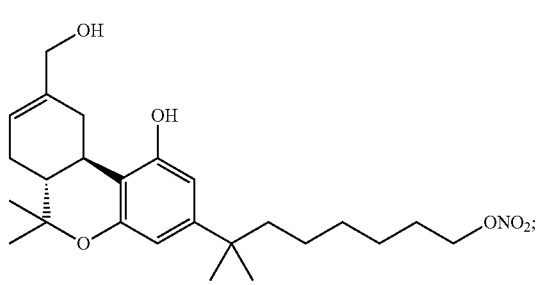

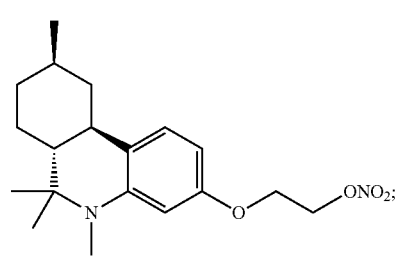

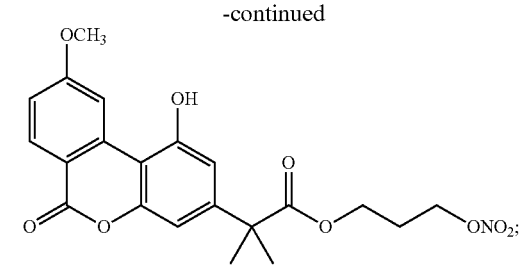
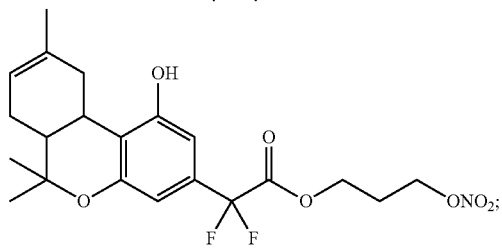
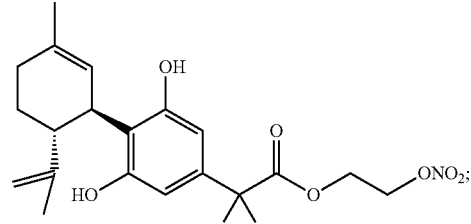
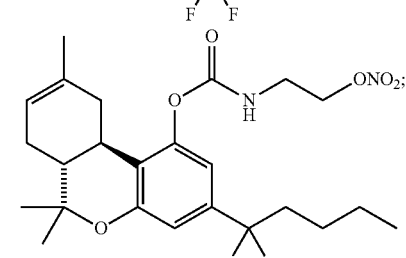
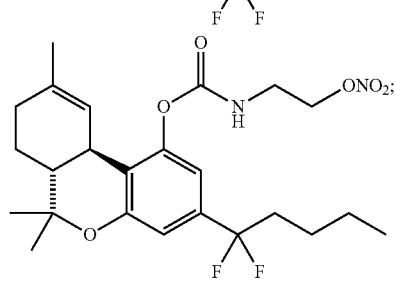
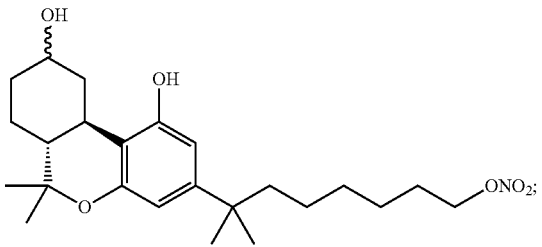
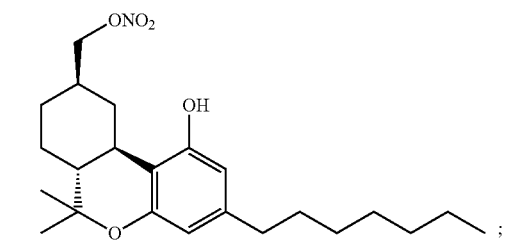
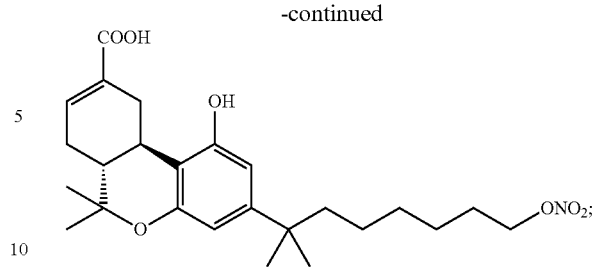
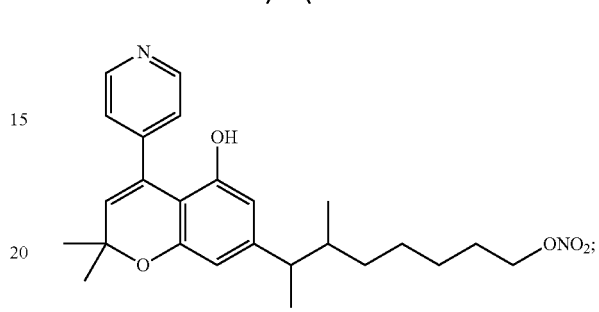
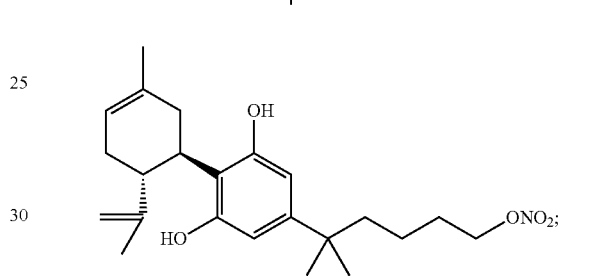
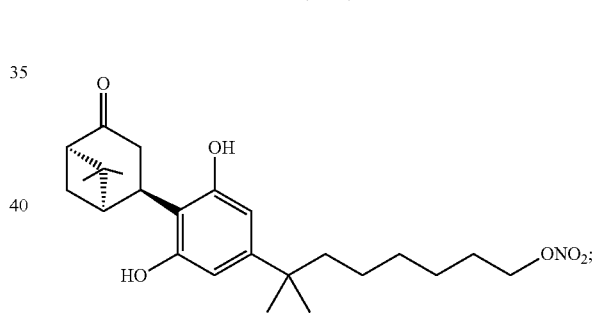
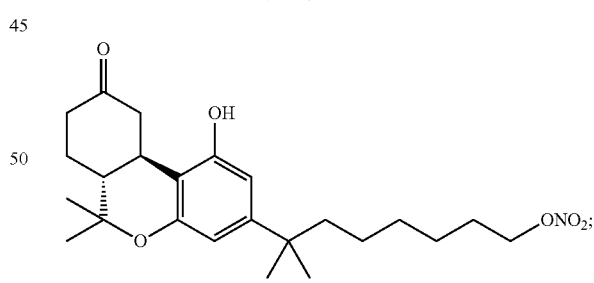
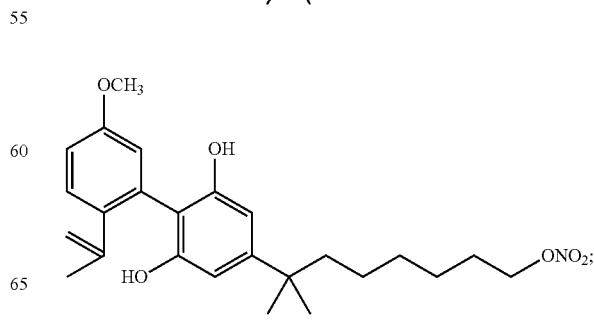
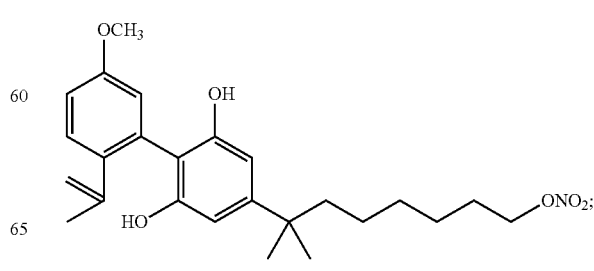

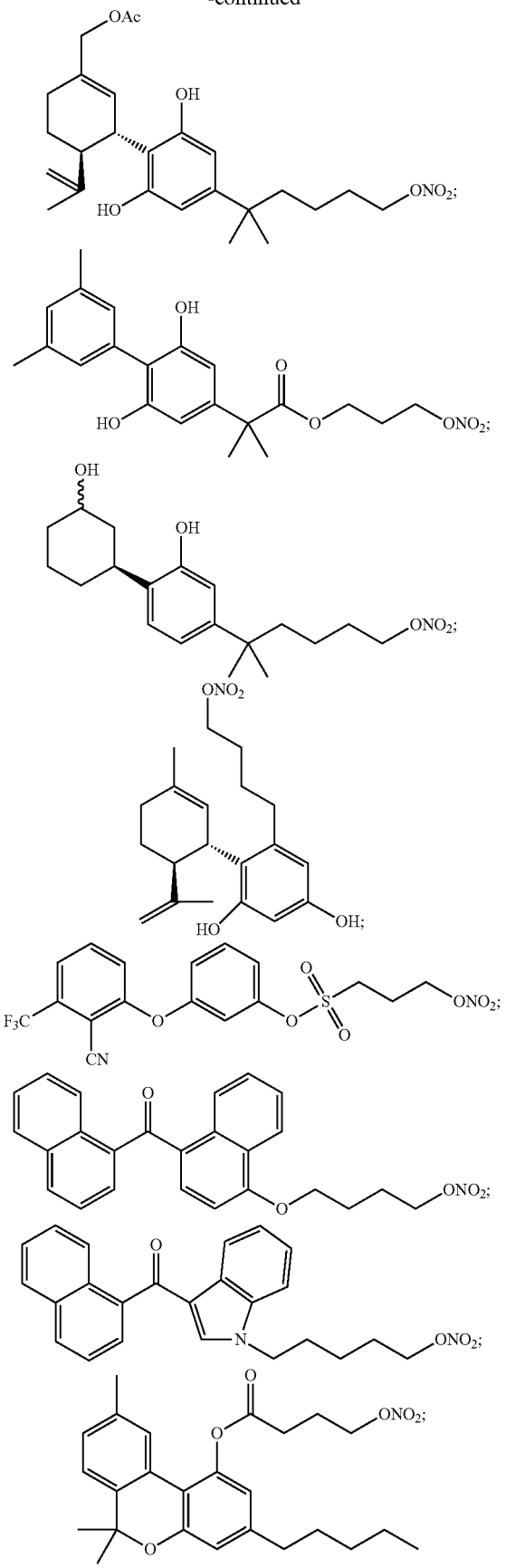
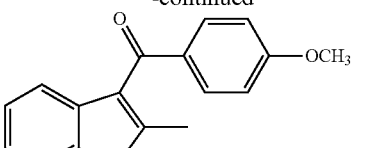
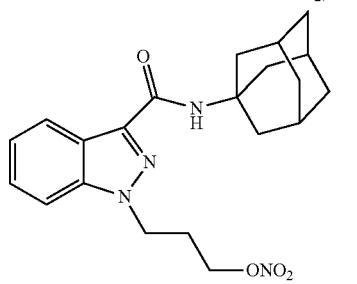

In further aspects of the technology, a composition is provided comprising any of the compounds described herein, and at least a pharmaceutically acceptable excipient.

Pharmaceutically acceptable excipients are non-toxic, aid administration, and do not adversely affect the therapeutic benefit of the compound. Such excipients may be any solid, liquid, semi-solid or, in the case of an aerosol composition, gaseous excipient that is generally available to one of skill in the art. Pharmaceutical compositions in accordance with the technology are prepared by conventional means using methods known in the art.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. In certain embodiments, the compositions provided herein comprises one or more of α-tocopherol, gum arabic, and/or hydroxypropyl cellulose.

In some embodiments, the CNE compounds are formulated into pharmaceutical compositions for administration to subjects in a biologically compatible form suitable for administration in vivo. According to another aspect, the present technology provides a pharmaceutical composition comprising a CNE compound described herein in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans. When administered to a subject, the compound and pharmaceutically acceptable carrier can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

Surfactants such as, for example, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sufate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine and the like.

The pharmaceutical formulations of the present technology are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Such compositions can be formulated for different routes of administration. Although compositions suitable for oral delivery will probably be used most frequently, other routes that may be used include transdermal, intravenous, intraarterial, pulmonary, rectal, nasal, vaginal, lingual, intramuscular, intraperitoneal, intracutaneous, intracranial, and subcutaneous routes. Suitable dosage forms for administering any of the compounds described herein include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16th ed., A. Oslo editor, Easton Pa. 1980).

The compounds and/or compositions of the present technology are administered to a human or animal subject by known procedures including oral administration, sublingual or buccal administration. In some embodiments, the compound or composition is administered orally.

For oral administration, a formulation of the compounds of the technology may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants.

Compounds and pharmaceutical compositions described herein may be used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the CNE compound described herein and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present technology.

In some embodiments, the technology relates to novel cannabinoid receptor modulators, and uses thereof for treating diseases, conditions and/or disorders modulated by a cannabinoid receptor.

In one aspects, a method is provided for treating a condition modulated by CB1, CB2 receptors and/or the GPR55 receptor activity, the method comprising administering to a subject in need thereof a therapeutically effective amount of any of the compounds or compositions described herein.

In some embodiments, the compounds show a high affinity for at least one of the cannabinoid receptors, CB1, CB2 or GPR55. Thus, another aspect of the technology is use of at least one of the compounds to interact with a cannabinoid receptor, CB1, CB2 or GPR55.

In some embodiments, the CNE compounds disclosed herein show a high affinity for more than one of the cannabinoid receptors, CB1, CB2 or GPR55. Thus, another aspect of the technology is use of the CNE compounds to interact with more than one of cannabinoid receptor, CB1, CB2 or GPR55.

In some embodiments, a method of agonizing and/or antagonizing or inhibiting activity of cannabinoid 1 (CB1), cannabinoid 2 (CB2) or GPR55 receptors is provided. The method includes contacting the cannabinoid 1 (CB1), cannabinoid 2 (CB2) or GPR55 receptors with a compound comprising a nitrate ester moiety. In some embodiments, a compound comprising a nitrate ester moiety includes any of the compounds or compositions described herein.

In some embodiments, provided is the use of a cannabinoid receptor agonist or a cannabinoid receptor antagonist for the manufacture of a medicament for the treatment of a condition modulated by CB1, CB2 receptors and/or the GPR55 receptor activity, wherein the cannabinoid receptor agonist or antagonist is compound comprising a nitrate ester moiety. In some embodiments, a compound comprising a nitrate ester moiety includes any of the compounds or compositions described herein. In some embodiments, the compound comprising a nitrate ester moeity is an agonist of antagonist of CB1, CB2 or GPR55 receptors and combinations thereof. In some embodiments, the compound comprising a nitrate ester moeity is a full agonist, a partial agonist, a neutral agonist, an inverse agonist, a full antagonist, a partial antagonist, a neutral antagonist, or an inverse antagonist. In certain embodiments, the cannabinoid receptor inverse agonist or cannabinoid receptor neutral antagonist is a CB1 inverse agonist or a CB1 neutral antagonist or a CB2 inverse agonist or a CB2 neutral antagonist.

In some embodiments, the compound exhibit fluorescent properties. The fluorescent compounds are typically endogenously fluorescent and do not rely on linking the cannabinoid compound to a fluorescent moiety.

In certain embodiments, the compound is covalently linked via a linker to an immmunogen such as Bovine Serum Albumin, polypeptides or polysaccharides in order to produce a physiological effect.

In some embodiments, the compounds interact with the cannabinoid receptors present in the CNS without affecting the receptors in the periphery to the same degree. Therefore, still another aspect of the technology is use of the CNE compounds to preferentially interact with cannabinoid receptors present either in the CNS or the periphery. In some embodiments, the CNE compounds affect the receptors in the periphery as well as in the CNS. Therefore, still another aspect of the technology is use of at least one of the CNE compounds that affect the receptors in the periphery without substantially affecting the receptors in the CNS.

The compounds described herein, and pharmaceutically acceptable salts thereof, have pharmacological properties when administered in therapeutically effective amounts for providing a physiological response. Thus, another aspect of the technology is the administration of a therapeutically effective amount of the CNE compounds, or a pharmaceutically acceptable salt thereof, to a subject to provide a physiological response.

In some embodiments, a "therapeutically effective amount" of a compound, is the quantity of a compound which, when administered to a subject, results in a sufficiently high level of that compound in the subject to cause a physiological response, for example a discernible increase or decrease in stimulation of cannabinoid receptors. The compounds described herein, and pharmaceutically acceptable salts thereof, have pharmacological properties when administered in therapeutically effective amounts individually or in combination for providing a physiological response useful to treat CNS neuro-inflammation, inflammatory pain, peripheral neuropathic pain associated with allodynia, autoimmune diabetes, obesity, diabetes, metabolic syndrome, metabolic disorders including cardiovascular disorders, diabetic nephropathy, cardiomyopathy including diabetic cardiomyopathy, sexual behavior, inflammatory bowel disease and other gastrointestinal allergic disorders including colonic inflammation, nausea and vomiting associated with cancer chemotherapy, rheumatoid arthritis, atopic dermatitis, psoriasis, autoimmune disorders including diabetes, angiogenesis, anorexia and weight loss in patients with AIDS, HIV-Wasting syndrome, HIV neuropathy, cervical dystonia, chronic pain in patients with acute complex regional pain syndromes, fibromyalgia, atherosclerosis, convulsions, cancer including cancers of the immune system, diabetic neuropathic pain, inflammatory nociception, nociception in persistent pain states, mesentery pain, amyotrophic lateral sclerosis, brain tumors, Tourette's syndrome, intraocular pressure, treatment of cramps during amyotrophic lateral sclerosis, non-GERD related non-cardiac chest pain, trichotillomania, interstitial cystitis, experimental colitis, wound healing, hepatic encephalopathy, liver cirrhosis, hepatitis, graft-versus-host-disease, insomnia, inflammatory hyperalgesia, tissue anoxia and related illness, europathic nociception and pain during cancer chemotherapy, chronic obstructive lung disease, postherpetic neuralgia, chronic pain which includes lower-back pain, brachial plexus injury, phantom limb pain, pain of neurological origin, asthma, osteoarthritis, chronic respiratory diseases, allergic diseases including allergic asthma, anorexia nervosa, cachexia, orexigenic therapy in advanced cancer patients with chemosensory abnormalities, primary gliomas, neuronal damage due to hyperglycemia, angiogenesis, gastrointestinal conditions and osteoporosis, persistent abdominal pain, postsurgical abdominal pain, sleep apnea, headache, migraine, glaucoma or ocular hypertension, epilepsy, stress, Crohn's disease, systemic lupus erythematosus, renal ischemia, lower urinary tract dysfunction, overactive bladder, detrusor overactivity, nephritis, psychosomatic disorders, thymic disorders, dyskinesia, kinetic disorder, anxiety disorders, psychotic disorders, cognitive disorders, appetite disorders, mood disorders, bipolar affective disorder, delirious disorders, benign prostatic hyperplasia, angina pectoris, anal fissure, chronic neuroinflammatory conditions, acute radiation toxicity, neurodegeneration, posttraumatic stress disorders, multiple sclerosis, central neuropathic pain in multiple sclerosis, detrusor overactivity in patients with multiple sclerosis, spasticity in multiple sclerosis, Alzheimer's disease, Huntington's disease, pro-neurogenic effects in areas of adult neurogenesis, neurotoxicity, sedation during outpatient surgical procedures, scleroderma, post-surgical pain, reduction of secondary damage following acute injury and neurodegenerative events such as depression, prevent rejection of foreign tissue during organ transplant, schizophrenia, obsessive-compulsive disorder, stroke, seizures, toxin exposure, ischemia, hypoxia, traumatic brain injury, comatose conditions, spinal cord injury, ischemic brain damage, fatty liver, Rett syndrome, cannabis dependence, alcohol, opioid, nicotine cocaine addiction and dementia. Additionally, these analogs can be useful in cancer chemotherapy. Typically, a "therapeutically effective amount" of an compound is believed to range from about 0.01 mg/day to about 1,000 mg/day.

In some embodiments, the compounds disclosed in the technology can be used in combination with other acceptable pharmaceutical substances. As will be apparent, the compounds of the technology can be used alone or in combination with other well-known agents, isomers thereof and pharmaceutically acceptable salts thereof, such as $\Delta^9$-tetrahydrocannabinol, nabilone, $\Delta^8$-tetrahydrocannabinol, (+)-cannabidiol, (−)-cannabidiol, $\Delta^8$-tetrahydrocannabivarin, $\Delta^9$-tetrahydrocannabivarin, CP-47,497, Cannabidivarin, dexanabinol, Ajulemic acid, HU-210, 8-β-OH-tetrahydrocannabinol, 8-α-OH-tetrahydrocannabinol, SAB-378, nabitan, mcnabitan, A-40174, Org 28611, nonabine, BAY38-7271, GRC10693, S-777469, AZD$^1$940, GW-842, 166X, GW-405,833, levonantradol, dimethylheptylpyran, AM1710, PRS-211,375, JD-5037, AM6545, 5-(4-(4-cyanobut-1-yn-1-yl)phenyl)-1-(2,4-dichlorophenyl)-4-methyl-N-morpholino-1H-pyrazole-3-carboxamide, 5-(4-(4-cyanobut-1-yn-1-yl)phenyl)-1-(2,4-dichlorophenyl)-4-methyl-N-(piperidin-1-yl)-1H-pyrazole-3-carboxamide, MePPEP, AM10009, AM10027, AM1241, A-796260, A-836339, Xenical® (Orlistat), Meridia® (Sibutramine), Phentermine, SR147778 (Surinabant), AVE-1625, CP-945,598 (Otenabant), Qnexa®, Contrave, Empatic, rosonabant, lorcaserin, MK-0364 (Taranabant), SLV-319 (Ibipinabant), JD5037, JD-5006 and SR141716A (Acomplia®/Rimonabant).

In some embodiments, compounds of the technology can also be used in combination with a CNS active CB1 neutral antagonist, peripherally restricted CB1 neutral antagonist, CNS active CB1 inverse agonist, peripherally restricted CB1 inverse agonist, opioid agonist, opioid antagonist, vanilloid receptor agonist, non-steroidal anti-inflammatory drug, approved local anesthetic, CB2 agonist, CB1 agonist, CB1 and CB2 mixed agonist, α2-adrenoceptor agonist, dopamine receptor agonist, adenosine receptor agonist, neurotensin receptor agonist, thyroxine derivative, cytochrome c inhibitor, oxygen tension reducer, GABA, a cholinergic drug, a nucleoside drug, serotoninergic agent, NMDA receptor antagonist, potassium channel modulator, anticonvulsant agent, contraceptive agent, an allosteric modulator, antipsychotic agent, an immunosuppressive agent, anticonstipation agent and/or a cyclooxygenase-2 inhibitor. In some embodiments, this combination comprising the two pharmaceutically active ingredients can be in ratios ranging from 1:99 to 99:1. In some embodiments, this combination can comprise three pharmaceutically active ingredients in safe acceptable ratios that can cause a physiological response.

In some embodiments, any of the CNE compound disclosed herein could in itself act as a drug with a combination effect. For example compounds disclosed in the technology could dually act as a CB2 agonist as well as CB1 antagonist.

In some embodiments, the CNE compounds disclosed herein could exist in various solid forms. The solid forms can be crystalline or amorphous forms including, but not limited to, solvates, hydrates, and N-oxides. These solid forms can be obtained by treating either the free base or their salts at a certain adjusted pH and certain temperature with a solvent or a combination of solvents. The solvents can be, for example, a hydrocarbon solvent such as toluene, xylene, hexanes, heptane, or petroleum ether, alcohol such as methanol, ethanol, n-butanol, n-propanol and 2-propanol, di-isopropyl ether, ethyl-acetate, dichloromethane, acetic acid, acetone, tetrahydrofuran, dichloromethane, and water.

In some embodiments, the CNE compounds exist as isomers comprising of constitutional isomers and stereoisomers including enantiomers, diastereomers, geometric isomers, racemates, tautomers, rotamers, or atropisomers.

In some embodiments, compounds disclosed herein are nitric oxide donors.

In some embodiments, compounds disclosed herein produce long lasting duration of action as they form a covalent bond to the cannabinoid receptors.

In some embodiments, the compounds disclosed herein act covalently on the receptors.

In some embodiments, compounds disclosed herein are capable of labeling the amino acid residues within the cannabinoid receptor. Examples of the amino acid residues include, but are not limited to, cystines, serines, and tyrosines.

In some embodiments, compounds disclosed herein have a prolonged and extended duration of action. In some embodiments, compounds disclosed herein have a drug residence time ranging from 60 minutes to 340 hours.

The compounds of the present technology can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

The overall therapeutic opportunities available through cannabinoid-related medications individually or as combination therapy are very diverse and include CNS neuro-inflammation, inflammatory pain, peripheral neuropathic pain associated with allodynia, autoimmune diabetes, obesity, diabetes, metabolic syndrome, metabolic disorders including cardiovascular disorders, diabetic nephropathy, cardiomyopathy including diabetic cardiomyopathy, acute radiation toxicity, sexual behavior, inflammatory bowel disease and other gastrointestinal allergic disorders including colonic inflammation, nausea and vomiting associated with cancer chemotherapy, rheumatoid arthritis, atopic dermatitis, psoriasis, autoimmune disorders including diabetes, scleroderma, systemic lupus erythematosus, angiogenesis, anorexia and weight loss in patients with AIDS, HIV-Wasting syndrome, HIV neuropathy, cervical dystonia, chronic pain in patients with acute complex regional pain syndromes, fibromyalgia, atherosclerosis, convulsions, trichotillomania, interstitial cystitis, wound healing, colitis, cancer including cancers of the immune system, diabetic neuropathic pain, inflammatory nociception, nociception in persistent pain states, mesentery pain, amyotrophic lateral sclerosis, brain tumors, treatment of cramps during amyotrophic lateral sclerosis, non-GERD related non-cardiac chest pain, hepatic encephalopathy, liver cirrhosis, hepatitis, graft-versus-host-disease, insomnia, inflammatory hyperalgesia, tissue anoxia and related illness, europathic nociception and pain during cancer chemotherapy, chronic obstructive lung disease, post-therpetic neuralgia, chronic pain which includes lower-back pain, brachial plexus injury, phantom limb pain, pain of neurological origin, asthma, osteoarthritis, chronic respiratory diseases, allergic diseases including allergic asthma, anorexia nervosa, cachexia, orexigenic therapy in advanced cancer patients with chemosensory abnormalities, primary gliomas, neuronal damage due to hyperglycemia, angiogenesis, gastrointestinal conditions and osteoporosis, persistent abdominal pain, post-surgical abdominal pain, sleep apnea, headache, migraine, glaucoma or ocular hypertension, epilepsy, stress, Crohn's disease, renal ischemia, lower urinary tract dysfunction, overactive bladder, detrusor overactivity, nephritis, psychosomatic disorders, thymic disorders, dyskinesia, kinetic disorder, anxiety disorders, psychotic disorders, cognitive disorders, appetite disorders, mood disorders, bipolar affective disorder, delirious disorders, benign prostatic hyperplasia, angina pectoris, anal fissure, chronic neuroinflammatory conditions, neurodegeneration, post-traumatic stress disorders, multiple sclerosis, central neuropathic pain in multiple sclerosis, detrusor overactivity in patients with multiple sclerosis, spasticity in multiple sclerosis, ischemic brain damage, Alzheimer's disease, Huntington's disease, pro-neurogenic effects in areas of adult neurogenesis, neurotoxicity, sedation during outpatient surgical procedures, post-surgical pain, reduction of secondary damage following acute injury and neurodegenerative events such as depression, prevent rejection of foreign tissue during organ transplant, schizophrenia, obsessive-compulsive disorder, stroke, seizures, toxin exposure, ischemia, hypoxia, traumatic brain injury, spinal cord injury, fatty liver, Rett syndrome, cannabis dependence, alcohol, opioid, nicotine cocaine addiction and dementia.

In addition to the CB1 and CB2 receptors, recently, GPR55 has been newly identified as a putative cannabinoid (or "CB3") receptor and a de-orphanized δ type GPCR that belongs to group of the rhodopsin-like receptors. GPR55 has high levels of expression in the human striatum, visceral and subcutaneous adipose tissue, as well as in the liver, and shows low sequence identity to both CB1 (13.5%) and CB2 (14.4%) receptors. GPR55 is activated by the by the only known endogenous lipid ligand L-α-lysophosphatidylinositol (LPI). In addition several CB1 and CB2 ligands are known to be recognized by GPR55 as antagonists, some of which are $\Delta^9$-THC, cannabidiol, and Abnormal-cannabidiol, all with very weak affinity. Though the physiological function of GPR55 in vivo remains largely unknown, and it was recently shown that the LPI/GPR55 system is positively associated with obesity in humans. As having a potential role in inflammation, it has been suggested that GPR55 and CB2R interfere with each other's signaling pathways in a way such that CB2-mediated responses are modulated. It has also been shown that GPR55 mediates the effects of LPI in prostate and ovarian cancer cells as well. Evidence continues to suggest that elevated levels of GPR55 and LPI present in most cancer cells can promote oncogenecity. Due to the therapeutic potential of GPR55 of this magnitude, efforts are being devoted in finding GPR55 compounds that deactivate the receptor and slow the progression of cancer cells. In addition, the GPR55 receptor has been implicated in conditions such as anorexia nervosa, angiogenesis, gastrointestinal conditions and osteoporosis.

Nitric Oxide "NO" is a ubiquitous signaling molecule within the human physiology that is able to diffuse readily across cell membranes and modulate a myriad of biological responses such as gene induction/activation, apoptosis, cytostasis, immune stimulation, platelet inhibition, smooth muscle relaxation. NO is known to play a critical role in the prevention and repair of injury to gastrointestinal (GI) tissue and perhaps acting as a local anti-inflammatory agent and a complement to gastroprotective prostaglandins. NO effectively reduces gastric mucosal injury and facilitates GI healing following chemical insult and is therefore considered a prime therapeutic candidate for reducing NSAID-induced GI toxicity. Historically, NO is known to be the most potent endogenous vasodilator and has proven to be beneficial in treating cardiovascular diseases. The NO-producing therapeutic and nitrovasodilator glyceryl trinitrate ("nitroglycerine") was among the first compounds used to treat coronary atherosclerosis accompanied by hypertension and chest pain ("angina") in patients with ischemic heart-disease. Organic nitrate esters (R—ONO$_2$) are NO donating compounds and when the ONO$_2$ functional group is tethered to an active pharmaceutical substance, may enhance and improve some of its pharmacological and phyisicochemical features. Commonly used and proposed organic nitrate based medications that can also act as NO donors include isosorbide dinitrate, isosorbide mononitrate, nicorandil and naproxcinod. In addition to reducing GI toxicity, important therapeutic areas for organic nitrate ester based therapies include angina pectoris, anal fissure, erectile dysfunction, osteoarthritis and neuroprotection.

The disclosure is further illustrated by the following examples, which are not to be construed as limiting this disclosure in scope or spirit to the specific procedures described in this disclosure. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

It will be recognized that one or more features of any embodiments disclosed herein may be combined and/or rearranged within the scope of the technology to produce further embodiments that are also within the scope of the technology.

EXAMPLES

Example 1: Synthesis of Compound 1

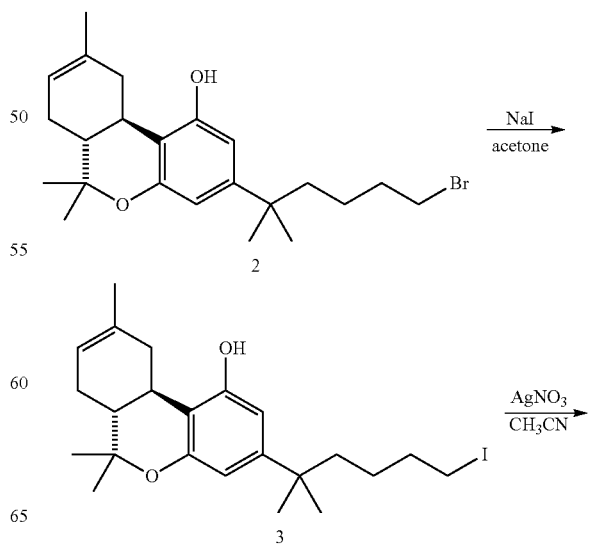

-continued

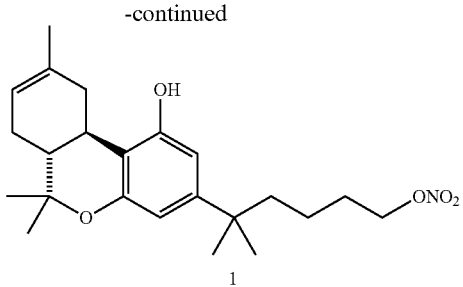

1

Step 1: To a flask containing (6aR,10aR)-3-(6-bromo-2-methylhexan-2-yl)-6,6,9-trimethyl-6a,7,10,10a-tetrahydro-6H-benzo[c]chromen-1-ol (2, 300 mg, 0.71 mmol) (prepared as in *AAPS J.* 2004 Oct. 19; 6(4):e30 and procedures based on *J. Med. Chem.* 1984, 27, 67-7; herein incorporated by reference in its entirety)) is added sodium iodide (320 mg, 2.13 mmol) and acetone (25 ml) and the contents are refluxed for 3 hours. The solvent is evaporated in vacuo and the residue is taken in dichloromethane (25 ml), washed with water (2×25 ml), dried over MgSO$_4$ and then purified by column chromatography to afford the iodo derivative 3 as a dark brown syrup (200 mg, 60%): $^1$H NMR (500 MHz, CDCl$_3$) δ 6.38 (d, J=1.46 Hz, 1H), 6.22 (d, J=0.98 Hz, 1H), 5.44 (br. s., 1H), 4.67 (s, 1H), 3.15-3.23 (dd, 1H), 3.12 (t, J=7.08 Hz, 2H), 2.61-2.78 (td, 1H), 2.08-2.28 (m, 1H), 1.75-1.97 (m, 3H), 1.59-1.67 (m, 2H), 1.51-1.58 (m, 5H), 1.40 (s, 3H), 1.23 (s, 6H), 1.14-1.20 (m, 2H), 1.12 (s, 3H); MS (ESI$^+$) for m/z 469 (M+H).

Step 2: (6aR,10aR)-3-(6-iodo-2-methylhexan-2-yl)-6,6,9-trimethyl-6a,7,10,10a-tetrahydro-6H-benzo[c]chromen-1-ol, 3 obtained from the previous step is suspended in acetonitrile (20 ml) and to it silver nitrate (217 mg, 1.28 mmol) is added and the contents are heated to 70° C. for 1 hour. The solvents are evaporated in vacuo and the residue is suspended in dichloromethane (25 ml), washed with water (2×25 ml), dried over MgSO$_4$ and then purified by column chromatography to afford 5-(((6aR,10aR)-1-hydroxy-6,6,9-trimethyl-6a,7,10,10a-tetrahydro-6H-benzo[c]chromen-3-yl)-5-methylhexyl nitrate as a yellow syrup (Compound 1, 89 mg, 52%): $^1$H NMR (500 MHz, CDCl$_3$) δ 6.38 (d, J=1.46 Hz, 1H), 6.22 (d, J=1.46 Hz, 1H), 5.45 (br. s., 1H), 4.67 (s, 1H), 4.38 (t, J=6.84 Hz, 2H), 3.19 (dd, J=4.64, 16.85 Hz, 1H), 2.70 (td, J=5.55, 10.86 Hz, 1H), 2.08-2.28 (m, 1H), 1.75-1.97 (m, 3H), 1.59-1.67 (m, 2H), 1.51-1.58 (m, 5H), 1.40 (s, 3H), 1.23 (s, 6H), 1.14-1.20 (m, 2H), 1.12 (s, 3H); MS (ESI$^+$) for m/z 404 (M+H).

Example 2: Synthesis of Compound 10

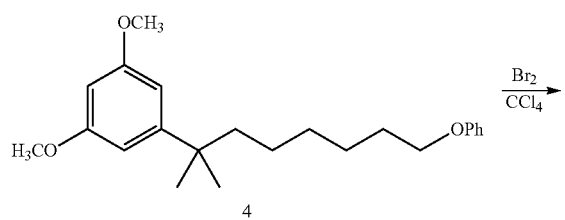

4

-continued

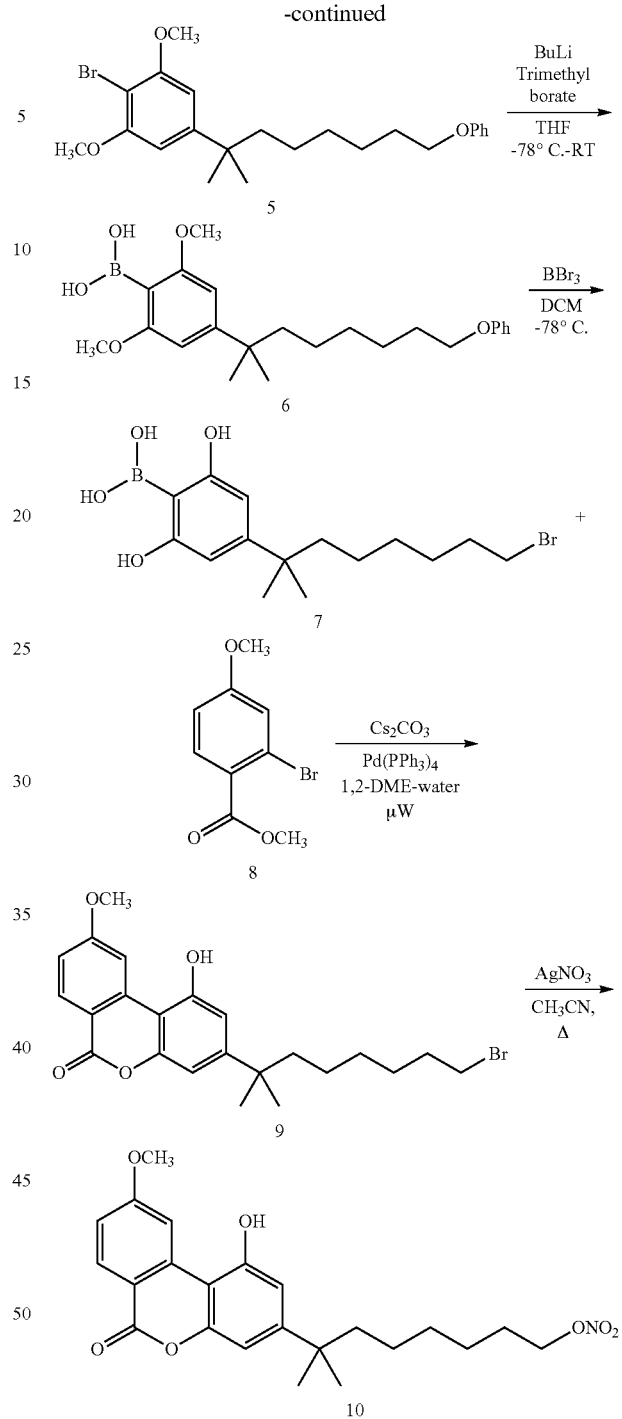

Step 1: To a mixture of 2-(3,5-dimethoxyphenyl)-2-methyl-8-phenoxyoctane (4, 10 mmol, prepared as in *AAPS J.* 2004 Oct. 19; 6(4):e30, and procedures based on *J. Med. Chem.* 1984, 27, 67-71, herein incorporated by reference in its entirety) in CCl$_4$ (35 ml) is added a solution of Br$_2$ (10 mmol) in CCl$_4$ (4 ml) during 2 h at 0° C. (procedures adopted from *J. Chem. Soc., Perkin Trans.* 2, 1997, 2219-2228, herein incorporated by reference in its entirety). After addition the solution is stirred for 1 h at 0° C. followed by evaporation to dryness to give compound 5.

Step 2: To a stirred solution of 2-bromo-1,3-dimethoxy-5-(2-methyl-8-phenoxyoctan-2-yl)benzene (5, 8.0 mmol) in anhydrous THF (40 ml) under an argon atmosphere at −78° C. is added n-BuLi (8.8 mmol using 1.6 M solution in hexane) over a 30 min period. Stirring is continued at −78° C. for 15 min and then trimethyl borate (24 mmol) is added (procedures adopted from WO 2008013963, herein incorporated by reference in its entirety). Following addition, the reaction mixture is allowed to warm to room temperature over 12 hours period. The pH is adjusted to 6.5 by addition of 5% aqueous HCl solution at 0° C., and the mixture is extracted with DCM. The organic layer is washed with brine, dried over $MgSO_4$ and the solvent is evaporated under reduced pressure. The residue is purified by flash column chromatography on silica gel to give compound 6.

Step 3: To a solution of (2,6-dimethoxy-4-(2-methyl-8-phenoxyoctan-2-yl)phenyl)boronic acid (6, 1 mmol) in anhydrous DCM (15 mL) is added boron tribromide (1.2 mmol) at −78° C. under nitrogen atmosphere. The resulting solution is stirred for 15 minutes at −78° C. The cooling bath is removed and the reaction mixture is continued to stir for 30 minutes at room temperature. The reaction is quenched with anhydrous methanol (1 mL) at −78° C., concentrated in vacuo to dryness. The desired corresponding o-hydroxy boronic acid 7 is carried to the next step without further purification (procedures adopted from *J. Comb. Chem.* 2010, 12, 664-669, herein incorporated by reference in its entirety).

Step 4: A solution of methyl 2-bromo-4-methoxybenzoate (8, prepared as described in WO 2010033643, herein incorporated by reference in its entirety) (0.5 mmol), (4-(8-bromo-2-methyloctan-2-yl)-2,6-dihydroxyphenyl)boronic acid (7, 0.65 mmol), cesium carbonate (2 mmol) in a mixture of dimethoxyethane (5 mL) and water (0.75 mL) is degassed with argon for 5 minutes. Tetrakis (triphenylphosphine) palladium (O) (10 mol %) is added, the reaction tube is sealed. The reaction is heated in a microwave (Emrys optimizer from Personal Chemistry) at 125° C. (power 300 W) for 15 minutes. After cooling at room temperature, the reaction mixture is diluted with water (30 mL), extracted with DCM (2×15 mL). The combined organic layers are passed through a phase separator and concentrated in vacuo. The residue is purified using WATERS preparative LC/MS autopurification system to afford the title compound 9 (procedures adopted from *J. Comb. Chem.* 2010, 12, 664-669, herein incorporated by reference in its entirety).

Step 5: 3-(8-bromo-2-methyloctan-2-yl)-1-hydroxy-9-methoxy-6H-benzo[c]chromen-6-one (9, 1 mmol) is taken in acetonitrile (20 ml) and to it silver nitrate (1.28 mmol) is added and the contents are heated to 70° C. for 1 hour. The solvents are evaporated in vacuo and the residue is taken in DCM (25 ml), washed with water (2×25 ml), dried over $MgSO_4$ and then purified by column chromatography to afford 7-(1-hydroxy-9-methoxy-6-oxo-6H-benzo[c]chromen-3-yl)-7-methyloctyl nitrate (Compound 10).

Example 3: Synthesis of Compound 13

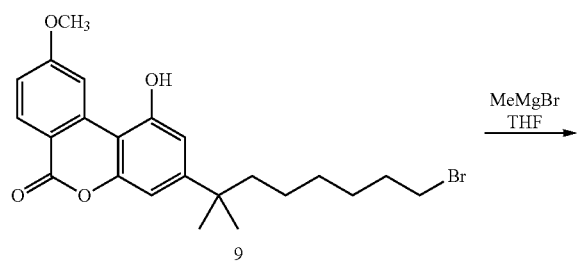

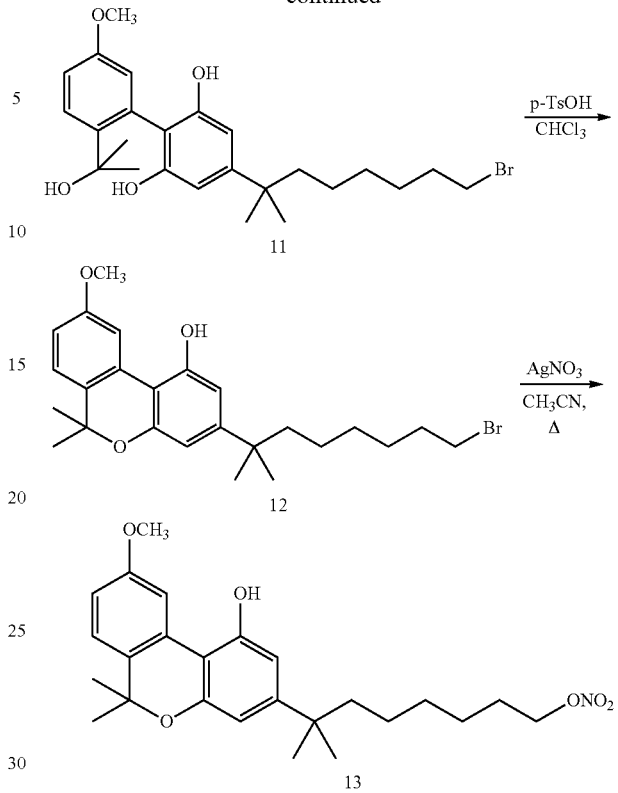

Step 1: To a solution of 3-(8-bromo-2-methyloctan-2-yl)-1-hydroxy-9-methoxy-6H-benzo[c]chromen-6-one (9, 1.0 mmol) obtained from scheme 2 in anhydrous THF (20 mL) is added methylmagnesium iodide (3 mmol, 3.0 M in $Et_2O$) at room temperature under an argon atmosphere. The reaction mixture is stirred at room temperature for 30 min and then refluxed for 1.5 h. The reaction is cooled to room temperature and quenched by the addition of 20 mL of saturated aqueous $NH_4Cl$. The THF is removed and the residue is dissolved in anhydrous $Et_2O$ (50 mL). The ether solution is washed with water and brine, dried over $MgSO_4$, and the solvent is evaporated to give the crude product 11 (procedures adopted from *J. Med. Chem.* 2007, 50, 6493-6500 and *J. Med. Chem*, 1973, 16 (11), 1200-1206; each herein incorporated by reference in its entirety).

Step 2: Without further purification 4-(8-bromo-2-methyloctan-2-yl)-2'-(2-hydroxypropan-2-yl)-5'-methoxy-[1,1'-biphenyl]-2,6-diol (11) is dissolved in anhydrous $CHCl_3$ (10-15 mL) and catalytic of p-toluenesulfonic acid monohydrate is then added under an argon atmosphere. The reaction mixture is stirred at room temperature for 6-8 h and then treated with 10 mL of water. The organic phase is separated and washed with water, 15% aqueous $NaHCO_3$, water and brine, dried over MgSO4, the solvent evaporated and the residue is purified by column chromatography to afford 12 (procedures adopted from *J. Med. Chem.* 2007, 50, 6493-6500 and *J. Med. Chem.*, 1973, 16 (11), 1200-1206; each herein incorporated by reference in its entirety).

Step 3: 3-(8-bromo-2-methyloctan-2-yl)-9-methoxy-6,6-dimethyl-6H-benzo[c]chromen-1-ol (12, 1 mmol) is taken in acetonitrile (20 ml) and to it silver nitrate (217 mg, 1.28 mmol) is added and the contents are heated to 70° C. for 1 hour. The solvents are evaporated in vacuo and the residue is taken in DCM (25 ml), washed with water (2×25 ml), dried over MgSO₄ and then purified by column chromatography to afford 7-(1-hydroxy-9-methoxy-6,6-dimethyl-6H-benzo[c]chromen-3-yl)-7-methyloctyl nitrate (Compound 13).

Example 4: Synthesis of Compound 18

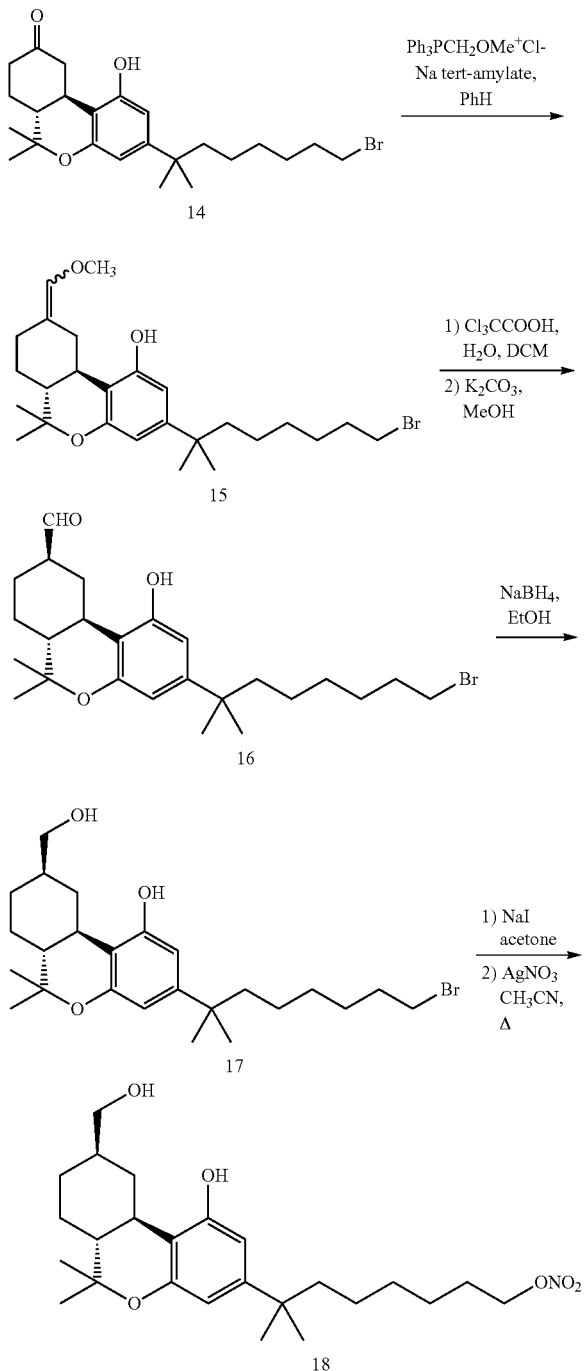

Step 1: To a suspension of (methoxymethyl)triphenylphosphonium chloride (14, 4.3 mmol, dried at 60° C./0.1 mmHg for 1 h) in 25 mL of benzene is added sodium tert-amylate (5.0 mL, 4.3 mmol; 0.85 M solution in benzene), and the mixture is stirred at room temperature for 15 min until a clear, deep red solution is obtained. A solution of (6aR,10aR)-3-(8-bromo-2-methyloctan-2-yl)-1-hydroxy-6,6-dimethyl-7,8,10,10a-tetrahydro-6H-benzo[c]chromen-9 (6aH)-one (1.5 mmol, prepared as in WO 2003005960; herein incorporated by reference in its entirety) in 15 mL of benzene is added dropwise to the ylide, and the reaction stirred at 70° C. for 3 h. The reaction is quenched by drop wise addition of saturated aqueous NH₄Cl and diluted with 40 mL of ether and the organic phase separated. The aqueous phase is extracted with of ether, the combined ethereal extracts are dried over MgSO₄, and the solvent is evaporated and the residue is purified by flash chromatography to give 15 (mixture of geometric isomers) (procedures adopted from *J. Med. Chem.* 1996, 39, 3790-3796, herein incorporated by reference in its entirety).

Step 2: To a solution of (6aR,10aR)-3-(8-bromo-2-methyloctan-2-yl)-9-(methoxymethylene)-6,6-dimethyl-6a,7,8,9,10,10a-hexahydro-6H-benzo[c]chromen-1-ol (15, 0.57 mmol) in 34 mL of DCM is added aqueous trichloroacetic acid (1.96 mmol), and the solution is stirred for 10 min at room temperature. The reaction is quenched by addition of saturated aqueous NaHCO₃, washed with brine, and dried (K₂CO₃) and the solvent evaporated. ¹H NMR spectrum of the crude product indicated the formation of aldehyde. The crude product is dissolved in 20 mL of absolute ethanol and stirred with anhydrous K₂CO₃ (1.14 mmol) for 24 h at room temperature. Examination of an aliquot by ¹H NMR showed that epimerization is complete (procedures adopted from *J. Med. Chem.* 1996, 39, 3790-3796, herein incorporated by reference in its entirety) to give the β-aldehyde 16.

Step 3: To a solution of (6aR,9R,10aR)-3-(8-bromo-2-methyloctan-2-yl)-1-hydroxy-6,6-dimethyl-6a,7,8,9,10,10a-hexahydro-6H-benzo[c]chromene-9-carbaldehyde (16, 0.42 mmol) in 42 mL of absolute ethanol at 0° C. is added 63 mg of NaBH₄ (1.68 mmol). The mixture is warmed to room temperature, stirred for 2 h, and then quenched by drop wise addition of saturated aqueous NH₄Cl and the solvent is evaporated. The residue is dissolved in water and extracted with ethyl acetate. The combined organic extracts are washed with brine and dried over MgSO₄, and the solvent is evaporated and the residue is purified by flash chromatography to give 17 (procedures adopted from *J. Med. Chem.* 1996, 39, 3790-3796, herein incorporated by reference in its entirety).

Step 4: To a flask containing (6aR,9R,10aR)-3-(8-bromo-2-methyloctan-2-yl)-9-(hydroxymethyl)-6,6-dimethyl-6a,7,8,9,10,10a-hexahydro-6H-benzo[c]chromen-1-ol (17, 0.71 mmol) is added sodium iodide (2.13 mmol) and acetone (25 ml) and the contents are refluxed for 3 hours. The solvent is evaporated in vacuo and the residue is taken in DCM (25 ml), washed with water (2×25 ml), dried over MgSO₄ and then purified by column chromatography to afford the iodo compound.

Step 5: (6aR,9R,10aR)-3-(8-iodo-2-methyloctan-2-yl)-9-(hydroxymethyl)-6,6-dimethyl-6a,7,8,9,10,10a-hexahydro-6H-benzo[c]chromen-1-ol (1 mmol) is taken in acetonitrile (20 ml) and to it silver nitrate (1.28 mmol) is added and the contents are heated to 70° C. for 1 hour. The solvents are evaporated in vacuo and the residue is taken in DCM (25 ml), washed with water (2×25 ml), dried over MgSO₄ and then purified by column chromatography to afford 7-((6aR,9R,10aR)-1-hydroxy-9-(hydroxymethyl)-6,6-dimethyl-6a,7,8,9,10,10a-hexahydro-6H-benzo[c]chromen-3-yl)-7-methyloctyl nitrate (Compound 18).

Example 5: Synthesis of Compound 19

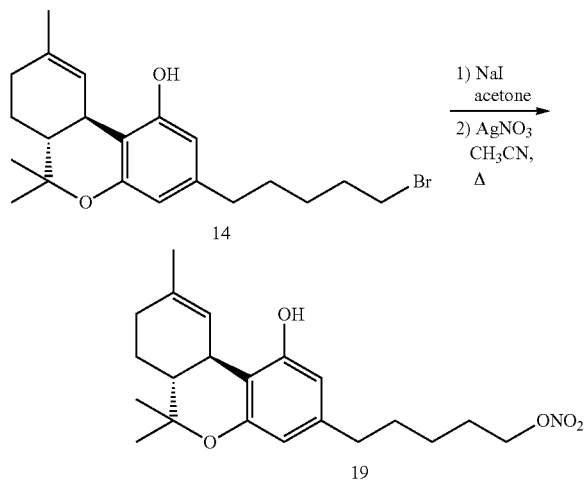

Step 1: To a flask containing 3-(5-bromopentyl)-6,6,9-trimethyl-6a,7,8,10a-tetrahydro-6H-benzo[c]chromen-1-ol (14, 0.71 mmol, prepared a *J. Med. Chem.* 2005, 48, 7389-7399, herein incorporated by reference in its entirety) is added sodium iodide (2.13 mmol) and acetone (25 ml) and the contents are refluxed for 3 hours. The solvent is evaporated in vacuo and the residue is taken in DCM (25 ml), washed with water (2×25 ml), dried over MgSO$_4$ and then purified by column chromatography to afford the iodo derivative.

Step 2: 3-(5-iodopentyl)-6,6,9-trimethyl-6a,7,8,10a-tetrahydro-6H-benzo[c]chromen-1-ol (1 momol) is taken in acetonitrile (20 ml) and to it silver nitrate (217 mg, 1.28 mmol) is added and the contents were heated to 70° C. for 1 hour. The solvent are evaporated in vacuo and the residue is taken in DCM (25 ml), washed with water (2×25 ml), dried over MgSO$_4$ and then purified by column chromatography to afford 5-(1-hydroxy-6,6,9-trimethyl-6a,7,8,10a-tetrahydro-6H-benzo[c]chromen-3-yl)pentyl nitrate (Compound 19).

Example 6: Synthesis of Compounds 23 and 26

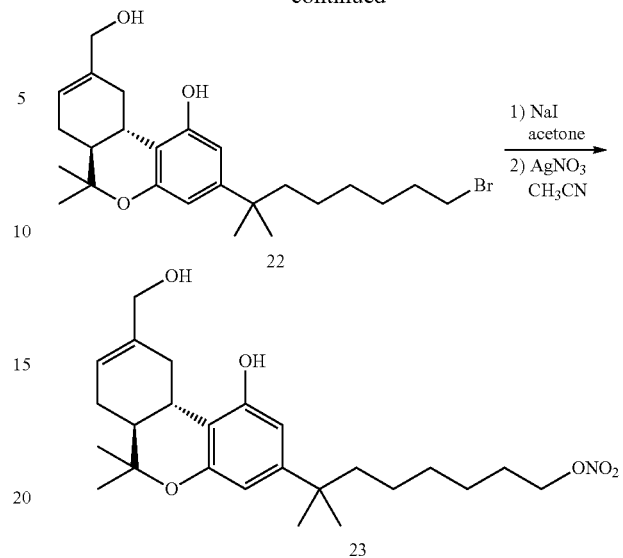

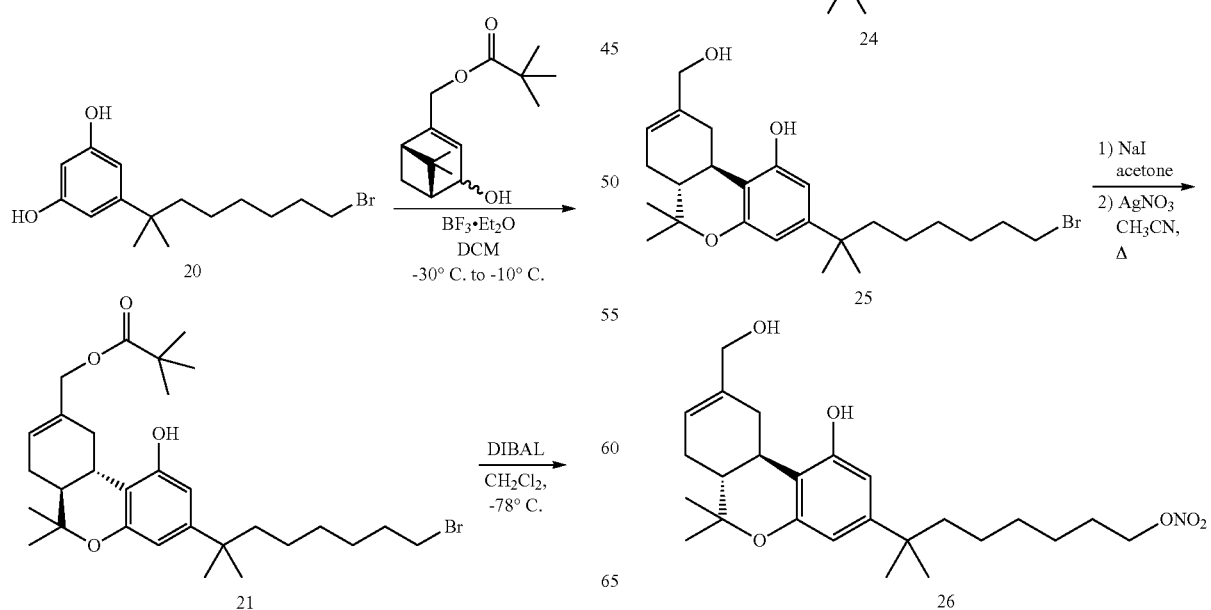

Step 1: Using known procedures (adopted from U.S. Pat. No. 5,440,052, US 2007060636 and *J. Med. Chem.* 1994, 37, 3867-3870, herein incorporated by reference in its entirety), the 6aS,10aS isomer compound 21 and the 6aR,10aR isomer compound 24 of 3-(8-bromo-2-methyloctan-2-yl)-1-hydroxy-6,6-dimethyl-6a,7,10,10a-tetrahydro-6H-benzo[c]chromen-9-yl)methyl pivalate are prepared starting from ((1S,5R)-4-hydroxy-6,6-dimethylbicyclo[3.1.1]hept-2-en-2-yl)methyl pivalate or (1R,5S)-4-hydroxy-6,6-dimethylbicyclo[3.1.1]hept-2-en-2-yl)methyl pivalate and 5-(8-bromo-2-methyloctan-2-yl)benzene-1,3-diol (20, prepared as in prepared as in *AAPS J.* 2004 Oct. 19; 6(4):e30 and procedures based on *J. Med. Chem.* 1984, 27, 67-71; each herein incorporated by reference in its entirety).

Step 2: To a solution of compound 20 or 23 (0.955 mmol) in anhydrous DCM (9.5 mL) is added 1M solution of DIBAL-H in toluene (2 mmol) dropwise at −78° C. The reaction mixture is stirred for 2.5 h and then quenched by drop wise addition of potassium sodium tartrate (10% solution in water) at −78° C. The reaction contents are warmed to room temperature, extracted with ethyl acetate and the organic layer is dried over MgSO$_4$. The crude product is purified by flash chromatography to give the corresponding 6aS,10aS isomer 22 or the 6aR,10aR isomer 25.

Step 3: To a flask containing the 6aS,10aS isomer 22 or the 6aR,10aR isomer 25 of 3-(8-bromo-2-methyloctan-2-yl)-9-(hydroxymethyl)-6,6-dimethyl-6a,7,10,10a-tetrahydro-6H-benzo[c]chromen-1-ol (0.71 mmol) is added sodium iodide (2.13 mmol) and acetone (25 ml) and the contents are refluxed for 3 hours. The solvent is evaporated in vacuo and the residue is taken in DCM (25 ml), washed with water (2×25 ml), dried over MgSO$_4$ and then purified by column chromatography to afford the iodo compound.

Step 3: The 6aS,10aS isomer or the 6aR,10aR isomer of 3-(8-iodo-2-methyloctan-2-yl)-9-(hydroxymethyl)-6,6-dimethyl-6a,7,10,10a-tetrahydro-6H-benzo[c]chromen-1-ol is taken in acetonitrile (20 ml) and to it silver nitrate (1.28 mmol) is added and the contents are heated to 70° C. for 1 hour. The solvent is evaporated in vacuo and the residue is taken in DCM (25 ml), washed with water (2×25 ml), dried over MgSO$_4$ and then purified by column chromatography to afford the 6aS,10aS isomer (compound 23) or the 6aR,10aR isomer of 7-((6aS,10aS)-1-hydroxy-9-(hydroxymethyl)-6,6-dimethyl-6a,7,10,10a-tetrahydro-6H-benzo[c]chromen-3-yl)-7-methyloctyl nitrate (compound 26).

Example 7: Synthesis of Compound 33

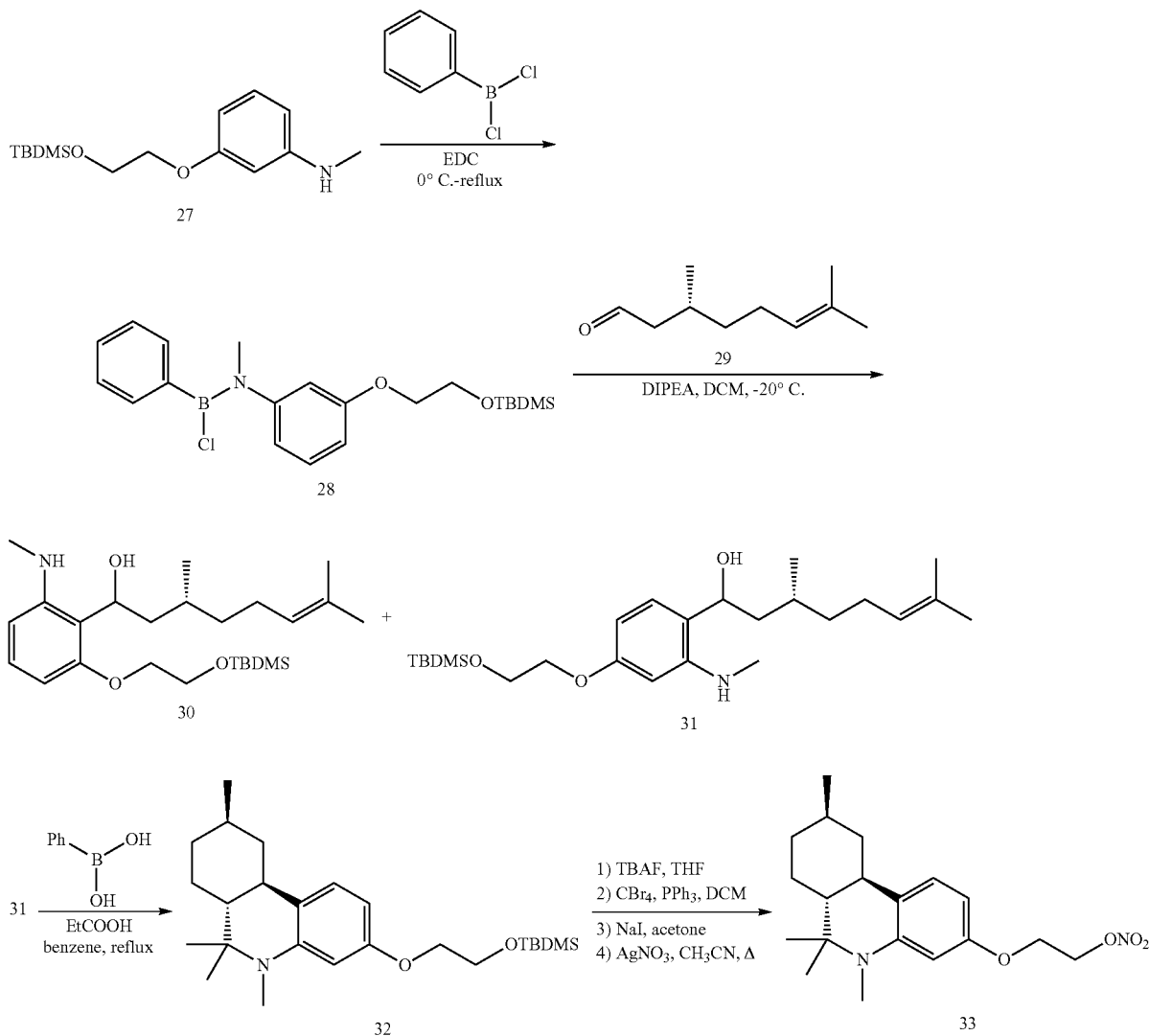

Step 1: To a solution of 3-(2-((tert-butyldimethylsilyl)oxy)ethoxy)-N-methylaniline (27, 25 mmol, prepared starting from 2-(tert-butyldimethylsilyloxy)ethanol and 3-nitro phenol based on procedures adopted from *J. Med. Chem.,* 2007, 50 (20), pp 4898-4908, herein incorporated by reference in its entirety) in 1,2-dichloroethane (25 mL) is added dichlorophenylborane (25 mmol) at 0° C. The resulting mixture is refluxed for 2 h under a rapid stream of nitrogen to remove the HCl formed. The mixture is cooled to give the title compound 28 (based on procedures adopted from CA2170850, herein incorporated by reference in its entirety).

Step 2: A solution of N-(3-(2-((tert-butyldimethylsilyl)oxy)ethoxy)phenyl)-1-chloro-N-methyl-1-phenylboranamine (28, 11 mmol) in 1,2-dichloroethane is added dropwise to a mixture of (R)-(±)-citronellal (29, 1.54 g, 10 mmol) and diisopropylethylamine (20 mmol) in DCM at −20° C. The mixture is stirred at −20° C. for 2 h and at 20° C. for 0.5 hours, quenched with ammonium acetate and then filtered through a short pad of silica gel. The filtrate is concentrated and the residue is chromatographed on silica gel to give compounds 30 and 31 as diastereomeric mixtures (based on procedures adopted from CA2170850, herein incorporated by reference in its entirety).

Step 3: A mixture of (3R)-1-(4-(2-((tert-butyldimethylsilyl)oxy)ethoxy)-2-(methylamino)phenyl)-3,7-dimethyloct-6-en-1-ol (31, 1 mmol), phenylboronic acid (3 mmol) and propionic acid (0.3 mmol) in benzene (10 mL) is refluxed for 20 h to give, after chromatography compound 32 (based on procedures adopted from CA2170850, herein incorporated by reference in its entirety).

Step 4: Tetrabutylammonium fluoride (0.6 mmol from a 1.0 M solution in THF) is added under a nitrogen atmosphere to a cold solution (ice bath) of the (6aR,9R,10aR)-3-(2-((tert-butyldimethylsilyl)oxy)ethoxy)-5,6,6,9-tetramethyl-5,6,6a,7,8,9,10,10a-octahydrophenanthridine (32, 0.54 mmol) in tetrahydrofuran (THF) (3 mL). The resulting solution is stirred at 0° C. for 15 min. Water is added, and the mixture is extracted ethyl acetate. The organic layer is dried over MgSO$_4$ and evaporated to give the crude product.

Step 5: 2-(((6aR,9R,10aR)-5,6,6,9-tetramethyl-5,6,6a,7,8,9,10,10a-octahydrophenanthridin-3-yl)oxy)ethanol (0.33 mmol) is dissolved in anhydrous DCM (3 mL), cooled to 0° C. and triphenylphosphine (0.26 g, 0.99 mmol) and tetrabromomethane (0.4 mL; 1.41 mmol) are added. The reaction mixture is stirred for 3 h after which a portion of methanol and water are sequentially added, and the mixture is extracted with DCM, sequentially washed with aqueous NaS$_2$O$_3$ and brine, and dried over MgSO$_4$. After removal of solvents, the residue is purified by silica gel column chromatography to afford the bromo compound.

Step 6: To a flask containing (6aR,9R,10aR)-3-(2-bromoethoxy)-5,6,6,9-tetramethyl-5,6,6a,7,8,9,10,10a-octahydrophenanthridine (0.71 mmol) is added sodium iodide (2.13 mmol) and acetone (25 ml) and the contents are refluxed for 3 hours. The solvent is evaporated in vacuo and the residue is taken in DCM (25 ml), washed with water (2×25 ml), dried over MgSO$_4$ and then purified by column chromatography to afford the iodo compound.

Step 7: (6aR,9R,10aR)-3-(2-iodoethoxy)-5,6,6,9-tetramethyl-5,6,6a,7,8,9,10,10a-octahydrophenanthridine (1 mmol) is taken in acetonitrile (20 ml) and to it silver nitrate (217 mg, 1.28 mmol) is added and the contents are heated to 70° C. for 1 hour. The solvent is evaporated in vacuo and the residue is taken in DCM (25 ml), washed with water (2×25 ml), dried over MgSO$_4$ and then purified by column chromatography to afford the title compound 2-((((6aR,9R,10aR)-5,6,6,9-tetramethyl-5,6,6a,7,8,9,10,10a-octahydrophenanthridin-3-yl)oxy)ethyl nitrate (Compound 33).

Example 8: Synthesis of Compound 40

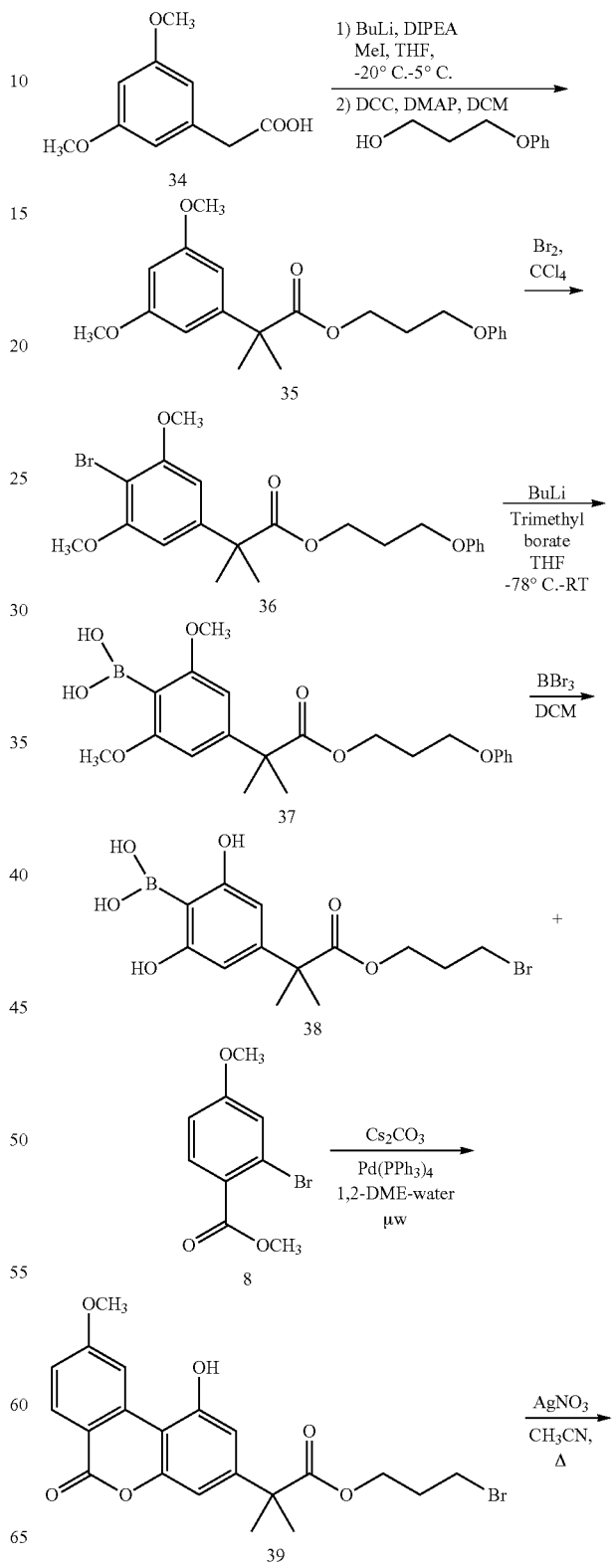

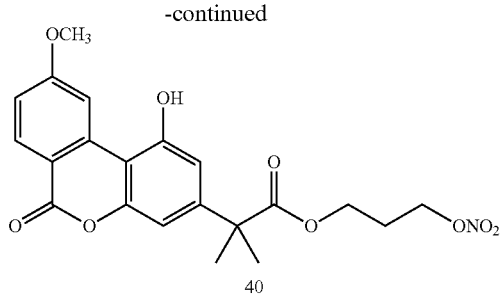

40

Step 1: To a flask containing diisopropylamine (218 mmol) is added anhydrous THF ([0.24 M]) and the reaction is cooled to −20° C. To this a solution of n-BuLi in hexanes (solution titrated at 2.48 M) (212 mmol) is added dropwise at −20° C. and the reaction is stirred for 2 hours at −20° C. 2-(3,5-dimethoxyphenyl)acetic acid (34, 53 mmol) is dissolved in anhydrous THF and is added dropwise to the LDA solution at 20° C. The reaction is slowly warmed to −5° C. using a brine/ice cooling bath and stirred for 2 hours at −5° C. Iodomethane (318 mmol) is then added dropwise at −5° C. and the reaction is gradually warmed up to room temperature and stirred for 15 hours at room temperature. The reaction is quenched by adding 100 mL of an aqueous solution of HCl 1N and diluted with Et₂O (200 mL). The Et₂O layer is separated and the aqueous layer is extracted with Et₂O (3×) and the organic layers are combined, dried over MgSO₄, and evaporated to dryness. The crude acid is purified by flash chromatography over silica gel to give the product (procedure adopted from *Nature Chemistry*, 4(3), 228-234; 2012, herein incorporated by reference in its entirety).

Step 2: To a solution 2-(3,5-dimethoxyphenyl)-2-methylpropanoic acid (35, 4.5 mmol) in dry DCM (20 mL) at room temperature are added dicyclohexylcarbodiimide (9.0 mmol) and 4-(dimethylamino)pyridine (0.9 mmol). To this is added, 3-phenoxypropan-1-ol (1.2 eq) and the resulting mixture is stirred for 12 h before it is quenched with NaHCO₃ (20 mL, sat. aq.). The layers are separated, and the aqueous layer is extracted with Et₂O (3×20 mL). The combined organic layers are washed with brine (20 mL), dried over MgSO₄ and concentrated in vacuo. The residue is purified by flash chromatography over silica gel to give the ester 35 (procedures adopted from *Chinese Journal of Chemistry*, 28(6), 1041-1043; 2010, herein incorporated by reference in its entirety).

Step 3: A solution of Br₂ (10 mmol) in CCl₄ (4 ml) is added to 3-phenoxypropyl 2-(3,5-dimethoxyphenyl)-2-methylpropanoate (10 mmol) in CCl₄ (35 ml) during 2 h at 0° C. (procedures adopted from *J. Chem. Soc., Perkin Trans. 2*, 1997, 2219-2228, herein incorporated by reference in its entirety) After addition the solution is stirred for 1 h at 0° C. followed by evaporation to dryness to give the bromo derivative 36.

Step 3: To a stirred solution of 3-phenoxypropyl 2-(4-bromo-3,5-dimethoxyphenyl)-2-methylpropanoate (36, 8.0 mmol) in anhydrous THF (40 ml) under an argon atmosphere at −78° C. is added n-BuLi (8.8 mmol using 1.6 M solution in hexane) over a 30 min period. Stirring is continued at −78° C. for 15 min and then trimethyl borate (24 mmol) is added (procedures adopted from WO 2008013963, herein incorporated by reference in its entirety). Following addition, the reaction mixture is allowed to warm to room temperature over 12 hours period. The pH is adjusted to 6.5 by addition of 5% aqueous HCl solution at 0° C., and the mixture is extracted with DCM. The organic layer is washed with brine, dried over MgSO₄ and the solvent is evaporated under reduced pressure. The residue is purified by flash column chromatography on silica gel to give compound 37.

Step 4: To a solution of (2,6-dimethoxy-4-(2-methyl-1-oxo-1-(3-phenoxypropoxy)propan-2-yl)phenyl)boronic acid (37, 1 mmol) in anhydrous DCM (15 mL), is added boron tribromide (1.2 mmol) at −78° C. under nitrogen atmosphere. The resulting solution is stirred for 15 minutes at −78° C. The cooling bath is removed and the reaction mixture is continued to stir for 30 minutes at room temperature. The reaction is quenched with anhydrous methanol (1 mL) at −78° C., concentrated in vacuo to dryness. The corresponding o-hydroxy boronic acid 38 is confirmed by LC/MS and is carried to the next step without further purification (procedures adopted from *J. Comb. Chem.* 2010, 12, 664-669, herein incorporated by reference in its entirety).

Step 5: A solution of methyl 2-bromo-4-methoxybenzoate (8, 0.5 mmol), (4-(1-(3-bromopropoxy)-2-methyl-1-oxopropan-2-yl)-2,6-dihydroxyphenyl)boronic acid (38, 0.65 mmol), cesium carbonate (2 mmol) in a mixture of dimethoxyethane (5 mL) and water (0.75 mL) is degassed with argon for 5 minutes. Tetrakis(triphenylphosphine)-palladium (0) (10 mol %) is added, the reaction tube is sealed. The reaction is heated in a microwave (Emrys optimizer from Personal Chemistry) at 125° C. (power 300 W) for 15 minutes. After cooling, the reaction mixture is diluted with water (30 mL), acidified to pH 5, extracted with DCM (2×15 mL). The combined organic layers are passed through a phase separator and concentrated in vacuo. The residue is purified with WATERS preparative LC/MS autopurification system to afford the title compound 39 (procedures adopted from *J. Comb. Chem.* 2010, 12, 664-669, herein incorporated by reference in its entirety).

Step 6: 3-bromopropyl 2-(1-hydroxy-9-methoxy-6-oxo-6H-benzo[c]chromen-3-yl)-2-methylpropanoate (39, 1 mmol) is taken in acetonitrile (20 ml) and to it silver nitrate (1.28 mmol) is added and the contents are heated to 70° C. for 1 hour. The solvents are evaporated in vacuo and the residue is taken in DCM (25 ml), washed with water (2×25 ml), dried over MgSO₄ and then purified by column chromatography to afford the title compound 3-(nitrooxy)propyl 2-(1-hydroxy-9-meth oxy-6-oxo-6H-benzo[c]chromen-3-yl)-2-methylpropanoate (compound 40).

Example 9: Synthesis of Compound 46

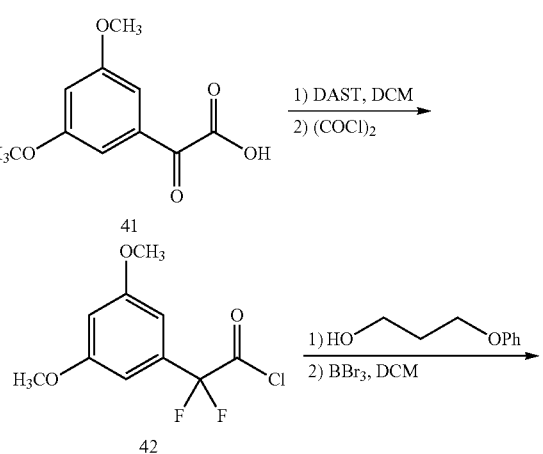

-continued

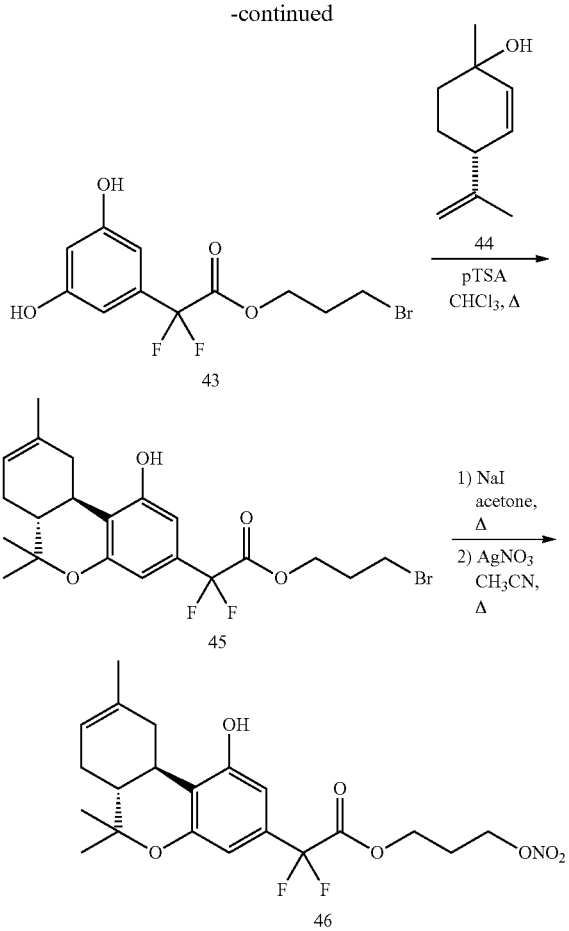

Step 1: To a stirred solution of 2-(3,5-dimethoxyphenyl)-2-oxoacetic acid (41, prepared as in *Journal of the American Chemical Society*, 132(21), 7540-7548, 2010, herein incorporated by reference in its entirety) (15.8 mmol) in anhydrous DCM (30 mL) at room temperature is added (diethylamino)sulfur trifluoride (127 mmol) under nitrogen and the mixture is stirred overnight. The mixture is then cooled in an ice bath and excess (diethylamino)sulfur trifluoride is quenched by drop wise addition of water. Ethyl acetate (300 mL) is added and the organic layer is washed with saturated aqueous sodium bicarbonate (2×100 mL) followed by water (100 mL). The residue obtained after drying and evaporation is purified by silica gel chromatography to give the N,N-diethylamide derivative. This is hydrolyzed to the title acid by heating a solution in ethanol (5 mL) with 10% sodium hydroxide (13 mL) at reflux for 4 h. This sequence is followed by acidification and then extractive work up with ethyl acetate to give the acid 58 (procedures adopted from *Org. Lett.*, 2001, 3 (25), pp 3987-3990, herein incorporated by reference in its entirety).

Step 2: A stirred solution of 2-(3,5-dimethoxyphenyl)-2,2-difluoroacetic acid (6.63 mmol) in anhydrous DCM (20 mL) is treated with oxalyl chloride (19.8 mmol) and 1 drop of dimethylformamide. After vigorous effervescence ceased, the reaction mixture is stirred for 3 h. The solvent is evaporated and traces of oxalyl chloride are removed by repeated evaporation with anhydrous DCM to give the acid chloride 42.

Step 3: To a stirred solution of 2-(3,5-dimethoxyphenyl)-2,2-difluoroacetyl chloride (1 mmol) in MeCN (10 ml) is added 3-phenoxypropan-1-ol (3.5 mmol) at 0° C. and the reaction is allowed to warm to room temperature overnight. The product is extracted into DCM and washed with water. The organics are dried with $MgSO_4$ and filtered through celite. The solvent is removed in vacuo and the residue is subjected to column chromatography on silica gel to give the required phenoxy ester 43.

Step 4: Step 4: To a solution of 3-phenoxypropyl 2-(3,5-dimethoxyphenyl)-2,2-difluoroacetate (43, 1 mmol) in anhydrous DCM (15 mL), is added boron tribromide (1.2 mmol) at −78° C. under nitrogen atmosphere. The resulting solution is stirred for 15 minutes at −78° C. The cooling bath is removed and the reaction mixture is continued to stir for 30 minutes at room temperature. The reaction is quenched with anhydrous methanol (1 mL) at 0° C., washed with water and the organics are dried with $MgSO_4$ and filtered through celite. The solvents are removed by rotary evaporation and the residue is subjected to column chromatography on silica gel to give the required compound 44.

Step 5: 3-bromopropyl 2-(3,5-dihydroxyphenyl)-2,2-difluoroacetate (44, 2 mmol) is taken in $CHCl_3$ (75 ml) and to it is added (+)-cis/trans-p-mentha-2,8-dien-1-ol (2.5 mmol) and p-TSA (38 mg) and the contents are refluxed for 1 hour. The reaction mixture is cooled to room temperature, washed with water (2×50 ml), dried over $MgSO_4$ and then purified by column chromatography to afford compound 45.

Step 6: To a flask containing 3-bromopropyl 2,2-difluoro-2-(1-hydroxy-6,6,9-trimethyl-6a,7,10,10a-tetrahydro-6H-benzo[c]chromen-3-yl)acetate (45, 0.71 mmol) is added sodium iodide (2.13 mmol) and acetone (25 ml) and the contents are refluxed for 3 hours. The solvent is evaporated in vacuo and the residue is taken in DCM (25 ml), washed with water (2×25 ml), dried over $MgSO_4$ and then purified by column chromatography to afford the iodo compound.

Step 7: 3-iodopropyl 2,2-difluoro-2-(1-hydroxy-6,6,9-trimethyl-6a,7,10,10a-tetrahydro-6H-benzo[c]chromen-3-yl)acetate (1 mmol) is taken in acetonitrile (20 ml) and to it silver nitrate (1.28 mmol) is added and the contents are heated to 70° C. for 1 hour. The solvent is evaporated in vacuo and the residue is taken in DCM (25 ml), washed with water (2×25 ml), dried over $MgSO_4$ and the residue is purified by column chromatography to afford 3-(nitrooxy) propyl 2,2-difluoro-2-(1-hydroxy-6,6,9-trimethyl-6a,7,10,10a-tetrahydro-6H-benzo[c]chromen-3-yl)acetate (compound 46).

Example 10: Synthesis of Compound 49

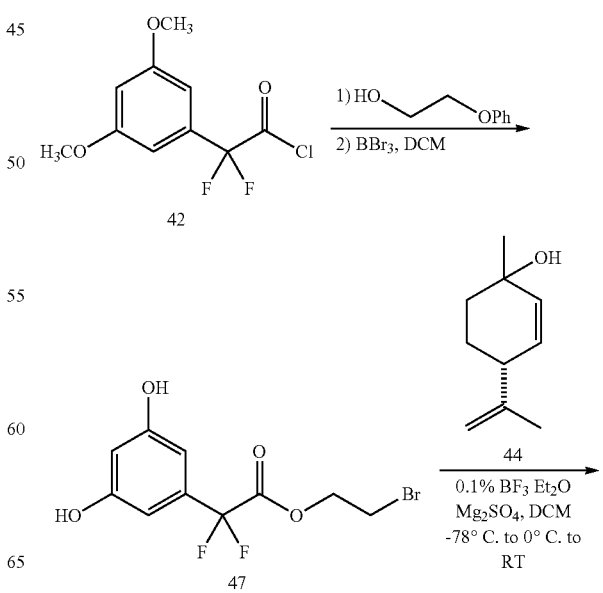

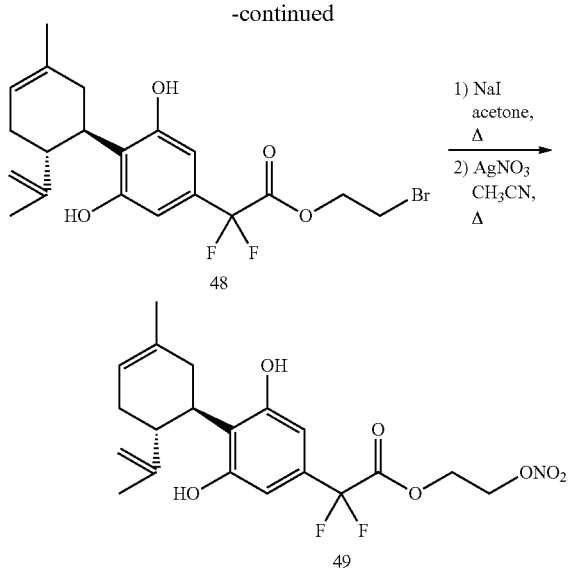

Step 1: To a stirred solution of 2-(3,5-dimethoxyphenyl)-2,2-difluoroacetyl chloride (1 mmol) in MeCN (10 ml) is added 2-phenoxyethan-1-ol (3.5 mmol) at 0° C. and the reaction is allowed to warm to room temperature overnight. The product is extracted into DCM and washed with water. The organics are dried with $MgSO_4$ and filtered through celite. The solvent is removed in vacuo and the residue is subjected to column chromatography on silica gel to give the required phenoxy ester.

Step 2: To a solution of 2-phenoxyethyl 2-(3,5-dihydroxyphenyl)-2,2-difluoroacetate (47, 1 mmol) in anhydrous DCM (15 mL), is added boron tribromide (1.2 mmol) at −78° C. under nitrogen atmosphere. The resulting solution is stirred for 15 minutes at −78° C. The cooling bath is removed and the reaction mixture is continued to stir for 30 minutes at room temperature. The reaction is quenched with anhydrous methanol (1 mL) at 0° C., washed with water and the organics are dried with $MgSO_4$ and filtered through celite. The solvents are removed by rotary evaporation and the residue is subjected to column chromatography on silica gel to give the required compound 48.

Step 3: To a solution of 2-bromoethyl 2-(3,5-dihydroxyphenyl)-2,2-difluoroacetate (1 mmol,) in 50 ml DCM is added ((+)-cis/trans-p-mentha-2,8-dien-1-ol (44, 1 mmol) and 1.5 g of anhydrous $Mg_2SO_4$ under an atmosphere of $N_2$. The contents are cooled to −78° C. and then 0.1% $BF_3.Et_2O$ is added. The mixture is stirred for 1.5 hr, brought to 0° C. and then room temperature over 1.5 hr and 2 g of anhydrous $NaHCO_3$ is added. Stirring is continued until the reaction mixture is colorless. The reaction contents are filtered, the filtrate is evaporated in vacuo and the residue is purified by column chromatography to afford cannabidiol 48 (procedures adopted from *J. Am. Chem. Soc.*, 1974, 96 (18), pp 5860-5865 and *Tetrahedron Letters* 54 (2013) 52-54; each herein incorporated by reference in its entirety).

Step: 4: To a flask containing 2-bromoethyl 2-((1'R,2'R)-2,6-dihydroxy-5'-methyl-2'-(prop-1-en-2-yl)-1',2',3',4'-tetrahydro-[1,1'-biphenyl]-4-yl)-2,2-difluoroacetate (48, 1 mmol) is added sodium iodide (2 mmol) and acetone (25 ml) and the contents are refluxed for 3 hours. The solvent is evaporated in vacuo and the residue is taken in DCM (25 ml), washed with water (2×25 ml), dried over $MgSO_4$ and then purified by column chromatography to afford the iodo compound.

Step 5: 2-iodoethyl 2-((1'R,2'R)-2,6-dihydroxy-5'-methyl-2'-(prop-1-en-2-yl)-1',2',3',4'-tetrahydro-[1,1'-biphenyl]-4-yl)-2,2-difluoroacetate (1 mmol) obtained from the previous step is taken in acetonitrile (20 ml) and to it silver nitrate (1.28 mmol) is added and the contents are heated to 70° C. for 1 hour. The solvent is evaporated in vacuo and the residue is taken in DCM (25 ml), washed with water (2×25 ml), dried over $MgSO_4$ and then purified by column chromatography to afford 2-(nitrooxy)ethyl 2-((1'R,2'R)-2,6-dihydroxy-5'-methyl-2'-(prop-1-en-2-yl)-1',2',3',4'-tetrahydro-[1,1'-biphenyl]-4-yl)-2,2-difluoroacetate (compound 49).

Example 11: Synthesis of Compound 53a and 53b

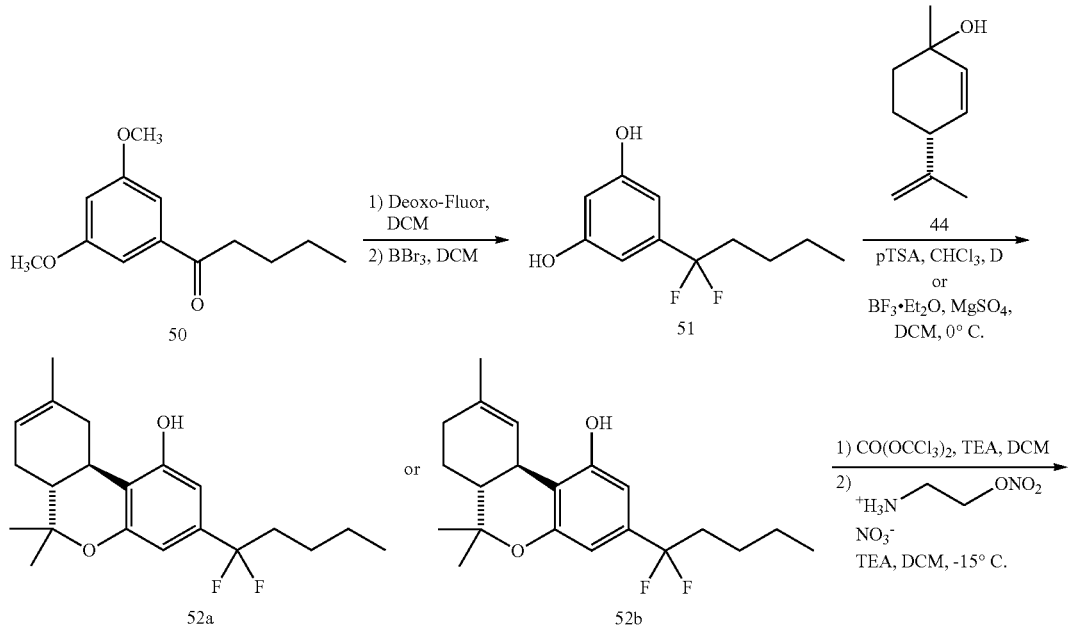

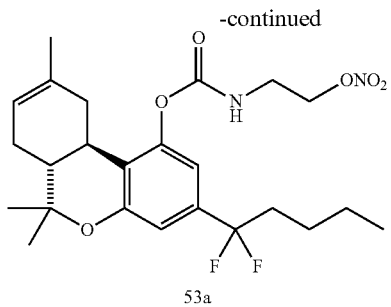 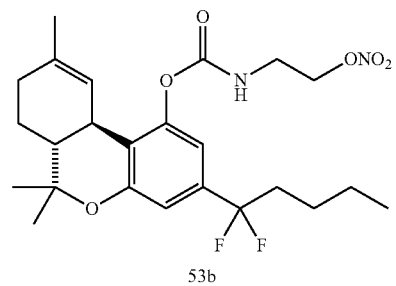

53a      53b

Step 1: A mixture of 1-(3,5-dimethoxyphenyl)pentan-1-one (50, 15.8 mmol), bis(2-methoxyethyl)aminosulfur trifluoride (127 mmol) and one drop of ethanol is stirred at 85° C. for 72 hours in a Teflon bottle and quenched by slow addition of water. The mixture is poured into water (100 mL) and extracted with ethyl acetate (100 mL). The organic layer is washed with water, dried over $MgSO_4$ and filtered. The filtrate is concentrated in vacuo and the residue is purified by flash column chromatography to afford the gem-difluoro compound (procedures adopted from WO 2008060789, herein incorporated by reference in its entirety).

Step 2: To a solution of 1-(1,1-difluoropentyl)-3,5-dimethoxybenzene (1 mmol) in anhydrous DCM (15 mL), is added boron tribromide (1.2 mmol) at −78° C. under nitrogen atmosphere. The resulting solution is stirred for 15 minutes at −78° C. The cooling bath is removed and the reaction mixture is continued to stir for 30 minutes at room temperature. The reaction is quenched with anhydrous methanol (1 mL) at 0° C., washed with water and the organics are dried with $MgSO_4$ and filtered through celite. The solvent is removed in vacuo and the residue is purified by column chromatography on silica gel to give the required compound 51.

Step 3a: To a mixture of 5-(1,1-difluoropentyl)benzene-1,3-diol (51, 3.2 mmol) and (+)-cis/trans-p-mentha-2,8-dien-1-ol (44, 3.2 mmol) in benzene (35 ml) is added p-TsOH.$H_2O$ (12 mol %) and the mixture heated to reflux for 2 h. To this reaction mixture was added a saturated aqueous $NaHCO_3$ solution (25 ml). The mixture is extracted with EtOAc (3×25 ml). Combined organic extracts were washed with water (20 ml) and brine (20 ml), dried over $MgSO_4$, filtered and concentrated under reduced pressure. The crude product is purified by column chromatography to obtain compound 52a (procedures based on US 20110312903; herein incorporated by reference in its entirety).

Step 3b: To a mixture of 5-(1,1-difluoropentyl)benzene-1,3-diol (51, 3.2 mmol) and (+)-cis/trans-p-mentha-2,8-dien-1-ol (44, 3.2 mmol) in anhydrous DCM (25 ml) is added anhydrous $MgSO_4$ (500 mg) under an atmosphere of $N_2$. The mixture is cooled to 0° C. followed by the addition of $BF_3.Et_2O$ (1 mol %) at 0° C. The contents are stirred for 1.5 h and subsequently anhydrous $NaHCO_3$ (1 g) is added, the reaction mixture is filtered and the solvent removed under reduced pressure. The crude product is purified by column chromatography to obtain the compound 52b.

Step 4: To a solution of (6aR,10aR)-3-(1,1-difluoropentyl)-6,6,9-trimethyl-6a,7,10,10a-tetrahydro-6H-benzo[c]chromen-1-ol (52a, 3 mmol) or (6aR,10aR)-3-(1,1-difluoropentyl)-6,6,9-trimethyl-6a,7,8,10a-tetrahydro-6H-benzo[c]chromen-1-ol (52b, 3 mmol) in DCM (25 ml) is added triphosgene (1 mmol) at 0° C. under an atmosphere of $N_2$ (based on procedures adopted from U.S. Pat. No. 4,327,028 and J. Org. Chem. 1991,56, 1549-1553; herein incorporated by reference in its entirety). The contents are stirred for 1 hour after which they are slowly added via a cannula to a flask containing 2-nitroxyethylammonium nitrate (3 mmol, prepared as in US 20130041001; herein incorporated by reference in its entirety) and triethylamine (6.6 mmol) in DCM (25 ml) at −15° C. The mixture is stirred at −10° C. for 1 h after which water (25 ml) is added, and the organic phase is washed with aqueous citric acid (10%) and saturated aqueous $NaHCO_3$, dried over $MgSO_4$, and evaporated. The crude product is purified by column chromatography to obtain compound (6aR,10 aR)-3-(1,1-difluoropentyl)-6,6,9-trimethyl-6a,7,10,10a-tetrahydro-6H-benzo[c]chromen-1-yl (2-(nitrooxy)ethyl)carbamate (compound 53a) or (6aR,10aR)-3-(1,1-difluoropentyl)-6,6,9-trimethyl-6a,7,8,10a-tetrahydro-6H-benzo[c]chromen-1-yl(2-(nitrooxy)ethyl)carbamate (compound 53b).

Example 12: Synthesis of Compounds 55a and 55b

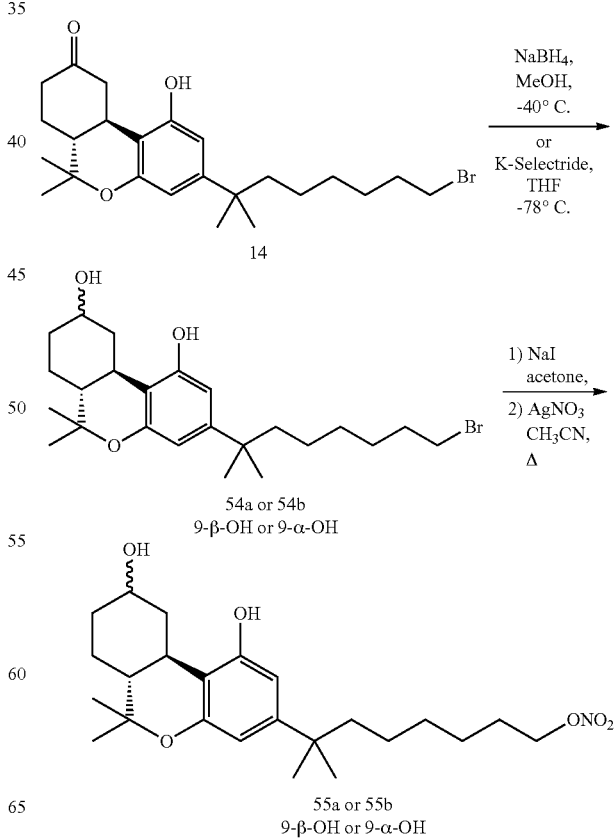

54a or 54b
9-β-OH or 9-α-OH 55a or 55b
9-β-OH or 9-α-OH

Step 1: To a solution of (6aR,10aR)-3-(8-bromo-2-methyloctan-2-yl)-1-hydroxy-6,6-dimethyl-7,8,10,10a-tetrahydro-6H-benzo[c]chromen-9(6aH)-one (14, 0.09 mmol, prepared as in WO 2003005960; herein incorporated by reference in its entirety) in 4.5 mL THF and 500 μL i-PrOH at rt is added NaBH$_4$ (0.14 mmol). The resulting reaction mixture is stirred at room temperature for 40 min and quenched with water and extracted with Et$_2$O (3×). The combined organic extracts are dried over MgSO$_4$, solvent is removed in vacuo and the residue is purified by flash column chromatography on silica gel to afford the 9-β-hydroxy compound 54a.

Alternatively, to a solution of (6aR,10aR)-3-(8-bromo-2-methyloctan-2-yl)-1-hydroxy-6,6-dimethyl-7,8,10,10a-tetrahydro-6H-benzo[c]chromen-9(6aH)-one (0.16 mmol, prepared as in WO 2003005960; herein incorporated by reference in its entirety) in 1 mL of THF at −78° C. is added of 1.0 M potassium tri-sec-butylborohydride (K-Selectride, 0.32 mmol) in THF. The reaction mixture is stirred at −78° C. for 2 h, allowed to warm to room temperature and stirred for 1 h. The reaction is quenched with 1 mL of water and 5 mL of ethanol followed by 2 ml of 15% aqueous NaOH and 2 mL of 30% water. After extraction with Et$_2$O, the combined extracts are washed with brine and dried over MgSO$_4$, solvent is removed in vacuo and the residue is purified by flash column chromatography on silica gel to afford the 9-α-hydroxy compound 54b.

Step 2: To a flask containing the 9-α or the 9-β isomer of (6aR,10aR)-3-(8-bromo-2-methyloctan-2-yl)-6,6-dimethyl-6a,7,8,9,10,10a-hexahydro-6H-benzo[c]chromene-1,9-diol (69, 0.71 mmol) is added sodium iodide (320 mg, 2.13 mmol) and acetone (25 ml) and the contents are refluxed for 3 hours. The solvent is evaporated in vacuo and the residue is taken in DCM (25 ml), washed with water (2×25 ml), dried over MgSO$_4$ and then purified by column chromatography to afford the iodo compound.

Step 3: (6aR,10aR)-3-(8-iodo-2-methyloctan-2-yl)-6,6-dimethyl-6a,7,8,9,10,10a-hexahydro-6H-benzo[c]chromene-1,9-diol obtained is taken in acetonitrile (20 ml) and to it silver nitrate (217 mg, 1.28 mmol) is added and the contents are heated to 70° C. for 1 hour. The solvent is evaporated in vacuo and the residue is taken in DCM (25 ml), washed with water (2×25 ml), dried over MgSO$_4$ and then purified by column chromatography to afford the 7-((6aR,9R,10aR)-1,9-dihydroxy-6,6-dimethyl-6a,7,8,9,10,10a-hexahydro-6H-benzo[c]chromen-3-yl)-7-methyloctyl nitrate (compound 55a) or 7-((6aR,9S,10aR)-1,9-dihydroxy-6,6-dimethyl-6a,7,8,9,10,10a-hexahydro-6H-benzo[c]chromen-3-yl)-7-methyloctyl nitrate (compound 55b).

Example 13: Synthesis of Compound 57

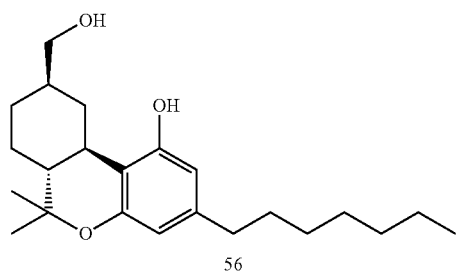

56

1) CBr$_4$, PPh$_3$ DCM
2) NaI acetone
3) AgNO$_3$ CH$_3$CN, Δ

-continued

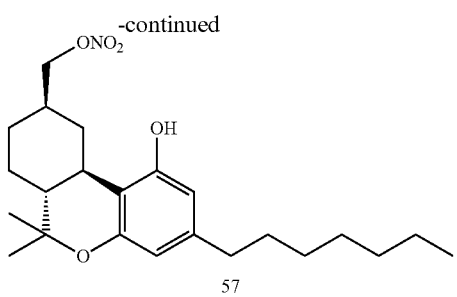

57

Step 1: (6aR,9R,10aR)-3-heptyl-9-(hydroxymethyl)-6,6-dimethyl-6a,7,8,9,10,10a-hexahydro-6H-benzo[c]chromen-1-ol (56, 0.33 mmol, prepared as in J. Med. Chem. 1996, 39, 3790-3796; herein incorporated by reference in its entirety) is dissolved in anhydrous DCM (3 mL), cooled to 0° C. and triphenylphosphine (0.26 g, 0.99 mmol) and tetrabromomethane (0.4 mL; 1.41 mmol) are added. The reaction mixture is stirred for 3 h after which a portion of methanol and water are sequentially added, and the mixture is extracted with DCM, sequentially washed with aqueous NaS$_2$O$_3$ and brine, dried over MgSO$_4$, solvent is removed in vacuo and the residue is purified by flash column chromatography on silica gel to afford the bromo compound.

Step 2: To a flask containing (6aR,9R,10aR)-9-(bromomethyl)-3-heptyl-6,6-dimethyl-6a,7,8,9,10,10a-hexahydro-6H-benzo[c]chromen-1-ol (0.71 mmol) is added sodium iodide (2.13 mmol) and acetone (25 ml) and the contents are refluxed for 3 hours. The solvent is evaporated in vacuo and the residue is taken in DCM (25 ml), washed with water (2×25 ml), dried over MgSO$_4$ and then purified by column chromatography to afford the iodo compound.

Step 3: (6aR,9R,10aR)-9-(iodomethyl)-3-heptyl-6,6-dimethyl-6a,7,8,9,10,10a-hexahydro-6H-benzo[c]chromen-1-ol (1 mmol) is taken in acetonitrile (20 ml) and to it silver nitrate (1.28 mmol) is added and the contents are heated to 70° C. for 1 hour. The solvent is evaporated in vacuo and the residue is taken in DCM (25 ml), washed with water (2×25 ml), dried over MgSO$_4$ and then purified by column chromatography to afford the title compound 2-(((6aR,9R,10aR)-5,6,6,9-tetramethyl-5,6,6a,7,8,9,10,10a-octahydrophenanthridin-3-yl)oxy)ethyl nitrate (Compound 57).

Example 14: Synthesis of Compound 62

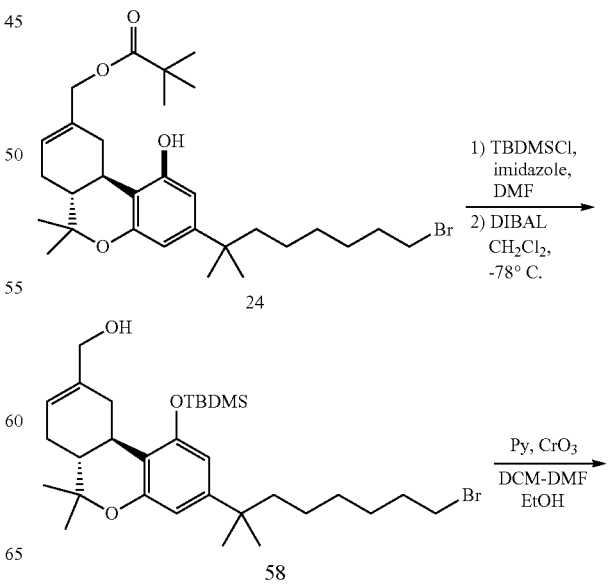

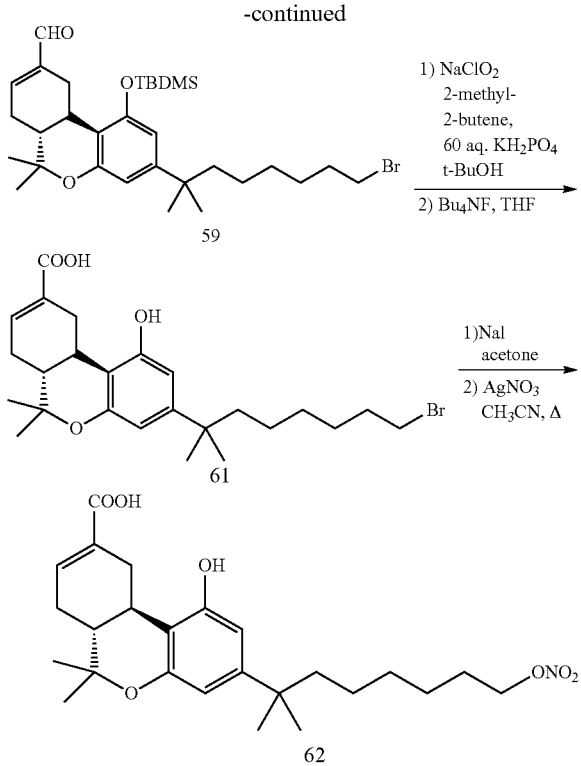

Step 1: ((6aR,10aR)-3-(8-bromo-2-methyloctan-2-yl)-1-hydroxy-6,6-dimethyl-6a,7,10,10a-tetrahydro-6H-benzo[c]chromen-9-yl)methyl pivalate (24, prepared as in *J. Med. Chem.* 1994,37, 3867-3870; herein incorporated by reference in its entirety) (12 mmol) is dissolved in dry dimethylformamide (6 mL) and to this dimethyl-tert-butylsilyl chloride (12.27 mmol) and imidazole (24.6 mmol) are added, and the resulting mixture is stirred for 48 h at room temperature. Water (30 mL) is added, and the mixture is as extracted with Et₂O, dried over MgSO₄, and the solvent evaporated in vacuo to give the product.

Step 2: To a solution of ((6aR,10aR)-3-(8-bromo-2-methyloctan-2-yl)-1-((tert-butyldimethylsilyl)oxy)-6,6-dimethyl-6a,7,10,10a-tetrahydro-6H-benzo[c]chromen-9-yl) methyl pivalate (0.955 mmol) in anhydrous DCM (9.5 mL) is added 1M solution of DIBAL-H in toluene (1.2 mmol) dropwise at −78° C. The reaction mixture is stirred for 2.5 h and then quenched by dropwise addition of potassium sodium tartrate (10% solution in water) at −78° C. The reaction contents are warmed to room temperature, extracted with ethyl acetate, the organic layer is dried over MgSO₄, the solvent evaporated in vacuo and the residue is purified by flash chromatography to give the product 58.

Step 3: Dry pyridine (2.3 mL) followed by chromic oxide (14.4 mmol) is added to a solution of DCM-DMF (4:1) (36 mL). The mixture is stirred for 15 min and to this ((6aR,10aS)-3-(8-bromo-2-methyloctan-2-yl)-1-((tert-butyldimethylsilyl)oxy)-6,6-dimethyl-6a,7,10,10a-tetrahydro-6H-benzo[c]chromen-9-yl)methanol (58, 3.6 mmol) in DCM-DMF (4:1) (7.2 mL) is added, and the reaction mixture is stirred at room temperature for 1 h. Ethanol (1.8 mL) is added, and the mixture is stirred for an additional 10 min and is then diluted with ethyl acetate (180 mL). The resulting mixture is filtered through a sintered-glass funnel, packed with silica (3 cm), with a layer of anhydrous MgSO₄ on top, and eluted with ethyl acetate (600 mL). The ethyl acetate filtrate is washed with dilute hydrochloric acid (1N) and then with sodium bicarbonate solution and water. The solvent is evaporated in vacuo to give the aldehyde 59.

Step 4: Using the Pinnick oxidation methodology, sodium chlorite (1 mmol) is added portion wise with vigorous stirring to a mixture of (6aR,10aS)-3-(8-bromo-2-methyloctan-2-yl)-1-((tert-butyldimethylsilyl)oxy)-6,6-dimethyl-6a,7,10,10a-tetrahydro-6H-benzo[c]chromene-9-carbaldehyde (59, 1 mmol), 2-methyl-2-butene (60, 1 mmol), saturated aqueous potassium dihydrogen phosphate (1 mmol), and tert-butyl alcohol (22 mL). The reaction mixture is stirred at room temperature for 5 h. Water (20 mL) is added, and the mixture is extracted several times with ethyl acetate, dried over MgSO₄, and the solvent is evaporated in vacuo to give the required product.

Step 5: Tetrabutylammonium fluoride (0.6 mmol from a 1.0 M solution in THF) is added under a nitrogen atmosphere to a cold solution (ice bath) of (6aR,10aS)-3-(8-bromo-2-methyloctan-2-yl)-1-((tert-butyldimethylsilyl)oxy)-6,6-dimethyl-6a,7,10,10a-tetrahydro-6H-benzo[c]chromene-9-carboxylic acid (0.54 mmol) in tetrahydrofuran (THF) (3 mL). The resulting solution is stirred at 0° C. for 15 min. Water is added, and the mixture is extracted several times with Et₂O. The Et₂O layer is dried, evaporated in vacuo and the residue is purified by column chromatography to give the acid 61.

Step 6: To a flask containing (6aR,10aS)-3-(8-bromo-2-methyloctan-2-yl)-1-hydroxy-6,6-dimethyl-6a,7,10,10a-tetrahydro-6H-benzo[c]chromene-9-carboxylic acid (61, 0.71 mmol) is added sodium iodide (2.13 mmol) and acetone (25 ml) and the contents are refluxed for 3 hours. The solvent is evaporated in vacuo and the residue is taken in DCM (25 ml), washed with water (2×25 ml), dried over MgSO₄ and then purified by column chromatography to afford the iodo compound.

Step 7: (6aR,10aS)-3-(8-iodo-2-methyloctan-2-yl)-1-hydroxy-6,6-dimethyl-6a,7,10,10a-tetrahydro-6H-benzo[c]chromene-9-carboxylic acid (1 mmol) is taken in acetonitrile (20 ml) and to it silver nitrate (1.28 mmol) is added and the contents are heated to 70° C. for 1 hour. The solvents is evaporated in vacuo and the residue is taken in DCM (25 ml), washed with water (2×25 ml), dried over MgSO₄ and then purified by column chromatography to afford the title compound (6aR,10aR)-1-hydroxy-6,6-dimethyl-3-(2-methyl-8-(nitrooxy)octan-2-yl)-6a,7,10,10a-tetrahydro-6H-benzo[c]chromene-9-carboxylic acid (Compound 62).

Example 15: Synthesis of Compound 74

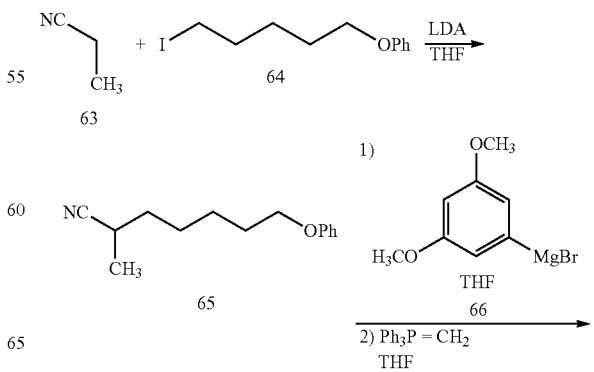

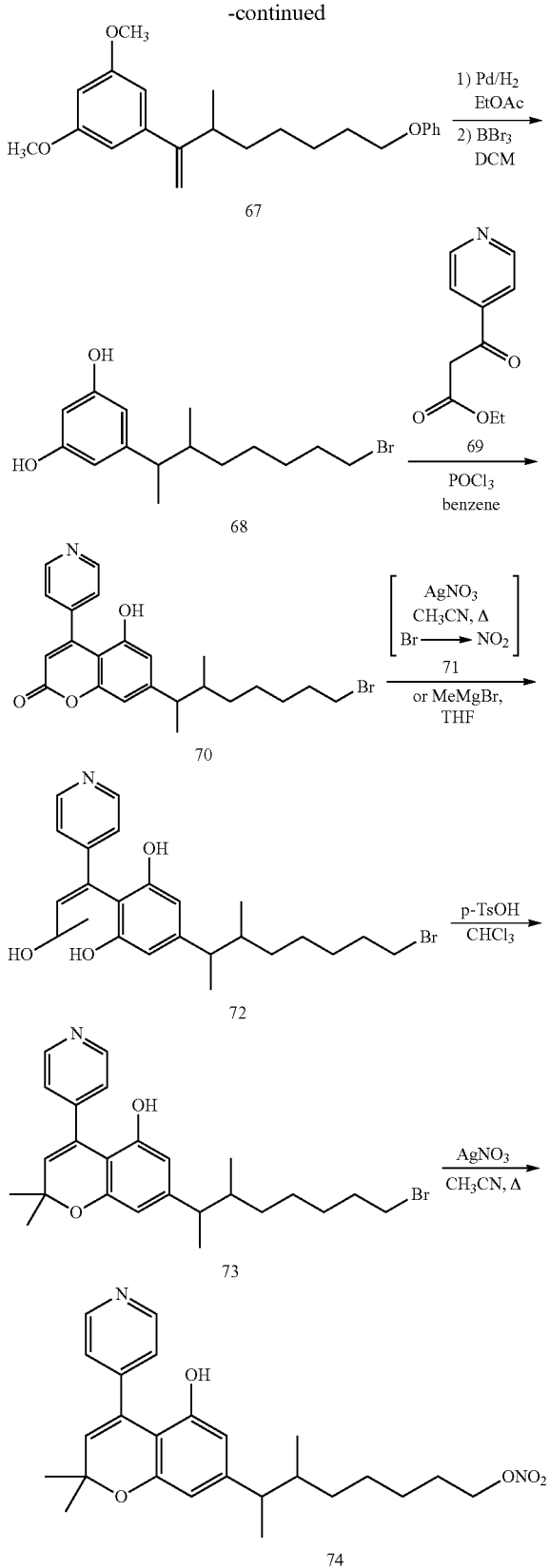

solution is cooled to −78° C. and propionitrile (63, 30.0 mmol) is added. The mixture is stirred for 2 h, and 5-phenoxypentyl iodide (64, 30.0 mmol) is added. The mixture is then is warmed to room temperature and stirred for 24 h. To the reaction mixture is added 50 mL of 1N HCl, and the resulting mixture is extracted 3×EtOAc. The combined organic layers are washed with an aqueous solution of NaHCO₃, dried over MgSO₄, filtered and concentrated and the resulting residue is purified by flash chromatography to give the product 65 (procedure adopted from *J. Am. Chem. Soc.*, 2007, 129 (29), pp 8948-8949; herein incorporated by reference in its entirety).

Step 2: 2-methyl-7-phenoxyheptanenitrile (65, 12 mmol) in Et₂O (50 mL) at 0° C. is treated with (3,5-dimethoxyphenyl)magnesium bromide (66, 14 mmol) and the mixture is stirred for 2 h at 0° C., then at room temperature overnight. 3M HCl is added, and after stirring for an additional 12 h, the mixture is extracted with DCM, washed with brine, dried over MgSO₄, filtered and concentrated in vacuo to give the desired ketone (procedures adopted from U.S. Pat. No. 3,278,606; herein incorporated by reference in its entirety).

Step 3: To a solution of methyltriphenylphosphonium bromide (32 mmol) in THF (80 mL) under nitrogen atmosphere is added n-BuLi (15 wt % in hexane, 32 mmol) at 0° C. After stirring for 20 min, 1-(3,5-dimethoxyphenyl)-2-methyl-7-phenoxyheptan-1-one (21 mmol) is added dropwise and after stirring for 24 h and the precipitated solid materials are removed by filtration. The filtrate is poured into H₂O (50 mL), and extracted with Et₂O (2×50 mL). The combined organic layers are washed with brine, and dried over anhydrous MgSO₄. The organic layer is concentrated in vacuo and the residue obtained is used for next step without further purification (procedures adopted from U.S. Pat. No. 3,278,606; herein incorporated by reference in its entirety).

Step 4: To a solution of 1,3-dimethoxy-5-(3-methyl-8-phenoxyoct-1-en-2-yl)benzene (67, 8.13 mmol) in ethanol (45 mL) is added palladium on carbon (10 mol %) and pressurized to 30 psi of hydrogen for 3 h. The reaction mixture is then filtered through a pad of celite, washed with diethyl ether and concentrated in vacuo to give reduced product (procedures adopted from U.S. Pat. No. 3,278,606, herein incorporated by reference in its entirety)

Step 5: To a solution of 1 1,3-dimethoxy-5-(3-methyl-8-phenoxyoctan-2-yl)benzene (1 mmol) in anhydrous DCM (15 mL), is added boron tribromide (1.2 mmol) at −78° C. under nitrogen atmosphere. The resulting solution is stirred for 15 minutes at −78° C. The cooling bath is removed and the reaction mixture is continued to stir for 30 minutes at room temperature. The reaction is quenched with anhydrous methanol (1 mL) at 0° C., washed with water and the organics are dried with MgSO₄ and filtered through celite. The solvent is removed in vacuo and the residue is purified by column chromatography on silica gel to give the required compound 68.

Step 6: To a mixture of ethyl isonicotinoylacetate (69, 0.11 mol) and 5-(8-bromo-3-methyloctan-2-yl)benzene-1,3-diol (68, 0.11 mole) is added concentrated sulfuric acid (46 ml) followed by phosphorus oxychloride (28 ml), the mixture being cooled during the addition. After stirring for 24 hours, the brown oil is poured into a stirred solution of NaHCO₃ and the resulting residue is extracted into DCM. The organic layer is washed with brine, dried over MgSO₄ and the solvent is evaporated in vacuo pressure to give 70 (procedures adopted from U.S. Pat. No. 3,726,883; herein incorporated by reference in its entirety).

Step 7: In a certain modification, 7-(8-bromo-3-methyl-octan-2-yl)-5-hydroxy-4-(pyridin-4-yl)-2H-chromen-2-one Step 1: To a solution of iPr₂NH (29.9 mmol) in 20 mL of THF is added a 1.57 M solution of butyllithium in hexanes (29.8 mmol) at 0° C. and the mixture is stirred for 5 min. The (70, 1 mmol) obtained in the previous step is taken in acetonitrile (20 ml) and to it silver nitrate (1.28 mmol) is added and the contents are heated to 70° C. for 1 hour. The solvents are evaporated in vacuo and the residue is taken in DCM (25 ml), washed with water (2×25 ml), dried over MgSO$_4$ and then purified by column chromatography to afford 7-(5-hydroxy-2-oxo-4-(pyridin-4-yl)-2H-chromen-7-yl)-6-methyloctyl nitrate 71.

Step 8: Alternatively, to a solution of 7-(8-bromo-3-methyloctan-2-yl)-5-hydroxy-4-(pyridin-4-yl)-2H-chromen-2-one (9, 1.0 mmol) taken in anhydrous THF (20 mL) is added methylmagnesium iodide (3 mmol, 3.0 M in Et$_2$O) at room temperature under an argon atmosphere. The reaction mixture is stirred at room temperature for 30 min and then refluxed for 1.5 h. The reaction is cooled to room temperature and quenched by the addition of 20 mL of saturated aqueous NH$_4$Cl. The THF is removed in vacuo and the residue is dissolved in anhydrous Et$_2$O (50 mL). The ether solution is washed with water and brine, dried over MgSO$_4$, and the solvent is evaporated in vacuo to give 72 (procedures adopted from U.S. Pat. No. 3,726,883, *J. Med. Chem.* 2007, 50, 6493-6500, and *J. Med. Chem.*, 1973, 16 (11), 1200-1206; each herein incorporated by reference in its entirety).

Step 9: 5-(8-bromo-3-methyloctan-2-yl)-2-(3-hydroxy-3-methyl-1-(pyridin-4-yl)but-1-en-1-yl)benzene-1,3-diol 72 obtained from the previous step is refluxed in glacial acetic acid (20 ml) for 2 hours. The reaction mixture is cooled to room temperature and poured into water with stirring. The residue that separates is extracted with DCM, washed with water, 15% aqueous NaHCO$_3$, water and brine, dried over MgSO$_4$, the solvent is evaporated in vacuo and the residue is purified by column chromatography to afford 73 (procedures adopted from U.S. Pat. No. 3,726,883; herein incorporated by reference in its entirety).

Step 10: 7-(8-bromo-3-methyloctan-2-yl)-2,2-dimethyl-4-(pyridin-4-yl)-2H-chromen-5-ol (73, 1 mmol) is taken in acetonitrile (20 ml) and to it silver nitrate (1.28 mmol) is added and the contents are heated to 70° C. for 1 hour. The solvents are evaporated in vacuo and the residue is taken in DCM (25 ml), washed with water (2×25 ml), dried over MgSO$_4$ and then purified by column chromatography to afford 7-(5-hydroxy-2,2-dimethyl-4-(pyridin-4-yl)-2H-chromen-7-yl)-6-methyloctyl nitrate (Compound 74).

Example 16: Synthesis of Compound 78

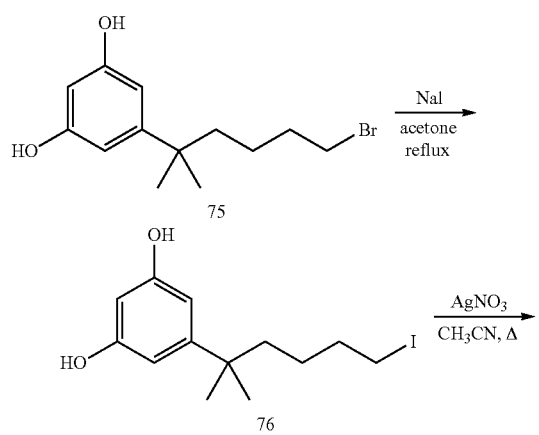

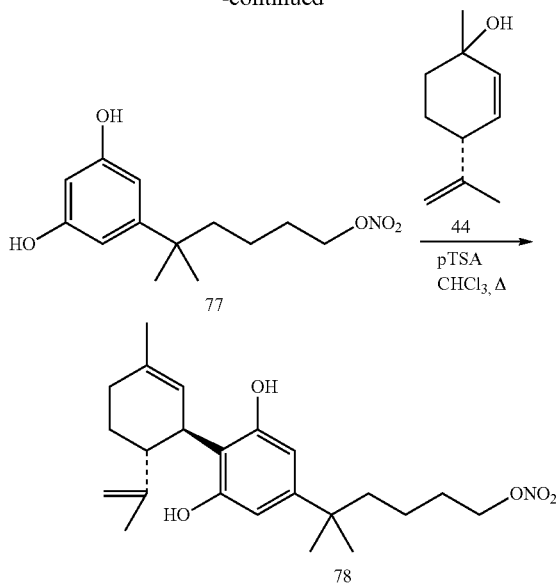

Step 1: To a flask containing 5-(6-bromo-2-methylhexan-2-yl)benzene-1,3-diol (75, 600 mg, 2.08 mmol) (prepared as in *AAPS J.* 2004 Oct. 19; 6(4):e30 and procedures based on *J. Med. Chem.* 1984,27, 67-71; each herein incorporated by reference in its entirety) is added sodium iodide (936.8 mg, 6.24 mmol) and acetone (25 ml) and the contents are refluxed for 3 hours. The solvent is evaporated in vacuo and the residue taken in DCM (25 ml), washed with water (2×25 ml), dried over MgSO$_4$ and the solvent evaporated in vacuo to afford 76 as a dark brown syrup in quantitative yield.

Step 2: 5-(6-iodo-2-methylhexan-2-yl)benzene-1,3-diol (76, 696 mg, 2.08 mmol) is taken in acetonitrile (20 ml) and to it silver nitrate (1.06 g, 6.24 mmol) is added and the contents are heated to 70° C. for 1 hour. The solvent is evaporated in vacuo and the residue taken in DCM (25 ml), washed with water (2×25 ml), dried over MgSO$_4$ and the solvent evaporated in vacuo to obtain 77 as a dark brown syrup (560 mg).

Step 3: 5-(3,5-dihydroxyphenyl)-5-methylhexyl nitrate (77, 560 mg, 2.08 mmol) is taken in CHCl$_3$ (75 ml) and to it is added (+)-cis/trans-p-mentha-2,8-dien-1-ol (44,

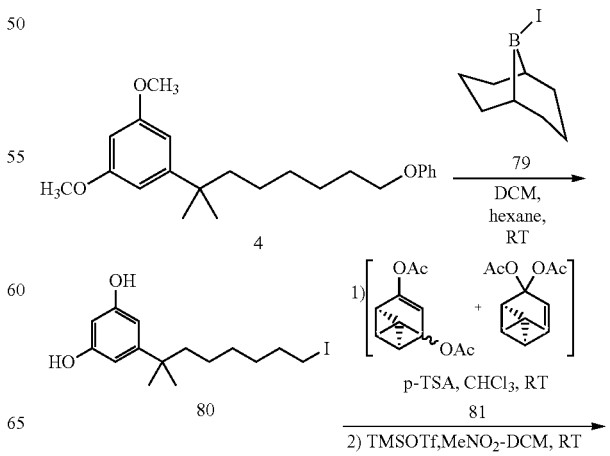

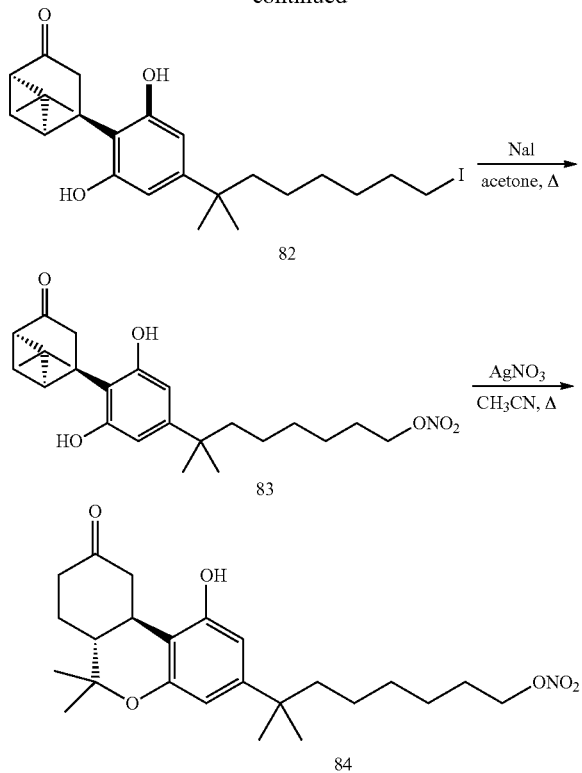

380 mg, 2.5 mmol) and p-TSA (38 mg) and the contents are refluxed for 1 hour. The reaction contents are cooled to room temperature, washed with water (2×50 ml), dried over MgSO₄ and then purified by column chromatography to afford 5-((1'R,2'R)-2,6-dihydroxy-5'-methyl-2'-(prop-1-en-2-yl)-1',2',3',4'-tetrahydro-[1,1'-biphenyl]-4-yl)-5-methylhexyl nitrate as a light brown syrup (compound 78, 110 mg): $^1$H NMR (500 MHz, CDCl₃) δ 6.17-6.53 (2H), 6.02 (s, 1H), 5.59 (br. s., 1H), 4.68 (s, 1H), 4.64 (br. s., 1H), 4.57 (s, 1H), 4.35 (t, J=6.59 Hz, 2H), 3.83 (m as b.d., J=8.79 Hz, 1H), 2.38 (ddd, J=2.93, 11, 10.99 Hz, 1H), 2.18-2.31 (m, 1H), 2.05-2.17 (m, 1H), 2.02 (s, 1H), 1.72-1.93 (m, 5H), 1.47-1.63 (m, 5H), 1.23 (d, J=1.95 Hz, 6H), 1.04-1.18 (m, 2H); MS (ESI⁺) for m/z 426 (M+Na).

Example 17: Synthesis of Compounds 83 and 84

Step 1: To a mixture of 2-(3,5-dimethoxyphenyl)-2-methyl-8-phenoxyoctane (4, 2 mmol) in DCM (20 ml) is added a 1M solution of 9-iodo-9-BBN in hexane (79, 6 mmol, 6.1 ml) at 0° C. and then stirred for 3 h at ambient temperature. To the reaction mixture is added a solution of ethanolamine (7 mmol) in DCM (10 mL to precipitate the 9-BBN.ethanolamine adduct. The mixture is stirred for 1 hour at RT. The reaction is diluted with DCM (50 ml), washed with water (2×25 ml), dried over MgSO₄ and then purified by column chromatography to afford the iodoresorcinol 80 (550 mg, 76%). $^1$H NMR (500 MHz, CDCl₃) δ 6.38 (d, J=1.95 Hz, 2H), 6.18 (s, 1H), 4.75 (s, 2H), 3.15 (t, J=6.84 Hz, 2H), 1.69-1.81 (m, 2H), 1.50-1.54 (m, 2H), 1.32 (m, 2H), 1.23 (s, 6H), 1.17-1.22 (m, 2H), 1.01-1.11 (m, 2H); MS (ESI⁺) for m/z 363 (M+H).

Step 2: To a solution of 5-(8-iodo-2-methyloctan-2-yl)benzene-1,3-diol (80, 550 mg, 1.5 mmol) and diacetates 81 (prepared in two steps as in Aust. J. Chem., 1970, 23, 1069-71 and J. Org. Chem. 1977, 42, 2277-2284; each herein incorporated by reference in its entirety (423 mg, ~2 mmol, purity) in of CHCl₃ (20 mL) is added p-toluenesulfonic acid monohydrate (380 mg, 2 mmol), and the solution stirred in dark and at room temperature for 24 hours. The reaction is diluted with DCM (25 ml), washed sequentially with saturated aqueous NaHCO₃ (1×25 ml), water (2×25 ml), dried over MgSO₄ and then purified by column chromatography to afford the bicyclic iodo-derivative 82 (300 mg, 40%). $^1$H NMR (500 MHz, CDCl₃) δ 6.28 (s, 2H), 5.19 (s, 2H), 3.95 (t, J=7.81 Hz, 1H), 3.51 (dd, J=19.04, 7.81 Hz, 1H), 3.15 (t, J=6.84 Hz, 2H), 2.61-2.68 (m, 1H), 2.56-2.61 (m, 1H), 2.49-2.55 (m, 1H), 2.43-2.48 (m, 1H), 2.28-2.35 (m, 1H), 1.75 (m, 2H), 1.44-1.57 (m, 2H), 1.36 (s, 3H), 1.28-1.35, (m, 2H), 1.21-1.25 (m, 2H), 1.20 (s, 6H), 1.02-1.13 (m, 2H), 0.99 (s, 3H); MS (ESI⁺) for m/z 499 (M+H).

Step 3: (1R,4R,5R)-4-(2,6-dihydroxy-4-(8-iodo-2-methyloctan-2-yl)phenyl)-6,6-dimethylbicyclo[3.1.1]heptan-2-one obtained from the previous step (82, 250 mg, 0.5 mmol) is taken in acetonitrile (20 ml) and to it silver nitrate (126 mg, 0.75 mmol) is added and the contents are heated to 70° C. for 1 hour. The solvent are evaporated in vacuo and the residue taken in DCM (25 ml), washed with water (2×25 ml), dried over MgSO₄ and the solvent evaporated in vacuo and the residue purified by column chromatography to afford to obtain the bicyclic nitrateester derivative, 7-(4-((1R,2R,5R)-6,6-dimethyl-4-oxobicyclo[3.1.1]heptan-2-yl)-3,5-dihydroxyphenyl)-7-methyloctyl nitrate (Compound 83, 120 mg, 55%). $^1$H NMR (500 MHz, CDCl₃) δ 6.27 (s, 2H), 5.10 (s, 2H), 4.41 (t, J=6.59 Hz, 2H), 3.94 (t, J=8.06 Hz, 1H), 3.50 (dd, J=18.56, 7.81 Hz, 1H), 2.61-2.67 (m, 1H), 2.57-2.61 (m, 1H), 2.49-2.55 (m, 1H), 2.42-2.48 (m, 1H), 2.31 (t, J=5.37 Hz, 1H), 1.62-1.70 (m, 2H), 1.46-1.55 (m, 2H), 1.36 (s, 3H), 1.34 (m., 2H), 1.21-1.28 (m, 2H), 1.20 (s, 6H), 1.03-1.13 (m, 2H), 1.00 (s, 3H); MS (ESI⁺) for m/z 434 (M+H).

Step 4: Compound 83 (120 mg, 0.28 mmol) is dissolved in a 3:1 mixture of dry DCM and nitromethane (20 mL) and, and the solution is cooled to 0° C. To this is added trimethylsilyl triflate as a 0.29M solution in nitromethane (0.34 mL, 0.1 mmol) was added dropwise (procedures adopted from J. Med. Chem. 1996, 39, 3790-3796 and Chem. Commun., 1996, 2085-2086; herein incorporated by reference in its entirety). Stirring is continued for 2 h while the temperature is allowed to rise to 25° C. The reaction is quenched with saturated aqueous NaHCO₃/brine (1:1) and 60 mL of ether is added and the contents stirred, and the organic layer is separated. The aqueous layer is extracted again with DCM (25 ml), the combined organic extracts washed with water (2×25 ml), dried over MgSO₄ and the solvent evaporated in vacuo and the residue purified by column chromatography to afford to obtain
the nabilone nitrate ester, 7-((6aR,10aR)-1-hydroxy-6,6-dimethyl-9-oxo-6a,7,8,9,10,10a-hexahydro-6H-benzo[c]chromen-3-yl)-7-methyloctyl nitrate (Compound 83, 65 mg, 54%). $^1$H NMR (500 MHz, CDCl₃) δ 6.37 (d, J=1.46 Hz, 1H), 6.29 (d, J=1.47 Hz, 1H), 6.25 (s, 1H), 4.40 (t, J=6.84 Hz, 2H), 4.02 (d, J=14.16 Hz, 1H), 2.83-2.95 (m, 1H), 2.57-2.69 (m, 1H), 2.41-2.53 (m, 1H), 2.10-2.24 (m, 2H), 1.91-2.04 (m, 1H), 1.60-1.70 (m, 2H), 1.50-1.60 (m, 3H), 1.48 (s, 3H), 1.28-1.40 (m, 2H) 1.23-1.28 (m, 2H), 1.21 (s, 6H), 1.13 (s, 3H), 1.08 (dt, J=7.81, 3.91 Hz, 2H); MS (ESI⁺) for m/z 434 (M+H).

Example 18: Synthesis of Compound 87

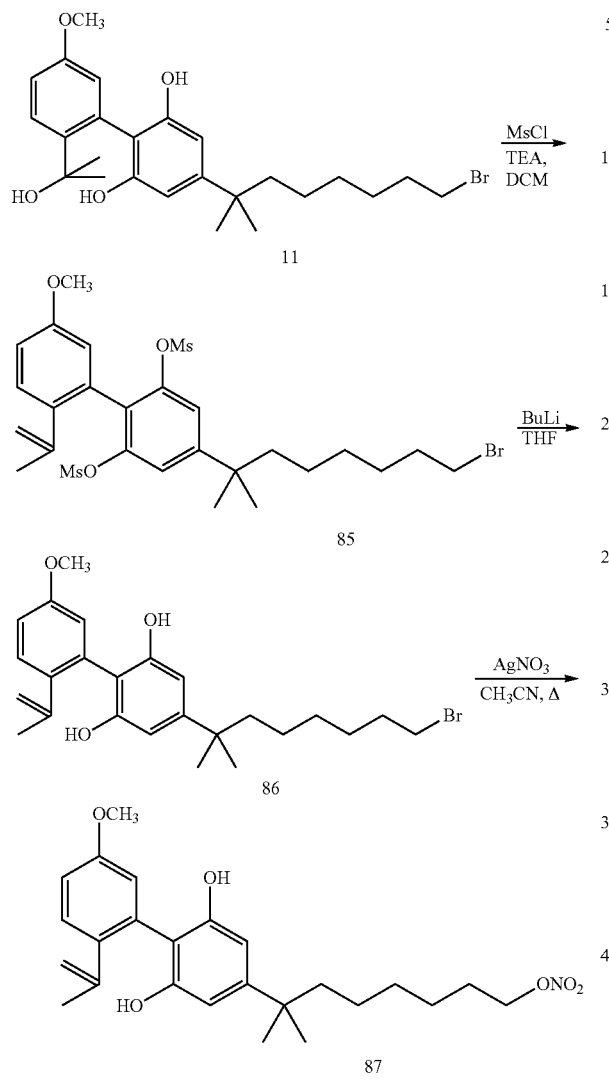

Step 1: To a solution of 4-(8-bromo-2-methyloctan-2-yl)-2'-(2-hydroxypropan-2-yl)-5'-methoxy-[1,1'-biphenyl]-2,6-diol (11, 1.0 mmol) obtained from scheme 2, in DCM at 0° C. is added triethylamine (4 mmol) then methanesulfonyl chloride (3 mmol) dropwise. The mixture is allowed to stir for 75 min at 0° C. then diluted with H$_2$O and Et$_2$O and the layers are separated. The aqueous layer is extracted with 2×Et$_2$O, and the combined organic extracts are washed with water (2×25 ml), dried over MgSO$_4$, the solvents are evaporated in vacuo and the residue is purified by column chromatography to product 85 (procedures adopted from *Org. Lett.*, 2008, 10 (11), pp 2195-2198; herein incorporated by reference in its entirety).

Step 2: To a solution of 4-(8-bromo-2-methyloctan-2-yl)-5'-methoxy-2'-(prop-1-en-2-yl)-[1,1'-biphenyl]-2,6-diyl dimethanesulfonate (85, 1 mmol) in THF is added MeLi (1.6 M in Et$_2$O, 10 mmol) dropwise at 0° C. The reaction is stirred for 30 minutes and then quenched with 10% NH$_4$Cl. The aqueous layer is extracted with 3×Et$_2$O and the combined organic extracts are washed with water (2×25 ml), dried over MgSO$_4$, the solvents are evaporated in vacuo and the residue is purified by column chromatography to product 86 (procedures adopted from *Org. Lett.*, 2008, 10 (11), pp 2195-2198; herein incorporated by reference in its entirety).

Step 3: 4-(8-bromo-2-methyloctan-2-yl)-5'-methoxy-2'-(prop-1-en-2-yl)-[1,1'-biphenyl]-2,6-diol (86, 1 mmol) is taken in acetonitrile (20 ml) and to it silver nitrate (1.28 mmol) is added and the contents are heated to 70° C. for 1 hour. The solvents are evaporated in vacuo and the residue is taken in DCM (25 ml), washed with water (2×25 ml), dried over MgSO$_4$, the solvents are evaporated in vacuo and the residue is purified by column chromatography to afford 7-(2,6-dihydroxy-5'-methoxy-2'-(prop-1-en-2-yl)-[1,1'-biphenyl]-4-yl)-7-methyloctyl nitrate (compound 87).

Example 19: Synthesis of Compound 88

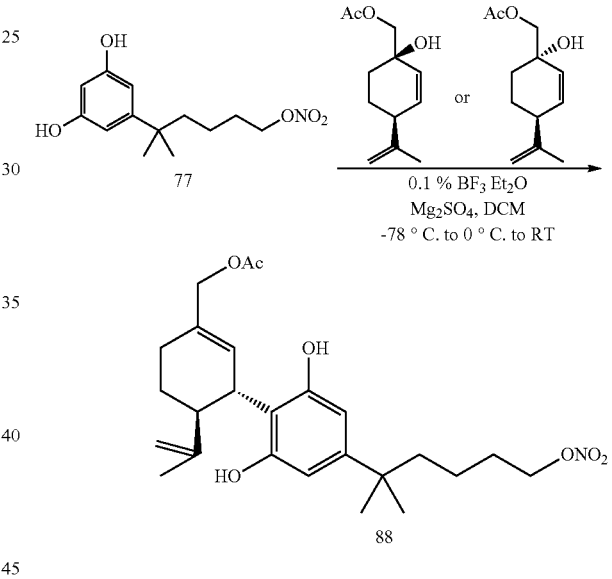

To a solution of 5-(3,5-dihydroxyphenyl)-5-methylhexyl nitrate (16.0 mmol, prepared as in example 16) in 100 ml DCM is added (1R,4S) or (1S,4S) 1-hydroxy-4-(prop-1-en-2-yl)cyclohex-2-en-1-yl)methyl acetate (16.1 mmol, prepared as in ProQuest Ph.D Dissertation 8902359, 1988, 120 p; herein incorporated by reference in its entirety) and 2 g of anhydrous Mg$_2$SO$_4$ under an atmosphere of N$_2$. The contents are cooled to 0° C. and then 0.1% BF$_3$.Et$_2$O is added. The mixture is stirred for 3 hr at room temperature and 5 g of anhydrous NaHCO$_3$ is then added. Stirring is continued until the reaction mixture is colorless. The reaction contents are filtered, the filtrate is evaporated in vacuo and the residue is purified by column chromatography to afford ((1S,6S)-2',6'-dihydroxy-4'-(2-methyl-6-(nitrooxy)hexan-2-yl)-6-(prop-1-en-2-yl)-1,4,5,6-tetrahydro-[1,1'-biphenyl]-3-yl)methyl acetate (compound 88) (procedures adopted from *J. Am. Chem. Soc.*, 1974, 96 (18), pp 5860-5865 and *Tetrahedron Letters* 54 (2013) 52-54; each herein incorporated by reference in its entirety).

Example 20: Synthesis of Compound 91

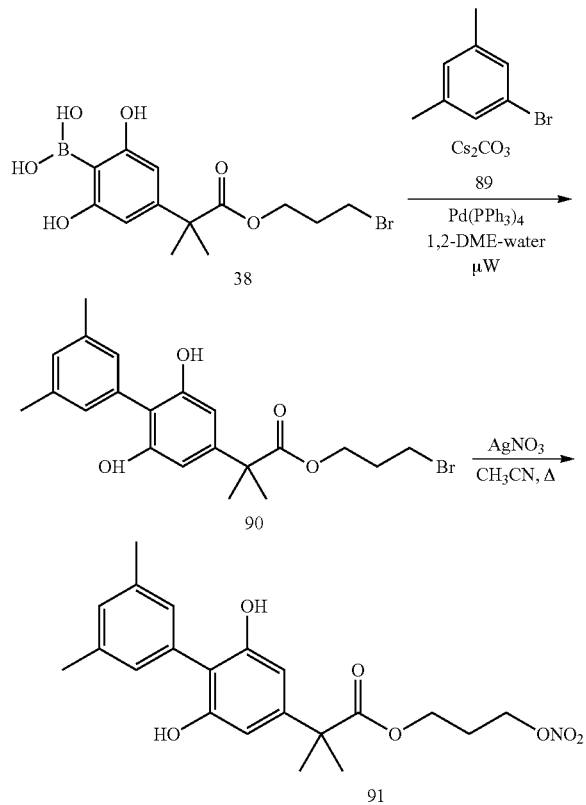

Step 1: A solution of methyl 1-bromo-3,5-dimethylbenzene (89, 0.5 mmol), (4-(1-(3-bromopropoxy)-2-methyl-1-oxopropan-2-yl)-2,6-dihydroxyphenyl)boronic acid (38, 0.65 mmol), cesium carbonate (2 mmol) in a mixture of dimethoxyethane (5 mL) and water (0.75 mL) is degassed with argon for 5 minutes. Tetrakis(triphenylphosphine)-palladium (0) (10 mol %) is added, the reaction tube is sealed. The reaction is heated in a microwave (Emrys optimizer from Personal Chemistry) at 125° C. (power 300 W) for 15 minutes. After cooling, the reaction mixture is diluted with water (30 mL), acidified to pH 5, extracted with DCM (2×15 mL). The combined organic layers are passed through a phase separator and concentrated in vacuo. The residue is purified with WATERS preparative LC/MS autopurification system to afford the title compound 90 (procedures adopted from *J. Comb. Chem.* 2010, 12, 664-669; herein incorporated by reference in its entirety).

Step 2: 3-bromopropyl 2-(2,6-dihydroxy-3',5'-dimethyl-[1,1'-biphenyl]-4-yl)-2-methylpropanoate (90, 1 mmol) is taken in acetonitrile (20 ml) and to it silver nitrate (1.28 mmol) is added and the contents are heated to 70° C. for 1 hour. The solvent is evaporated in vacuo and the residue is taken in DCM (25 ml), washed with water (2×25 ml), dried over MgSO4 and then purified by column chromatography to afford the title compound 3-(nitrooxy)propyl 2-(2,6-dihydroxy-3',5'-dimethyl-[1,1'-biphenyl]-4-yl)-2-methylpropanoate (compound 91).

Example 21: Synthesis of Compound 95

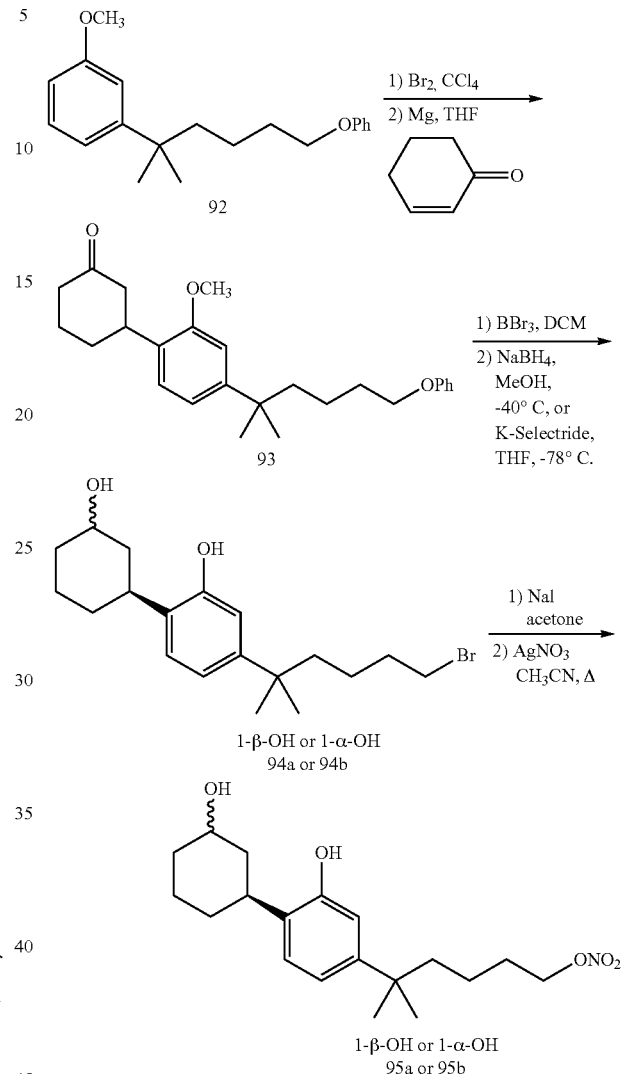

Step 1: To a stirred solution of 1-methoxy-3-(2-methyl-6-phenoxyhexan-2-yl)benzene (92, 6.35 mmol) (prepared as in *Bioorganic & Medicinal Chemistry* 15 (2007) 7850-7864 and procedures adopted from *J. Med. Chem.* 1984, 27, 67-71; herein incorporated by reference in its entirety) in AcOH (30 ml) is added $Br_2$ (12.7 mmol) in AcOH (10 ml) dropwise at room temperature. The mixture is stirred for 4 h at the same temperature. Then, the reaction mixture is quenched with 10% aqueous $Na_2S_2O_3$ and extracted with 1×25 ml $Et_2O$, washed with 1×25 ml $H_2O$, the organic extract is washed with 1×25 ml brine, dried over $MgSO_4$, and concentrated in vacuo. The residue is chromatographed to give the brominated product.

Step 2: A solution of 1-bromo-2-methoxy-4-(2-methyl-6-phenoxyhexan-2-yl)benzene (0.193 mol) in 200 mL of THF is slowly added to magnesium turnings (0.386 mol). The resultant mixture is refluxed for 20 min and then cooled to −18° C. CuI (9.7 mmol) is added, and stirring is continued for 10 min. To the resultant mixture is slowly added a solution of 2-cyclohexen-1-one (0.193 mol) in 40 mL of THF at such a rate that the reaction temperature is maintained at <−3° C. The reaction is stirred 30 min and then added to 500 mL of 2N HCl and 2 L of ice-water. The mixture is extracted 3× 50 mL ether and the combined extract is washed with 2×100 mL of water, 2×100 mL of saturated NaCl, dried over MgSO₄, and evaporated in vacuo. The residue is purified via column chromatography to give the product 93.

Step 3: To a solution of 3-(2-methoxy-4-(2-methyl-6-phenoxyhexan-2-yl)phenyl)cyclohexanone (93, 1 mmol) in anhydrous DCM (15 mL), is added boron tribromide (1.2 mmol) at −78° C. under nitrogen atmosphere. The resulting solution is stirred for 15 minutes at −78° C. The cooling bath is removed and the reaction mixture is continued to stir for 30 minutes at room temperature. The reaction is quenched with anhydrous methanol (1 mL) at 0° C., washed with water and the organics are dried with MgSO₄ and filtered through celite. The solvent is removed in vacuo and the residue is purified by column chromatography on silica gel to give the bromo phenol intermediate.

Step 4: To a solution of 3-(4-(6-bromo-2-methylhexan-2-yl)-2-hydroxyphenyl)cyclohexanone (0.09 mmol) in 4.5 mL THF and 500 μL i-PrOH at rt is added NaBH₄ (0.14 mmol). The resulting reaction mixture is stirred at room temperature for 40 min and quenched with water and extracted with 3×Et₂O. The combined organic extracts are dried over MgSO₄, solvent is removed in vacuo and the residue is purified by flash column chromatography on silica gel to afford the 1-β-hydroxy compound 94a.

Alternatively, to a solution of 3-(4-(6-bromo-2-methyl-hexan-2-yl)-2-hydroxyphenyl)-cyclohexanone (0.16 mmol) in 1 mL of THF at −78° C. is added of 1.0 M potassium tri-sec-butylborohydride (K-Selectride, 0.32 mmol) in THF. The reaction mixture is stirred at −78° C. for 2 h, allowed to warm to room temperature and stirred for 1 h. The reaction is quenched with 1 mL of water and 5 mL of ethanol followed by 2 ml of 15% aqueous NaOH and 2 mL of 30% water. After extraction with Et₂O, the combined extracts are washed with brine and dried over MgSO₄, solvent is removed in vacuo and the residue is purified by flash column chromatography on silica gel to afford the 1-α-hydroxy compound 94b.

Step 5: To a flask containing the 1-α or the 1-β isomer of 5-(6-bromo-2-methylhexan-2-yl)-2-((1S)-3-hydroxycyclohexyl)phenol (94, 0.71 mmol) is added sodium iodide (320 mg, 2.13 mmol) and acetone (25 ml) and the contents are refluxed for 3 hours. The solvent is evaporated in vacuo and the residue taken in DCM (25 ml), washed with water (2×25 ml), dried over MgSO₄ and then purified by column chromatography to afford the iodo compound.

Step 6: 2-((1S)-3-hydroxycyclohexyl)-5-(6-iodo-2-methylhexan-2-yl)phenol is taken in acetonitrile (20 ml) and to it silver nitrate (217 mg, 1.28 mmol) is added and the contents are heated to 70° C. for 1 hour. The solvent is evaporated in vacuo and the residue is taken in DCM (25 ml), washed with water (2×25 ml), dried over MgSO₄ and then purified by column chromatography to afford 5-(3-hydroxy-4-((1S,3R)-3-hydroxycyclohexyl)phenyl)-5-methylhexyl nitrate (Compound 95a) or 5-(3-hydroxy-4-((1S,3S)-3-hydroxycyclohexyl)phenyl)-5-methylhexyl nitrate (Compound 95b).

Example 22: Synthesis of Compound 98

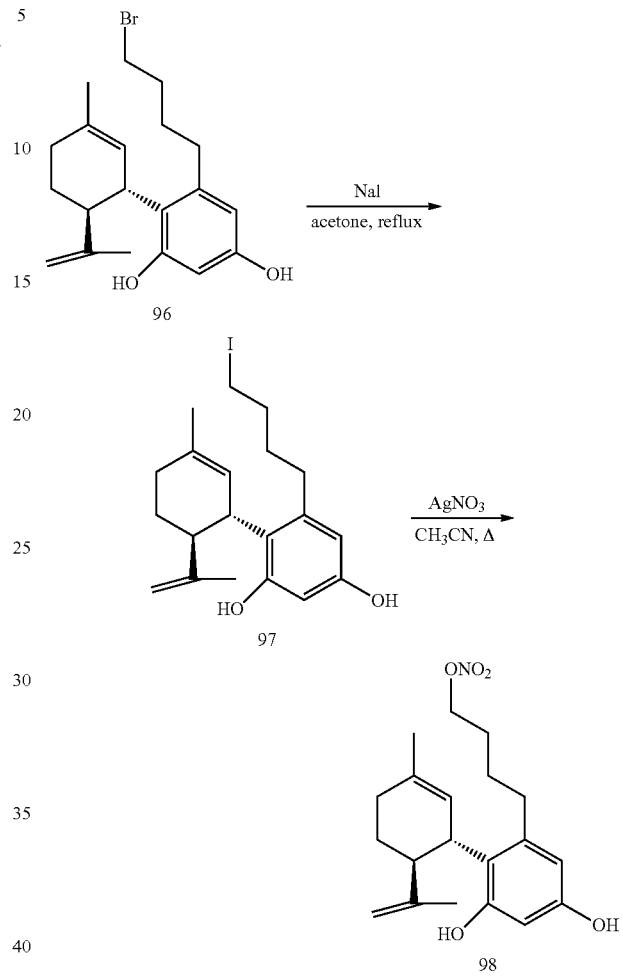

Step 1: To a flask containing the 5-(4-bromobutyl)-4-[(1R, 6R)-3-methyl-6-(1-methylethenyl)-2-cyclohexen-1-yl]-1,3-benzenediol (prepared as in *J. Label Compd. Radiopharm* 2011, 54 180-184; herein incorporated by reference in its entirety) (96, 0.71 mmol) is added sodium iodide (2.13 mmol) and acetone (25 ml) and the contents are refluxed for 3 hours. The solvent is evaporated in vacuo and the residue is taken in DCM (25 ml), washed with water (2×25 ml), dried over MgSO₄ and then purified by column chromatography to afford the iodo compound.

Step 2: (1'S,2'S)-6-(4-iodobutyl)-5'-methyl-2'-(prop-1-en-2-yl)-F,2',3',4'-tetrahydro-[1,1'-biphenyl]-2,4-diol (97, 1 mmol) is taken in acetonitrile (20 ml) and to it silver nitrate (1.28 mmol) is added and the contents are heated to 70° C. for 1 hour. The solvents are evaporated in vacuo and the residue is taken in DCM (25 ml), washed with water (2×25 ml), dried over MgSO₄, the solvents are evaporated in vacuo and the residue is purified by column chromatography to afford 4-((1'S,2'S)-4,6-dihydroxy-5'-methyl-2'-(prop-1-en-2-yl)-1',2',3',4'-tetrahydro-[1,1'-biphenyl]-2-yl)butyl nitrate (compound 98).

Example 23: Synthesis of Compound 100

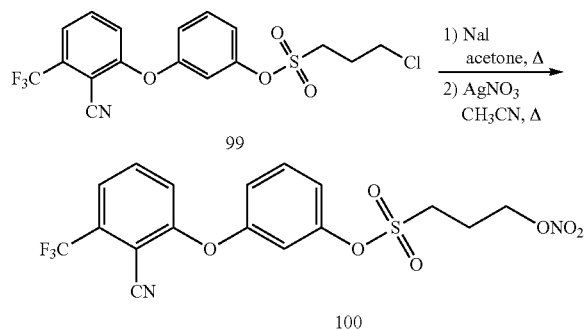

Step 1: To a flask containing the 3-(2-cyano-3-(trifluoromethyl)phenoxy)phenyl 3-chloropropane-1-sulfonate (prepared as in ProQuest Ph.D Dissertation 3468427, 2011, 207 p and procedures adopted from WO 2002026702; each herein incorporated by reference in its entirety) (99, 0.71 mmol) is added sodium iodide (2.13 mmol) and acetone (25 ml) and the contents are refluxed for 3 hours. The solvent is evaporated in vacuo and the residue taken in DCM (25 ml), washed with water (2×25 ml), dried over MgSO$_4$ and then purified by column chromatography to afford the iodo compound.

Step 2: (1'S,2'S)-6-(4-iodobutyl)-5'-methyl-2'-(prop-1-en-2-yl)-1',2',3',4?-tetrahydro-[1,1'-biphenyl]-2,4-diol (97, 1 mmol) is taken in acetonitrile (20 ml) and to it silver nitrate (1.28 mmol) is added and the contents are heated to 70° C. for 1 hour. The solvents are evaporated in vacuo and the residue is taken in DCM (25 ml), washed with water (2×25 ml), dried over MgSO$_4$, the solvents are evaporated in vacuo and the residue is purified by column chromatography to afford 3-(2-cyano-3-(trifluoromethyl)phenoxy)phenyl 3-(nitrooxy)propane-1-sulfonate (compound 100).

Example 24: Synthesis of Compound 103

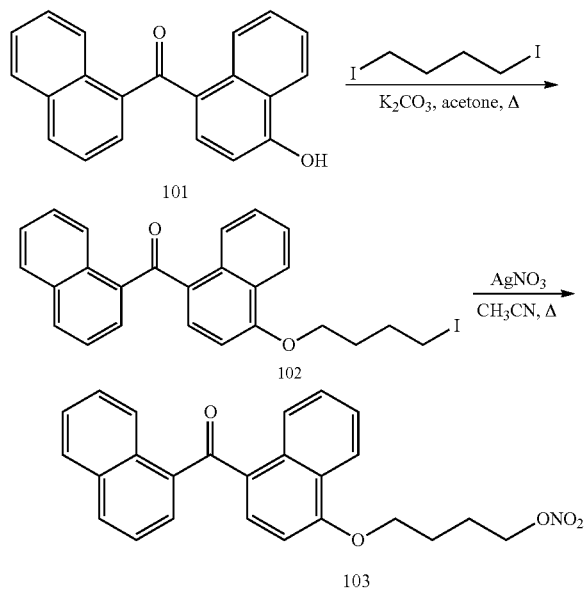

Step 1: To a flask containing 4-hydroxynaphthalen-1-yl)(naphthalen-1-yl)methanone (101, 10 mmol, prepared as in WO 2002/042248; herein incorporated by reference in its entirety) taken in 100 ml of acetone is added 1,4-diiodobutane (20 mmol) and potassium carbonate (20 mmol), and the mixture is refluxed 24 h. The solvent is evaporated in vacuo and the residue is taken in DCM (25 ml), washed with water (2×25 ml), dried over MgSO$_4$, the solvents are evaporated in vacuo and the residue again is purified by column chromatography to afford the desired O-alkylated compound 102.

Step 2: (4-(4-iodobutoxy)naphthalen-1-yl)(naphthalen-1-yl)methanone (102, 1 mmol) is taken in acetonitrile (20 ml) and to it silver nitrate (1.28 mmol) is added and the contents are heated to 70° C. for 1 hour. The solvents are evaporated in vacuo and the residue is taken in DCM (25 ml), washed with water (2×25 ml), dried over MgSO$_4$, the solvents are evaporated in vacuo and the residue again is purified by column chromatography to afford 4-((4-(1-naphthoyl)naphthalen-1-yl)oxy)butyl nitrate (compound 103).

Example 25: Synthesis of Compound 106

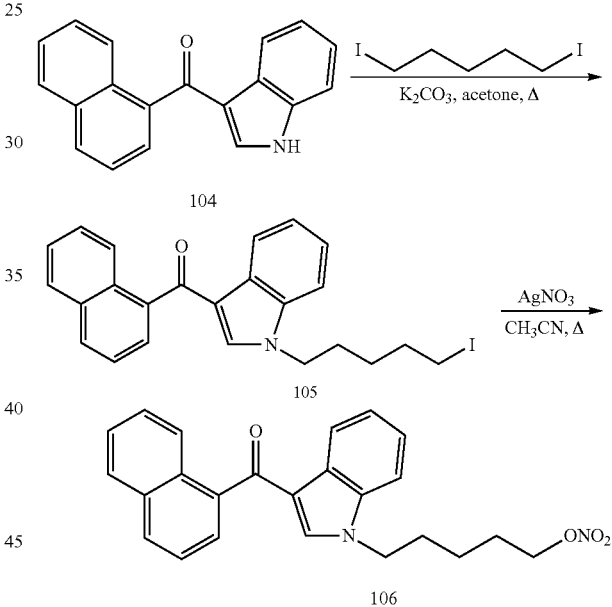

Step 1: To a flask containing 4 (1H-indol-3-yl)(naphthalen-1-yl)methanone (104, 10 mmol) taken in 100 ml of acetone is added 1,4-diiodopentane (20 mmol) and potassium carbonate (20 mmol), and the mixture is refluxed 24 h. The solvent is evaporate in vacuo and the residue is taken in DCM (25 ml), washed with water (2×25 ml), dried over MgSO$_4$, the solvents are evaporated in vacuo and the residue again is purified by column chromatography to afford the desired N-alkylated compound 105.

Step 2: (1-(5-iodopentyl)-1H-indol-3-yl)(naphthalen-1-yl)methanone (105, 1 mmol) is taken in acetonitrile (20 ml) and to it silver nitrate (1.28 mmol) is added and the contents are heated to 70° C. for 1 hour. The solvents are evaporated in vacuo and the residue is taken in DCM (25 ml), washed with water (2×25 ml), dried over MgSO$_4$, the solvents are evaporated in vacuo and the residue again is purified by column chromatography to afford 5-(3-(1-naphthoyl)-1H-indol-1-yl)pentyl nitrate (compound 106).

Example 26: Synthesis of Compound 109

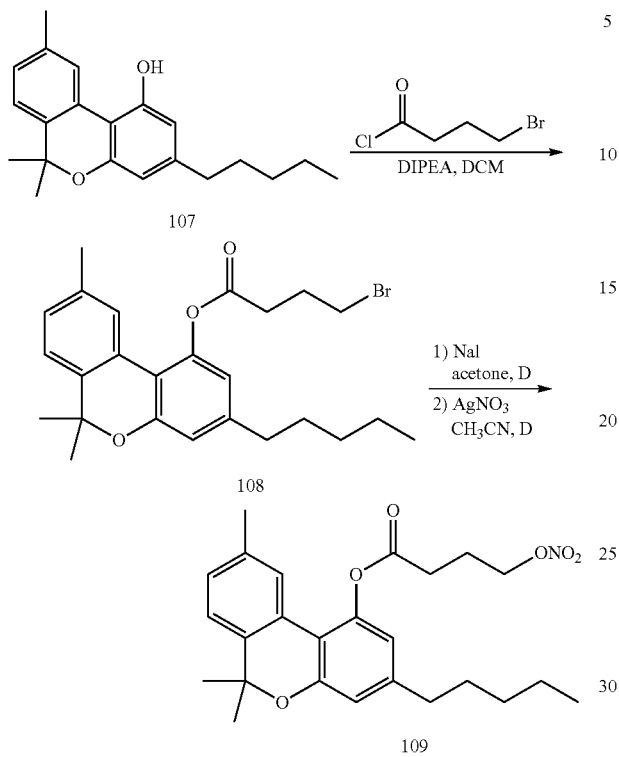

Step 1: To a mixture of 6,6,9-trimethyl-3-pentyl-6H-benzo[c]chromen-1-ol (107, 12.8 mmol) and DIPEA (14.08 mmol) in 100 mL dry DCM at 0° C. is added dropwise a solution of 4-bromobutyryl chloride (12.8 mmol) taken in 20 mL dry DCM under an inert atmosphere. The reaction mixture is allowed to warm up to ambient temperature. After stirring for 16 h, water and DCM were added. The two layers were separated and the organic layer is dried over $MgSO_4$, the solvents are evaporated in vacuo and the residue is purified by column chromatography to afford the bromo derivative 108.

Step 2: To a flask containing the 6,6,9-trimethyl-3-pentyl-6H-benzo[c]chromen-1-yl 4-bromobutanoate (108, 0.71 mmol) is added sodium iodide (2.13 mmol) and acetone (25 ml) and the contents are refluxed for 3 hours. The solvent is evaporated in vacuo and the residue taken in DCM (25 ml), washed with water (2×25 ml), dried over $MgSO_4$ and then purified by column chromatography to afford the iodo intermediate.

Step 3: 6,6,9-trimethyl-3-pentyl-6H-benzo[c]chromen-1-yl 4-iodobutanoate (1 mmol) from the previous step is taken in acetonitrile (20 ml) and to it silver nitrate (1.28 mmol) is added and the contents are heated to 70° C. for 1 h. The solvents are evaporated in vacuo and the residue is taken in DCM (25 ml), washed with water (2×25 ml), dried over $MgSO_4$, the solvents are evaporated in vacuo and the residue again is purified by column chromatography to afford 6,6,9-trimethyl-3-pentyl-6H-benzo[c]chromen-1-yl 4-(nitrooxy)butanoate (compound 109). $^1H$ NMR (500 MHz, $CDCl_3$) δ 7.73 (s, 1H), 7.12-7.18 (m, 1H), 7.05-7.12 (m, 1H), 6.73 (s, 1H), 6.56 (s, 1H), 4.53 (t, J=6.35 Hz, 2H), 2.75 (t, J=7.32 Hz, 2H), 2.57 (t, J=7.81 Hz, 2H), 2.36 (s, 3H), 2.15 (t, J=6.59 Hz, 2H), 1.61-1.66 (m, 2H), 1.60 (s, 6H), 1.28-1.38 (m, 4H), 0.86-0.94 (m, 3H); MS ($ESI^+$) for m/z 442 (M+H).

Example 27: Synthesis of Compound 112

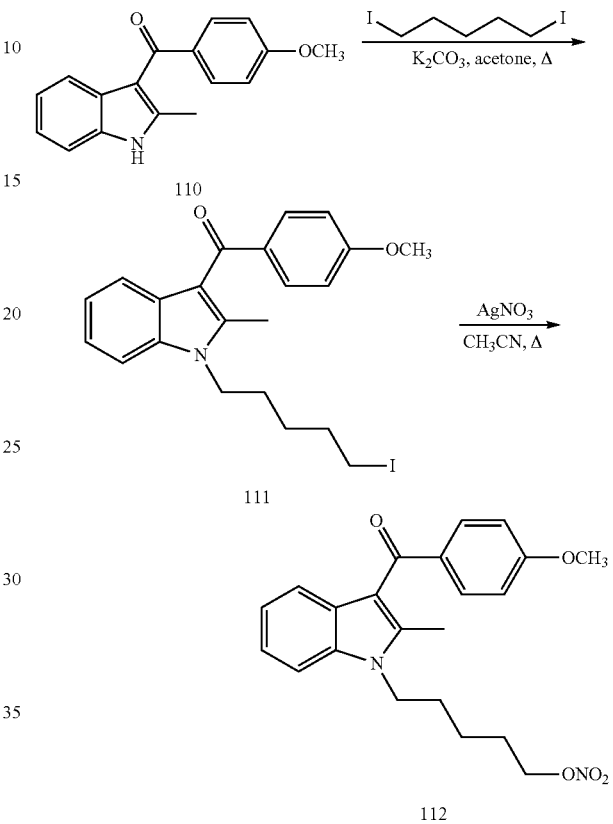

Step 1: To a flask containing (4-methoxyphenyl)(2-methyl-1H-indol-3-yl)methanone (110, prepared as in *J. Med. Chem.* 1991,34, 1099-1110, herein incorporated by reference in its entirety) (10 mmol) taken in 100 ml of acetone is added 1,4-diiodopentane (20 mmol) and potassium carbonate (20 mmol), and the mixture is refluxed 24 h. The solvent is evaporate in vacuo and the residue is taken in DCM (25 ml), washed with water (2×25 ml), dried over $MgSO_4$, the solvents are evaporated in vacuo and the residue again is purified by column chromatography to afford the desired N-alkylated compound 111.

Step 2: (1-(5-iodopentyl)-2-methyl-1H-indol-3-yl)(4-methoxyphenyl)methanone (111, 1 mmol) is taken in acetonitrile (20 ml) and to it silver nitrate (1.28 mmol) is added and the contents are heated to 70° C. for 1 h. The solvents are evaporated in vacuo and the residue is taken in DCM (25 ml), washed with water (2×25 ml), dried over $MgSO_4$, the solvents are evaporated in vacuo and the residue again is purified by column chromatography to afford 5-(3-(4-methoxybenzoyl)-2-methyl-1H-indol-1-yl)pentyl nitrate (compound 112). $^1H$ NMR (500 MHz, $CDCl_3$) δ 7.79 (d, J=8.79 Hz, 2H), 7.32 (dd, J=14.89, 8.06 Hz, 2H), 7.20 (t, J=7.57 Hz, 1H), 7.03-7.11 (m, 1H), 6.94 (d, J=8.79 Hz, 2H), 4.45 (t, J=6.35 Hz, 2H), 4.18 (t, J=7.32 Hz, 2H), 3.89 (s, 3H), 2.61 (s, 3H), 2.01 (s, 1H), 1.87 (t, J=7.81 Hz, 2H), 1.73-1.82 (m, 2H), 1.47-1.56 (m, 2H); MS ($ESI^+$) for m/z 397 (M+H).

Example 28: Synthesis of Compound 117

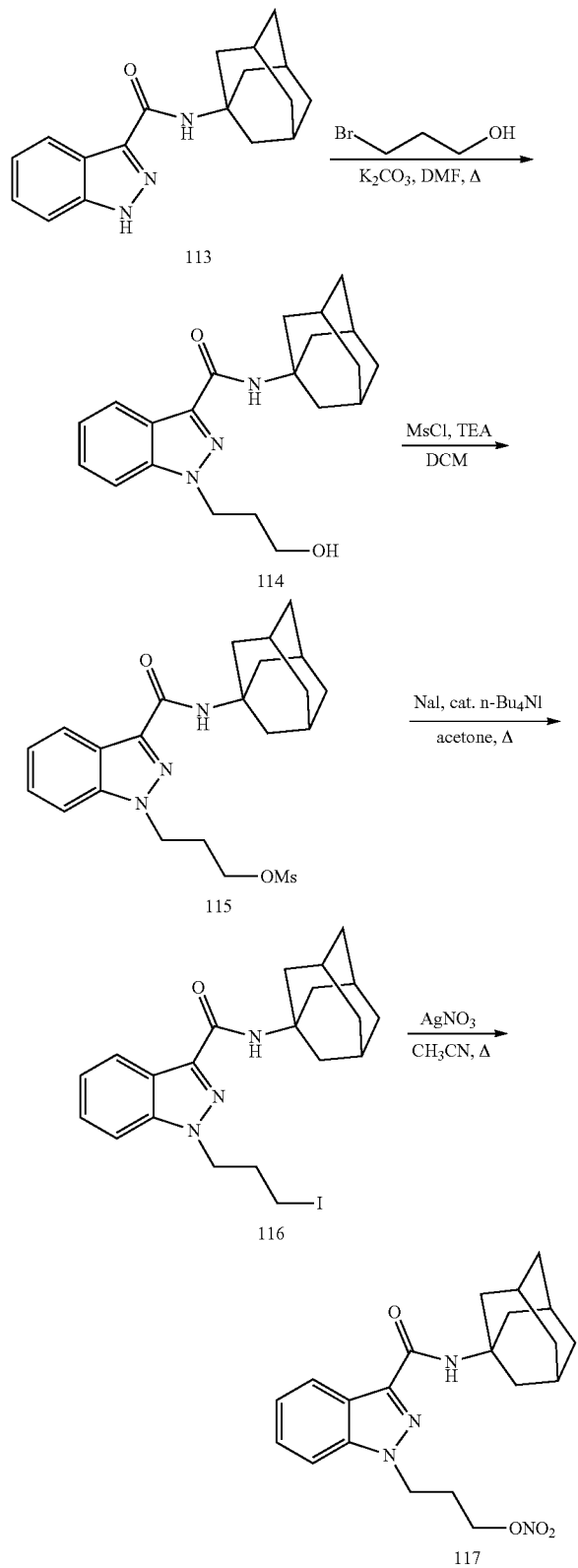

Step 1: To a magnetically stirred solution of N-((1s,3s)-adamantan-1-yl)-1H-indazole-3-carboxamide (113, prepared as in U.S. Pat. No. 7,666,867, herein incorporated by reference in its entirety) (0.51 mmol) in DMF at room temperature is added $K_2CO_3$ (1.1 mmol) and 3-bromopropan-1-ol (0.6 mmol). The resulting mixture is allowed to stir at 90° C. for 1 h. The DMF is evaporated under reduced pressure, and the residue is dissolved in DCM (25 ml), washed with water (2×25 ml), dried over $MgSO_4$, the solvents are evaporated in vacuo and the residue (compound 114) is taken directly to the next reaction.

Step 2: To a solution of N-((1 s,3s)-adamantan-1-yl)-1-(3-hydroxypropyl)-1H-indazole-3-carboxamide (114, 0.4 mmol) obtained from scheme 2, in DCM at 0° C. is added triethylamine (0.6 mmol) then methanesulfonyl chloride (0.5 mmol) dropwise. The mixture is allowed to stir for 75 min at 0° C. then diluted with $H_2O$ and $Et_2O$ and the layers are separated. The aqueous layer is extracted with $2 \times Et_2O$, and the combined organic extracts are washed with water (2×25 ml), dried over $MgSO_4$, the solvents are evaporated in vacuo and the residue is purified by column chromatography to product 115. $^1H$ NMR (500 MHz, $CDCl_3$) δ 8.39 (d, J=7.81 Hz, 1H), 7.42 (d, J=3.42 Hz, 2H), 7.26 (m, 1H), 6.82 (s, 1H), 4.19 (t, J=5.86 Hz, 2H), 2.94 (s, 3H), 2.39 (quin, J=6.10 Hz, 2H), 2.20 (br. s., 6H), 2.14 (br. s., 3H), 1.67-1.82 (m, 6H); MS (ESI') for m/z 432 (M+H).

Step 3: To a flask containing the 3-(3-(((1s,3s)-adamantan-1-yl)carbamoyl)-1H-indazol-1-yl)propyl methanesulfonate (115, 0.4 mmol) is added sodium iodide (2 mmol) and acetone (20 ml) and the contents are refluxed for 3 hours. The solvent is evaporated in vacuo and the residue taken in DCM (25 ml), washed with water (2×25 ml), dried over $MgSO_4$ and then purified by column chromatography to afford the iodo intermediate 116. $^1H$ NMR (500 MHz, $CDCl_3$) δ 8.39 (d, J=8.30 Hz, 1H), 7.47-7.52 (m, 1H), 7.39-7.46 (m, 1H), 7.28 (s, 1H), 6.78 (s, 1H), 4.49 (t, J=6.59 Hz, 2H), 3.12 (t, J=6.59 Hz, 2H), 2.46 (quin, J=6.47 Hz, 2H), 2.20 (s, 6H), 2.15 (br. s., 3H), 1.67-1.84 (m, 6H); MS (ESI$^+$) for m/z 464 (M+H).

Step 4: N-((1s,3s)-adamantan-1-yl)-1-(3-iodopropyl)-1H-indazole-3-carboxamide (116, 0.4 mmol) is taken in acetonitrile (20 ml) and to it silver nitrate (0.6 mmol) is added and the contents are heated to 70° C. for 1 h. The solvents are evaporated in vacuo and the residue is taken in DCM (25 ml), washed with water (2×25 ml), dried over $MgSO_4$, the solvents are evaporated in vacuo and the residue again is purified by column chromatography to afford 3-(3-(((1s,3s)-adamantan-1-yl)carbamoyl)-1H-indazol-1-yl)propyl nitrate (compound 117). $^1H$ NMR (500 MHz, $CDCl_3$) δ 8.40 (d, J=7.81 Hz, 1H), 7.35-7.47 (m, 2H), 7.27 (br. s., 1H), 6.75 (br. s., 1H), 4.50 (t, J=6.59 Hz, 2H), 4.42 (t, J=6.10 Hz, 2H), 2.38 (quin, J=6.23 Hz, 2H), 2.20 (s, 6H), 2.15 (br. s., 3H), 1.67-1.84 (m, 6H); MS (ESI$^+$) for m/z 399 (M+H).

Example 29: Membrane Preparations from Tissue Culture Sources

HEK293 cells expressing hCB1, hCB2 or mCB2 receptor are used for membrane preparations according to the method described in J Neurochem 1999, 72, (5), 2032-8, herein incorporated by reference in its entirety. The resulting pellet is resuspended in 10 mM Tris-chloride, pH 7.4 with 5 mM $MgCl_2$ and 2 mM EDTA (TME), and stored at −80° C. for no longer than two months. Protein content is assayed by using the Bio-Rad DC protein assay according to the manufacturer's protocol.

Example 30: Membrane Preparations from Tissue Sources

Frozen rat brains (CB1 source) are obtained from Pel-Freeze Biologicals (Rogers, Ak.) and stored at −80° C. until use. Membranes are prepared according to the method described in *Brain Res* 1981, 226, (1-2), 107-18 and adapted as previously reported in *J Med Chem* 1994, 37, (23), 3867-70 and *Life Sci* 1995, 56, (23-24), 1957-62; each herein incorporated by reference in its entirety.

Example 31: rCB1, hCB2, and mCB2 Binding Assays

Figure 3:
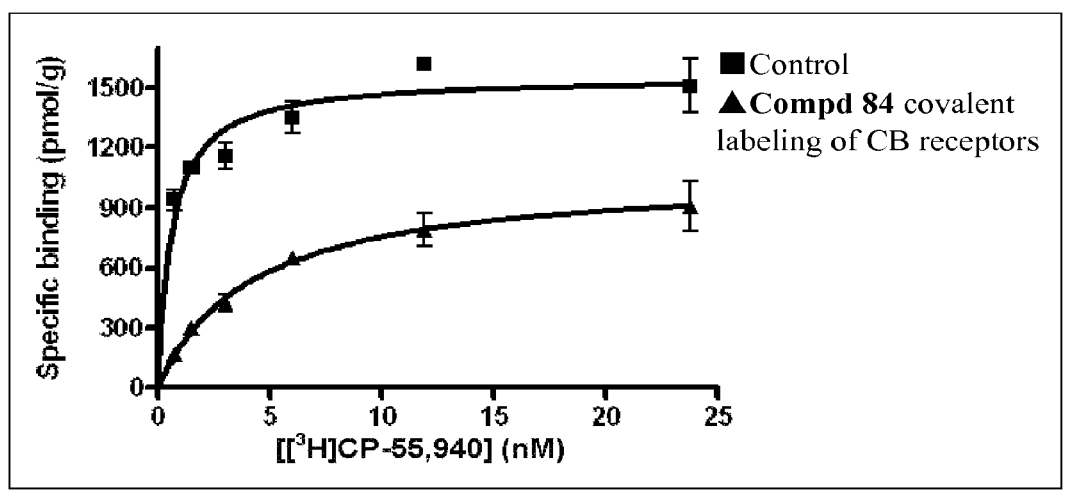
FIG. 3 illustrates covalent binding of compound 84 to rCB1.
Figure 4:
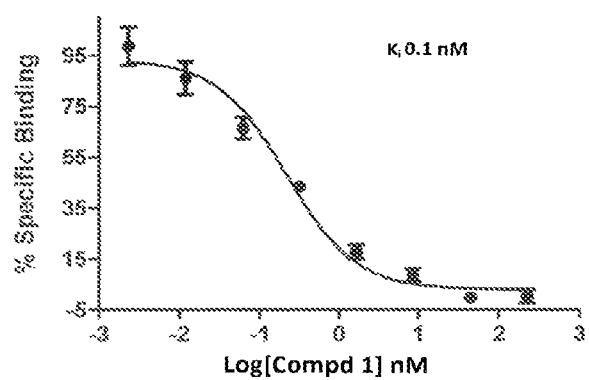
FIG. 4 illustrates rCB1 competition binding for compound 1.
Figure 5:
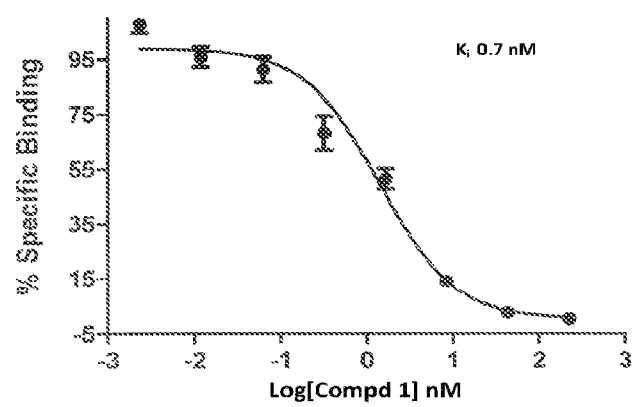
FIG. 5 illustrates mCB2 competition binding for compound 1.
Figure 6:
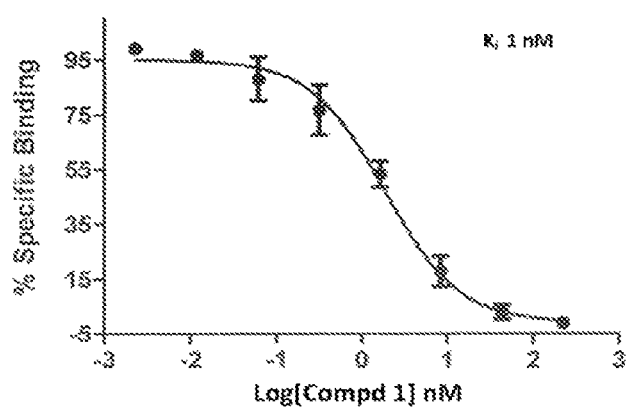
FIG. 6 illustrates hCB2 competition binding for compound 1.

The compounds are tested for their ability to bind to CB1 and CB2 receptors using rat brain or HEK293 cell membranes expressing hCB2 and mCB2 membrane preparations, respectively, as described in *J Med Chem* 1999, 42, (4), 769-776, *J Med Chem* 1994, 37, (23), 3867-70 and *Life Sci* 1995, 56, (23-24), 1957-62 (each herein incorporated by reference in its entirety) via competition-equilibrium binding using [$^3$H]CP-55,940. The results are analyzed using nonlinear regression to determine the actual $IC_{50}$ of the ligand (Prizm by GraphPad Software, Inc.) and the Ki values are calculated from the $IC_{50}$ as described in *Biochemical Pharmacology* 1973, 22, (23), 3099-3108; herein incorporated by reference in its entirety. For example, the rCB1 affinity data for $\Delta^8$-THC, $\Delta^9$-THC, compound 1 and compound 78 are 47 nM, 39 nM, 0.1 nM and 60 nM respectively; and the hCB2 affinity data for $\Delta^8$-THC, $\Delta^9$-THC, compound 1 and compound 78 are 39 nM, 40 nM, 1 nM and 35 nM respectively. Competition binding for Compound 1 in rCB1, mCB2 and hCB2 are shown in FIGS. 3, 4 and 5, respectively

Example 32: Covalent Binding Assessment Assay and Electrophilic Labeling

Figure 2:
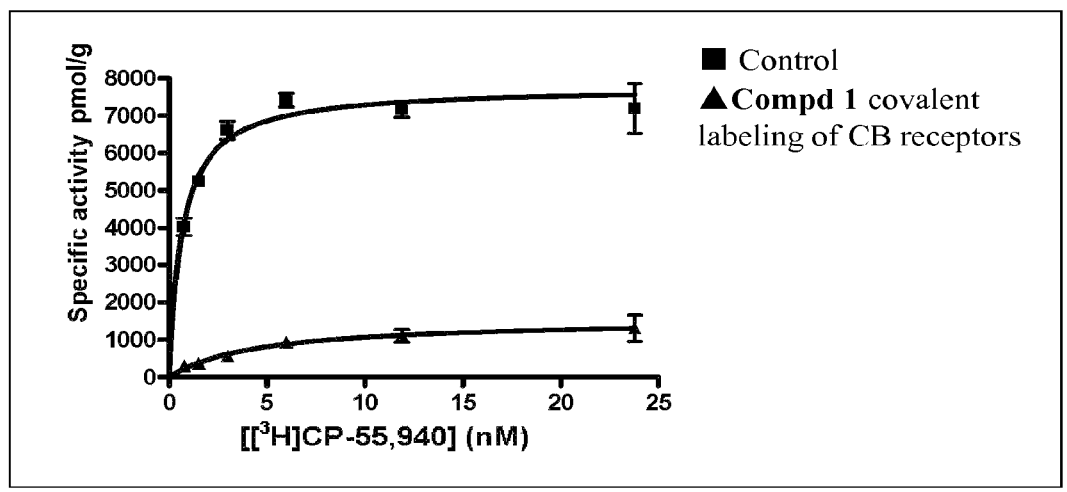
FIG. 2 illustrates covalent binding of compound 1 to hCB2.

The electrophilic covalent ligand possessing sufficiently high affinities for the receptors in the competition binding assays are evaluated for their abilities to irreversibly occupy CB1 and/or CB2 receptor sites using similar methods described in *J Proteome Res.* 2011, 10(10):4789-98, *Chem Biol.* 2010, 17(10):1132-42, *Chem Biol.* 2008, 5(11):1207-19, *Mol Pharm*, 2005, 68(6), 1623-1635, *J Med Chem.* 2005, 48(20):6423-9, *J. Org. Chem.* 2003, 68 (1), 55-61, *J Neurochem.* 2000, 74(5):2174-81), *Life Sci.* 1995, 56(23-24): 1957-62, *J. Med. Chem.* 1994, 37 (23), 3867-3870, *J Med. Chem.* 1992, 35 (16), 3076-3079; each herein incorporated by reference in its entirety. For example, the covalent binding for Compound 1 to hCB2 is shown in FIG. 2 and the covalent binding for Compound 84 to rCB1 is shown in FIG. 3.

Example 33: Signal Transduction Assays (cAMP Assay)

Figure 7:
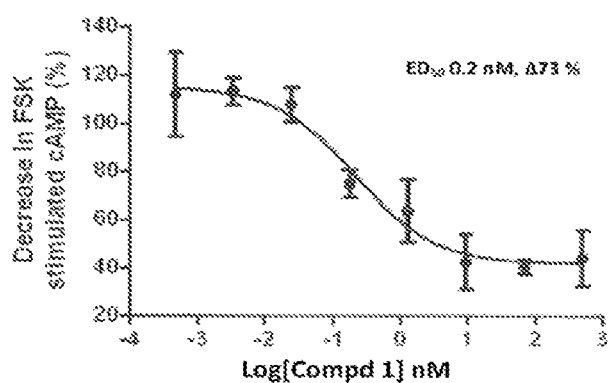
FIG. 7 illustrates rCB1 cAMP data for compound 1.
Figure 8:
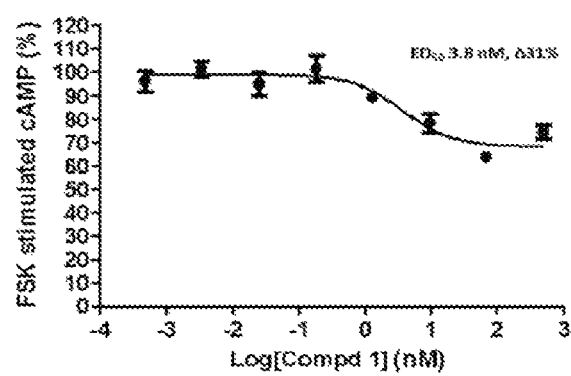
FIG. 8 illustrates hCB2 cAMP data for compound 1.
Figure 9:
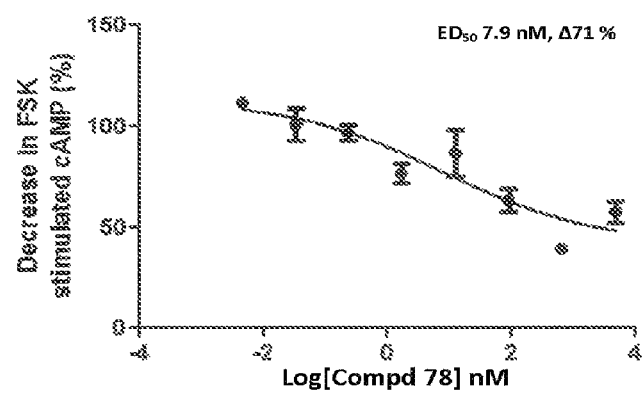
FIG. 9 illustrates rCB1 cAMP data for compound 78.
Figure 10:
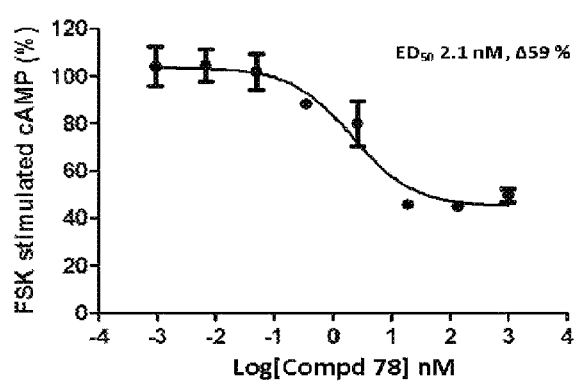
FIG. 10 illustrates hCB2 cAMP data for compound 78.

Ligands are evaluated for their abilities to behave as agonists, partial-agonists, neutral antagonists, or inverse agonists at CB1 and CB2 sites. HEK293 cells transfected with rCB1, mCB2, or hCB2 receptor are used with the PerkinElmer's Lance ultra cAMP kit following the protocol as described in *J Biomol Screen* 1999, 4, (6), 303-308; herein incorporated by reference in its entirety. The assays are carried out in 384-well format using 1000 cells/well. Test compounds are added to wells containing stimulation buffer and 2 µM forskolin followed by cell suspension. After 30 minutes stimulation, the Eu-cAMP tracer and Ulight-anti-cAMP are added to the plate and incubated at room temperature for 1 h prior to detection via PerkinElmer Envision; data are analyzed using GraphPad Prism software. For example the cAMP data for compound 1 and compound 78 using rCB1 is shown in FIG. 7 and FIG. 9. cAMP data for compound 1 and compound 78 using hCB2 is shown in FIG. 8 and FIG. 10 respectively.

Example 34: Antinociception in Male Mice

Figure 11:
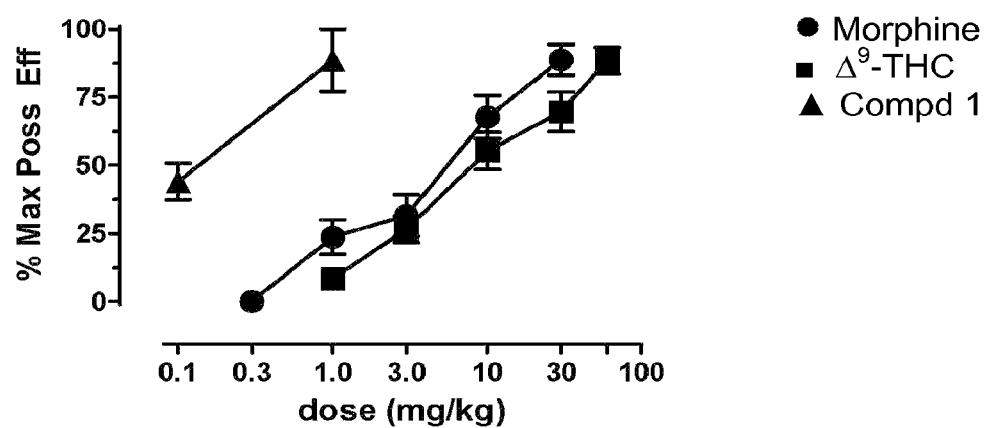
FIG. 11 is a comparison of antinociception data (tail immersion test) between morphine, $\Delta^9$-THC and compound 1 in mice.
Figure 12:
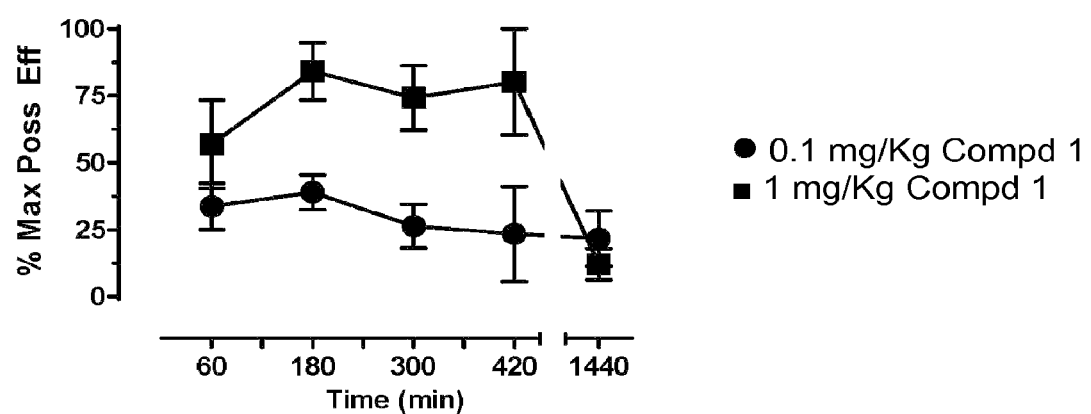
FIG. 12 illustrates antinociception data (tail immersion test) for compound 1 at 0.1 mg/kg and 1 mg/kg over 24 hours in mice.
Figure 13:
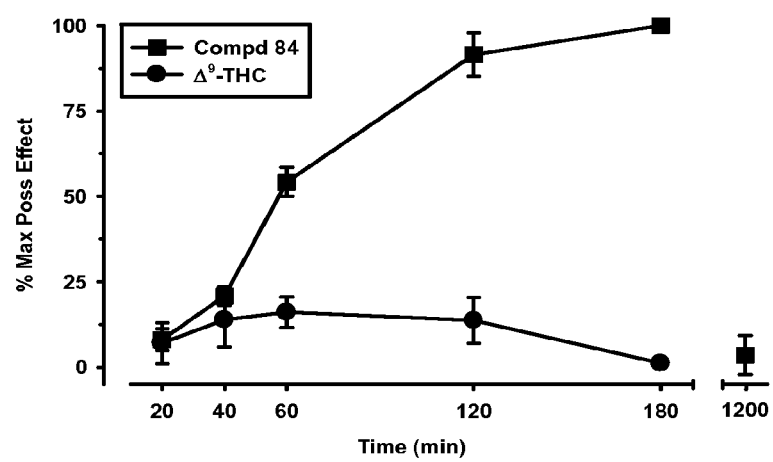
FIG. 13 illustrates antinociception data (tail immersion test) for compound 84 cumulatively dosed up to 1 mg/kg in mice.
Figure 14:
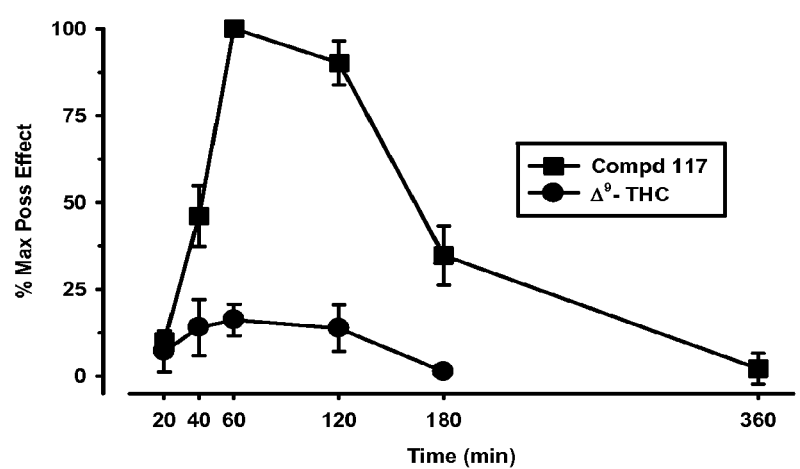
FIG. 14 illustrates antinociception data (tail immersion test) for compound 117 cumulatively dosed up to 10 mg/kg in mice.

Antinociception is evaluated by measuring response latencies in the warm water tail-immersion (tail flick) assay using similar methods as described in *Arzneimittelforschung* 13:502-507 and *J Neurosci* 17:7157-7165; each herein incorporated by reference in its entirety. Response latencies are measured as the amount of time the animal takes to respond to the thermal stimuli. Male CD-1 mice (n=6, Charles River Breeding Laboratories, Wilmington, Mass., USA) weighing 30-35 g are group housed, 4 to a cage, in a temperature controlled (~20° C.), animal facility. Mice are habituated to the vivarium for at least 1 week prior to experiments with a light/dark cycle of 12:12 h (lights on at 7 a.m.) and are acclimatized to study procedures twice, prior to testing. Mice are given food and water ad libitum. Experimentally nave mice are used for all procedures and tested during the light phase. All procedures are approved by The Animal Care and Use Committee of Northeastern University, Boston, Mass., USA. The "Principles of Animal Laboratory Care" (National Institute of Health 1996) is followed.

a) Fixed dosing: Mice are injected at T=0; and at 1, 3, 5, 7, 24 hours their tails are placed into a 52° C. water bath and the time they take to move "flick" their tails are recorded. Data is expressed as a % of an 8 second maximum. For example, FIG. 11 shows comparison of tail immersion test results for morphine, $\Delta^9$-THC, and compound 1 in mice. FIG. 12 shows tail immersion test results for compound 1 at 0.1 mg/kg and 1 mg/kg over 24 hours in mice.

b) Cumulative dosing: Drugs are administered at 0 min i.e. subsequent to base-line determinations, 0.1 mg/kg, 1 mg/kg or 1 mg/kg of compound 84, compound 117 or $\Delta^9$-THC respectively; after 20 min, 0.2 mg/kg, 2 mg/kg or 2 mg/kg of compound 84, compound 117 or $\Delta^9$-THC respectively; and after 40 min, 0.7 mg/kg, 7 mg/kg or 7 mg/kg of compound 84, compound 117 or $\Delta^9$-THC respectively. FIG. 13 and FIG. 14 show tail immersion test results for compound 84 and compound 117 in comparison to $\Delta^9$-THC in mice, respectively. FIG. 13 shows tail immersion test results for compound 84 cumulatively dosed at 1 mg/kg in comparison to $\Delta^9$-THC cumulatively dosed at 10 mg/kg in mice respectively. FIG. 14 shows tail immersion test results for compound 117 cumulatively dosed at 10 mg/kg in comparison to $\Delta^9$-THC cumulatively dosed at 10 mg/kg in mice.

Example 35: Arrestin Assay

Test compounds were screened in U2OS cells permanently expressing β-arrestin 2-GFP and human GPR55 receptor modified with human vasopressin V2 receptor tail [GPR55(E)].

β-arrestin2 translocation: For both agonist and antagonist assays, the U2OS cells permanently transfected with β-arrestin 2-GFP and human GPR55(E) were used to trace β-arrestin translocation upon compound treatment. U2OS cells permanently expressing HA-GPR55E and βarr2-GFP were plated into 96 or 384 glass bottomed well plates in clear MEM. For the antagonist assay, compounds in DMSO (final concentration<1%) were added to cells 15 min prior to LPI (agonist) addition and the plates were placed in a 5% 37 degree CO2 incubator (LPI was used at 6 µM). For agonist evaluation only the compound of interest is placed on the wells. Following 40 minute incubation, the cells are fixed by adding paraformaldehyde to 4%.

Figure 15:
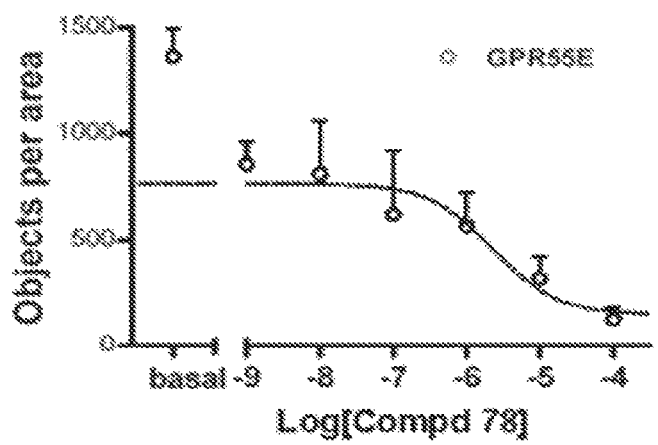
FIG. 15 illustrates the biochemical assay for compound 78 wherein the β-arresting assessment of GPR55 activation is shown.

Image acquisition is performed using the Cellomics Arrayscan VTI High Content (HC) cell based imaging system and a ×40 lens. Image analysis is done by using the Batchmode computer software evaluating wavelet information which reflects the number and intensity of fluorescent aggregation (procedures performed at Duke University and adopted from http://www.ncbi.nlm.nih.gov/books/NBK66153/and *J. Biol. Chem.* 2009; 284(43):29817-27 herein incorporated by reference in its entirety). Comparison of GPR55 antagonist data for $\Delta^9$-THC, cannabidiol, abn-cannabidiol and compound 78 are shown in Table 1. FIG. 15 describes the biochemical assay for compound 78 wherein the β-arrestin assessment of GPR55 activation is shown.

TABLE 1

GPR55 (antagonist assay) data for $\Delta^9$-THC, cannabidiol, abn-cannabidiol and compound 78.

| | GPR55 EC$_{50}$ (µM) |
|---|---|
| $\Delta^9$-THC | none |
| cannabidiol | none |
| abn-cannabidiol | none |
| compound 78 | 2-4 |
| LPI (agonist) | 6 |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:
1. A compound represented by formula (II):

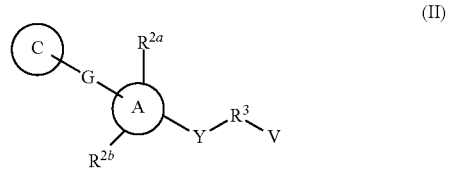

or a pharmaceutically acceptable salt thereof;
wherein:
  C is a terpene;
  G is a bond;
  A is a phenyl ring;
  $R^{2a}$ and $R^{2b}$ are each independently H, OH, SH, NH$_2$, CF$_3$, COOH, alkoxy, halogen, ONO$_2$, alkyl-ONO$_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;
  Y is a bond, C(CH$_3$)$_2$, CF$_2$, C=O, CH(alkyl), C(O)O, NHCO, CONH, alkyl, cycloalkyl, heterocyclyl, lactone, lactam, sultam, O, S, SO, SO$_2$, OSO$_2$, amine, diazine, alkenyl, or alkynyl group;
  $R^3$ is absent, or is O, S, SO$_2$, SO$_2$NH, NHSO$_2$, OSO$_2$, alkyl, alkenyl, alkynyl, cycloalkyl, a carbocyclic, a spirocyclic, heterocyclyl, aryl, heteroaryl, carboxyl, acetate, amine, amide, or imide; and
  V is ONO$_2$.

2. A compound of claim 1 represented by formula (III):

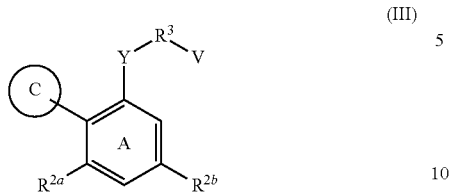
(III)

or a pharmaceutically acceptable salt thereof.

3. A compound of claim 1 represented by formula (IV):

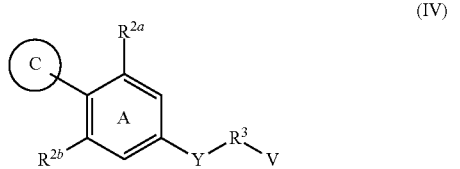
(IV)

or a pharmaceutically acceptable salt thereof.

4. The compound of claim 1, wherein C is:

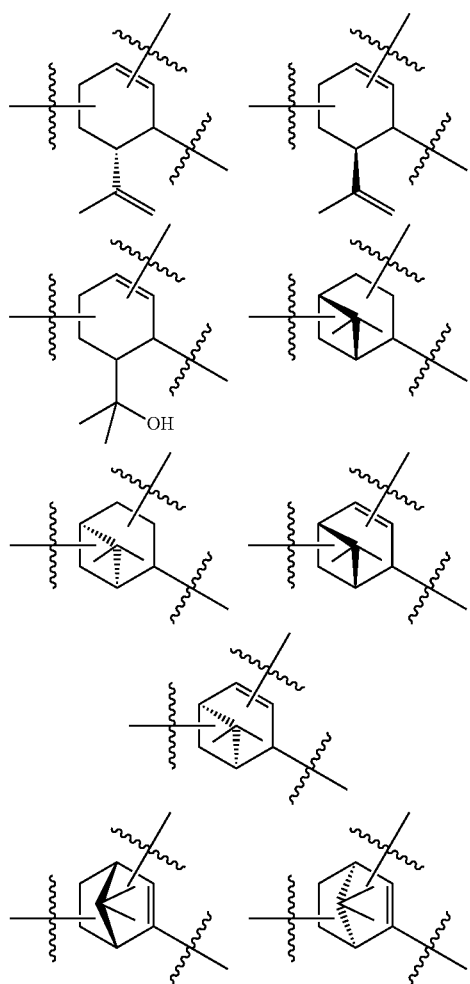

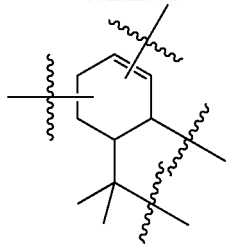

5. A composition comprising a compound of claim 1 and at least one pharmaceutically acceptable excipient.

6. A method of modulating activity of a cannabinoid 1 (CB1), cannabinoid 2 (CB2) or GPR55 receptor, the method comprising contacting the cannabinoid 1 (CB1), cannabinoid 2 (CB2), or GPR55 receptor with the compound of claim 1.

7. A compound represented by formula (V):

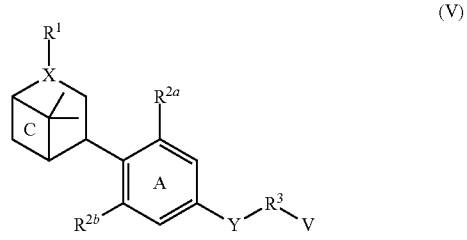
(V)

or a pharmaceutically acceptable salt thereof;
wherein:
C has zero or one double bond and, if present, the double bond is in the C2-C3 position or C3-C4 position;
X is C, CH, N, or NH; and
$R^1$ is H, OH, =O, halogen, COOH, nitro, $ONO_2$, alkyl, haloalkyl, alkenyl, alkynyl, acyl, aryl, heterocyclyl, heteroaryl, alkoxy, aryloxy, heteroalkoxy, heteroaryloxy, alkenyl, amino, thio, cyano, thiocynato, isothiocynato, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate; or
$X-R^1$ is S, O, SO, $SO_2$, or $CF_2$;
$R^{2a}$ and $R^{2b}$ are each independently H, OH, SH, $NH_2$, $CF_3$, COOH, alkoxy, halogen, $ONO_2$, alkyl-$ONO_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;
Y is a bond, $C(CH_3)_2$, $CF_2$, C=O, CH(alkyl), C(O)O, NHCO, CONH, alkyl, cycloalkyl, heterocyclyl, lactone, lactam, sultam, O, S, SO, $SO_2$, $OSO_2$, amine, diazine, alkenyl, or alkynyl group;
$R^3$ is absent, or is O, S, $SO_2$, $SO_2NH$, $NHSO_2$, $OSO_2$, alkyl, alkenyl, alkynyl, cycloalkyl, a carbocyclic, a spirocyclic, heterocyclyl, aryl, heteroaryl, carboxyl, acetate, amine, amide, or imide; and V is ONO$_2$.

8. A compound represented by formula (VI):

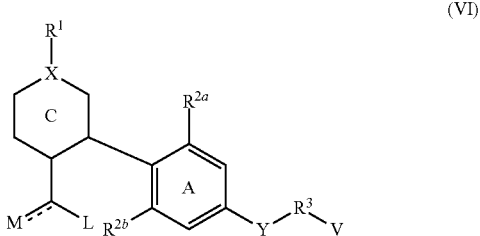

(VI)

or a pharmaceutically acceptable salt thereof; wherein:

C has zero, one or three double bonds and, if present, at least one double bond is in the C1-C2 position;

$R^{2a}$ and $R^{2b}$ are each independently H, OH, SH, NH$_2$, CF$_3$, COOH, alkoxy, halogen, ONO$_2$, alkyl-ONO$_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;

Y is a bond, C(CH$_3$)$_2$, CF$_2$, C=O, CH(alkyl), C(O)O, NHCO, CONH, alkyl, cycloalkyl, heterocyclyl, lactone, lactam, sultam, O, S, SO, SO$_2$, OSO$_2$, amine, diazine, alkenyl, or alkynyl group;

$R^3$ is absent, or is O, S, SO$_2$, SO$_2$NH, NHSO$_2$, OSO$_2$, alkyl, alkenyl, alkynyl, cycloalkyl, a carbocyclic, a spirocyclic, heterocyclyl, aryl, heteroaryl, carboxyl, acetate, amine, amide, or imide;

V is ONO$_2$;

===== represents a single bond or a double bond;

M is CH$_2$ or alkyl-T$^1$, and M is only CH$_2$ when ===== represents a double bond;

L is CH$_3$ or alkyl-T$^1$; and

X is C, CH, N, or NH; and $R^1$ is H, OH, =O, halogen, COOH, nitro, ONO$_2$, alkyl, haloalkyl, alkenyl, alkynyl, acyl, aryl, heterocyclyl, heteroaryl, alkoxy, aryloxy, heteroalkoxy, heteroaryloxy, alkenyl, amino, thio, cyano, thiocynato, isothiocynato, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate; or X—R$^1$ is S, O, SO, SO$_2$, or CF$_2$;

T$^1$ is H, alkyl, halogen, OH, CF$_3$, CF$_2$H, COOH, COOalkyl, alkaloid, immunogen, terpene, O—PO(OX$^1$)(OY$^1$), SO$_3$H, ONO$_2$ a heterocyclic ring, NQ$^1$Q$^1$, or T$^1$ is an ammonium group, wherein said ammonium group can be independently substituted one or more times with a C1 to C6 alkyl radical, or is a C3 to C7 heterocycle containing a nitrogen heteroatom for bond formation, wherein the heterocycle can contain one or more heteroatoms independently selected from N, O or S, and wherein said heterocycle can be substituted with one or more independently chosen substituents;

Q$^1$ and Q$^1$ are each independently H, alkyl, or alkyl-ONO$_2$, or Q$^1$ and Q$^1$ together are part of a heterocyclic ring having about 4 to about 7 ring members and optionally one additional heteroatom selected from O, N or S, or Q$^1$ and Q$^1$ together are part of an imide ring having about 5 to about 6 members; and X$^1$ and Y$^2$ are independently H, alkyl-OCO-alkyl, alkyl-O—CO—O-alkyl, alkali metals or alkaline earth metals.

9. A compound represented by formula (VII):

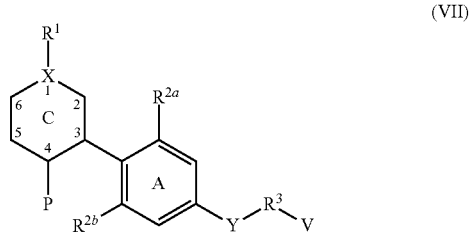

(VII)

or a pharmaceutically acceptable salt thereof, wherein:

C has zero, one or three double bonds;

$R^{2a}$ and $R^{2b}$ are each independently H, OH, SH, NH$_2$, CF$_3$, COOH, alkoxy, halogen, ONO$_2$, alkyl-ONO$_2$, or optionally substituted alkyl, haloalkyl, amine, amide, imide, alkoxy, alkoxy thio, phosphate, phosphonate, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate;

Y is a bond, C(CH$_3$)$_2$, CF$_2$, C=O, CH(alkyl), C(O)O, NHCO, CONH, alkyl, cycloalkyl, heterocyclyl, lactone, lactam, sultam, O, S, SO, SO$_2$, OSO$_2$, amine, diazine, alkenyl, or alkynyl group;

$R^3$ is absent, or is O, S, SO$_2$, SO$_2$NH, NHSO$_2$, OSO$_2$, alkyl, alkenyl, alkynyl, cycloalkyl, a carbocyclic, a spirocyclic, heterocyclyl, aryl, heteroaryl, carboxyl, acetate, amine, amide, or imide;

V is ONO$_2$;

P is alkyl, alkyl-OH or alkyl-ONO$_2$;

X is C, CH, N, or NH; and $R^1$ is H, OH, =O, halogen, COOH, nitro, ONO$_2$, alkyl, haloalkyl, alkenyl, alkynyl, acyl, aryl, heterocyclyl, heteroaryl, alkoxy, aryloxy, heteroalkoxy, heteroaryloxy, alkenyl, amino, thio, cyano, thiocynato, isothiocynato, carboxyl, formyl, carbamyl, amino, acylamino, amido, imido, aminoalkyl, aminoaryl, heteroarylamino, heterocyclylamino, sulfonate, sulfonamide, sulfonyl, thioalkyl, thioaryl, heteroarylthio, heterocyclylthio, phosphonate, phosphate, or acetate; or X—R$^1$ is S, O, SO, SO$_2$, or CF$_2$.

* * * * *